US008871205B2

(12) United States Patent  
Ting et al.

(10) Patent No.: US 8,871,205 B2  
(45) Date of Patent: Oct. 28, 2014

(54) METHODS AND COMPOSITIONS FOR THE TREATMENT OF IMMUNE DISORDERS

(75) Inventors: Jenny P.-Y. Ting, Chapel Hill, NC (US); Haitao Wen, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 10 days.

(21) Appl. No.: 13/511,933

(22) PCT Filed: Nov. 23, 2010

(86) PCT No.: PCT/US2010/057807
§ 371 (c)(1),
(2), (4) Date: Jun. 12, 2012

(87) PCT Pub. No.: WO2011/066284
PCT Pub. Date: Jun. 3, 2011

(65) Prior Publication Data
US 2012/0251539 A1 Oct. 4, 2012

Related U.S. Application Data

(60) Provisional application No. 61/264,338, filed on Nov. 25, 2009.

(51) Int. Cl.
*A61K 39/395* (2006.01)
*C07K 14/705* (2006.01)
*C07K 16/28* (2006.01)

(52) U.S. Cl.
CPC .............. *C07K 16/28* (2013.01); *C07K 14/705* (2013.01); *C07K 2319/30* (2013.01)
USPC .................... 424/134.1; 424/143.1; 424/145.1

(58) Field of Classification Search
None
See application file for complete search history.

(56) References Cited

U.S. PATENT DOCUMENTS

| 8,409,577 B2 * | 4/2013 | Thompson et al. ........ 424/134.1 |
| 2003/0032070 A1 * | 2/2003 | Good et al. ................ 435/7.21 |
| 2009/0304693 A1 * | 12/2009 | Ghayur et al. ............. 424/133.1 |

FOREIGN PATENT DOCUMENTS

WO   WO 0114420 A2 *   3/2001

OTHER PUBLICATIONS

Expert Opin Biol Ther. Sep. 2005;5 Suppl 1:S37-47. Pharmacokinetics and concentration—effect relationships of therapeutic monoclonal antibodies and fusion proteins. Ternant D, Paintaud G.*
Goshima, Y. et al., "Class 3 semaphorins as a therapeutic target", *Expert Opin. Ther. Targets*, vol. 16(9), 2012, pp. 933-944.
Holl, E.K. et al., "Plexin-B2 and Plexin-D1 in Dendritic Cells: Expression and IL-12/IL-23p40 Production", *PLoS ONE*, Aug. 2012, vol. 7, Issue 8, e43333.
Hota, P.K. et al., "Plexin structures are coming: opportunities for multilevel investigations of semaphoring guidance receptors, their cell signaling mechanisms, and functions", *Cellular and Molecular Life Sciences*, 2012, 41 pages.
Kikutani, H. et al., "Semaphorins in Interactions Between T Cells and Antigen-Presenting Cells", *Nature Reviews Immunology*, vol. 3, Feb. 2003, pp. 159-167.
Kruger, R.P. et al., "Semaphorins Command Cells to Move", *Nature Reviews Molecular Cell Biology*, vol. 6, Oct. 2005, pp. 789-800.
Kumanogoh, A. et al., "Class IV semaphoring Sema4A enhances T-cell activation and interacts with Tim-2", *Nature*, vol. 419, Oct. 10, 2002, pp. 629-633.
Kumanogoh, A. et al., "Identification of CD72 as a Lymphocyte Receptor for the Class IV Semaphorin CD100: A Novel Mechanism for Regulating B Cell Signaling", *Immunity*, vol. 13, Nov. 2000, pp. 621-631.
Kumanogoh, A. et al., "Nonredundant Roles of Sema4A in the Immune System: Defective T-Cell Priming and Th1/Th2 Regulation in Sema4A-Deficient Mice", *Immunity*, vol. 22, Mar. 2005, pp. 305-316.
Neufeld, G. et al., "The semaphorins: versatile regulators of tumour progression and tumour angiogenesis", *Nature Reviews Cancer*, vol. 8, Aug. 2008, pp. 632-645.
Okada, A. et al., "Plexin-A4 is expressed in oligodendrocyte precursor cells and acts as a mediator of semaphoring signals", *Biochemical and Biophysical Research Communications*, vol. 352, 2007, pp. 158-163.
Perälä, N. et al., "More than nervous: The emerging roles of plexins", *Differentiation*, vol. 83, 2012, pp. 71-91.
Perrot, V. et al., "Plexin B Regulates Rho through the Guanine Nucleotide Exchange Factors Leukemia-associated Rho GEF (LARG) and PDZ-RhoGEF", *The Journal of Biological Chemistry*, vol. 277, No. 45, Nov. 8, 2002, pp. 43115-43120.
Roney, K.E. et al., "Plexin-B2 Negatively Regulates Macrophage Motility, Rac, and Cdc42 Activation", *PLoS ONE*, Sep. 2011, vol. 6, Issue 9, e24795.
Saban, M.R. et al., "VEGF signaling mediates bladder neuroplasticity and inflammation in response to BCG", *BMC Physiology*, 2011, 11:16, 20 pages.
Shi, W. et al., "The Class IV Semaphorin CD100 Plays Nonredundant roles in the Immune System: Defective B and T Cell Activation in CD100-Deficient Mice", *Immunity*, vol. 13, Nov. 2000, pp. 633-642.
Suto, F. et al., "Interactions between Plexin-A2, Plexin-A4, and Semaphorin 6A Control Lamina-Restricted Projection of Hippocampal Mossy Fibers", *Neuron*, vol. 53, Feb. 15, 2007, pp. 535-547.

(Continued)

*Primary Examiner* — Brian J Gangle
*Assistant Examiner* — Andrea McCollum
(74) *Attorney, Agent, or Firm* — Myers Bigel Sibley & Sajovec, P.A.

(57) ABSTRACT

The present invention provides a method of treating an immune-related disorder in a subject, comprising administering to the subject an effective amount of an inhibitor of plexin-A4 activity, which results in reducing the plexin-A4 activity in the subject, and thereby treating the immune-related disorder. Inhibitors of plexin-A4 activity include, for example, plexin-A4 antibodies and plexin-A4 fusion proteins. The present invention further provides a method of treating an immune-related disorder in a subject, comprising administering to the subject an effective amount of an inhibitor of semaphorin-3A (Sema3A) activity, which results in reducing the Sema3A activity in the subject, thereby treating the immune-related disorder. Inhibitors of Sema3A activity include, for example, Sema3A antibodies and Sema3A fusion proteins.

3 Claims, 39 Drawing Sheets

(56) References Cited

OTHER PUBLICATIONS

Suzuki, K. et al., "Semaphorins and their receptors in immune cell interactions", *Nature Immunology*, vol. 9, No. 1, Jan. 2008, pp. 17-23.

Swiercz, J.M. et al., "Plexin-B1 Directly Interacts with PDZ-RhoGEF/LARG to Regulate RhoA and Growth Cone Morphology", *Neuron*, vol. 35, Jul. 3, 2002, pp. 51-63.

Takamatsu, H. et al., "Diverse roles for semaphoring-plexin signaling in the immune system", *Trends in Immunology*, Mar. 2012, vol. 33, No. 3, pp. 127-135.

Takegahara, N. et al., "Plexin-Al and its interaction with DAP12 in immune responses and bone homeostasis", *Nature Cell Biology*, vol. 8, No. 6, Jun. 2006, pp. 615-622.

Tran, T.S. et al., "Semaphorin Regulation of Cellular Morphology", *Annu. Rev. Cell Dev. Biol.*, vol. 23, 2007, pp. 263-292.

Turner, L.J. et al., "The Activity of the Plexin-A1 Receptor Is Regulated by Rac", *The Journal of Biological Chemistry*, vol. 279, No. 32, Aug. 6, 2004, pp. 33199-33205.

UniProtKB/Swiss-Prot, Database Accession No. Q9HCM2 (PLXA4_HUMAN), Retrieved from the internet http://www.uniprot.org/uniprot/q9hcm2.

Vadasz, Z. et al., "Semaphorin 3A is a marker for disease activity and a potential immunoregulator in systemic lupus erythematosus", *Arthritis Research & Therapy*, 2012, 14:R146, 8 pages.

Wong, A.W. et al., "CIITA-regulated plexin-A1 affects T-cell-dendritic cell interactions", *Nature Immunology*, vol. 4, No. 9, Sep. 2003, pp. 891-898.

Yamamoto, M. et al., "Plexin-A4 negatively regulates T lymphocyte responses", *International Immunology*, vol. 20, No. 3, Jan. 2008, pp. 413-420.

Yaron, A. et al., "Differential Requirement for Plexin-A3 and-A4 in Mediating Responses of Sensory and Sympathetic Neurons to Distinct Class 3 Semaphorins", *Neuron*, vol. 45, Feb. 17, 2005, pp. 513-523.

Zhu, Y. et al., "Cell Surface Signaling Molecules in the Control of Immune Responses: A Tide Model", *Immunity*, vol. 34, Apr. 22, 2011, pp. 466-478.

Coussens et al., "Inflammation and Cancer," *Nature*, vol. 410(6917), Dec. 19, 2002, pp. 860-867.

Koenig, W., "Heart Disease and the Inflammatory Response,"*BMJ*, Jul. 22, 2000, vol. 321, pp. 187-188.

Wellens et al., "Obesity-induced Inflammatory Changes in Adipose Tissue," *The Journal of Clinical Investigation*, Dec. 2003, vol. 112(12), pp. 1785-1788.

\* cited by examiner

Figure 12A.

MKAMPWNWTCLLSHLLMVGMGSSTLLTRQPAPLSQKQRSFVTFRGEPAEG
FNHLVVDERTGHIYLGAVNRIYKLSSDLKVLVTHETGPDEDNPKCYPPRI
VQTCNEPLTTTNNVNKMLLIDYKENRLIACGSLYQGICKLLRLEDLFKLG
EPYHKKEHYLSGVNESGSVFGVIVSYSNLDDKLFIATAVDGKPEYFPTIS
SRKLTKNSEADGMFAYVFHDEFVASMIKIPSDTFTIIPDFDIYYVYGFSS
GNFVYFLTLQPEMVSPPGSTTKEQVYTSKLVRLCKEDTAFNSYVEVPIGC
ERSGVEYRLLQAAYLSKAGAVLGRTLGVHPDDDLLFTVFSKGQKRKMKSL
DESALCIFILKQINDRIKERLQSCYRGEGTLDLAWLKVKDIPCSSALLTI
DDNFCGLDMNAPLGVSDMVRGIPVFTEDRDRMTSVIAYVYKNHSLAFVGT
KSGKLKKIRVDGPRGNALQYETVQVVDPGPVLRDMAFSKDHEQLYIMSER
QLTRVPVESCGQYQSCGECLGSGDPHCGWCVLHNTCTRKERCERSKEPRR
FASEMKQCVRLTVHPNNISVSQYNVLLVLETYNVPELSAGVNCTFEDLSE
MDGLVVGNQIQCYSPAAKEVPRIITENGDHHVVQLQLKSKETGMTFASTS
FVFYNCSVHNSCLSCVESPYRCHWCKYRHVCTHDPKTCSFQEGRVKLPED
CPQLLRVDKILVPVEVIKPITLKAKNLPQPQSGQRGYECILNIQGSEQRV
PALRFNSSSVQCQNTSYSYEGMEINNLPVELTVVWNGHFNIDNPAQNKVH
LYKCGAMRESCGLCLKADPDFACGWCQGPGQCTLRQHCPAQESQWLELSG
AKSKCTNPRITEIIPVTGPREGGTKVTIRGENLGLEFRDIASHVKVAGVE
CSPLVDGYIPAEQIVCEMGEAKPSQHAGFVEICVAVCRPEFMARSSQLYY
FMTLTLSDLKPSRGPMSGGTQVTITGTNLNAGSNVVVMFGKQPCLFHRRS
PSYIVCNTTSSDEVLEMKVSVQVDRAKIHQDLVFQYVEDPTIVRIEPEWS
IVSGNTPIAVWGTHLDLIQNPQIRAKHGGKEHINICEVLNATEMTCQAPA
LALGPDHQSDLTERPEEFGFILDNVQSLLILNKTNFTYYPNPVFEAFGPS
GILELKPGTPIILKGKNLIPPVAGGNVKLNYTVLVGEKPCTVTVSDVQLL
CESPNLIGRHKVMARVGGMEYSPGMVYIAPDSPLSLPAIVSIAVAGGLLI
IFIVAVLIAYKRKSRESDLTLKRLQMQMDNLESRVALECKEAFAELQTDI
HELTSDLDGAGIPFLDYRTYTMRVLFPGIEDHPVLRDLEVPGYRQERVEK
GLKLFAQLINNKVFLLSFIRTLESQRSFSMRDRGNVASLIMTVLQSKLEY
ATDVLKQLLADLIDKNLESKNHPKLLLRRTESVAEKMLTNWFTFLLYKFL
KECAGEPLFSLFCAIKQQMEKGPIDAITGEARYSLSEDKLIRQQIDYKTL
VLSCVSPDNANSPEVPVKILNCDTITQVKEKILDAIFKNVPCSHRPKAAD
MDLEWRQGSGARMILQDEDITTKIENDWKRLNTLAHYQVPDGSVVALVSK
QVTAYNAVNNSTVSRTSASKYENMIRYTGSPDSLRSRTPMITPDLESGVK
MWHLVKNHEHGDQKEGDRGSKMVSEIYLTRLLATKGTLQKFVDDLFETIF
STAHRGSALPLAIKYMFDFLDEQADKHGIHDPHVRHTWKSNCLPLRFWVN
MIKNPQFVFDIHKNSITDACLSVVAQTFMDSCSTSEHRLGKDSPSNKLLY
AKDIPSYKNWVERYYSDIGKMPAISDQDMNAYLAEQSRMHMNEFNTMSAL
SEIFSYVGKYSEEILGPLDHDDQCGKQKLAYKLEQVITLMSLDS (SEQ
ID NO:1)

Figure 12B.

MKAMPWNWTCLLSHLLMVGMGSSTLLTRQPAPLSQKQRSFVTFRGEPAEG
FNHLVVDERTGHIYLGAVNRIYKLSSDLKVLVTHETGPDEDNPKCYPPRI
VQTCNEPLTTTNNVNKMLLIDYKENRLIACGSLYQGICKLLRLEDLFKLG
EPYHKKEHYLSGVNESGSVFGVIVSYSNLDDKLFIATAVDGKPEYFPTIS
SRKLTKNSEADGMFAYVFHDEFVASMIKIPSDTFTIIPDFDIYYVYGFSS
GNFVYFLTLQPEMVSPPGSTTKEQVYTSKLVRLCKEDTAFNSYVEVPIGC
ERSGVEYRLLQAAYLSKAGAVLGRTLGVHPDDDLLFTVFSKGQKRKMKSL
DESALCIFILKQINDRIKERLQSCYRGEGTLDLAWLKVKDIPCSSALLTI
DDNFCGLDMNAPLGVSDMVRGIPVFTEDRDRMTSVIAYVYKNHSLAFVGT
KSGKLKKSFGTPQGGITQEWIGVEGDPPGANIASQEQMLCVYLQCSSHK
AISDQRVQPLLCCFLNVPGNSS(SEQ ID NO:2)

Figure 12C.

MKAMPWNWTCLLSHLLMVGMGSSTLLTRQPAPLSQKQRSFVTFRGEPAEG
FNHLVVDERTGHIYLGAVNRIYKLSSDLKVLVTHETGPDEDNPKCYPPRI
VQTCNEPLTTTNNVNKMLLIDYKENRLIACGSLYQGICKLLRLEDLFKLG
EPYHKKEHYLSGVNESGSVFGVIVSYSNLDDKLFIATAVDGKPEYFPTIS
SRKLTKNSEADGMFAYVFHDEFVASMIKIPSDTFTIIPDFDIYYVYGFSS
GNFVYFLTLQPEMVSPPGSTTKEQVYTSKLVRLCKEDTAFNSYVEVPIGC
ERSGVEYRLLQAAYLSKAGAVLGRTLGVHPDDDLLFTVFSKGQKRKMKSL
DESALCIFILKQINDRIKERLQSCYRGEGTLDLAWLKVKDIPCSSALLTI
DDNFCGLDMNAPLGVSDMVRGIPVFTEDRDRMTSVIAYVYKNHSLAFVGT
KSGKLKKMPGTSLCPTLELQTGPRSHRATVTLELLFSSCSSN(SEQ ID
NO:3)

```
ATGAAAGCCATGCCCTGGAACTGGACCTGCCTTCTCTCCCACCTCCTCATGGTGGGCATGGGCTCCTCCA
CTTTGCTCACCCGGCAGCCAGCCCCGCTGTCCCAGAAGCAGCGGTCATTTGTCACATTCCGAGGAGAGCC
CGCCGAGGGTTTCAATCACCTGGTGGTGGATGAGAGGACAGGACACATTTACTTGGGGCCGTCAATCGG
ATTTACAAGCTCTCCAGCGACCTGAAGGTCTTGGTGACGCATGAGACAGGGCCGGACGAGGACAACCCCA
AGTGTTACCCACCCCGCATCGTCCAGACCTGCAATGAGCCCCTGACCACCACCAACAATGTCAACAAGAT
GCTCCTCATAGACTACAAGGAGAACAGGCTGATTGCCTGTGGGAGCCTGTACCAAGGCATCTGCAAGCTG
CTGAGGCTGGAGGACCTCTTCAAGCTGGGGGAGCCTTATCATAAGAAGGAGCACTATCTGTCAGGTGTCA
ACGAGAGCGGCTCAGTCTTTGGAGTGATCGTCTCCTACAGCAACCTGGATGACAAGCTGTTCATTGCCAC
GGCAGTGGATGGGAAGCCCGAGTATTTTCCCACCATCTCCAGCCGGAAACTGACCAAGAACTCTGAGGCG
GATGGCATGTTCGCGTACGTCTTCCATGATGAGTTCGTGGCCTCGATGATTAAGATCCCTTCGGACACCT
TCACCATCATCCCTGACTTTGATATCTACTATGTCTATGGTTTTAGCAGTGGCAACTTTGTCTACTTTTT
GACCCTCCAACCTGAGATGGTGTCTCCACCAGGCTCCACCACCAAGGAGCAGGTGTATACATCCAAGCTC
GTGAGGCTTTGCAAGGAGGACACAGCCTTCAACTCCTATGTAGAGGTGCCCATTGGCTGTGAGCGCAGTG
GGGTGGAGTACCGCCTGCTGCAGGCTGCCTACCTGTCCAAAGCGGGGGCCGTGCTTGGCAGGACCCTTGG
AGTCCATCCAGATGATGACCTGCTCTTCACCGTCTTCTCCAAGGGCCAGAAGCGGAAAATGAAATCCCTG
GATGAGTCGGCCCTGTGCATCTTCATCTTGAAGCAGATAAATGACCGCATTAAGGAGCGGCTGCAGTCTT
GTTACCGGGCGAGGGCACGCTGGACCTGGCCTGGCTCAAGGTGAAGGACATCCCCTGCAGCAGTGCGCT
CTTAACCATTGACGATAACTTCTGTGGCCTGGACATGAATGCTCCCCTGGGAGTGTCCGACATGGTGCGT
GGAATTCCCGTCTTCACGGAGGACAGGGACCGCATGACGTCTGTCATCGCATATGTCTACAAGAACCACT
CTCTGGCCTTTGTGGGCACCAAAAGTGGCAAGCTGAAGAAGATCCGGGTGGATGGACCCAGGGCAACGC
CCTCCAGTATGAGACGGTGCAGGTGGTGGACCCCGGCCCAGTCCTCCGGGATATGGCCTTCTCCAAGGAC
CACGAGCAACTCTACATCATGTCAGAGAGGCAGCTCACCAGAGTCCCTGTGGAGTCCTGTGGTCAGTATC
AGAGCTGCGGCGAGTGCCTTGGCTCAGGCGACCCCCACTGTGGCTGGTGTGTGCTGCACAACACTTGCAC
CCGGAAGGAGCGGTGTGAGCGGTCCAAGGAGCCCCGCAGGTTTGCCTCGGAGATGAAGCAGTGTGTCCGG
CTGACGGTCCATCCCAACAATATCTCCGTCTCTCAGTACAACGTGCTGCTGGTCCTGGAGACGTACAATG
TCCCGGAGCTGTCAGCTGGCGTCAACTGCACCTTTGAGGACCTGTCAGAGATGGATGGGCTGGTCGTGGG
CAATCAGATCCAGTGCTACTCCCCTGCAGCCAAGGAGGTGCCCCGGATCATCACAGAGAATGGGGACCAC
CATGTCGTACAGCTTCAGCTCAAATCAAAGGAGACCGGCATGACCTTCGCCAGCACCAGCTTTGTCTTCT
ACAATTGCAGCGTCCACAATTCGTGCCTGTCCTGCGTGGAGAGTCCATACCGCTGCCACTGGTGTAAATA
CCGGCATGTCTGCACCCATGACCCCAAGACCTGCTCCTTCCAGGAAGGCCGAGTGAAGCTGCCCGAGGAC
TGCCCCCAGCTGCTGCGAGTGGACAAGATCCTGGTGCCCGTGGAGGTGATCAAGCCTATCACGCTGAAGG
CCAAGAACCTCCCCCAGCCCCAGTCTGGGCAGCGTGGCTACGAATGCATCCTCAACATTCAGGGCAGCGA
GCAGCGAGTGCCCGCCCTGCGCTTCAACAGCTCCAGCGTACAGTGCCAGAACACCTCTTATTCCTATGAA
GGGATGGAGATCAACAACCTGCCCGTGGAGTTGACAGTCGTGTGGAATGGGCACTTCAACATTGACAACC
CAGCTCAGAATAAAGTTCACCTCTACAAGTGTGGAGCCATGCGTGAGAGCTGCGGGCTGTGCCTCAAGGC
TGACCCAGACTTCGCATGTGGCTGGTGCCAGGGCCCAGGCCAGTGCACCCTGCGCCAGCACTGCCCTGCC
CAGGAGAGCCAGTGGCTGGAGCTGTCTGGTGCCAAAAGCAAGTGCACAAACCCCGCATCACAGAGATAA
TCCCGGTGACAGGCCCCGGGAAGGGGCACCAAGGTCACTATCCGAGGGGAGAACCTGGGCCTGGAATT
TCGCGACATCGCCTCCCATGTCAAGGTTGCTGGCGTGGAGTGCAGCCCTTTAGTGGATGGTTACATCCCT
GCAGAACAGATCGTGTGTGAGATGGGGAGGCCAAGCCCAGCCAGCATGCAGGCTTCGTGGAGATCTGCG
TGGCTGTGTGTCGGCCTGAATTCATGGCCCGGTCCTCACAGCTCTATTACTTCATGACACTGACTCTCTC
AGATCTGAAGCCCAGCCGGGGGCCCATGTCCGGAGGGACCCAAGTGACCATCACAGGCACCAACCTGAAT
GCCGGAAGCAACGTGGTGGTGATGTTTGGAAAGCAGCCCTGTCTCTTCCACAGGCGATCTCCATCCTACA
```

FIG. 13

```
TTGTCTGCAACACCACATCCTCAGATGAGGTGCTAGAGATGAAGGTGTCGGTGCAGGTGGACAGGGCCAA
GATCCACCAGGACCTGGTCTTTCAGTATGTGGAAGACCCCACCATCGTGCGGATTGAGCCAGAATGGAGC
ATTGTCAGTGGAAACACACCCATCGCCGTATGGGGACCCACCTGGACCTCATACAGAACCCCCAGATCC
GTGCCAAGCATGGAGGGAAGGAGCACATCAATATCTGTGAGGTTCTGAACGCTACTGAGATGACCTGTCA
GGCGCCCGCCCTCGCTCTGGGTCCTGACCACCAGTCAGACCTGACCGAGAGGCCCGAGGAGTTTGGCTTC
ATCCTGGACAACGTCCAGTCCCTGCTCATCCTCAACAAGACCAACTTCACCTACTATCCCAACCCGGTGT
TTGAGGCCTTTGGTCCCTCAGGAATCCTGGAGCTCAAGCCTGGCACGCCCATCATCCTAAAGGGCAAGAA
CCTGATCCCGCCTGTGGCTGGGGGCAACGTGAAGCTGAACTACACTGTGCTGGTTGGGGAGAAGCCGTGC
ACCGTGACCGTGTCAGATGTCCAGCTGCTCTGCGAGTCCCCCAACCTCATCGGCAGGCACAAAGTGATGG
CCCGTGTCGGTGGCATGGAGTACTCCCCGGGGATGGTGTACATTGCCCCGGACAGCCCGCTCAGCCTGCC
CGCCATCGTCAGCATCGCAGTGGCTGGCGGCCTCCTCATCATTTTCATCGTGGCCGTGCTCATTGCCTAT
AAACGCAAGTCCCGCGAAAGTGACCTCACGCTGAAGCGGCTGCAGATGCAGATGGACAACCTGGAGTCCC
GTGTGGCCCTGGAGTGCAAGGAAGCCTTTGCCGAGCTGCAGACGGACATCCATGAGCTGACCAGTGACCT
GGATGGAGCCGGGATTCCGTTCCTGGACTATAGAACTTACACCATGCGGGTGCTGTTCCCAGGAATTGAA
GACCACCCTGTCCTCCGGGACCTTGAGGTCCCGGGCTACCGGCAGGAGCGTGTGGAGAAAGGCCTGAAGC
TCTTCGCCCAGCTCATCAACAACAAGGTGTTCCTGCTGTCCTTCATCCGCACGCTTGAGTCCCAGCGTAG
CTTCTCCATGCGCGACCGTGGCAACGTGGCCTCACTCATCATGACCGTGCTGCAGAGCAAGCTGGAGTAC
GCCACTGATGTGCTGAAGCAGCTGCTGGCCGACCTCATTGACAAGAACCTGGAGAGCAAGAACCACCCTA
AGCTGCTGCTCAGGAGGACTGAGTCAGTGGCTGAGAAGATGCTGACCAATTGGTTTACTTTCCTCCTCTA
CAAGTTCCTCAAGGAGTGTGCTGGGGAGCCCCTCTTCTCCCTGTTCTGTGCCATCAAGCAGCAGATGGAG
AAGGGCCCCATTGACGCCATCACGGGCGAGGCCCGCTACTCCTTGAGCGAGGACAAGCTCATCCGCCAGC
AGATTGACTACAAAACCCTGGTCCTGAGCTGTGTCAGCCCAGACAATGCCAACAGCCCCGAGGTCCCAGT
AAAGATCCTCAACTGTGACACCATCACTCAGGTCAAGGAGAAGATTCTGGATGCCATCTTCAAGAATGTG
CCTTGCTCCCACCGGCCCAAAGCTGCAGATATGGATCTGGAGTGGCGACAAGGAAGTGGGGCAAGGATGA
TCTTGCAGGATGAAGACATCACCACCAAGATTGAGAATGATTGGAAGCGACTGAACACACTGGCCCACTA
CCAGGTGCCAGATGGTTCCGTGGTGGCATTAGTGTCCAAGCAGGTGACAGCCTATAACGCAGTGAACAAC
TCCACCGTCTCCAGGACCTCAGCAAGTAAATATGAAAACATGATCCGGTACACGGGCAGCCCCGACAGCC
TCCGCTCACGGACACCTATGATCACTCCTGACCTGGAGAGTGGAGTCAAGATGTGGCACCTAGTGAAGAA
CCACGAGCACGGAGACCAGAAGGAGGGGGACCGGGGAGCAAGATGGTGTCTGAAATCTACCTGACCCGA
CTCCTGGCCACTAAGGGCACACTGCAGAAGTTTGTGGATGACCTCTTTGAGACCATCTTCAGCACGGCAC
ACCGTGGCTCTGCCCTGCCCCTGGCCATCAAGTACATGTTTGACTTCCTGGATGAGCAGGCTGATAAACA
TGGCATTCATGACCCGCACGTCCGCCATACCTGGAAGAGCAATTGCCTGCCCCTGAGGTTTTGGGTCAAC
ATGATCAAGAACCCGCAGTTTGTGTTTGACATCCATAAGAACAGCATCACAGACGCCTGCCTCTCTGTGG
TGGCTCAGACCTTCATGGACTCTTGCTCCACGTCAGAGCACCGGCTGGGCAAGGACTCGCCCTCCAACAA
GCTGCTGTATGCCAAGGACATCCCCAGCTACAAGAATTGGGTGGAGAGGTATTACTCAGACATAGGGAAG
ATGCCAGCCATCAGCGACCAAGACATGAACGCATACCTGGCTGAGCAGTCCCGGATGCACATGAATGAGT
TCAACACCATGAGTGCACTCTCAGAGATCTTCTCCTATGTGGGCAAATACAGCGAGGAGATCCTTGGACC
TCTGGACCACGATGACCAGTGTGGGAAGCAGAAACTGGCCTACAAACTAGAACAAGTCATAACCCTCATG
AGCTTAGACAGCTGA (SEQ ID NO:4)
```

*FIG. 13 (CONT'D.)*

```
TGCGTTCGGGGCTGGGGCTGGAGGAGGCAGCCACACGCGCGCACACGCACACGTTCAGAGGAGGGCGAGA
GGCAGCGGCATAGGCTCCATCTGCAGTGTCAATGCGGCGCTCCCGCTGAAGGAGGGAAACGCGGCGCGTC
CAGTAGGGGAGACTGCATTGCTGAGTCCTGGCCCTCTGAGGGGACGACTGTGCCTGAGTGCTGCTGTGCC
ACTGGGACCCGCCTCTGCCATGAAAGCCATGCCCTGGAACTGGACCTGCCTTCTCTCCCACCTCCTCATG
GTGGGCATGGGCTCCTCCACTTTGCTCACCCGGCAGCCAGCCCCGCTGTCCCAGAAGCAGCGGTCATTTG
TCACATTCCGAGGAGAGCCCGCCGAGGGTTTCAATCACCTGGTGGTGGATGAGAGGACAGGACACATTTA
CTTGGGGGCCGTCAATCGGATTTACAAGCTCTCCAGCGACCTGAAGGTCTTGGTGACGCATGAGACAGGG
CCGGACGAGGACAACCCCAAGTGTTACCCACCCCGCATCGTCCAGACCTGCAATGAGCCCCTGACCACCA
CCAACAATGTCAACAAGATGCTCCTCATAGACTACAAGGAGAACAGGCTGATTGCCTGTGGGAGCCTGTA
CCAAGGCATCTGCAAGCTGCTGAGGCTGGAGGACCTCTTCAAGCTGGGGGAGCCTTATCATAAGAAGGAG
CACTATCTGTCAGGTGTCAACGAGAGCGGCTCAGTCTTTGGAGTGATCGTCTCCTACAGCAACCTGGATG
ACAAGCTGTTCATTGCCACGGCAGTGGATGGAAGCCCGAGTATTTTCCCACCATCTCCAGCCGGAAACT
GACCAAGAACTCTGAGGCGGATGGCATGTTCGCGTACGTCTTCCATGATGAGTTCGTGGCCTCGATGATT
AAGATCCCTTCGGACACCTTCACCATCATCCCTGACTTTGATATCTACTATGTCTATGGTTTTAGCAGTG
GCAACTTTGTCTACTTTTTGACCCTCCAACCTGAGATGGTGTCTCCACCAGGCTCCACCACCAAGGAGCA
GGTGTATACATCCAAGCTCGTGAGGCTTTGCAAGGAGGACACAGCCTTCAACTCCTATGTAGAGGTGCCC
ATTGGCTGTGAGCGCAGTGGGGTGGAGTACCGCCTGCTGCAGGCTGCCTACCTGTCCAAAGCGGGGCCG
TGCTTGGCAGGACCCTTGGAGTCCATCCAGATGATGACCTGCTCTTCACCGTCTTCTCCAAGGGCCAGAA
GCGGAAAATGAAATCCCTGGATGAGTCGGCCCTGTGCATCTTCATCTTGAAGCAGATAAATGACCGCATT
AAGGAGCGGCTGCAGTCTTGTTACCGGGGCGAGGGCACGCTGGACCTGGCCTGGCTCAAGGTGAAGGACA
TCCCCTGCAGCAGTGCGCTCTTAACCATTGACGATAACTTCTGTGGCCTGGACATGAATGCTCCCCTGGG
AGTGTCCGACATGGTGCGTGGAATTCCCGTCTTCACGGAGGACAGGGACCGCATGACGTCTGTCATCGCA
TATGTCTACAAGAACCACTCTCTGGCCTTTGTGGGCACCAAAAGTGGCAAGCTGAAGAAGATCCGGGTGG
ATGGACCCAGGGGCAACGCCCTCCAGTATGAGACGGTGCAGGTGGTGGACCCCGGCCCAGTCCTCCGGGA
TATGGCCTTCTCCAAGGACCACGAGCAACTCTACATCATGTCAGAGAGGCAGCTCACCAGAGTCCCTGTG
GAGTCCTGTGGTCAGTATCAGAGCTGCGGCGAGTGCCTTGGCTCAGGCGACCCCCACTGTGGCTGGTGTG
TGCTGCACAACACTTGCACCCGGAAGGAGCGGTGTGAGCGGTCCAAGGAGCCCCGCAGGTTTGCCTCGGA
GATGAAGCAGTGTGTCCGGCTGACGGTCCATCCCAACAATATCTCCGTCTCTCAGTACAACGTGCTGCTG
GTCCTGGAGACGTACAATGTCCCGGAGCTGTCAGCTGGCGTCAACTGCACCTTTGAGGACCTGTCAGAGA
TGGATGGGCTGGTCGTGGGCAATCAGATCCAGTGCTACTCCCCTGCAGCCAAGGAGGTGCCCCGGATCAT
CACAGAGAATGGGGACCACCATGTCGTACAGCTTCAGCTCAAATCAAAGGAGACCGGCATGACCTTCGCC
AGCACCAGCTTTGTCTTCTACAATTGCAGCGTCCACAATTCGTGCCTGTCCTGCGTGGAGAGTCCATACC
GCTGCCACTGGTGTAAATACCGGCATGTCTGCACCCATGACCCCAAGACCTGCTCCTTCCAGGAAGGCCG
AGTGAAGCTGCCCGAGGACTGCCCCAGCTGCTGCGAGTGGACAAGATCCTGGTGCCCGTGGAGGTGATC
AAGCCTATCACGCTGAAGGCCAAGAACCTCCCCCAGCCCCAGTCTGGGCAGCGTGGCTACGAATGCATCC
TCAACATTCAGGGCAGCGAGCAGCGAGTGCCCGCCCTGCGCTTCAACAGCTCCAGCGTACAGTGCCAGAA
CACCTCTTATTCCTATGAAGGGATGGAGATCAACAACCTGCCCGTGGAGTTGACAGTCGTGTGGAATGGG
CACTTCAACATTGACAACCCAGCTCAGAATAAAGTTCACCTCTACAAGTGTGGAGCCATGCGTGAGAGCT
GCGGGCTGTGCCTCAAGGCTGACCCAGACTTCGCATGTGGCTGGTGCCAGGGCCCAGGCCAGTGCACCCT
GCGCCAGCACTGCCCTGCCCAGGAGAGCCAGTGGCTGGAGCTGTCTGGTGCCAAAAGCAAGTGCACAAAC
CCCCGCATCACAGAGATAATCCCGGTGACAGGCCCCGGGAAGGGGCACCAAGGTCACTATCCGAGGGG
AGAACCTGGGCCTGGAATTTCGCGACATCGCCTCCCATGTCAAGGTTGCTGGCGTGGAGTGCAGCCCTTT
AGTGGATGGTTACATCCCTGCAGAACAGATCGTGTGTGAGATGGGGGAGGCCAAGCCCAGCCAGCATGCA
```

*FIG. 14*

```
GGCTTCGTGGAGATCTGCGTGGCTGTGTGTCGGCCTGAATTCATGGCCCGGTCCTCACAGCTCTATTACT
TCATGACACTGACTCTCTCAGATCTGAAGCCCAGCCGGGGGCCCATGTCCGGAGGGACCCAAGTGACCAT
CACAGGCACCAACCTGAATGCCGGAAGCAACGTGGTGGTGATGTTTGGAAAGCAGCCCTGTCTCTTCCAC
AGGCGATCTCCATCCTACATTGTCTGCAACACCACATCCTCAGATGAGGTGCTAGAGATGAAGGTGTCGG
TGCAGGTGGACAGGGCCAAGATCCACCAGGACCTGGTCTTTCAGTATGTGGAAGACCCCACCATCGTGCG
GATTGAGCCAGAATGGAGCATTGTCAGTGGAAACACACCCATCGCCGTATGGGGGACCCACCTGGACCTC
ATACAGAACCCCCAGATCCGTGCCAAGCATGGAGGGAAGGAGCACATCAATATCTGTGAGGTTCTGAACG
CTACTGAGATGACCTGTCAGGCGCCCGCCCTCGCTCTGGGTCCTGACCACCAGTCAGACCTGACCGAGAG
GCCCGAGGAGTTTGGCTTCATCCTGGACAACGTCCAGTCCCTGCTCATCCTCAACAAGACCAACTTCACC
TACTATCCCAACCCGGTGTTTGAGGCCTTTGGTCCCTCAGGAATCCTGGAGCTCAAGCCTGGCACGCCCA
TCATCCTAAAGGGCAAGAACCTGATCCCGCCTGTGGCTGGGGGCAACGTGAAGCTGAACTACACTGTGCT
GGTTGGGGAGAAGCCGTGCACCGTGACCGTGTCAGATGTCCAGCTGCTCTGCGAGTCCCCCAACCTCATC
GGCAGGCACAAAGTGATGGCCCGTGTCGGTGGCATGGAGTACTCCCCGGGGATGGTGTACATTGCCCCGG
ACAGCCCGCTCAGCCTGCCCGCCATCGTCAGCATCGCAGTGGCTGGCGGCCTCCTCATCATTTTCATCGT
GGCCGTGCTCATTGCCTATAAACGCAAGTCCCGCGAAAGTGACCTCACGCTGAAGCGGCTGCAGATGCAG
ATGGACAACCTGGAGTCCCGTGTGGCCCTGGAGTGCAAGGAAGCCTTTGCCGAGCTGCAGACGGACATCC
ATGAGCTGACCAGTGACCTGGATGGAGCCGGGATTCCGTTCCTGGACTATAGAACTTACACCATGCGGGT
GCTGTTCCCAGGAATTGAAGACCACCCTGTCCTCCGGGACCTTGAGGTCCCGGGCTACCGGCAGGAGCGT
GTGGAGAAAGGCCTGAAGCTCTTCGCCCAGCTCATCAACAACAAGGTGTTCCTGCTGTCCTTCATCCGCA
CGCTTGAGTCCCAGCGTAGCTTCTCCATGCGCGACCGTGGCAACGTGGCCTCACTCATCATGACCGTGCT
GCAGAGCAAGCTGGAGTACGCCACTGATGTGCTGAAGCAGCTGCTGGCCGACCTCATTGACAAGAACCTG
GAGAGCAAGAACCACCCTAAGCTGCTGCTCAGGAGGACTGAGTCAGTGGCTGAGAAGATGCTGACCAATT
GGTTTACTTTCCTCCTCTACAAGTTCCTCAAGGAGTGTGCTGGGGAGCCCCTCTTCTCCCTGTTCTGTGC
CATCAAGCAGCAGATGGAGAAGGGCCCCATTGACGCCATCACGGGCGAGGCCCGCTACTCCTTGAGCGAG
GACAAGCTCATCCGCCAGCAGATTGACTACAAAACCCTGGTCCTGAGCTGTGTCAGCCCAGACAATGCCA
ACAGCCCCGAGGTCCCAGTAAAGATCCTCAACTGTGACACCATCACTCAGGTCAAGGAGAAGATTCTGGA
TGCCATCTTCAAGAATGTGCCTTGCTCCCACCGGCCCAAAGCTGCAGATATGGATCTGGAGTGGCGACAA
GGAAGTGGGGCAAGGATGATCTTGCAGGATGAAGACATCACCACCAAGATTGAGAATGATTGGAAGCGAC
TGAACACACTGGCCCACTACCAGGTGCCAGATGGTTCCGTGGTGGCATTAGTGTCCAAGCAGGTGACAGC
CTATAACGCAGTGAACAACTCCACCGTCTCCAGGACCTCAGCAAGTAAATATGAAAACATGATCCGGTAC
ACGGGCAGCCCCGACAGCCTCCGCTCACGGACACCTATGATCACTCCTGACCTGGAGAGTGGAGTCAAGA
TGTGGCACCTAGTGAAGAACCACGAGCACGGAGACCAGAAGGAGGGGGACCGGGGAGCAAGATGGTGTC
TGAAATCTACCTGACCCGACTCCTGGCCACTAAGGGCACACTGCAGAAGTTTGTGGATGACCTCTTTGAG
ACCATCTTCAGCACGGCACACCGTGGCTCTGCCCTGCCCCTGGCCATCAAGTACATGTTTGACTTCCTGG
ATGAGCAGGCTGATAAACATGGCATTCATGACCCGCAGTTTGTGTTTGACATCCATAAGAACAGCATCACA
GACGCCTGCCTCTCTGTGGTGGCTCAGACCTTCATGGACTCTTGCTCCACGTCAGAGCACCGGCTGGGCA
AGGACTCGCCCTCCAACAAGCTGCTGTATGCCAAGGACATCCCCAGCTACAAGAATTGGGTGGAGAGGTA
TTACTCAGACATAGGGAAGATGCCAGCCATCAGCGACCAAGACATGAACGCATACCTGGCTGAGCAGTCC
CGGATGCACATGAATGAGTTCAACACCATGAGTGCACTCTCAGAGATCTTCTCCTATGTGGGCAAATACA
GCGAGGAGATCCTTGGACCTCTGGACCACGATGACCAGTGTGGGAAGCAGAAACTGGCCTACAAACTAGA
ACAAGTCATAACCCTCATGAGCTTAGACAGCTGAGAACCGTCCTTCCAGGGCCGCCCTGGAGGGGGACAC
ACCAAGCCGTGCCTCAGTCTAGATTATCATCTTTACCAAGTGCAAGTTCCGACTGGCATCAGCAGCATCC
```

*FIG. 14 (CONT'D.)*

```
CCTGAGCAGCGCTGTTTCTCTCTCTTTCTCTCTGCCTCTTTCCGTTTCTCCCTCCTTCCTGGATCTCTTC
TCTTCCAGTTGCTCTGCCAACACGATTGGACCAAGCCACTGACCCTCAGTTAGTCCAAGAATGGCCAGGC
CCATGGCAAGGGAGCTGACCAGAAGATGTCAGAGAGGCCTCTGTCTCCCAGGTGCTCCTGACCCTGTGCA
TGTCAGCAGCAGGGTGCAAATAACGAATGAGGAGCCAGGGACAGGGGACATTTCTGTGCTGCTACTTCAC
CTTCCACTTTGGCAGCCCCTGCTTTGGTCTGAGCCTTGGCCTAGGGAAGAGGCAAGGAAGGACTTCAGTA
TTATCTTTACTGGGAAGACATCACCTGGCTCTCCCTTCCCACAGTTCCATCTCCAGTGGTTCAGCCAGTG
GTCTGATCGCTTTGCAGCTGTGAGAAGAAAGGCTACACCTCCTGCATGTGGCTGGAGCAGGGCATGTGTG
GGCAGCTGGGAGGTGCTCCTTGAGGCTCCTTCTCCCCACTGGGCTGGTGTCCAGAGGCTTCCTGTCCTT
TTCCAGGTCTCCAGAGGGACCTGCCTGCCCTGCCTGCTCCCCCGCCAGTAGAAAGCCAGGCAGGAGAAAG
AATAGCAATTACATTCCACCATGGAGATGCTCCTGACCTTTTCATCTGAATCCTAGTAGCAGAAATGTAA
CACAGGGGGAGAAAAGGAAAGAGAGTTGCATCTACCCTGGAAGCAGAATTTGTTTTTCCATTTACCCTCAA
ATTCAAATGAGTCACAATCATAGTCATAGGTCTAGTCCACTACCAGAGCCCTGAGTGCTGTCAAGAGAAA
GCATCTATCTCCACCCTCCTTTGTCAACCTTCATCAAGGGTCAACGTGAAATGCAGAGTGCATCTAGGAG
ATTCTACCTCCAGCCATCTCCATGGCTCCATCCCCATCATCCTTCCTGAGAACTCCATAGACGGCTGGGG
CCAACAGCCAGTCCCTGTTCCCTCTGCAGAATCCGGTGCCATTGCTATGCAGATGACTTTGTCACTGGG
CTGTCCAGACCTCTTTGGGAATGATTTCATCAACATCTCAGCTGTCTCTCATCATTCTCCTTCCTCATCT
CTTCAGCAGTCATCCTTGAAAGAAACAGACTTAAGCAAAGCCTCACGGAGACAGCCCAAAATGCCAGCCA
ACCTCAGCCTCCAGCTTGTCAGATCTGGGAGGGACAAAGAGTCGAGCTGATGGGCCTGGCTGGAATTAAG
AAGAGGGACATACAAATGACCTTGGCCTTGGCATCCATCTCCCCATCTGTTCTTACATCTACAGATGCAC
GATTTTAGCCAGGCAGGCAAATGTGTGCCTAGAAATTGATACTAGGTAAGCAGAGGCTATGGGAGAGAT
GGTCTAATGGAGGGTTCTAGGAACCTTTCATCCTAAGGAGACCTTAGGTGCTGTCTGGTGCAGTCTCCCA
TCCTAAGCAGGAGTCTCTGTTGGCACCTCTGCTCTGGAGTTGTTCACCACTATGGGAGACAAGGAGAAAC
ATCTTAGGTGAGGTTGAGGAGAAGGATTCACAGTCTTGCCTTCACTCCCCAAACATCAGACATCATTCCT
TGTCACCCACTCAGAATGAGCCCCCCTTGGGGAAGAAACCACACCATTTCCAGCAAAGTCCATGGAGCAT
CCGGTACTTTTAAGAACACTTGCCCCTTTGGATATGAATATGTGCACATGTGTGTGAGCACATGTATGTG
TGTGTGTGTCTGCCCCAGGTGTAGGCGGAAAGCTCAAAAGGATTTCTTGTCCTTTGTAGGAGGATTTT
TGAAGTGTTCCCCTTCTCTTTCCCCTTGCTCATCCATTCATCCTGCAGCTTCAGGACATTTCAACACTTA
CTTGCTTTCTATGCTGAGAGCTGGTGGGTGGAAGGAGAGGGCGCTTGTCCATAGGAAATCAGGGTGGTCG
CCTGCCGAGGCCTGGACCTTGGAACAGGGCATCATGTGACATCGCAGAGGACAGATGGTGGAAAAGACAT
GAGCAACCTAATGGGAAGAGGAAAATGGGAAACAATGCATTGGAAGAGGAAGAAAAAAAATAAATAACCA
AAGGTTTTGGCAAGTGCAGTACCAGGTGGAGAAGCTTGACTTTTCTATCCTTGATCATTTTATTCCCTCC
CAAGAAGTCAGTCACAGGACCTGGAAGGCCAGAAAGGGTACATGTGGGAGACGGTCTGAGGAAGTACCTC
GGTCACTACAATATTTTTGCACATATAAAGGGTTGGGGAGGAAAGAGACACAAACGTATTTAACACAGAT
TTGCTGGATGGAAGCTGCGTGTGTGAACGTGTGTATGAGTGAGTGCATTTTGATTTTTTTTTTTTTTTT
TGCACAGTTAAGAGAAAAAATCAAACAAGCAGAAAAAAAAAAGAAAAAAGACTTATCACGGTTCTGCTGA
AGCTTTTATTTTTTACTGGATGATGATTATTGTTATTGTTACTTTGGCGGTACAGGACTTTATTTTATTC
CATGTTTTTGTTATAAGAAAAATTTCAAACACCTCAGAGAAATAGAAAGGTTAGGAAGAAAGAGGAGACA
AGGACAGACAAATTTTCTGGCTGTCCCCATTTCTCCTGGGGAGGGGTTTGGGGCTGGTTTGACTTTAAT
TGGTGGGTGGGTTGTTTCTGCCGCTCTGTTTGCTGCAGTCCCCGTGGCCTGCTTGGGGACTGAGAAATTT
GAGCCAGGTATCCAGAGCCACAGCCCATCTTGCTTATAAAAATTATCTTCTGCTGTTTGTTTTCCATTTC
TTCCGTTTGGATTCTTGGTGCACGTGTGATATGGTATTTAAAAGCAAAGACAAGCAACATTGTCAAAAAG
CTGTCCTTGCCCCCATCCCCCACCCAAATCTTTTTTCCAAACTCCCCCAGGGATCTTCCTTACCCCACT
GGCAGAGCAAACATCCAGGGGCTGTCCATGTGGCTTGCGGGCTCCCAGAGAAAGGAATTGGGCCAACTTT
```

*FIG. 14 (CONT'D.)*

```
GTCCTGTGGGATGGAGGCCCCTTCACGGCCTCCCTCGAGGCAAAGTTAATTTGTAGGGTCACCATTATGT
TGAGTCATGAGCAGACAGAAGGAGAGAAAAGGCCATCTTCCTTACCTTCCCCTCCAACTTATCCCGTACC
CTCCCAGGGAAAATGGTACCAGACTGAGCCATCAAAATCACTGACAAAGTTTAGGTGGGAATTTTTTTTG
CATGTTGGAGAGAGAAGGGCTTAAGGTAGCAGGGAAGAAGGGGGCTTTGTGGGGTCCTAAATTTTAAGGA
ATAAGTAGAGGAAGACAAGAAACAGAGTGGTAGGCTGGTCATTTCTCCTGGCCACAAGTCCCCCCAGATG
CAGCTTTTACCCATTCTTTGTCCTTCCCCATAAGGAGAGACCCTGACATTTCTTGGTAGCTGCAAATAGT
GCCACTAAGTGAAGGTGGCCATCATGCCAGTTACTTCCTCAGGAAAATATTTTCTTGCCTTCTTCTTTCA
GTATGGTTTTAAATTTGGGAACAGTGGATAACCCAAGTGTCCCACAGGCCAAGGTACATTCCAATGGCAG
CATGATCCCTGCACCCAAAGCCAGCCCCTAAAGCCTACCCCTTGTGCACCCGCAGCCTGGTAAGTGAGCT
TGGCTGCTTGTGAGGAGCTACAAGTGAAAGAGAAGTTATTTTAAATAAATCCCAAAGTTTGAGGCAGACT
GTCCAGGACTGTTCCCAGGAAGAAGCAGGAGTTACCCACAGGAAAAGTCTCTGACCTGGTCCCCTCAGGC
CCAGCTACCTGCGCCCACCAGCAGTGAAGGTTGATGTACTGGCCCAGCATCTCCACCTCCCCCATGCAAC
CAGGTCCCTGGTACCGTGTCTCCCGTTGCATGTCTGGCTTCTGCCTGTGCTCCTCCTGCCACGAGCATCC
TCCCTGTCCCTCCTCATTCCACCGTGTCTCTCCTGCACACATAGCCTCTGTCCCAGGGCGATTTATCCAC
TTGAGTACAGGAGCTGCTCAGACCTCTCAGCCCAGCCCTCTGTGACTGCCCCAGCCCCATCCTACCCCAC
CCAAAGCTGCCTTCCTGGCTGTAGGAGCTCCCTCGTCTAGCCAAGGCCCTATGGGTCCCCATCCGAGGAT
CCACAAGCAATGACTTCCCAAATGACCTCCACTGCAAGAAGAATCCTTACCACTGTTTCCAGAGCCGTGA
ACGATGCTGTGATGGGCCCAGGTCTCAGCACCACCCTCTGTGACCTAAAAAGAAAAGCTCAATTTCCATC
TGTCTTCTTTCCCAGGACCAAGGGGACACAGTAATGTGAAGTCAAATACTTAACCGAGCAAAGGGCCAGT
ATTGTTATCAGTCAAGGACAAACCTCCCACCTCACAGACAGCCAAGCAGTGAGGGAAAGACAGACAGACA
TAGGTAGGAAGGTGCTCTGCAGGCACAAGGCCCAGAGAAGCCCCTCTCCGGGAACTTCCCCTGCTCCTTC
CAGGAACAGTGAGCCCAGTGAGCAGCCCAGCCAGCTCTTCAAGGCCTTCAAGGGGTCTTTCCATGACTG
AGTCACCTCCAGGAGCTCACCTGACCCCAGAGAAGACCTACCCCAGGCAGCTCCGTGCCCTGGCTTCTC
CCCATGCCCCAAATCCCCCCCGCCATCCCTCCTGGTCCTCGTCTACATCAAGGGCCTCTTCCCCTCTTC
CTGCCAGCTCTCAGGACAGGTGACTGGGAGGCCTTGAACCCTCAGCCTCTTCCTTTAAAAAAAACAAAAC
AAAACAAAACTGTGGGCCATTTATTTGGGATTTTGGAGTTGTTTGGTTTTTGTTTGTATATCTTAATAGT
TCGAAAGTAAGAAGGGAGCCCTGCTATGGATGTTAAGTCCAAATTACTCGGTTAGTGGGAGCAAAACCTA
TGACTTCCAAGGGGATGAGGAGAGGTTCAGAGGACAGGAGGAGCCTCCCCCATTGAAAAAAAAAAATGGG
TCAGGACATTCCCTGGATGAGGACAATGCTAGGGGTGGCATCTCACATGGCTGCTGCTATTCCTGGTGCT
TCCCCACACTTTTGACAGATGGAGTCCTTCTCCTACCGCCTCCTGCCACCTCACCCTACAGGCATTCTCT
ATGTAGGAAACAAGAGCCTTATTTTATAGAGTGGGGAGCTGAGACACAGCCTCAGGTAACACTGACACAG
CTCCCGAATGAGGCTGGGACACTCTGCAAACCTCTCCTCATGGTGCTAAGGGTGGCATGCTCTTGACAGG
AAACCTAAATGACCACTCCTCTCATTTGGAAAGTAATCCACTGCAGTAAAAGTTTCAGACATGCAAGAGA
GAGTTTTTTTTTTTTACTACAAATTTTTGCTCCCCATAAAATTATTTTATTAGAGGGAGTATCCAAGT
TTTAAAAGTATATAGAATTTTTTGGTTGTAAGAGAAATACATACTCATTAGGATCCCGATTAAATTCCTT
GAGTAGACTGGTGCCTACCAGAAAGCAAAGCAAAGTTAAACAAAACGAAACAAAATCCTTCATATACAAA
AAGAACTTTCTGTTTGTATTGGCAGAGGTAGTGAGGTGATTCAGGTAGGCTGAAAATCCTGGGTTGCGGG
AGCCTCACTTTATTCCATTCCACCCGCTTTGATGTCTATGCTTGGCTCTCTGGGCTGCCCCTGGTACTG
CCGAATCCTACACATCTCTTATCAGCTTTCCTCAAACTTTAAGGAGGCTCTGTGAGGGATGGGTCATGGG
AAGACCCAAGCTTTCCCTCCGCCAGGATTGCAAAAGCAAGTAGACTTGGTCTATGCAGCTCTTCTTCCAG
CAATTTCTTTATTTGGAATTAGAACTTCCTTTGTTAGTATCTTTGATCTTTTGACTCAAGCACATTTTGG
AAGGGCTCCCTTACAAAAGTAGAATTTAAAACAGAGGATACAGTTAAAGAGCAACCCAAAGGACGCTTAA
GAAACCGAGACCACTTCACCAAACAGGACTAAGGAACACTTTCGTGCACAGAAGTCAGCCGCAATCCAGG
```

*FIG. 14 (CONT'D.)*

```
CACAGGACGAAGATGGGATACACGTGCTCATCTGTCTGTCCTCCTTTCCTCTCCCTCCCCGACGTTCTAG
TTAGCTTGTTGACTTGTTAAACCTTCTGTTCTTAAAATGAAAAGCTAGCTTACCTCAAAGAATCTTGTTT
CCATTCGGAAACCAACGATTTTGTGTTTTAGAATGGACAGCCCTCCCCTCACCACTCCCTACCTTGGCCT
GGTGTCCTTGAGACATACGGTCTTTGCTTAGTCGTGTGTTGGCTGCTTTGAGCAGGAACAAGGCCTCCAG
GCCCTGAGGTGGGAAGGAAGGATTGGATGCCACTGCCCTCCTCCCCACTTTAGCATGTAGGGGCCAGCCC
ATCTCTTCCAGCAGGGTCCTGCTGAGTTACCATAGCAACCAGCAACTCCAGGGTACCACAACAGACAATG
GCTCAGCGAGCCGACGTGTGGGATGATGCAGGGGTTTTGGCCCAGCCAGAGGACCCAGAGTTGAGCTTC
AAATGCTAGAGAAGGGGAGAAACAGGATGGAAGGGTGGTTTAAGGAACCGGCAGGGGTCTTTGAGTCACA
TAGAGAAGCCGTTGAAGGAGGTAGGGCAGGTTATCTCTGTTCCAGTCACCCCCTTCCAGCCCCATCCCAC
TTCTGTTTCAAACTAAAGCTCCCACCTCGAACATTGACCCTTTGTTAGAACAAAGCAAAGCATATCTTTA
GACAACAGTGTTAAAATGAGCCTCAAATGTATGTGGATGAGATCTCTAAGAAGAGGGTCTTCTGGTTTTG
ATTTTTAAAGAAGAGTATCCTAGTAAAATATTAAAAAAAAATTAAAAAGTTTTTAAAAAGGAAACCTGTG
CTATTTAAATTGGAGCCCAGTTGTAACTTGGTAAAGGCAAGCTTCTGTACCTTTGTTATAATTAATTGTA
TACCTGTGTATGTAAATATAAGGCATTCCTATTTTGCAGTTCAGAACAAAAAAAACTTATTTGTAATATA
GAATAAAGTTTATTAAAAAATAATAAAAATGCAGTTTGGGA (SEQ ID NO:5)
```

*FIG. 14 (CONT'D.)*

```
MKAMPWNWTCLLSHLLMVGMGSSTLLTRQPAPLSQKQRSFVTFRGEPAEGFNHLVVDERTGHIY
LGAVNRIYKLSSDLKVLVTHETGPDEDNPKCYPPRIVQTCNEPLTTTNNVNKMLLIDYKENRLI
ACGSLYQGICKLLRLEDLFKLGEPYHKKEHYLSGVNESGSVFGVIVSYSNLDDKLFIATAVDGK
PEYFPTISSRKLTKNSEADGMFAYVFHDEFVASMIKIPSDTFTIIPDFDIYYVYGFSSGNFVYF
LTLQPEMVSPPGSTTKEQVYTSKLVRLCKEDTAFNSYVEVPIGCERSGVEYRLLQAAYLSKAGA
VLGRTLGVHPDDDLLFTVFSKGQKRKMKSLDESALCIFILKQINDRIKERLQSCYRGEGTLDLA
WLKVKDIPCSSALLTIDDNFCGLDMNAPLGVSDMVRGIPVFTEDRDRMTSVIAYVYKNHSLAFV
GTKSGKLKKIRVDGPRGNALQYETVQVVDPGPVLRDMAFSKDHEQLYIMSERQLTRVPVESCGQ
YQSCGECLGSGDPHCGWCVLHNTCTRKERCERSKEPRRFASEMKQCVRLTVHPNNISVSQYNVL
LVLETYNVPELSAGVNCTFEDLSEMDGLVVGNQIQCYSPAAKEVPRIITENGDHHVVQLQLKSK
ETGMTFASTSFVFYNCSVHNSCLSCVESPYRCHWCKYRHVCTHDPKTCSFQEGRVKLPEDCPQL
LRVDKILVPVEVIKPITLKAKNLPQPQSGQRGYECILNIQGSEQRVPALRFNSSSVQCQNTSYS
YEGMEINNLPVELTVVWNGHFNIDNPAQNKVHLYKCGAMRESCGLCLKADPDFACGWCQGPGQC
TLRQHCPAQESQWLELSGAKSKCTNPRITEIIPVTGPREGGTKVTIRGENLGLEFRDIASHVKV
AGVECSPLVDGYIPAEQIVCEMGEAKPSQHAGFVEICVAVCRPEFMARSSQLYYFMTLTLSDLK
PSRGFMSGGTQVTITGTNLNAGSNVVVMFGKQPCLFHRRSPSYIVCNTTSSDEVLEMKVSVQVD
RAKIHQDLVFQYVEDPTIVRIEPEWSIVSGNTPIAVWGTHLDLIQNPQIRAKHGGKEHINICEV
LNATEMTCQAPALALGPDHQSDLTERPEEFGFILDNVQSLLILNKTNFTYYPNPVFEAFGPSGI
LELKPGTPIILKGKNLIPPVAGGNVKLNYTVLVGEKPCTVTVSDVQLLCESPNLIGRHKVMARV
GGMEYSPGMVYIAPDGCVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK (SEQ
ID NO:6)
```

*FIG. 15A*

MKAMPWNWTCLLSHLLMVGMGSSTLLTRQPAPLSQKQRSFVTFRGEPAEGFNHLVVDERTGHIY
LGAVNRIYKLSSDLKVLVTHETGPDEDNPKCYPPRIVQTCNEPLTTTNNVNKMLLIDYKENRLI
ACGSLYQGICKLLRLEDLFKLGEPYHKKEHYLSGVNESGSVFGVIVSYSNLDDKLFIATAVDGK
PEYFPTISSRKLTKNSEADGMFAYVFHDEFVASMIKIPSDTFTIIPDFDIYYVYGFSSGNFVYF
LTLQPEMVSPPGSTTKEQVYTSKLVRLCKEDTAFNSYVEVPIGCERSGVEYRLLQAAYLSKAGA
VLGRTLGVHPDDDLLFTVFSKGQKRKMKSLDESALCIFILKQINDRIKERLQSCYRGEGTLDLA
WLKVKDIPCSSALLTIDDNFCGLDMNAPLGVSDMVRGIPVFTEDRDRMTSVIAYVYKNHSLAFV
GTKSGKLKKIRVDGPRGNALQYETVQVVDPGPVLRDMAFSKDHEQLYIMSERQLTRVPVESCGQ
YQSCGECLGSGDPHCGWCVLHNTCTRKERCERSKEPRRFASEMKQCVRLTVHPNNISVSQYNVL
LVLETYNVPELSAGVNCTFEDLSEMDGLVVGNQIQCYSPAAKEVPRIITENGDHHVVQLQLKSK
ETGMTFASTSFVFYNCSVHNSCLSCVESPYRCHWCKYRHVCTHDPKTCSFQEGRVKLPEDCPQL
LRVDKILVPVEVIKPITLKAKNLPQPQSGQRGYECILNIQGSEQRVPALRFNSSSVQCQNTSYS
YEGMEINNLPVELTVVWNGHFNIDNPAQNKVHLYKCGAMRESCGLCLKADPDFACGWCQGPGQC
TLRQHCPAQESQWLELSGAKSKCTNPRITEIIPVTGPREGGTKVTIRGENLGLEFRDIASHVKV
AGVECSPLVDGYIPAEQIVCEMGEAKPSQHAGFVEICVAVCRPEFMARSSQLYYFMTLTLSDLK
PSRGPMSGGTQVTITGTNLNAGSNVVVMFGKQPCLFHRRSPSYIVCNTTSSDEVLEMKVSVQVD
RAKIHQDLVFQYVEDPTIVRIEPEWSIVSGNTPIAVWGTHLDLIQNPQIRAKHGGKEHINICEV
LNATEMTCQAPALALGPDHQSDLTERPEEFGFILDNVQSLLILNKTNFTYYPNPVFEAFGPSGI
LELKPGTPIILKGKNLIPPVAGGNVKLNYTVLGEKPCTVTVSDVQLLCESPNLIGRHKVMARV
GGMEYSPGMVYIAPD (SEQ ID NO:7)

*FIG. 15B*

VEPKSCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGK (SEQ ID NO:8)

*FIG. 15C*

```
ATGAAAGCCATGCCCTGGAACTGGACCTGCCTTCTCTCCCACCTCCTCATGGTGGGCATGGGCT
CCTCCACTTTGCTCACCCGGCAGCCAGCCCCGCTGTCCCAGAAGCAGCGGTCATTTGTCACATT
CCGAGGAGAGCCCGCCGAGGGTTTCAATCACCTGGTGGTGGATGAGAGGACAGGACACATTTAC
TTGGGGGCCGTCAATCGGATTTACAAGCTCTCCAGCGACCTGAAGGTCTTGGTGACGCATGAGA
CAGGGCCGGACGAGGACAACCCCAAGTGTTACCCACCCCGCATCGTCCAGACCTGCAATGAGCC
CCTGACCACCACCAACAATGTCAACAAGATGCTCCTCATAGACTACAAGGAGAACAGGCTGATT
GCCTGTGGGAGCCTGTACCAAGGCATCTGCAAGCTGCTGAGGCTGGAGGACCTCTTCAAGCTGG
GGGAGCCTTATCATAAGAAGGAGCACTATCTGTCAGGTGTCAACGAGAGCGGCTCAGTCTTTGG
AGTGATCGTCTCCTACAGCAACCTGGATGACAAGCTGTTCATTGCCACGGCAGTGGATGGGAAG
CCCGAGTATTTTCCACCATCTCCAGCCGGAAACTGACCAAGAACTCTGAGGCGGATGGCATGT
TCGCGTACGTCTTCCATGATGAGTTCGTGGCCTCGATGATTAAGATCCCTTCGGACACCTTCAC
CATCATCCCTGACTTTGATATCTACTATGTCTATGGTTTTAGCAGTGGCAACTTTGTCTACTTT
TTGACCCTCCAACCTGAGATGGTGTCTCCACCAGGCTCCACCACCAAGGAGCAGGTGTATACAT
CCAAGCTCGTGAGGCTTTGCAAGGAGGACACAGCCTTCAACTCCTATGTAGAGGTGCCCATTGG
CTGTGAGCGCAGTGGGGTGGAGTACCGCCTGCTGCAGGCTGCCTACCTGTCCAAAGCGGGGGCC
GTGCTTGGCAGGACCCTTGGAGTCCATCCAGATGATGACCTGCTCTTCACCGTCTTCTCCAAGG
GCCAGAAGCGGAAAATGAAATCCCTGGATGAGTCGGCCCTGTGCATCTTCATCTTGAAGCAGAT
AAATGACCGCATTAAGGAGCGGCTGCAGTCTTGTTACCGGGGCGAGGGCACGCTGGACCTGGCC
TGGCTCAAGGTGAAGGACATCCCCTGCAGCAGTGCGCTCTTAACCATTGACGATAACTTCTGTG
GCCTGGACATGAATGCTCCCCTGGGAGTGTCCGACATGGTGCGTGGAATTCCCGTCTTCACGGA
GGACAGGGACCGCATGACGTCTGTCATCGCATATGTCTACAAGAACCACTCTCTGGCCTTTGTG
GGCACCAAAAGTGGCAAGCTGAAGAAGATCCGGGTGGATGGACCCAGGGGCAACGCCCTCCAGT
ATGAGACGGTGCAGGTGGTGGACCCCGGCCCAGTCCTCCGGGATATGGCCTTCTCCAAGGACCA
CGAGCAACTCTACATCATGTCAGAGAGGCAGCTCACCAGAGTCCCTGTGGAGTCCTGTGGTCAG
TATCAGAGCTGCGGCGAGTGCCTTGGCTCAGGCGACCCCACTGTGGCTGGTGTGCTGCACA
ACACTTGCACCCGGAAGGAGCGGTGTGAGCGGTCCAAGGAGCCCCGCAGGTTTGCCTCGGAGAT
GAAGCAGTGTGTCCGGCTGACGGTCCATCCCAACAATATCTCCGTCTCTCAGTACAACGTGCTG
CTGGTCCTGGAGACGTACAATGTCCCGGAGCTGTCAGCTGGCGTCAACTGCACCTTTGAGGACC
TGTCAGAGATGGATGGGCTGGTCGTGGGCAATCAGATCCAGTGCTACTCCCCTGCAGCCAAGGA
GGTGCCCCGGATCATCACAGAGAATGGGGACCACCATGTCGTACAGCTTCAGCTCAAATCAAAG
GAGACCGGCATGACCTTCGCCAGCACCAGCTTTGTCTTCTACAATTGCAGCGTCCACAATTCGT
GCCTGTCCTGCGTGGAGAGTCCATACCGCTGCCACTGGTGTAAATACCGGCATGTCTGCACCCA
TGACCCCAAGACCTGCTCCTTCCAGGAAGGCCGAGTGAAGCTGCCCGAGGACTGCCCCAGCTG
CTGCGAGTGGACAAGATCCTGGTGCCCGTGGAGGTGATCAAGCCTATCACGCTGAAGGCCAAGA
ACCTCCCCCAGCCCCAGTCTGGGCAGCGTGGCTACGAATGCATCCTCAACATTCAGGGCAGCGA
GCAGCGAGTGCCCGCCCTGCGCTTCAACAGCTCCAGCGTACAGTGCCAGAACACCTCTTATTCC
TATGAAGGGATGGAGATCAACAACCTGCCCGTGGAGTTGACAGTCGTGTGGAATGGGCACTTCA
ACATTGACAACCCAGCTCAGAATAAAGTTCACCTCTACAAGTGTGGAGCCATGCGTGAGAGCTG
CGGGCTGTGCCTCAAGGCTGACCCAGACTTCGCATGTGGCTGGTGCCAGGGCCCAGGCCAGTGC
```

*FIG. 16A*

ACCCTGCGCCAGCACTGCCCTGCCCAGGAGAGCCAGTGGCTGGAGCTGTCTGGTGCCAAAAGCA
AGTGCACAAACCCCGCATCACAGAGATAATCCCGGTGACAGGCCCCGGGAAGGGGGCACCAA
GGTCACTATCCGAGGGGAGAACCTGGGCCTGGAATTTCGCGACATCGCCTCCCATGTCAAGGTT
GCTGGCGTGGAGTGCAGCCCTTTAGTGGATGGTTACATCCCTGCAGAACAGATCGTGTGTGAGA
TGGGGGAGGCCAAGCCCAGCCAGCATGCAGGCTTCGTGGAGATCTGCGTGGCTGTGTGTCGGCC
TGAATTCATGGCCCGGTCCTCACAGCTCTATTACTTCATGACACTGACTCTCTCAGATCTGAAG
CCCAGCCGGGGGCCCATGTCCGGAGGGACCCAAGTGACCATCACAGGCACCAACCTGAATGCCG
GAAGCAACGTGGTGGTGATGTTTGGAAAGCAGCCCTGTCTCTTCCACAGGCGATCTCCATCCTA
CATTGTCTGCAACACCACATCCTCAGATGAGGTGCTAGAGATGAAGGTGTCGGTGCAGGTGGAC
AGGGCCAAGATCCACCAGGACCTGGTCTTTCAGTATGTGGAAGACCCCACCATCGTGCGGATTG
AGCCAGAATGGAGCATTGTCAGTGGAAACACACCCATCGCCGTATGGGGGACCCACCTGGACCT
CATACAGAACCCCCAGATCCGTGCCAAGCATGGAGGGAAGGAGCACATCAATATCTGTGAGGTT
CTGAACGCTACTGAGATGACCTGTCAGGCGCCCGCCCTCGCTCTGGGTCCTGACCACCAGTCAG
ACCTGACCGAGAGGCCCGAGGAGTTTGGCTTCATCCTGGACAACGTCCAGTCCCTGCTCATCCT
CAACAAGACCAACTTCACCTACTATCCCAACCCGGTGTTTGAGGCCTTTGGTCCCTCAGGAATC
CTGGAGCTCAAGCCTGGCACGCCCATCATCCTAAAGGGCAAGAACCTGATCCCGCCTGTGGCTG
GGGGCAACGTGAAGCTGAACTACACTGTGCTGGTTGGGGAGAAGCCGTGCACCGTGACCGTGTC
AGATGTCCAGCTGCTCTGCGAGTCCCCCAACCTCATCGGCAGGCACAAAGTGATGGCCCGTGTC
GGTGGCATGGAGTACTCCCCGGGGATGGTGTACATTGCCCCGGACGGATCCgagcccaaatctt
gtgacaaaactcacacatgcccaccgtgcccagcacctgaactcctggggggaccgtcagtctt
cctcttccccccaaaacccaaggacaccctcatgatctcccggacccctgaggtcacatgcgtg
gtggtggacgtgagccacgaagaccctgaggtcaagttcaactggtacgtggacggcgtggagg
tgcataatgccaagacaaagccgcgggaggagcagtacaacagcacgtaccgtgtggtcagcgt
cctcaccgtcctgcaccaggactggctgaatggcaaggagtacaagtgcaaggtctccaacaaa
gccctcccagcccccatcgagaaaaccatctccaaagccaaagggcagccccgagaaccacagg
tgtacaccctgcccccatcccgggatgagctgaccaagaaccaggtcagcctgacctgcctggt
caaaggcttctatcccagcgacatcgccgtggagtgggagagcaatgggcagccggagaacaac
tacaagaccacgcctcccgtgctggactccgacggctccttcttcctctacagcaagctcaccg
tggacaagagcaggtggcagcaggggaacgtcttctcatgctccgtgatgcatgaggctctgca
caaccactacacgcagaagagcctctccctgtctccgggtaaatga (SEQ ID NO:9)

*FIG. 16A (CONT'D.)*

```
ATGAAAGCCATGCCCTGGAACTGGACCTGCCTTCTCTCCCACCTCCTCATGGTGGGCATGGGCT
CCTCCACTTTGCTCACCCGGCAGCCAGCCCGCTGTCCCAGAAGCAGCGGTCATTTGTCACATT
CCGAGGAGAGCCCGCCGAGGGTTTCAATCACCTGGTGGTGGATGAGAGGACAGGACACATTTAC
TTGGGGGCCGTCAATCGGATTTACAAGCTCTCCAGCGACCTGAAGGTCTTGGTGACGCATGAGA
CAGGGCCGGACGAGGACAACCCCAAGTGTTACCCACCCCGCATCGTCCAGACCTGCAATGAGCC
CCTGACCACCACCAACAATGTCAACAAGATGCTCCTCATAGACTACAAGGAGAACAGGCTGATT
GCCTGTGGGAGCCTGTACCAAGGCATCTGCAAGCTGCTGAGGCTGGAGGACCTCTTCAAGCTGG
GGGAGCCTTATCATAAGAAGGAGCACTATCTGTCAGGTGTCAACGAGAGCGGCTCAGTCTTTGG
AGTGATCGTCTCCTACAGCAACCTGGATGACAAGCTGTTCATTGCCACGGCAGTGGATGGGAAG
CCCGAGTATTTTCCCACCATCTCCAGCCGGAAACTGACCAAGAACTCTGAGGCGGATGGCATGT
TCGCGTACGTCTTCCATGATGAGTTCGTGGCCTCGATGATTAAGATCCCTTCGGACACCTTCAC
CATCATCCCTGACTTTGATATCTACTATGTCTATGGTTTTAGCAGTGGCAACTTTGTCTACTTT
TTGACCCTCCAACCTGAGATGGTGTCTCCACCAGGCTCCACCACCAAGGAGCAGGTGTATACAT
CCAAGCTCGTGAGGCTTTGCAAGGAGGACACAGCCTTCAACTCCTATGTAGAGGTGCCCATTGG
CTGTGAGCGCAGTGGGGTGGAGTACCGCCTGCTGCAGGCTGCCTACCTGTCCAAAGCGGGGCC
GTGCTTGGCAGGACCCTTGGAGTCCATCCAGATGATGACCTGCTCTTCACCGTCTTCTCCAAGG
GCCAGAAGCGGAAAATGAAATCCCTGGATGAGTCGGCCCTGTGCATCTTCATCTTGAAGCAGAT
AAATGACCGCATTAAGGAGCGGCTGCAGTCTTGTTACCGGGGCGAGGGCACGCTGGACCTGGCC
TGGCTCAAGGTGAAGGACATCCCCTGCAGCAGTGCGCTCTTAACCATTGACGATAACTTCTGTG
GCCTGGACATGAATGCTCCCCTGGGAGTGTCCGACATGGTGCGTGGAATTCCCGTCTTCACGGA
GGACAGGGACCGCATGACGTCTGTCATCGCATATGTCTACAAGAACCACTCTCTGGCCTTTGTG
GGCACCAAAAGTGGCAAGCTGAAGAAGATCCGGGTGGATGGACCCAGGGGCAACGCCCTCCAGT
ATGAGACGGTGCAGGTGGTGGACCCCGGCCCAGTCCTCCGGGATATGGCCTTCTCCAAGGACCA
CGAGCAACTCTACATCATGTCAGAGAGGCAGCTCACCAGAGTCCCTGTGGAGTCCTGTGGTCAG
TATCAGAGCTGCGGCGAGTGCCTTGGCTCAGGCGACCCCCACTGTGGCTGGTGTGTGCTGCACA
ACACTTGCACCCGGAAGGAGCGGTGTGAGCGGTCCAAGGAGCCCCGCAGGTTTGCCTCGGAGAT
GAAGCAGTGTGTCCGGCTGACGGTCCATCCCAACAATATCTCCGTCTCTCAGTACAACGTGCTG
CTGGTCCTGGAGACGTACAATGTCCCGGAGCTGTCAGCTGGCGTCAACTGCACCTTTGAGGACC
TGTCAGAGATGGATGGGCTGGTCGTGGGCAATCAGATCCAGTGCTACTCCCCTGCAGCCAAGGA
GGTGCCCCGGATCATCACAGAGAATGGGACCACCATGTCGTACAGCTTCAGCTCAAATCAAAG
GAGACCGGCATGACCTTCGCCAGCACCAGCTTTGTCTTCTACAATTGCAGCGTCCACAATTCGT
GCCTGTCCTGCGTGGAGAGTCCATACCGCTGCCACTGGTGTAAATACCGGCATGTCTGCACCCA
TGACCCCAAGACCTGCTCCTTCCAGGAAGGCCGAGTGAAGCTGCCCGAGGACTGCCCCAGCTG
CTGCGAGTGGACAAGATCCTGGTGCCCGTGGAGGTGATCAAGCCTATCACGCTGAAGGCCAAGA
ACCTCCCCCAGCCCCAGTCTGGGCAGCGTGGCTACGAATGCATCCTCAACATTCAGGGCAGCGA
GCAGCGAGTGCCCGCCCTGCGCTTCAACAGCTCCAGCGTACAGTGCCAGAACACCTCTTATTCC
TATGAAGGGATGGAGATCAACAACCTGCCCGTGGAGTTGACAGTCGTGTGGAATGGGCACTTCA
ACATTGACAACCCAGCTCAGAATAAAGTTCACCTCTACAAGTGTGGAGCCATGCGTGAGAGCTG
CGGGCTGTGCCTCAAGGCTGACCCAGACTTCGCATGTGGCTGGTGCCAGGGCCCAGGCCAGTGC
```

*FIG. 16B*

```
ACCCTGCGCCAGCACTGCCCTGCCCAGGAGAGCCAGTGGCTGGAGCTGTCTGGTGCCAAAAGCA
AGTGCACAAACCCCGCATCACAGAGATAATCCCGGTGACAGGCCCCCGGGAAGGGGGCACCAA
GGTCACTATCCGAGGGGAGAACCTGGGCCTGGAATTTCGCGACATCGCCTCCCATGTCAAGGTT
GCTGGCGTGGAGTGCAGCCCTTTAGTGGATGGTTACATCCCTGCAGAACAGATCGTGTGTGAGA
TGGGGGAGGCCAAGCCCAGCCAGCATGCAGGCTTCGTGGAGATCTGCGTGGCTGTGTGTCGGCC
TGAATTCATGGCCCGGTCCTCACAGCTCTATTACTTCATGACACTGACTCTCTCAGATCTGAAG
CCCAGCCGGGGCCCATGTCCGGAGGGACCCAAGTGACCATCACAGGCACCAACCTGAATGCCG
GAAGCAACGTGGTGGTGATGTTTGGAAAGCAGCCCTGTCTCTTCCACAGGCGATCTCCATCCTA
CATTGTCTGCAACACCACATCCTCAGATGAGGTGCTAGAGATGAAGGTGTCGGTGCAGGTGGAC
AGGGCCAAGATCCACCAGGACCTGGTCTTTCAGTATGTGGAAGACCCCACCATCGTGCGGATTG
AGCCAGAATGGAGCATTGTCAGTGGAAACACACCCATCGCCGTATGGGGACCCACCTGGACCT
CATACAGAACCCCCAGATCCGTGCCAAGCATGGAGGGAAGGAGCACATCAATATCTGTGAGGTT
CTGAACGCTACTGAGATGACCTGTCAGGCGCCCGCCCTCGCTCTGGGTCCTGACCACCAGTCAG
ACCTGACCGAGAGGCCCGAGGAGTTTGGCTTCATCCTGGACAACGTCCAGTCCCTGCTCATCCT
CAACAAGACCAACTTCACCTACTATCCCAACCCGGTGTTTGAGGCCTTTGGTCCCTCAGGAATC
CTGGAGCTCAAGCCTGGCACGCCCATCATCCTAAAGGGCAAGAACCTGATCCCGCCTGTGGCTG
GGGGCAACGTGAAGCTGAACTACACTGTGCTGGTTGGGGAGAAGCCGTGCACCGTGACCGTGTC
AGATGTCCAGCTGCTCTGCGAGTCCCCCAACCTCATCGGCAGGCACAAAGTGATGGCCCGTGTC
GGTGGCATGGAGTACTCCCCGGGGATGGTGTACATTGCCCCGGAC (SEQ ID NO:10)
```

*FIG. 16B (CONT'D.)*

```
gagcccaaatcttgtgacaaaactcacacatgcccaccgtgcccagcacctgaactcctggggg
gaccgtcagtcttcctcttccccccaaaacccaaggacaccctcatgatctcccggacccctga
ggtcacatgcgtggtggtggacgtgagccacgaagaccctgaggtcaagttcaactggtacgtg
gacggcgtggaggtgcataatgccaagacaaagccgcgggaggagcagtacaacagcacgtacc
gtgtggtcagcgtcctcaccgtcctgcaccaggactggctgaatggcaaggagtacaagtgcaa
ggtctccaacaaagccctcccagcccccatcgagaaaaccatctccaaagccaaagggcagccc
cgagaaccacaggtgtacaccctgcccccatcccgggatgagctgaccaagaaccaggtcagcc
tgacctgcctggtcaaaggcttctatcccagcgacatcgccgtggagtgggagagcaatgggca
gccggagaacaactacaagaccacgcctcccgtgctggactccgacggctccttcttcctctac
agcaagctcaccgtggacaagagcaggtggcagcaggggaacgtcttctcatgctccgtgatgc
atgaggctctgcacaaccactacacgcagaagagcctctccctgtctccgggtaaatga (SEQ
ID NO:11)
```

MEFGLSCVFLVAIFKGVHCEVQLVESGGGL
VQPGGSLRLSCVASAFTLSRHAMHWVRQA
PGKGLEYVSGISNSENSTYYADSVKGRFTI
SRDNYKNTLYLQLGSLRAEDKAVYYCARA
RCRGDTCLNFYYGLDVWGQGTTVIVSSAS
TKGPSVFPLAPSSKSTSGGTAALGCLVKDY
FPEPVTVSWNSGALTSGVHTFPAVLQSSG
LYSLSSVVTVPSSSLGTQTYICNVNHKPSN
TKVDKKVEPKSCDKTHTCPPCPAPELLGG
PSVFLFPPKPKDTLMISRTPEVTCVVVDVS
HEDPEVKFNWYVDGVEVHNAKTKPREEQY
NSTYRVVSVLTVLHQDWLNGKEYKCKVSN
KALPAPIEKTISKAKGQPREPQVYTLPPSR
DELTKNQVSLTCLVKGFYPSDIAVEWESN
GQPENNYKTTPPVLDSDGSFFLYSKLTVD
KSRWQQGNVFSCSVMHEALHNHYTQKSL
SLSPGK (SEQ ID NO:12)

MGWLTRIVCLFWGVLLTARANYQNGKNNVPRLKLSYKEMLESNNVITFNGLANSSSYHTFLLDE
ERSRLYVGAKDHIFSFDLVNIKDFQKIVWPVSYTRRDECKWAGKDILKECANFIKVLKAYNQTH
LYACGTGAFHPICTYIEIGHHPEDNIFKLENSHFENGRGKSPYDPKLLTASLLIDGELYSGTAA
DFMGRDFAIFRTLGHHHPIRTEQHDSRWLNDPKFISAHLISESDNPEDDKVYFFFRENAIDGEH
SGKATHARIGQICKNDFGGHRSLVNKWTTFLKARLICSVPGPNGIDTHFDELQDVFLMNFKDPK
NPVVYGVFTTSSNIFKGSAVCMYSMSDVRRVFLGPYAHRDGPNYQWVPYQGRVPYPRPGTCPSK
TFGGFDSTKDLPDDVITFARSHPAMYNPVFPMNNRPIVIKTDVNYQFTQIVVDRVDAEDGQYDV
MFIGTDVGTVLKVVSIPKETWYDLEEVLLEEMTVFREPTAISAMELSTKQQQLYIGSTAGVAQL
PLHRCDIYGKACAECCLARDPYCAWDGSACSRYFPTAKRRTRRQDIRNGDPLTHCSDLHHDNHH
GHSPEERIIYGVENSSTFLECSPKSQRALVYWQFQRRNEERKEEIRVDDHIIRTDQGLLLRSLQ
QKDSGNYLCHAVEHGFIQTLLKVTLEVIDTEHLEELLHKDDDGDGSKTKEMSNSMTPSQKVWYR
DFMQLINHPNLNTMDEFCEQVWKRDRKQRRQRPGHTPGNSNKWKHLQENKKGRNRRTHEFERAP
RSV (SEQ ID NO:13)

*FIG. 18A*

ATGGGCTGGTTAACTAGGATTGTCTGTCTTTTCTGGGGAGTATTACTTACAGCAAGAGCAAACT
ATCAGAATGGGAAGAACAATGTGCCAAGGCTGAAATTATCCTACAAAGAAATGTTGGAATCCAA
CAATGTGATCACTTTCAATGGCTTGGCCAACAGCTCCAGTTATCATACCTTCCTTTTGGATGAG
GAACGGAGTAGGCTGTATGTTGGAGCAAAGGATCACATATTTTCATTCGACCTGGTTAATATCA
AGGATTTTCAAAAGATTGTGTGGCCAGTATCTTACACCAGAAGAGATGAATGCAAGTGGGCTGG
AAAAGACATCCTGAAAGAATGTGCTAATTTCATCAAGGTACTTAAGGCATATAATCAGACTCAC
TTGTACGCCTGTGGAACGGGGGCTTTTCATCCAATTTGCACCTACATTGAAATTGGACATCATC
CTGAGGACAATATTTTTAAGCTGGAGAACTCACATTTTGAAAACGGCCGTGGGAAGAGTCCATA
TGACCCTAAGCTGCTGACAGCATCCCTTTTAATAGATGGAGAATTATACTCTGGAACTGCAGCT
GATTTTATGGGGCGAGACTTTGCTATCTTCCGAACTCTTGGGCACCACCACCCAATCAGGACAG
AGCAGCATGATTCCAGGTGGCTCAATGATCCAAAGTTCATTAGTGCCCACCTCATCTCAGAGAG
TGACAATCCTGAAGATGACAAAGTATACTTTTTCTTCCGTGAAAATGCAATAGATGGAGAACAC
TCTGGAAAAGCTACTCACGCTAGAATAGGTCAGATATGCAAGAATGACTTTGGAGGGCACAGAA
GTCTGGTGAATAAATGGACAACATTCCTCAAAGCTCGTCTGATTTGCTCAGTGCCAGGTCCAAA
TGGCATTGACACTCATTTTGATGAACTGCAGGATGTATTCCTAATGAACTTTAAAGATCCTAAA
AATCCAGTTGTATATGGAGTGTTTACGACTTCCAGTAACATTTTCAAGGGATCAGCCGTGTGTA
TGTATAGCATGAGTGATGTGAGAAGGGTGTTCCTTGGTCCATATGCCCACAGGGATGGACCCAA
CTATCAATGGGTGCCTTATCAAGGAAGAGTCCCCTATCCACGGCCAGGAACTTGTCCCAGCAAA
ACATTTGGTGGTTTTGACTCTACAAAGGACCTTCCTGATGATGTTATAACCTTTGCAAGAAGTC
ATCCAGCCATGTACAATCCAGTGTTTCCTATGAACAATCGCCCAATAGTGATCAAAACGGATGT
AAATTATCAATTTACACAAATTGTCGTAGACCGAGTGGATGCAGAAGATGGACAGTATGATGTT

*FIG. 18B*

```
ATGTTTATCGGAACAGATGTTGGGACCGTTCTTAAAGTAGTTTCAATTCCTAAGGAGACTTGGT
ATGATTTAGAAGAGGTTCTGCTGGAAGAAATGACAGTTTTTCGGGAACCGACTGCTATTTCAGC
AATGGAGCTTTCCACTAAGCAGCAACAACTATATATTGGTTCAACGGCTGGGGTTGCCCAGCTC
CCTTTACACCGGTGTGATATTTACGGGAAAGCGTGTGCTGAGTGTTGCCTCGCCCGAGACCCTT
ACTGTGCTTGGGATGGTTCTGCATGTTCTCGCTATTTTCCCACTGCAAAGAGACGCACAAGACG
ACAAGATATAAGAAATGGAGACCCACTGACTCACTGTTCAGACTTACACCATGATAATCACCAT
GGCCACAGCCCTGAAGAGAGAATCATCTATGGTGTAGAGAATAGTAGCACATTTTTGGAATGCA
GTCCGAAGTCGCAGAGAGCGCTGGTCTATTGGCAATTCCAGAGGCGAAATGAAGAGCGAAAAGA
AGAGATCAGAGTGGATGATCATATCATCAGGACAGATCAAGGCCTTCTGCTACGTAGTCTACAA
CAGAAGGATTCAGGCAATTACCTCTGCCATGCGGTGGAACATGGGTTCATACAAACTCTTCTTA
AGGTAACCCTGGAAGTCATTGACACAGAGCATTTGGAAGAACTTCTTCATAAAGATGATGATGG
AGATGGCTCTAAGACCAAAGAAATGTCCAATAGCATGACACCTAGCCAGAAGGTCTGGTACAGA
GACTTCATGCAGCTCATCAACCACCCCAATCTCAACACAATGGATGAGTTCTGTGAACAAGTTT
GGAAAAGGGACCGAAAACAACGTCGGCAAAGGCCAGGACATACCCCAGGGAACAGTAACAAATG
GAAGCACTTACAAGAAAATAAGAAAGGTAGAAACAGGAGGACCCACGAATTTGAGAGGGCACCC
AGGAGTGTCTGA (SEQ ID NO:14)
```

*FIG. 18B (CONT'D.)*

```
AAGCACCACTGCAGCAGACCTTGTTAATTTTTTTTTTTTTCTTTCCACACAACAGTTGTGCCTCATTAT
CCGGTGCCTGGCTCGGAATTTTTTTTTTTTTTTCTTTTTGGAGGGTTTGAAGTTTCTGTGCTTCAGTG
ACTGTTACAGAAGAAGAGGTGTTAGTGTTGCCATGAGGTCTTGATTGTCTGCATTTATGAATGAAACTGA
CCTAAATCACCTGTTACCTCCAGTTTCCAGATTGTTTGAACTTCTCTGCCCGCACAATACAGGAAGGAAG
ACTAAAGCAGCAAAGGGACCTACAGCGTCTGCAGCATGGGCTGGTTAACTAGGATTGTCTGTCTTTCTG
GGGAGTATTACTTACAGCAAGAGCAAACTATCAGAATGGGAAGAACAATGTGCCAAGGCTGAAATTATCC
TACAAAGAAATGTTGGAATCCAACAATGTGATCACTTTCAATGGCTTGGCCAACAGCTCCAGTTATCATA
CCTTCCTTTTGGATGAGGAACGGAGTAGGCTGTATGTTGGAGCAAAGGATCACATATTTTCATTCGACCT
GGTTAATATCAAGGATTTTCAAAAGATTGTGTGGCCAGTATCTTACACCAGAAGAGATGAATGCAAGTGG
GCTGGAAAAGACATCCTGAAGAATGTGCTAATTTCATCAAGGTACTTAAGGCATATAATCAGACTCACT
TGTACGCCTGTGGAACGGGGGCTTTTCATCCAATTTGCACCTACATTGAAATTGGACATCATCCTGAGGA
CAATATTTTTAAGCTGGAGAACTCACATTTTGAAAACGGCCGTGGGAAGAGTCCATATGACCCTAAGCTG
CTGACAGCATCCCTTTTAATAGATGGAGAATTATACTCTGGAACTGCAGCTGATTTTATGGGGCGAGACT
TTGCTATCTTCCGAACTCTTGGGCACCACCACCCAATCAGGACAGAGCAGCATGATTCCAGGTGGCTCAA
TGATCCAAAGTTCATTAGTGCCCACCTCATCTCAGAGAGTGACAATCCTGAAGATGACAAAGTATACTTT
TTCTTCCGTGAAAATGCAATAGATGGAGAACACTCTGGAAAAGCTACTCACGCTAGAATAGGTCAGATAT
GCAAGAATGACTTTGGAGGGCACAGAAGTCTGGTGAATAAATGGACAACATTCCTCAAAGCTCGTCTGAT
TTGCTCAGTGCCAGGTCCAAATGGCATTGACACTCATTTTGATGAACTGCAGGATGTATTCCTAATGAAC
TTTAAGATCCTAAAAATCCAGTTGTATATGGAGTGTTTACCACTTCCAGTAACATTTTCAAGGGATCAG
CCGTGTGTATGTATAGCATGAGTGATGTGAGAAGGGTGTTCCTTGGTCCATATGCCCACAGGGATGGACC
CAACTATCAATGGGTGCCTTATCAAGGAAGAGTCCCCTATCCACGGCCAGGAACTTGTCCCAGCAAAACA
TTTGGTGGTTTTGACTCTACAAAGGACCTTCCTGATGATGTTATAACCTTTGCAAGAAGTCATCCAGCCA
TGTACAATCCAGTGTTTCCTATGAACAATCGCCCAATAGTGATCAAAACGGATGTAAATTATCAATTTAC
ACAAATTGTCGTAGACCGAGTGGATGCAGAAGATGGACAGTATGATGTTATGTTTATCGGAACAGATGTT
GGGACCGTTCTTAAAGTAGTTTCAATTCCTAAGGAGACTTGGTATGATTTAGAAGAGGTTCTGCTGGAAG
AAATGACAGTTTTTCGGGAACCGACTGCTATTTCAGCAATGGAGCTTTCCACTAAGCAGCAACAACTATA
TATTGGTTCAACGGCTGGGGGTTGCCCAGCTCCCTTTACACCGGTGTGATATTTACGGGAAAGCGTGTGCT
GAGTGTTGCCTCGCCCGAGACCCTTACTGTGCTTGGGATGGTTCTGCATGTTCTCGCTATTTTCCCACTG
CAAAGAGACGCACAAGACGACAAGATATAAGAAATGGAGACCCACTGACTCACTGTTCAGACTTACACCA
TGATAATCACCATGGCCACAGCCCTGAAGAGAGAATCATCTATGGTGTAGAGAATAGTAGCACATTTTTG
GAATGCAGTCCGAAGTCGCAGAGAGCGCTGGTCTATTGGCAATTCCAGAGGCGAAATGAAGAGCGAAAAG
AAGAGATCAGAGTGGATGATCATATCATCAGGACAGATCAAGGCCTTCTGCTACGTAGTCTACAACAGAA
GGATTCAGGCAATTACCTCTGCCATGCGGTGGAACATGGGTTCATACAAACTCTTCTTAAGGTAACCCTG
GAAGTCATTGACACAGAGCATTTGGAAGAACTTCTTCATAAAGATGATGATGGAGATGGCTCTAAGACCA
AAGAAATGTCCAATAGCATGACACCTAGCCAGAAGGTCTGGTACAGAGACTTCATGCAGCTCATCAACCA
CCCCAATCTCAACACAATGGATGAGTTCTGTGAACAAGTTTGGAAAAGGGACCGAAAACAACGTCGGCAA
AGGCCAGGACATACCCCAGGGAACAGTAACAAATGGAAGCACTTACAAGAAAATAAGAAAGGTAGAAACA
GGAGGACCCACGAATTTGAGAGGGCACCCAGGAGTGTCTGAGCTGCATTACCTCTAGAAACCTCAAACAA
GTAGAAACTTGCCTAGACAATAACTGGAAAAACAAATGCAATATACATGAACTTTTTTCATGGCATTATG
TGGATGTTTACAATGGTGGGAAATTCAGCTGAGTTCCACCAATTATAAATTAAATCCATGAGTAACTTTC
CTAATAGGCTTTTTTTCCTAATACCACCACCTAACAGAGAACACAGGTGAATGCAGATGTTCACTTTAGC
AGACTTAATGTTTCCTATGAGATTTCACTGTACAGGTTTGTCTTTCTTCTTTGCCTGAGAAATAAAAATG
TCATTTGCCATATTGCCATCTAAAGGAGAAAAACTGCATCAGCAAAGCCATTGTATTGAACTAAAAGTTT
```

*FIG. 18C*

```
AAAATGAACTGCATGGATTTACTAAGCTGATGAATATTCCAAAACGTGGTTGGATTCAAGGATATATTTT
GTCTACCGGCCCTCATGTTTGTATGTACTTGAGGAGTAAAATGAGTAAAATGATACTGAATGAAATGTTC
TGTGGAAATATTAAAAAAAAAAAAAAACATAAGCCATCCATCATCCAGAAGAAAAATGGAATACACTGAT
CTACTACTGATGTCTTCTTTCAGCTTTGATCTAAAGATGTATTTTATTAAAACTATAATTTAAATGTACC
ATGAAAAATATGCAGTAAAAATTAGTTGTTTTCTAAGCTAGAGTAGGATTTGTCTTACAATTATTGTGCT
ATGTAGTTTTTGTTTTAAAAATTCCAATGGTGTGCTGCTTTCTTTGGACATTTTATTTTCAATTCTATAA
GAGGGATAGATGACATTGTTCTAGAAACACATATACATCATTAAGAGTGAATCTCTAAAACCAGGATATA
AATTATGCTTTATTTCTCTGAGAAAATCAAACAAATGGAAGCTGTTCACACCTCCCCTTCTTTAAGCATT
ATCTAAATTAATTTTTACTTGCATAATGTTCTTAGAAAAAAAAACAGAACATTTAAGCAGGAAAAAGGA
AGAAACAAGTTGATTTTTAAGTGCATTTTACTATAATGAATCAATGAAGGGAAAAGGAACTGCATATTTC
ATGAAAATAATAAGCATTGTCTTAATATACTGTTAATAGAAAATGTGTCTTAATTCCGTGCTTGAATCCC
TGCATGATATTTGAGACTAAGATCTCTCTTATGATTCTACCAAGAATTATATCTGTGTCACTTAATTTTT
TTAAAAGAGAGAGATCAATAACTATTCAGAGCAACATGTTAAAGGCAAAGTTTCCAATCATTTACATCTG
TATCAGGTGCCTCTTACCTTTCCTTATTTAAGACAATTATTTGTACAAGAAACACATGACTCTTTTCATA
TCAATGGGAGGGACTTTTCTACAAAGTATTTTCCAGGATGCAACCCACATTTAAACAATGTAAAATTCTT
TGTTTCCTGCAACAACTTACAAAATAAGGTAAAAGACTAAAATTCAAGATTTGCTTCCTTCATTGTCCTA
AGACGATTCGTTGAGAATCACTGACTTTGAGATATTTAAAACTTTCAGCATTATACTGTGGTTTCTTTTG
CACTGCACTCACCTATTCAGGACTCCTCCCCCAGGTTCCTCATCATGCACAAAAATGCAAAGAAAACATC
TTATTAGTAATTAATGAAGCAACATTGAAATTCTAACTCTAGCTGTCTTTGGATTCTAATTAACTCAGCA
TCAATTTCTCACCTCAGACTACAGTGAATTTTTATTTCCTATCAGCTGAAATATTTCACAGATGGAAGCT
CATGTTTCAGTTTTAATGACTGCCTTGAATAAACAAGTTGTTGCCACTTGTTTCAAACAAAAGCCTAAAA
ATAATCTACATTCAATTTTAGGCTCCATTGACTAATATGGTGTTGCTTTTGGAAGTACTGTATATCCTCA
CATGGAAGCCAAATTGTTAAATTATTTGAAGGACACACCACTGTACAGAAAGTAGTGTTTCAAATATAAA
TCGAAGAACAAAGAGTGCTCCAAAAAATAGGTCATTCTTTTATTTCATAAAGTATCTAAACTGTACTAA
CATTCAGTGTTGTGTTTCATTCTAAATTTGCAGCTGAAATAAATTTATTTGCGATAGCAGAAATATCTTA
TTATTCATCCTCAGAAATAAAGGATTTGAAGGGATAGAGATTATATGATAAATTTATAGAAGACTTTCAG
AATTTGAATGCATTTTGTTTAGTGTTATGAAATGACAATAGAAAAAGTCTCGACTTCAATTAAAAGTTA
CACAAACAAACAAATCTACAGGCATGTCTTTATATACCATCAGGTCTAAGTTTTCAAAGAAAATTGTAGA
TATAACTTGCAGATAACTCATTACAGTCATAATCTCTGCCCATGTGTATTGAGAGGGGGCAGTTTGCACG
AAAAAGAATTATTGGCCCATTTAATAATTCAGCTTTAAATAGACTTTGTCATATGCATGAATCATCAGAG
ATGAAACTGTTTGAGAGACTCATGTGACCTTACGAAAATTACAACAGCAGTCTTAAAGTATGAAAAGAT
GCATCACAGCAGAGACATTATGGCCCAGTTGATATCAAATGTAAAATGTAAATGCATGTAAATGCACACT
TCATTTTATGTATTATTTAGTAATTTGCAGTGGTATGTGTTTAATATTTTTGCTACCTACACATTAGGCA
AAAAAAAGATGTAAATAATTTGGGAGAAAAAGACGAAGAACAGTGTAAAATAAAACTTTCTATAAGTACT
CCATTTCAATGTGTTCAACATCATCCTAAAAGGCAAGATTTTCCCACGCAGGTGACAAGGTGGTTTATGT
ACTATTTAAGGGCGGAAGGTGCGTGCCCGTTCAATAAGCATGTTTTTTGCCAGGTAGGAAATATGTTCCA
TATCTTTACTTATCATTGCATTTCAGATGGGAACTAGAAAACTGGAGAGAAAATGTAATGAAACTGCT
GCTGTAAATTATTCCTTTTAGCATGTATTCACTTGCTAAATACACATTTCTTCAAAATAAAAAAAAAAAA
AA (SEQ ID NO:15)
```

*FIG. 18C (CONT'D.)*

MGWLTRIVCLFWGVLLTARANYQNGKNNVPRLKLSYKEMLESNNVITFNGLANSSSYHTFLLDE
ERSRLYVGAKDHIFSFDLVNIKDFQKIVWPVSYTRRDECKWAGKDILKECANFIKVLKAYNQTH
LYACGTGAFHPICTYIEIGHHPEDNIFKLENSHFENGRGKSPYDPKLLTASLLIDGELYSGTAA
DFMGRDFAIFRTLGHHHPIRTEQHDSRWLNDPKFISAHLISESDNPEDDKVYFFFRENAIDGEH
SGKATHARIGQICKNDFGGHRSLVNKWTTFLKARLICSVPGPNGIDTHFDELQDVFLMNFKDPK
NPVVYGVFTTSSNIFKGSAVCMYSMSDVRRVFLGPYAHRDGPNYQWVPYQGRVPYPRPGTCPSK
TFGGFDSTKDLPDDVITFARSHPAMYNPVFPMNNRPIVIKTDVNYQFTQIVVDRVDAEDGQYDV
MFIGTDVGTVLKVVSIPKETWYDLEEVLLEEMTVFREPTAISAMELSTKQQQLYIGSTAGVAQL
PLHRCDIYGKACAECCLARDPYCAWDGSACSRYFPTAKRRTRRQDIRNGDPLTHCSDLHHDNHH
GHSPEERIIYGVENSSTFLECSPKSQRALVYWQFQRRNEERKEEIRVDDHIIRTDQGLLLRSLQ
QKDSGNYLCHAVEHGFIQTLLKVTLEVIDTEHLEELLHKDDDGDGSKTKEMSNSMTPSQKVWYR
DFMQLINHPNLNTMDEFCEQVWKRDRKQRRQRPGHTPGNSNKWKHLQENKKGRNRRTHEFERAP
RSVGCVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK (SEQ ID NO:16)

*FIG. 18D*

ATGGGCTGGTTAACTAGGATTGTCTGTCTTTTCTGGGGAGTATTACTTACAGCAAGAGCAAACT
ATCAGAATGGGAAGAACAATGTGCCAAGGCTGAAATTATCCTACAAAGAAATGTTGGAATCCAA
CAATGTGATCACTTTCAATGGCTTGGCCAACAGCTCCAGTTATCATACCTTCCTTTTGGATGAG
GAACGGAGTAGGCTGTATGTTGGAGCAAAGGATCACATATTTTCATTCGACCTGGTTAATATCA
AGGATTTTCAAAAGATTGTGTGGCCAGTATCTTACACCAGAAGAGATGAATGCAAGTGGGCTGG
AAAAGACATCCTGAAAGAATGTGCTAATTTCATCAAGGTACTTAAGGCATATAATCAGACTCAC
TTGTACGCCTGTGGAACGGGGGCTTTTCATCCAATTTGCACCTACATTGAAATTGGACATCATC
CTGAGGACAATATTTTTAAGCTGGAGAACTCACATTTTGAAAACGGCCGTGGGAAGAGTCCATA
TGACCCTAAGCTGCTGACAGCATCCCTTTTAATAGATGGAGAATTATACTCTGGAACTGCAGCT
GATTTTATGGGGCGAGACTTTGCTATCTTCCGAACTCTTGGCACCACCACCCAATCAGGACAG
AGCAGCATGATTCCAGGTGGCTCAATGATCCAAAGTTCATTAGTGCCCACCTCATCTCAGAGAG
TGACAATCCTGAAGATGACAAAGTATACTTTTTCTTCCGTGAAAATGCAATAGATGGAGAACAC
TCTGGAAAAGCTACTCACGCTAGAATAGGTCAGATATGCAAGAATGACTTTGGAGGGCACAGAA
GTCTGGTGAATAAATGGACAACATTCCTCAAAGCTCGTCTGATTTGCTCAGTGCCAGGTCCAAA
TGGCATTGACACTCATTTTGATGAACTGCAGGATGTATTCCTAATGAACTTTAAAGATCCTAAA
AATCCAGTTGTATATGGAGTGTTTACGACTTCCAGTAACATTTTCAAGGGATCAGCCGTGTGTA
TGTATAGCATGAGTGATGTGAGAAGGGTGTTCCTTGGTCCATATGCCCACAGGGATGGACCCAA
CTATCAATGGGTGCCTTATCAAGGAAGAGTCCCCTATCCACGGCCAGGAACTTGTCCCAGCAAA

*FIG. 18E*

ACATTTGGTGGTTTTGACTCTACAAAGGACCTTCCTGATGATGTTATAACCTTTGCAAGAAGTC
ATCCAGCCATGTACAATCCAGTGTTTCCTATGAACAATCGCCCAATAGTGATCAAAACGGATGT
AAATTATCAATTTACACAAATTGTCGTAGACCGAGTGGATGCAGAAGATGGACAGTATGATGTT
ATGTTTATCGGAACAGATGTTGGGACCGTTCTTAAAGTAGTTTCAATTCCTAAGGAGACTTGGT
ATGATTTAGAAGAGGTTCTGCTGGAAGAAATGACAGTTTTTCGGGAACCGACTGCTATTTCAGC
AATGGAGCTTTCCACTAAGCAGCAACAACTATATATTGGTTCAACGGCTGGGGTTGCCCAGCTC
CCTTTACACCGGTGTGATATTTACGGGAAAGCGTGTGCTGAGTGTTGCCTCGCCCGAGACCCTT
ACTGTGCTTGGGATGGTTCTGCATGTTCTCGCTATTTTCCCACTGCAAAGAGACGCACAAGACG
ACAAGATATAAGAAATGGAGACCCACTGACTCACTGTTCAGACTTACACCATGATAATCACCAT
GGCCACAGCCCTGAAGAGAGAATCATCTATGGTGTAGAGAATAGTAGCACATTTTTGGAATGCA
GTCCGAAGTCGCAGAGAGCGCTGGTCTATTGGCAATTCCAGAGGCGAAATGAAGAGCGAAAAGA
AGAGATCAGAGTGGATGATCATATCATCAGGACAGATCAAGGCCTTCTGCTACGTAGTCTACAA
CAGAAGGATTCAGGCAATTACCTCTGCCATGCGGTGGAACATGGGTTCATACAAACTCTTCTTA
AGGTAACCCTGGAAGTCATTGACACAGAGCATTTGGAAGAACTTCTTCATAAAGATGATGATGG
AGATGGCTCTAAGACCAAAGAAATGTCCAATAGCATGACACCTAGCCAGAAGGTCTGGTACAGA
GACTTCATGCAGCTCATCAACCACCCCAATCTCAACACAATGGATGAGTTCTGTGAACAAGTTT
GGAAAAGGGACCGAAAACAACGTCGGCAAAGGCCAGGACATACCCCAGGGAACAGTAACAAATG
GAAGCACTTACAAGAAAATAAGAAAGGTAGAAACAGGAGGACCCACGAATTTGAGAGGGCACCC
AGGAGTGTCGGATCCgagcccaaatcttgtgacaaaactcacacatgcccaccgtgcccagcac
ctgaactcctggggggaccgtcagtcttcctcttccccccaaaacccaaggacaccctcatgat
ctcccggacccctgaggtcacatgcgtggtggtggacgtgagccacgaagaccctgaggtcaag
ttcaactggtacgtggacggcgtggaggtgcataatgccaagacaaagccgcgggaggagcagt
acaacagcacgtaccgtgtggtcagcgtcctcaccgtcctgcaccaggactggctgaatggcaa
ggagtacaagtgcaaggtctccaacaaagccctcccagcccccatcgagaaaaccatctccaaa
gccaagggcagccccgagaaccacaggtgtacaccctgcccccatcccgggatgagctgacca
agaaccaggtcagcctgacctgcctggtcaaaggcttctatcccagcgacatcgccgtggagtg
ggagagcaatgggcagccggagaacaactacaagaccacgcctcccgtgctggactccgacggc
tccttcttcctctacagcaagctcaccgtggacaagagcaggtggcagcaggggaacgtcttct
catgctccgtgatgcatgaggctctgcacaaccactacacgcagaagagcctctccctgtctcc
gggtaaatga (SEQ ID NO:17)

*FIG. 18E (CONT'D.)*

METHODS AND COMPOSITIONS FOR THE TREATMENT OF IMMUNE DISORDERS

STATEMENT REGARDING ELECTRONIC FILING OF A SEQUENCE LISTING

A Sequence Listing in ASCII text format, submitted under 37 C.F.R. §1.821, entitled 5470-536_ST25.txt, 129,540 bytes in size, generated on May 15, 2013 and filed via EFS-Web, is provided in lieu of a paper copy. This Sequence Listing is hereby incorporated herein by reference into the specification for its disclosures.

STATEMENT OF GOVERNMENT SUPPORT

This invention was made with government support under Grant Nos. 2-R37-AI029564-17 and U19-AI067798 awarded by the National Institutes of Health. The government has certain rights in the invention.

STATEMENT OF PRIORITY

This application is a 35 U.S.C. §371 national phase application of International Application Serial No. PCT/US2010/057807, filed Nov. 23, 2010, which claims the benefit, under 35 U.S.C. §119 (e), of U.S. Provisional Application Ser. No. 61/264,338, filed Nov. 25, 2009, the entire contents of which are incorporated by reference herein.

FIELD OF THE INVENTION

The present invention relates to methods and compositions for treatment of immune related disorders and diseases.

BACKGROUND OF THE INVENTION

The functions of plexins and their ligands, semaphorins, have been extensively studied in the central nervous system (CNS). They represent two large families of molecules that can transduce signals essential for the regulation of neuronal repulsion and attraction, cell shape, motility and cell-cell interactions (Kruger et al., 2005; Tran et al., 2007). In addition to their roles in the CNS, the diverse functions of plexins and semaphorins have also been identified in cardiac development (Toyofuku et al., 2004), vascularization and angiogenesis (Gu et al., 2003a; Serini et al., 2003), and tumorigenesis (Neufeld and Kessler, 2008; Sierra et al., 2008). More recent data strongly indicate a role for these molecules in the immune system (Kikutani and Kumanogoh, 2003; Suzuki et al., 2008). For example, plexin-A1 is expressed by dendritic cells (DCs) and regulates DC interaction with T cells to affect adaptive immunity (Takegahara et al., 2006; Wong et al., 2003). Plexin-C1 is also found on DCs, although its role is less defined and it only mildly affects T cell activation (Walzer et al., 2005). A further paper showed the high expression of plexin-D1 in double-positive (DP) thymocytes and a role for this protein in the control of intrathymic migration of these cells from the cortical to medullary region (Choi et al., 2008). Therefore, plexins are involved in diverse functions in the immune system.

Plexin-A4 belongs to the plexin A-type group (Kruger et al., 2005) and serves as a guidance cue molecule in sensory and sympathetic neurons (Waimey et al., 2008; Yaron et al., 2005) and hippocampal mossy fibers (Suto et al., 2007). One study identified plexin-A4 as a negative regulator in T cell activation (Yamamoto et al., 2008). T cells lacking plexin-A4 (Plxna4$^{-/-}$) exhibited hyperproliferative responses upon stimulations in vivo and in vitro. In addition, Plxna4$^{-/-}$ mice developed exacerbated experimental autoimmune encephalomyelitis (EAE) when immunized with myelin oligodendrocyte glycoprotein (MOG)-derived peptides. However, given the much higher expression of plexin-A4 in myeloid cells relative to lymphoid cells (Yamamoto et al., 2008), the role of plexin-A4 in cells of myeloid lineage such as macrophages and DCs needed to be elucidated.

The innate immune system constitutes the first line of defense by rapidly detecting invading pathogens and nonmicrobial danger signals through the pattern recognition receptors (PRRs). Several classes of PRRs have been identified; the best-characterized are the Toll-like receptors (TLRs) (Iwasaki and Medzhitov, 2004). TLR family members are localized either on the cell surface (TLRs 1, 2, 4, 5 and 6) or in endosomal compartments (TLRs 3, 7, 8, 9) to detect a multitude of pathogen-associated molecular patterns (PAMPs) (Akira et al., 2006; Iwasaki and Medzhitov, 2004). TLR activation leads to the direct interactions of the TLR toll-interleukin 1 receptor (TIR) domain with a cytoplasmic TIR-containing adaptive molecule such as Myd88, TRIF, TRAM or TIRAP. Activation of Myd88-dependent signaling pathway results in the activation of IRAK kinases, the ubiquitin ligase TRAF6, TAK1 kinase complex, NF-κB transcription factor, and mitogen-activated protein kinases (MAPKs) (Akira and Takeda, 2004; Akira et al., 2006; Iwasaki and Medzhitov, 2004). TRIF-dependent type I interferon (IFN) requires a cascade involving the adaptor TRAF3, the kinase TBK1, the inhibitor of κB kinase ε (IKKε), and the transcription factor interferon-regulatory factor 3 (IRF3) (Akira et al., 2006; Kawai and Akira, 2006).

The present invention addresses the shortcomings in the art by providing methods and compositions for the treatment of immune related and inflammatory disorders and diseases based on new therapeutic targets.

SUMMARY OF THE INVENTION

Provided herein is a method of treating an immune-related and/or inflammatory disorder in a subject (e.g., a subject in need thereof), comprising administering to the subject in need of treatment an effective amount of an inhibitor of plexin-A4 activity, whereby the plexin-A4 activity in said subject is reduced, thereby treating the immune-related disorder and/or inflammatory disorder. In some embodiments, the inhibitor of plexin-A4 activity is a plexin-A4 fusion protein, a plexin-A4 antibody or an active fragment thereof, or any combination thereof. In some embodiments, the plexin-A4 fusion protein comprises the extracellular domain of plexin-A4 and the Fc region of immunoglobulin G (IgG).

Also provided is a method of reducing cytokine production in a subject (e.g., a subject in need thereof), comprising administering to the subject an effective amount of an inhibitor of plexin-A4 activity. In some embodiments, the inhibitor of plexin-A4 activity is a plexin-A4 fusion protein, a plexin-A4 antibody or an active fragment thereof, or any combination thereof. In some embodiments, the plexin-A4 fusion protein comprises the extracellular domain of plexin-A4 and the Fc region of IgG.

Further provided is a method of identifying a substance having an inhibitory effect on plexin-A4 activity, comprising contacting the substance with macrophage/dendritic cells under conditions whereby plexin-A4 activity can occur and measuring the amount of plexin-A4 activity in the presence and absence of the substance, whereby a decrease in plexin-A4 activity in the presence of the substance as compared to the amount of plexin-A4 activity in the absence of the substance identifies a substance having an inhibitory effect on plexin-A4 activity.

BRIEF DESCRIPTION OF THE FIGURES

(FIG. 1A) Expression of Plxna4$^{-/-}$ mRNA in different immune cells was normalized to Actb mRNA level. T cells, B cells, NK cells, bone marrow (BM) plasmacytoid DCs (pDCs), and splenic myeloid DCs (mDCs) were isolated by fluorescence activated cell sorting (FACS) according to appropriate cell surface markers described in the Examples section, BM-derived macrophages (BMMs) and BM-derived dendritic cells (BMDCs) were respectively cultured from BM cells in the presence of L929 cell supernatant and granulocyte-macrophage colony-stimulating factor (GM-CSF) plus interleukin-4 (IL-4). Peritoneal and splenic macrophages were separated from other cells by adherence for 2 h at 37° C. FIG. 1B shows flow cytometry of WT and Plxna4$^{-/-}$ peritoneal macrophages stained with IgG control (gray filled) or antibody against mouse plexin-A4 (black lines). FIG. 1C and FIG. 1D illustrate stimulation of peritoneal macrophages with Pam3Cys (5 μg/ml), poly(I:C) (10 μg/ml), ultrapure lipopolysaccharide (LPS) (1 μg/ml), R837 (10 μg/ml), or CpG-B (4 μg/ml) for 4 h. Messenger RNA (FIG. 1C) and protein (FIG. 1D) levels of TNF-α, IL-6 and interferon-beta (IFN-β) were measured by RT-PCR and ELISA, respectively. The results shown are representative of five independent experiments and are expressed as mean±s.d. *P<0.05 compared to WT peritoneal macrophages.

FIG. 3B and FIG. 3C show chromatin immunoprecipitation (ChIP) assays of the binding of p65 or c-Jun at the promoter regions of Tnfa and Il6 gene in WT and Plxna4$^{-/-}$ peritoneal macrophages left untreated or treated with 10 μg/ml poly(I:C), 1 μg/ml ultrapure LPS (B), 5 μg/ml Pam3Cys or 4 μg/ml CpG (C) for 1 h. Rho family GTPase (Rac1, Cdc42 and RhoA) pull-down analyses in WT and Plxna4$^{-/-}$ peritoneal macrophages is shown in FIG. 3D. Cells were left untreated (0) or treated for 15 or 30 min with 1 μg/ml ultrapure LPS. Rac1, Cdc42 and RhoA pull-down analysis were performed as described in the Examples section. Total Rac1, Cdc42 and RhoA in cell lysate were used as controls. WT peritoneal macrophages were pretreated with or without a Rac1 inhibitor, NSC23766 (200 μM) for 1 h, or left untreated, followed by stimulation with 5 μg/ml Pam3Cys, 10 μg/ml poly(I:C), 1 μg/ml ultrapure LPS, 10 μg/ml R837, or 4 μg/ml CpG for 4 h as shown in FIG. 3E. IFN-β production in WT macrophages was not affected by Rac1 inhibition as shown in FIG. 3F. Protein levels of TNF-α and IL-6 were measured by ELISA. The results shown are representative of three independent experiments and are expressed as mean±s.d. * P<0.05 compared to WT peritoneal macrophages without NSC23766 pretreatment.

FIG. 4A illustrates the survival of WT and Plxna4$^{-/-}$ mice (n=8 per group) given intraperitoneal injection of poly(I:C) (20 mg per kg body weight; left panel) or LPS (12.5 mg per kg body weight; right panel). FIG. 4B and FIG. 4C show the results of ELISA of inflammatory cytokines in peritoneal lavage (FIG. 4B) and serum (FIG. 4C) 4 h after the administration of poly(I:C), LPS, or PBS control (n=4 per group). The results shown are representative of two experiments and are expressed as mean±s.d. * P<0.05 compared to WT mice.

FIG. 5A shows the survival of WT and Plxna4$^{-/-}$ mice (n=10 per group) after CLP procedure with two punctures (left panel) or nine punctures (right panel). Results are representative of three individual experiments. FIGS. 5B-D show the results of ELISA of inflammatory cytokines in peritoneal lavage (FIG. 5B), serum (FIG. 5C) and lung homogenate (FIG. 5D) before CLP or 4, 24, and 72 h after CLP (n=5 per group). The results are representative of at least two individual experiments. P<0.05 compared with cytokine levels measured in peritoneal lavage, serum, or lung homogenate from WT mice.

FIG. 6B provides FACS histograms showing phagocytosis of *E. coli*-GFP (MOI=100) by WT (black lines) or Plxna4$^{-/-}$ (tinted) peritoneal macrophages at 37° C. The two show a complete overlap. GFP fluorescence is plotted on the x axis, and cell number is plotted on they axis. FIG. 6C and FIG. 6D provide the mean fluorescence intensities (MFIs) of GFP showing phagocytosis of *E. coli*-GFP after various time periods (FIG. 6C) or at different MOI (FIG. 6D) by WT and Plxna4$^{-/-}$ peritoneal macrophages at 37° C. FIG. 6E shows the results of treatment of WT and Plxna4$^{-/-}$ peritoneal macrophages with *E. coli* (strain LF82) at a MOI of 10 (left panel) or 100 (right panel) for 1 h at 37° C., followed by the addition of 100 μg/ml gentamicin. Intracellular alive bacteria were determined by plate counting after various time periods (0, 1, 2 or 3 h).

FIG. 7F shows a schematic of the cellular interactions during cytokine storm. WT and Plxna4$^{-/-}$ mice (n=4 per group experiment) were pretreated with either Sema3A-Fc or IgG Fc control proteins at a dosage of 25 ug/kg body weight 1 hour before CLP procedure. Inflammatory cytokines in peritoneal lavage collected 4 h after CLP were determined by ELISA. *P<0.05 compared with peritoneal lavage from WT mice pretreated with Sema3A-Fc (FIG. 7G).

FIGS. 12A-C show amino acid sequences for three plexin-A4 proteins. The residues indicated in bold show the sequence for the extracellular domain of the protein.

FIG. 13 shows the nucleotide sequence of the plexin-A4 coding sequence.

FIG. 14 shows the nucleotide sequence of the plexin-A4 cDNA. The nucleotides in bold are the primer sites and start (ATG) and stop codons (TGA).

FIGS. 15A-C show the amino acid sequence of the plexin-A4 fusion protein. In FIG. 15A, the portion of the sequence in bold indicates the extracellular domain of plexin-A4 and the non-bolded portion indicates the Fc region of IgG1. The two residues in bold and larger font between the plexin-A4 extracellular domain and the IgG Fc comprise the linker peptide of the fusion protein. In FIG. 15B is shown the amino acid sequence of the extracellular domain of plexin-A4 and in FIG. 15C is shown the amino acid sequence of the Fc region of IgG1.

FIGS. 16A-C show the nucleotide sequence of the plexin-A4 fusion protein. In FIG. 16A, the portion of the sequence in bold indicates the plexin-A4 extracellular domain and the non-bolded portion indicates the Fc region of IgG1. The six nucleotides in bold and larger font between the plexin-A4 extracellular domain and the IgG Fc show the nucleotide sequence encoding the linker peptide. FIG. 16B shows the nucleotide sequence of the extracellular domain of plexin-A4 and FIG. 16C shows the nucleotide sequence of the Fc region of IgG1.

FIGS. 17A-C. FIG. 17A show plexin-A4 mRNA levels in a variety of different cell types. FIG. 17B shows the amino acid sequence for IgG with the Fc region of the sequence in bold. FIG. 17C shows a protein immunoblot for three different fusion proteins: plexin-A4/IgG Fc fusion protein (lanes 1, 2, 4, and 5), a Sema6D/IgG Fc fusion protein (lane 3) and a sema6D-IgG Fc fusion protein (lane 6). Lanes 1-3 were probed with antibody to plexin-A4 and lanes 5-6 were probed with antibody to hIgG.

FIGS. 18A-E. FIG. 18A shows the amino acid sequence for the Semaphorin 3A (Sema3A) polypeptide. FIG. 18B shows the nucleotide sequence of the Sema3A coding sequence. FIG. 18C shows nucleotide sequence of the Sema3A cDNA. The nucleotides in bold are the primer sites and start (ATG) and stop codons (TGA). FIG. 18I) shows the amino acid sequence of the fusion protein between full-length human Sema3A and human IgG Fc. Full-length human Sema3A is in bold and the non-bolded portion of the sequence indicates the Fc region of IgG1. The two residues in bold and larger font between the Sema3A and the IgG Fc comprise a linker peptide. FIG. 18E shows the nucleotide sequence encoding the fusion protein between full-length human Sema3A and human IgG Fc. In FIG. 18E, the portion of the sequence in bold indicates the full length human Sema3A nucleotide sequence and the non-bolded portion indicates nucleotide sequence of the Fc region of IgG1. The six nucleotides in bold and larger font between Sema3A and IgG Fc show the nucleotide sequence encoding a linker peptide.

DETAILED DESCRIPTION

Figure 1:
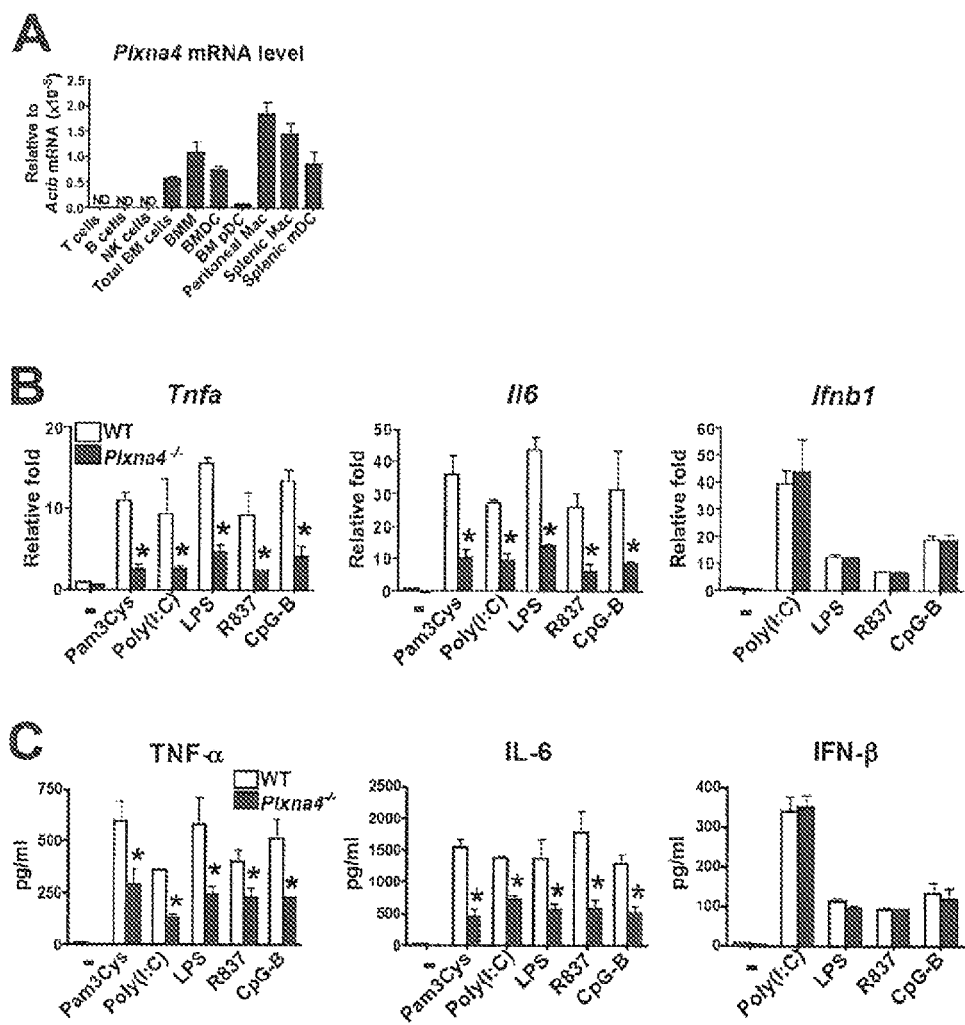
FIGS. 1A-D show that plexin-A4 is required for tumor necrosis factor-alpha (TNF-α) and interleukin-6 (IL-6) production in macrophages.

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a non-viral vector) and the like, is meant to encompass variations of ±20%, ±10%, ±5%, ±1%, ±0.5%, or even ±0.1% of the specified amount.

As used herein, the transitional phrase "consisting essentially of" (and grammatical variants) means that the scope of a claim is to be interpreted to encompass the specified materials or steps recited in the claim, "and those that do not materially affect the basic and novel characteristic(s)" of the claimed invention. Thus, the term "consisting essentially of" when used in a claim of this invention is not intended to be interpreted to be equivalent to "comprising."

Plexins are large (~200 Kd) transmembrane glycoproteins with a conserved extracellular "Sema" domain. Plexin binds to its ligand, semaphorin, through Sema-Sema domain interaction, and transduces signals essential for cell migration in various tissue types (Kruger et al., 2005; Tran et al., 2007). The cytoplasmic domains of plexins have two highly conserved regions that share homology with GTPase-activating proteins (GAPs) that are known to activate the Ras superfamily of small GTPases.

The present invention is based on the unexpected discovery that plexin-A4 in macrophages is required for optimal cytokine production upon TLR stimulation and bacterial challenge. Semaphorin 3A (Sema3A) serves as a ligand for plexin-A4 and enhances LPS-induced macrophage activation and cytokine production in a plexin-A4-dependent manner. Thus, through the inhibition of plexin-A4 activity, immune-related and/or inflammatory disorders including disorders/diseases that result in exacerbated production of proinflammatory cytokines and chemokines (those where TLR signaling is implicated) can be ameliorated.

Accordingly, in one embodiment, the present invention provides a method of treating an immune-related and/or inflammatory disorder in a subject in need thereof, comprising administering to the subject an effective amount of an inhibitor of plexin-A4 activity, whereby plexin-A4 activity in said subject is reduced, thereby treating the immune-related and/or inflammatory disorder.

Accordingly, in one embodiment, the present invention provides a method of treating an immune-related and/or inflammatory disorder in a subject in need thereof, comprising administering to the subject an effective amount of an inhibitor of plexin-A4 expression, whereby plexin-A4 expression in said subject is reduced, thereby treating the immune-related and/or inflammatory disorder.

Accordingly, in one embodiment, the present invention provides a method of treating an immune-related and/or inflammatory disorder in a subject in need thereof, comprising administering to the subject an effective amount of an inhibitor of Sema3A activity, whereby Sema3A activity in said subject is reduced, thereby treating the immune-related and/or inflammatory disorder.

Accordingly, in one embodiment, the present invention provides a method of treating an immune-related and/or inflammatory disorder in a subject in need thereof, comprising administering to the subject an effective amount of an inhibitor of Sema3A expression, whereby Sema3A expression in said subject is reduced, thereby treating the immune-related and/or inflammatory disorder.

As used herein, the terms "express," "expressing," or "expression" (or grammatical variants thereof) in reference to a gene or coding sequence can refer to transcription to produce an RNA and, optionally translation to produce a polypeptide. Thus, unless the context indicates otherwise, the terms "express," "expressing," "expression" and the like can refer to events at the transcriptional, post-transcriptional, translational and/or post-translational level.

In some embodiments of the present invention, the immune related and/or inflammatory disease or disorder can be, but is not limited to, sepsis; colitis; malignancies; systemic lupus erythematosis (SLE); arthritis, including, but not limited to, rheumatoid arthritis, osteoarthritis, juvenile chronic arthritis, and spondyloarthropathies; systemic sclerosis; idiopathic inflammatory myopathies; Sjogren's syndrome; systemic vasculitis; sarcoidosis; autoimmune hemolytic anemia; autoimmune thrombocytopenia; thyroiditis; diabetes mellitus; immune-mediated renal disease; demyelinating diseases of the central and peripheral nervous systems such as multiple sclerosis, idiopathic demyelinating polyneuropathy or Guillain-Barre syndrome, and chronic inflammatory demyelinating polyneuropathy; Alzheimer's disease; myocarditis; kidney disease; obesity; cardiovascular disease; hepatobiliary diseases such as infectious, autoimmune chronic active hepatitis, primary biliary cirrhosis, granulomatous hepatitis, and sclerosing cholangitis; inflammatory bowel disease; gluten-sensitive enteropathy; Whipple's disease; autoimmune or immune-mediated skin diseases including bullous skin diseases, erythema multiforme and contact dermatitis or hypersensitivity; psoriasis; allergic diseases such as asthma, allergic rhinitis, atopic dermatitis, food hypersensitivity and urticaria; immunologic diseases of the lung such as asthma, allergies, COPD (chronic obstructive pulmonary disease), eosinophilic pneumonias, idiopathic pulmonary fibrosis and hypersensitivity pneumonitis; transplantation associated diseases including graft rejection and graft-versus-host-disease; inflammation of the eye including but not limited to retinitis and uveitis; and any/or combination thereof.

In some embodiments, the immune related disease or disorder can be sepsis, arthritis, hepatitis, systemic lupus erythematosus (SLE), multiple sclerosis, Guillain-Barre syndrome, Alzheimer's disease, colitis, psoriasis, contact hypersensitivity, retinitis, uveitis, malignancies, systemic lupus erythematosis, asthma, myocarditis, hepatitis, kidney diseases, diabetes, obesity, cardiovascular diseases, inflammatory bowel disease and any/or combination thereof. In other embodiments, the immune-related disease or disorder is sepsis.

A "subject" of this invention includes any subject that is susceptible to the various diseases and/or disorders described herein. Nonlimiting examples of subjects of this invention include mammals, such as humans, nonhuman primates, domesticated mammals (e.g., dogs, cats, rabbits, guinea pigs, rats), livestock and agricultural mammals (e.g., horses, bovine, pigs, goats). In other embodiments, a subject may additionally be an animal such as a bird or reptile. Thus, in some embodiments, a subject can be any domestic, commercially or clinically valuable animal. Subjects may be male or female and may be any age including neonate, infant, juvenile, adolescent, adult, and geriatric subjects. In particular embodiments, the subject is a human. A human subject of this invention can be of any age, gender, race or ethnic group (e.g., Caucasian (white), Asian, African, black, African American, African European, Hispanic, Mideastern, etc.).

A "subject in need thereof" is a subject known to have, or suspected of having, diagnosed with, or at risk of having an immune related and/or inflammatory disease or disorder. A subject of this invention can also include a subject not previously known or suspected to have an immune related and/or inflammatory disease or disorder or in need of treatment for an immune related and/or inflammatory disease or disorder. For example, a subject of this invention can be administered the compositions of this invention even if it is not known or suspected that the subject has an immune related and/or inflammatory disease or disorder (e.g., prophylactically). A subject of this invention is also a subject known or believed to be at risk of developing an immune related and/or inflammatory disease or disorder. Accordingly, a subject in need thereof also includes a subject known to need, suspected of needing, or at risk of needing reduced cytokine production, reduced plexin-A4 activity or expression, or reduced Sema3A activity or expression. A subject of this invention can also include a subject not previously known or suspected to need reduced cytokine production, reduced plexin-A4 activity or expression, or reduced Sema3A activity or expression or to need treatment to reduce cytokine production, reduce plexin-A4 activity or expression, or reduce Sema3A activity or expression. For example, a subject of this invention can be administered the compositions of this invention even if it is not known or suspected that the subject needs reduced cytokine production or needs reduced plexin-A4 activity or expression or needs reduced Sema3A activity or expression (e.g., prophylactically). A subject of this invention is also a subject known or believed to be at risk of developing a need for reduced cytokine production, or for reduced plexin-A4 activity or expression, or for reduced Sema3A activity or expression.

A "subject in need thereof" is additionally a subject known to need, or suspected of needing, diagnosed with needing, or at risk of needing increased plexin-A4 activity or expression, or increased Sema3A activity or expression. A subject of this invention can also include a subject not previously known or suspected to need increased plexin-A4 activity or expression, or increased Sema3A activity or expression, or to need treatment to increase cytokine production, or to increase plexin-A4 activity or expression, or to increase Sema3A activity or expression. For example, a subject of this invention can be administered the compositions of this invention even if it is not known or suspected that the subject needs increased plexin-A4 activity or expression or increased Sema3A activity or expression (e.g., prophylactically). A subject of this invention is also a subject known or believed to be at risk of developing a need for increased plexin-A4 activity or expression or increased Sema3A activity or expression.

Also provided herein is a method of reducing cytokine production in a subject (e.g., a subject in need thereof), comprising administering to a subject an effective amount of an inhibitor of plexin-A4 activity. In other embodiments, a method of reducing plexin-A4 activity or expression in a subject is provided, comprising administering to a subject in need thereof an effective amount of an inhibitor of plexin-A4 activity. A subject in need thereof in these embodiments is a subject in need of reduced cytokine production or reduced plexin-A4 activity or expression, including, but not limited to, a subject having an immune-related and/or inflammatory disease or disorder including, but not limited to, those described herein.

Additionally provided herein is a method of reducing cytokine production in a subject (e.g., a subject in need thereof), comprising administering to a subject an effective amount of an inhibitor of Sema3A activity. In other embodiments, a method of reducing Sema3A activity or expression in a subject is provided, comprising administering to a subject in need thereof an effective amount of an inhibitor of Sema3A activity. A subject in need thereof in these embodiments is a subject in need of reduced cytokine production or reduced Sema3A activity or expression, including, but not limited to, a subject having an immune-related and/or inflammatory disease or disorder including, but not limited to, those described herein.

In further embodiments, an inhibitor of plexin-A4 activity includes, but is not limited to, a plexin-A4 fusion protein, a plexin-A4 antibody or an active fragment thereof or any combination thereof. In some embodiments, the plexin-A4 antibody is a monoclonal antibody and/or is derived from a monoclonal antibody. In other embodiments, the plexin-A4 antibody or active fragment thereof is a polyclonal antibody and/or is derived from a polyclonal antibody. In yet other embodiments, the present invention provides a composition comprising an inhibitor of plexin-A4 activity in an admixture with a pharmaceutically acceptable carrier. Thus, in some embodiments, a plexin-A4 antibody or active fragment thereof or a plexin-A4 fusion protein is provided in a composition further comprising a pharmaceutically acceptable carrier.

In still further embodiments, an inhibitor of Sema3A activity includes, but is not limited to, a Sema3A fusion protein, a Sema3A antibody or an active fragment thereof or any combination thereof. In some embodiments, the Sema3A antibody is a monoclonal antibody and/or is derived from a monoclonal antibody. In other embodiments, the Sema3A antibody or active fragment thereof is a polyclonal antibody and/or is derived from a polyclonal antibody. In yet other embodiments, the present invention provides a composition comprising an inhibitor of Sema3A activity in an admixture with a pharmaceutically acceptable carrier. Thus, in some embodiments, a Sema3A antibody or active fragment thereof or a Sema3A fusion protein is provided in a composition further comprising a pharmaceutically acceptable carrier.

In yet further embodiments, an inhibitor of plexin-A4 expression or Sema3A expression includes, but is not limited to, siRNA, shRNA, miRNA, antisense RNA and ribozymes.

The present invention further contemplates that enhancers or activators of plexin-A4 or Sema3A activity may be useful for treating subjects having immune deficiencies. Immune deficiencies can be inherited, or acquired through infection and/or other illness, and/or produced as an inadvertent side effect of particular drug treatments. Non-limiting examples of immune deficiencies include severe combined immunodeficiency disease (SCID), chronic fatigue and immune dysfunction syndrome (CFIDS), acquired immune deficiency syndrome (AIDS), and/or immune deficiencies resulting from chemotherapeutics administered to subjects (e.g., cancer patients) undergoing chemotherapy.

Accordingly, the present invention provides a method of treating an immune deficiency in a subject, comprising administering to a subject in need thereof an effective amount of an enhancer and/or activator of plexin-A4 or Sema3A activity or expression, whereby the plexin-A4 or Sema3A activity or expression in said subject is increased, thereby treating the immune deficiency. In some embodiments, the present invention provides a method for increasing cytokine production in a subject, comprising administering to a subject in need thereof an effective amount of an enhancer and/or activator of plexin-A4 activity or expression, or an effective amount of an enhancer and/or activator of Sema3A activity or expression. In other embodiments, a method is provided for increasing plexin-A4 activity or expression in a subject, comprising administering to a subject in need thereof an effective amount of an enhancer and/or activator of plexin-A4 activity or expression. In still other embodiments, a method is provided for increasing Sema3A activity or expression in a subject, comprising administering to a subject in need thereof an effective amount of an enhancer and/or activator of Sema3A activity or expression. The increase in cytokine production and/or in plexin-A4 activity and/or expression and/or in Sema3A activity and/or expression is any increase as compared to the level of cytokine production, and/or plexin-A4 activity and/or expression and/or in Sema3A activity and/or expression in the absence of the enhancer and/or activator.

As used herein an activator and/or enhancer of plexin-A4 activity and/or expression is a substance, or combination of substances that increase plexin-A4 activity and/or expression over the level of the plexin-A4 activity and/or expression in the absence of the substance. As used herein an activator and/or enhancer of Sema3A activity and/or expression is a substance, or combination of substances that increase Sema3A activity and/or expression over the level of the Sema3A activity and/or expression in the absence of the substance.

In some particular embodiments, an enhancer and/or activator of plexin-A4 activity and/or expression includes, but is not limited to, a plexin-A4 antibody or an active fragment thereof, or any combination thereof. In other particular embodiments, an enhancer and/or activator of Sema3A activity and/or expression includes, but is not limited to, a Sema3A antibody or an active fragment thereof, or any combination thereof.

As used herein, the term "antibody" includes intact immunoglobin molecules as well as active fragments thereof, such as Fab, F(ab')2, and Fc, which are capable of binding the epitopic determinant of an antigen (i.e., antigenic determinant). Antibodies that bind the polypeptides of this invention are prepared using intact polypeptides and/or fragments containing small peptides of interest as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize a host animal (e.g., a mouse, rat, goat, sheep, human or rabbit). The polypeptide or peptide antigens can also be administered with an adjuvant, as described herein and as otherwise known in the art.

The terms "antibody" and "antibodies" as used herein refer to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, and/or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980. The antibody can further be a single chain antibody or bispecific antibody.

Techniques for the production of chimeric antibodies or humanized antibodies by splicing mouse antibody genes to human antibody genes to obtain a molecule with appropriate antigen specificity and biological activity can be used (Morrison et al. 1984. *Proc. Natl. Acad. Sci.* 81:6851-6855; Neuberger et al. 1984. *Nature* 312:604-608; Takeda et al. 1985. *Nature* 314:452-454). Alternatively, techniques described for the production of single chain antibodies can be adapted, using methods known in the art, to produce single chain antibodies specific for the polypeptides and/or fragments and/or epitopes of this invention. Antibodies with related specificity, but of distinct idiotypic composition, can be generated by chain shuffling from random combinatorial immunoglobin libraries (Burton 1991. *Proc. Natl. Acad. Sci,* 88:11120-3).

Active antibody fragments included within the scope of the present invention include, for example, Fab, F(ab')2, and Fc fragments, and the corresponding fragments obtained from antibodies other than IgG, Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein (*Nature* 265:495-97 (1975)). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

Antibodies can also be obtained by phage display techniques known in the art or by immunizing a heterologous host with a cell containing an epitope or immunogen of interest.

In some embodiments of the present invention, the plexin-A4 fusion protein comprises, consists essentially of, or consists of an extracellular domain of plexin-A4 and an Fc region of IgG. The extracellular domain of plexin-A4 and the Fc region of IgG can be derived from a plexin-A4 or IgG from any species (e.g., mouse, human). In particular embodiments, the extracellular domain of plexin-A4 and the IgG Fc region are derived from human.

A plexin-A4 polypeptide of this invention includes, but is not limited to, the amino acid sequence of SEQ ID NO:1, SEQ ID NO:2 and SEQ ID NO:3. It is further contemplated that plexin-A4 polypeptides useful for the present invention include those known in the art, including the non-limiting examples of the plexin-A4 polypeptides having NCBI Accession Nos. NM_020911, NM_181775, and NM_001105543.

As discussed above, in some embodiments of the invention, the plexin-A4 fusion protein comprises the extracellular domain of a plexin-A4 polypeptide. Thus, in some embodiments, the extracellular domain of a plexin-A4 polypeptide includes, but is not limited to, the amino acid sequence of SEQ ID NO:7.

In some embodiments, the plexin-A4 fusion protein further comprises a region of an immunoglobulin, for example, IgG, IgM, IgA, IgD, and IgE. In further embodiments, the plexin-A4 fusion protein comprises a region of IgG. The amino acid sequence of a representative IgG is SEQ ID NO:12 (FIG. 17B). In other embodiments of the invention, the plexin-A4 fusion protein comprises the Fc region of an immunoglobulin. In yet other embodiments of the invention, the plexin-A4 fusion protein comprises the Fc region of IgG. Thus, in some embodiments of the present invention, the plexin-A4 fusion protein comprises IgG Fc having the amino acid sequence of SEQ ID NO:8 (FIG. 15C).

Accordingly, in some embodiments of the present invention a plexin-A4 fusion protein is provided comprising the amino acid sequences of SEQ ID NO:7 (FIG. 15B) and SEQ ID NO:8 (FIG. 15C).

In further embodiments of the present invention, the fusion protein comprises an extracellular domain of plexin-A4 and the Fc region of IgG, wherein the plexin-A4 extracellular domain and the IgG Fc region are linked by a peptide or peptide fragment. In some embodiments, the peptide or peptide fragment linker is a length from about 1 amino acid residue to about 20 amino acid residues. Thus, the peptide linker can be a length of about 1, 2, 3, 4, 5, 6, 7, 8, 9, 10, 11, 12, 13, 14, 15, 16, 17, 18, 19, or 20 amino acids in length, Thus, in further embodiments, the length of the peptide linker can be from about 1 to about 5 amino acid residues, from about 1 to about 10 amino acid residues, from about 1 to about 15 amino acid residues, from about 2 to about 5 amino acid residues, from about 2 to about 10 amino acid residues, from about 2 to about 15 amino acid residues, from about 2 to about 20 amino acid residues, from about 5 to about 10 amino acid residues, from about 5 to about 15 amino acid residues, from about 5 to about 20 amino acid residues, and the like. In some embodiments, the peptide linker comprises, consists essentially of, and/or consists of 2 amino acids in length. The peptide linker can be any amino acid residue or combination of amino acid residues in any order and/or in any multiplicity of the same amino acid residues. In some embodiments, the peptide linker of the present invention comprises glycine and/or cysteine. In particular embodiments, the peptide linker comprises a glycine residue and a cysteine residue (i.e., G-C; gly-cys).

Accordingly, the present invention further provides embodiments wherein the plexin-A4 fusion protein comprises the amino acid sequence of SEQ ID NO:6 (FIG. 15A).

In some embodiments of the present invention, the Sema3A fusion protein comprises, consists essentially of, or consists of full length Sema3A and an Fc region of IgG. The Sema3A and the Fc region of IgG can be derived from a Sema3A or IgG from any species (e.g., mouse, human). In particular embodiments, the Sema3A and the IgG Fc region are derived from human.

A Sema3A polypeptide of this invention includes, but is not limited to, the amino acid sequence of SEQ ID NO:13 (FIG. 18A). It is further contemplated that Sema3A polypeptides useful for the present invention include those known in the art, including the non-limiting example of a Sema3A polypeptide having NCBI Accession No. NM_006080.

As discussed above, in some embodiments of the invention, the Sema3A fusion protein comprises the full length polypeptide. In other embodiments, the Sema3A fusion protein comprises fragments of the full length polypeptide. Thus, in some embodiments, the Sema3A fusion protein includes, but is not limited to, fragments of the amino acid sequence of SEQ ID NO:13 (FIG. 18A).

In some embodiments, the fusion protein further comprises a region of an immunoglobulin, for example, IgG, IgM, IgA, IgD, and IgE. In further embodiments, the fusion protein comprises a region of IgG. The amino acid sequence of a representative IgG is SEQ ID NO:12 (FIG. 17B). In other embodiments of the invention, the fusion protein comprises the Fc region of an immunoglobulin. In yet other embodiments of the invention, the fusion protein comprises the Fc region of IgG. Thus, in some embodiments of the present invention, the fusion protein comprises IgG Fc region having the amino acid sequence of SEQ ID NO:8 (FIG. 15).

Accordingly, in some embodiments of the present invention a Sema3A fusion protein is provided comprising the amino acid sequences of SEQ ID NO:13 and SEQ ID NO:8.

In further embodiments of the present invention, the Sema3A fusion protein comprises a full length Sema3A and the Fc region of IgG, wherein the Sema3A and the IgG Fc region are linked by a peptide or peptide fragment. In some embodiments, the peptide or peptide fragment linker is a length from about 1 amino acid residue to about 20 amino acid residues. Thus, the peptide linker can be a length of about 1, 2, 3, 4, 5, 6, 7, 8, 9, 10, 11, 12, 13, 14, 15, 16, 17, 18, 19, or 20 amino acids in length, Thus, in further embodiments, the length of the peptide linker can be from about 1 to about 5 amino acid residues, from about 1 to about 10 amino acid residues, from about 1 to about 15 amino acid residues, from about 2 to about 5 amino acid residues, from about 2 to about 10 amino acid residues, from about 2 to about 15 amino acid residues, from about 2 to about 20 amino acid residues, from about 5 to about 10 amino acid residues, from about 5 to about 15 amino acid residues, from about 5 to about 20 amino acid residues, and the like. In some embodiments, the peptide linker comprises, consists essentially of, and/or consists of 2 amino acids in length. The peptide linker can be any amino acid residue or combination of amino acid residues in any order and/or in any multiplicity of the same amino acid residues. In some embodiments, the peptide linker of the present invention comprises glycine and/or cysteine. In particular embodiments, the peptide linker comprises a glycine residue and a cysteine residue (i.e., G-C; gly-cys).

Accordingly, the present invention further provides embodiments wherein the plexin-A4 fusion protein comprises the amino acid sequence of SEQ ID NO:16 (FIG. 18D).

As used herein, the term "polypeptide" encompasses both peptides and proteins, unless indicated otherwise.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. Polypeptides, proteins, and peptides may comprise naturally occurring amino acids, non-naturally occurring amino acids, or a combination of both. The polypeptides, proteins, and peptides may be isolated from sources (e.g., cells or tissues) in which they naturally occur, produced recombinantly in cells in vivo or in vitro or in a test tube in vitro, and/or synthesized chemically. Such techniques are known to those skilled in the art. See, e.g., Sambrook et al., *Molecular Cloning: A Laboratory Manual 2nd Ed.* (Cold Spring Harbor, N.Y., 1989); Ausubel et al. Current Protocols in Molecular Biology (Green Publishing Associates, Inc. and John Wiley & Sons, Inc., New York).

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical, or substantially identical, to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention (e.g., plexin-A4 binding to Sema3A) according to the methods described herein, which are routine methods for testing activities of polypeptides, and/or according to any art-known and routine methods for identifying such activities. Such production and testing to identify biologically active fragments of the polypeptides described herein would be well within the scope of one of ordinary skill in the art and would be routine.

Ribozymes are RNA-protein complexes that cleave nucleic acids in a site-specific fashion. Ribozymes have specific catalytic domains that possess endonuclease activity (Kiln et al. (1987); Gerlach et al. (1987); Forster et al. (1987)). For example, a large number of ribozymes accelerate phosphoester transfer reactions with a high degree of specificity, often cleaving only one of several phosphoesters in an oligonucleotide substrate (Michel et al. (1990); Reinhold-Hurek et al. (1992)). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce (1989)). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of nucleic acid expression may be particularly suited to therapeutic applications (Scanlon et al. (1991); Sarver et al. (1990); Sioud, M. et al. (1992)).

MicroRNAs (miRNA) are RNA molecules, generally 21-23 nucleotides long, that can down-regulate gene expression by hybridizing to miRNA. Over-expression or diminution of a particular miRNA can be used to treat a dysfunction and has been shown to be effective in a number of disease states and animal models of disease (Couzin 2008). Mature miRNAs are produced from a primary transcript (pri-miRNA) that is processed into a short stem-loop structure (a pre-miRNA) that then forms the final miRNA product.

The term "antisense oligonucleotide" (including "antisense RNA") as used herein, refers to a nucleic acid that is complementary to and specifically hybridizes to a specified DNA or RNA sequence such as a plexin-A4 or Sema3A DNA or RNA sequence. Antisense oligonucleotides and nucleic acids that encode the same can be made in accordance with conventional techniques. See, e.g., U.S. Pat. No. 5,023,243 to Tullis; U.S. Pat. No. 5,149,797 to Pederson et al.

Those skilled in the art will appreciate that it is not necessary that the antisense oligonucleotide be fully complementary to the target sequence as long as the degree of sequence similarity is sufficient for the antisense nucleotide sequence to specifically hybridize to its target (as defined above) and reduces production of the protein product (e.g., by at least about 30%, 40%, 50%, 60%, 70%, 80%, 90%, 95% or more).

To determine the specificity of hybridization, hybridization of such oligonucleotides to target sequences can be carried out under conditions of reduced stringency, medium stringency or even high stringency conditions, as described herein. Exemplary conditions for reduced, medium and high stringency hybridization are as follows: (e.g., conditions represented by a wash stringency of 35-40% Formamide with 5×Denhardt's solution, 0.5% SDS and 1×SSPE at 37° C.; conditions represented by a wash stringency of 40-45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively). See, e.g., Sambrook et al., *Molecular Cloning, A Laboratory Manual* (2d Ed. 1989) (Cold Spring Harbor Laboratory).

Alternatively stated, in particular embodiments, the antisense oligonucleotide has at least about 60%, 70%, 80%, 90%, 95%, 97%, 98% or higher sequence similarity with the complement of the target sequence and reduce production of the protein product (as defined above). In some embodiments, the antisense sequence contains 1, 2, 3, 4, 5, 6, 7, 8, 9 or 10 or more mismatches as compared with the target sequence.

Methods of determining percent identity of nucleic acid sequences are described in more detail elsewhere herein.

The length of the antisense oligonucleotide is not critical as long as it specifically hybridizes to the intended target and reduces production of the protein product and can be determined in accordance with routine procedures. In general, the antisense oligonucleotide is at least about eight, ten or twelve or fifteen nucleotides in length and/or less than about 20, 30, 40, 50, 60, 70, 80, 100 or 150 nucleotides in length.

An antisense oligonucleotide can be constructed using chemical synthesis and enzymatic ligation reactions by procedures known in the art. For example, an antisense oligonucleotide can be chemically synthesized using naturally occurring nucleotides or various modified nucleotides designed to increase the biological stability of the molecules and/or to increase the physical stability of the duplex formed between the antisense and sense nucleotide sequences, e.g., phosphorothioate derivatives and acridine substituted nucleotides can be used.

Examples of modified nucleotides which can be used to generate the antisense oligonucleotide include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluraci-1,5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotides can further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described.

As another non-limiting example, one or all of the nucleotides in the oligonucleotide can contain a 2' loweralkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al. (1989) *Nucleic Acids Res.* 17, 9193-9204; Agrawal et al. (1990) *Proc. Natl. Acad. Sci. USA* 87, 1401-1405; Baker et al. (1990) *Nucleic Acids Res.* 18, 3537-3543; Sproat et al. (1989) *Nucleic Acids Res.* 17, 3373-3386; Walder and Walder (1988) *Proc. Natl. Acad. Sci. USA* 85, 5011-5015.

The antisense oligonucleotide can be chemically modified (e.g., at the 3' and/or 5' end) to be covalently conjugated to another molecule. To illustrate, the antisense oligonucleotide can be conjugated to a molecule that facilitates delivery to a cell of interest, enhances absorption by the nasal mucosa (e.g., by conjugation to a lipophilic moiety such as a fatty acid), provides a detectable marker, increases the bioavailability of the oligonucleotide, increases the stability of the oligonucleotide, improves the formulation or pharmacokinetic characteristics, and the like. Examples of conjugated molecules include but are not limited to cholesterol, lipids, polyamines, polyamides, polyesters, intercalators, reporter molecules, biotin, dyes, polyethylene glycol, human serum albumin, an enzyme, an antibody or antibody fragment, or a ligand for a cellular receptor.

Other modifications to nucleic acids to improve the stability, nuclease-resistance, bioavailability, formulation characteristics and/or pharmacokinetic properties are known in the art.

RNA interference (RNAi) is another useful approach for reducing production of a protein product (e.g., shRNA or siRNA). RNAi is a mechanism of post-transcriptional gene silencing in which double-stranded RNA (dsRNA) corresponding to a target sequence of interest (e.g., plexin-A4 and/or Sema3A) is introduced into a cell or an organism, resulting in degradation of the corresponding mRNA. The mechanism by which RNAi achieves gene silencing has been reviewed in Sharp et al. (2001) *Genes Dev* 15: 485-490; and Hammond et al. (2001) *Nature Rev Gen* 2:110-119). The RNAi effect persists for multiple cell divisions before gene expression is regained. RNAi is therefore a powerful method for making targeted knockouts or "knockdowns" at the RNA level. RNAi has proven successful in human cells, including human embryonic kidney and HeLa cells (see, e.g., Elbashir et al., *Nature* (2001) 411:494-8).

The RNAi molecule (including an siRNA molecule) can be a short hairpin RNA (shRNA; see Paddison et al. (2002) *PNAS USA* 99:1443-1448), which is believed to be processed in the cell by the action of the RNase III like enzyme Dicer into 20-25mer siRNA molecules. The shRNAs generally have a stem-loop structure in which two inverted repeat sequences are separated by a short spacer sequence that loops out. There have been reports of shRNAs with loops ranging from 3 to 23 nucleotides in length. The loop sequence is generally not critical. Exemplary loop sequences include the following motifs: AUG, CCC, UUCG, CCACC, CTCGAG, AAGCUU, CCACACC and UUCAAGAGA.

The RNAi can further comprise a circular molecule comprising sense and antisense regions with two loop regions on either side to form a "dumbbell" shaped structure upon dsRNA formation between the sense and antisense regions. This molecule can be processed in vitro or in vivo to release the dsRNA portion, e.g., a siRNA.

International patent publication WO 01/77350 describes a vector for bi-directional transcription to generate both sense and antisense transcripts of a heterologous sequence in a eukaryotic cell. This technique can be employed to produce RNAi for use according to the invention.

Shinagawa et al, (2003) *Genes & Dev.* 17:1340 reported a method of expressing long dsRNAs from a CMV promoter (a pol II promoter), which method is also applicable to tissue specific pol II promoters, Likewise, the approach of Xia et al. (2002) *Nature Biotech.* 20:1006, avoids poly(A) tailing and can be used in connection with tissue-specific promoters.

Methods of generating RNAi include chemical synthesis, in vitro transcription, digestion of long dsRNA by Dicer (in vitro or in vivo), expression in vivo from a delivery vector, and expression in vivo from a PCR-derived RNAi expression cassette (see, e.g., TechNotes 10(3) "Five Ways to Produce siRNAs," from Ambion, Inc., Austin Tex.; available at www.ambion.com).

Guidelines for designing siRNA molecules are available (see e.g., literature from Ambion, Inc., Austin Tex.; available at www.ambion.com). In particular embodiments, the siRNA sequence has about 30-50% G/C content. Further, long stretches of greater than four T or A residues are generally avoided if RNA polymerase III is used to transcribe the RNA. Online siRNA target finders are available, e.g., from Ambion, Inc. (www.ambion.com), through the Whitehead Institute of Biomedical Research (www.jura.wi.mit.edu) or from Dharmacon Research, Inc. (www.dharmacon.com).

The antisense region of the RNAi molecule can be completely complementary to the target sequence (e.g., plexin-A4 and/or Sema3A), but need not be as long as it specifically hybridizes to the target sequence and reduces production of the protein product (e.g., by at least about 30%, 40%, 50%, 60%, 70%, 80%, 90%, 95% or more). In some embodiments, hybridization of such oligonucleotides to target sequences can be carried out under conditions of reduced stringency, medium stringency or even high stringency conditions, as defined herein.

In other embodiments, the antisense region of the RNAi has at least about 60%, 70%, 80%, 90%, 95%, 97%, 98% or higher sequence identity with the complement of the target sequence and reduces production of the protein product (e.g., by at least about 30%, 40%, 50%, 60%, 70%, 80%, 90%, 95% or more). In some embodiments, the antisense region contains 1, 2, 3, 4, 5, 6, 7, 8, 9 or 10 mismatches as compared with the target sequence. Mismatches are generally tolerated better at the ends of the dsRNA than in the center portion.

In particular embodiments, the RNAi is formed by intermolecular complexing between two separate sense and antisense molecules. The RNAi comprises a ds region formed by the intermolecular basepairing between the two separate strands. In other embodiments, the RNAi comprises a ds region formed by intramolecular basepairing within a single nucleic acid molecule comprising both sense and antisense regions, typically as an inverted repeat (e.g., a shRNA or other stem loop structure, or a circular RNAi molecule). The RNAi can further comprise a spacer region between the sense and antisense regions.

The RNAi molecule can contain modified sugars, nucleotides, backbone linkages and other modifications as described above for antisense oligonucleotides.

Generally, RNAi molecules are highly selective. If desired, those skilled in the art can readily eliminate candidate RNAi that are likely to interfere with expression of nucleic acids other than the target by searching relevant databases to identify RNAi sequences that do not have substantial sequence homology with other known sequences, for example, using BLAST (available at www.ncbi.nlm.nih.gov/BLAST).

Kits for the production of RNAi are commercially available, e.g., from New England Biolabs, Inc. and Ambion, Inc.

A further aspect of the present invention is an isolated nucleic acid encoding a plexin-A4 polypeptide, an extracellular domain of a plexin-A4 polypeptide, an immunoglobulin Fc fragment, and/or a plexin-A4 fusion protein (e.g., a plexin-A4/Fc IgG fusion protein). Examples include (a) nucleic acids as disclosed herein, such as isolated nucleic acids having the nucleotide sequence as set forth in SEQ ID NO:4, SEQ ID NO:5, SEQ ID NO:9, SEQ ID NO:10, or SEQ ID NO:11 (FIGS. 13, 14, 16A-C); (b) nucleic acids that hybridize to isolated nucleic acids of (a) above or the complement thereof (e.g., under stringent conditions), and/or have substantial sequence identity to nucleic acids of (a) above (e.g., are about 75, 80, 85, 90 95 or 99% identical to nucleic acids of (a) above), and encode a plexin-A4 polypeptide, an extracellular domain of a plexin-A4 polypeptide, an immunoglobulin Fc fragment, or a plexin-A4 fusion protein; and (c) nucleic acids that differ from the nucleic acids of (a) or (b) above due to the degeneracy of the genetic code, and code for a plexin-A4, an extracellular domain of plexin-A4, an immunoglobulin Fc fragment, or a plexin-A4 fusion protein.

Thus, in particular embodiments, the present invention provides an isolated plexin-A4 polypeptide, a plexin-A4 fusion protein, a nucleic acid comprising a nucleotide sequence encoding a plexin-A4 polypeptide or a plexin-A4 fusion protein of this invention, a vector comprising said nucleic acid and a cell containing said vector. The plexin-A4 polypeptide and fusion protein, the nucleic acid, the vector and/or the cell can be present singly and/or in any combination in a composition comprising a pharmaceutically acceptable carrier.

Accordingly, in some embodiments, a plexin-A4 coding sequence includes, but is not limited to, the nucleotide sequence of SEQ ID NO:4. In other embodiments, a plexin-A4 cDNA includes, but is not limited to, the nucleotide sequence of SEQ ID NO:5. The genomic sequence of the plexin-A4 gene is also contemplated to be a part of the present invention.

The present invention further provides a nucleic acid comprising an isolated nucleotide sequence encoding the extracellular domain of a plexin-4A polypeptide. Thus, in some embodiments, the extracellular domain of a plexin-4A polypeptide is encoded by the nucleotide sequence of SEQ ID NO:10. The present invention additionally provides a nucleic acid comprising a nucleotide sequence encoding the Fc region of IgG. In some embodiments, the IgG Fc region is encoded by the nucleotide sequence of SEQ ID NO:11. In still further embodiments, the present invention provides a nucleic acid comprising, consisting essentially of, and/or consisting of a nucleotide sequence encoding a plexin-A4/Fc IgG fusion protein. In additional embodiments of the invention, the nucleic acid comprising a nucleotide sequence encoding a plexin-A4/Fc IgG fusion protein comprises the nucleotide sequences of SEQ ID NO:10 and SEQ ID NO:11.

The present invention further provides a nucleic acid comprising a nucleotide sequence encoding a plexin-A4/Fc IgG fusion protein, wherein the plexin-A4/IgG Fc fusion protein comprises an extracellular domain of plexin-A4 fused to the Fc region of an IgG via a peptide linker. Thus, in some embodiments of the invention, the plexin-A4/IgG Fc fusion protein is encoded by the nucleotide sequence of SEQ ID NO:9.

An additional aspect of the present invention is an isolated nucleic acid encoding a Sema3A polypeptide, an immunoglobulin Fc fragment, and/or a Sema3A fusion protein (e.g., a Sema3A/Fc IgG fusion protein). Examples include (a) nucleic acids as disclosed herein, such as isolated nucleic acids having the nucleotide sequence as set forth in SEQ ID NO:11 (FIG. 16C), SEQ ID NO:14, SEQ ID NO:15, or SEQ ID NO: 17 (FIGS. 18B,C,E); (b) nucleic acids that hybridize to isolated nucleic acids of (a) above or the complement thereof (e.g., under stringent conditions), and/or have substantial sequence identity to nucleic acids of (a) above (e.g., are about 75, 80, 85, 90 95 or 99% identical to nucleic acids of (a) above), and encode a Sema3A polypeptide, an immunoglobulin Fc fragment, or a Sema3A fusion protein; and (c) nucleic acids that differ from the nucleic acids of (a) or (b) above due to the degeneracy of the genetic code, and code for a Sema3A polypeptide, an immunoglobulin Fc fragment, or a Sema3A fusion protein.

Thus, in particular embodiments, the present invention provides an isolated Sema3A polypeptide, a Sema3A fusion protein, a nucleic acid comprising a nucleotide sequence encoding a Sema3A polypeptide or a Sema3A fusion protein of this invention, a vector comprising said nucleic acid and a cell containing said vector. The Sema3A polypeptide and fusion protein, the nucleic acid, the vector and/or the cell can be present singly and/or in any combination in a composition comprising a pharmaceutically acceptable carrier.

Accordingly, in some embodiments, a Sema3A coding sequence includes, but is not limited to, the nucleotide sequence of SEQ ID NO:14 (FIG. 18B). In other embodiments, a Sema3A cDNA includes, but is not limited to, the nucleotide sequence of SEQ ID NO:15 (FIG. 18C). The genomic sequence of the Sema3A gene is also contemplated to be a part of the present invention.

As discussed above, the present invention additionally provides a nucleic acid comprising a nucleotide sequence encoding the Fc region of IgG. In some embodiments, the IgG Fc region is encoded by the nucleotide sequence of SEQ ID NO:11. In still further embodiments, the present invention provides a nucleic acid comprising, consisting essentially of, and/or consisting of a nucleotide sequence encoding a Sema3A/Fc IgG fusion protein. In additional embodiments of the invention, the nucleic acid comprising a nucleotide sequence encoding a Sema3A/Fc IgG fusion protein comprises the nucleotide sequences of SEQ ID NO:14 and SEQ ID NO:11.

The present invention further provides a nucleic acid comprising a nucleotide sequence encoding a Sema3A/Fc IgG fusion protein, wherein the Sema3A/IgG Fc fusion protein comprises Sema3A fused to the Fc region of an IgG via a peptide linker. Thus, in some embodiments of the invention, the Sema3A/IgG Fc fusion protein is encoded by the nucleotide sequence of SEQ ID NO:17.

As used herein, "nucleic acid," "nucleic acid molecule," "nucleotide sequence" and "polynucleotide" encompass both RNA and DNA, including cDNA, genomic DNA, mRNA, synthetic (e.g., chemically synthesized) DNA and chimeras of RNA and DNA [e.g., DNA-RNA hybrid sequences (including both naturally occurring and non-naturally occurring nucleotides)], but are typically either single or double stranded DNA or RNA sequences.

The term polynucleotide, nucleotide sequence, or nucleic acid refers to a chain of nucleotides without regard to length of the chain. The nucleic acid can be double-stranded or single-stranded (i.e., including the complementary nucleic acid). Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid or nucleotide sequence of this invention.

The term "nucleic acid fragment" will be understood to mean a nucleotide sequence of reduced length relative to a reference nucleic acid or nucleotide sequence and comprising, consisting essentially of and/or consisting of a nucleotide sequence of contiguous nucleotides identical or almost identical (e.g., about 75%, 80%, 82%, 85%, 88%, 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of and/or consist of, oligonucleotides having a length of at least about 6, 7, 8, 9, 10, 11, 12, 13, 14, 15, 16, 17, 18, 19, 20, 21, 22, 23, 24, 25, 50, 75, 100, 150, 200, 250, 300, 350, 400, 450, 500, 750, 1000 or more, consecutive nucleotides of a nucleic acid or nucleotide sequence according to the invention.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands. Similarly, a sequence "homologous" to a target nucleic acid can mean that the sequence is of exact, or nearly exact, identity to the nucleic acid, such that it would specifically hybridize to a nucleic acid exactly complementary to the target nucleic acid. As used herein, stringent hybridization conditions are those conditions that provide selective hybridization for a selected target(s). By "selective hybridization" as used herein is meant that a nucleic acid can hybridize to a target nucleic acid under sufficient stringency conditions without significant hybridization to a nucleic acid likely to be present in the reaction but not of interest. Conditions can be selected to allow for detection of, for example, one or more related nucleic acids having, e.g., one, two, or three mismatches, as in, for example, related strains of the same organism, or they can be selected to provide that hybridization only occurs with one selected target, e.g., such that it differentiates between two strains, depending upon the purpose of the hybridization, amplification and detection. Such conditions are well known to persons of ordinary skill in the art.

Hybridization is typically performed under stringent hybridization conditions. Stringent hybridization conditions are described in, e.g., Sambrook, et. al, *Molecular Cloning: A Laboratory Manual,* 2nd Ed. Cold Spring Lab. Press, December 1989. However, hybridization conditions can be modified and selected to suit the particular reaction design, including the $T_m$s of the selected primers and the temperature at which the amplification reaction is to be performed. One of skill in the art can suitably design the appropriate reaction conditions for the selected type of amplification and for the selected combination of targets and primers.

Thus, stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. Higher stringency conditions utilize buffers with lower ionic strength and/or a higher reaction temperature, and tend to require a more perfect match between probe/primer and a target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence.

Non-limiting examples of high stringency hybridization conditions include: (1) prehybridization with a solution containing 5× standard saline phosphate EDTA (SSPE), 0.5% $NaDodSO_4$ (SDS) at 55° C., and incubating probe with target nucleic acid molecules in the same solution at the same temperature, followed by washing with a solution containing 2×.SSPE, and 0.1% SDS at 55° C. or room temperature; (2) a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 60° C. for 30 min; (3) alternatively, the last two washes of (2) can be carried out at a higher temperature of 65° C.; and/or (4) a single wash at 0.1×SSC, 65° C.

Non-limiting examples of moderate stringency hybridization conditions include: (1) a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min; (2) a wash with a solution of about 50 mM KCl at about 46° C.; (3) a wash with a solution of about 100 mM KCl at about 46° C.; and/or (4) a wash with a solution of 2×SSC, 65° C.

Further exemplary conditions for reduced, medium and high stringency hybridization are as follows: (e.g., conditions represented by a wash stringency of 35-40% Formamide with 5×Denhardt's solution, 0.5% SDS and 1×SSPE at 37° C.; conditions represented by a wash stringency of 40-45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively). See, e.g., Sambrook et al., *Molecular Cloning, A Laboratory Manual* (2d Ed. 1989) (Cold Spring Harbor Laboratory).

The term "isolated" can refer to a nucleic acid, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose.

An "isolated nucleic acid" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins.

As is well known in the art, nucleic acid sequences can have changes in one or more nucleotide bases that results in substitution of one or more amino acids, but which do not affect the functional properties of the polypeptide encoded by the nucleotide sequence. It is therefore understood that the invention encompasses more than the specific exemplary nucleotide or amino acid sequences and includes functional equivalents thereof.

For example, alterations in the nucleotide sequence of a gene which result in the production of a chemically equivalent amino acid at a given site, but do not effect the functional properties of the encoded protein, are well known in the art. Such alterations include "conservative" changes, wherein a substituted amino acid has similar structural or chemical properties. In particular, such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function. Each of the proposed modifications is well within the routine skill in the art, as is determination of retention of biological activity of the encoded products.

Alternatively, alterations in the coding sequence of a gene may involve "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, such as for example, LASERGENE™ software.

In particular embodiments, a resultant variant polypeptide has at least about 60%, 70%, 75%, 80%, 85%, 90%, 95%, 98% or more amino acid sequence similarity or identity with the amino acid sequence of a naturally occurring protein or reference amino acid sequence (e.g., plexin-A4, Sema3A or IgG-Fc).

Thus, the invention further provides homologues, as well as methods of obtaining homologues, of the polypeptides and/or fragments of this invention from other organisms included in this invention. As used herein, an amino acid sequence or protein is defined as a homologue of a polypeptide or fragment of the present invention if it shares significant homology or identity to a polypeptide, peptide and/or fragment of the present invention. Significant homology or identity means at least 60%, 65%, 70%, 75%, 80%, 85%, 90%, 95%, 97%, 98%, 99%, and/or 100% homology or identity with another amino acid sequence. Specifically, by using the nucleic acids that encode the proteins, peptides and fragments of this invention, as a probe or primer, and techniques such as PCR amplification and colony/plaque hybridization, one skilled in the art can identify homologues of the polypeptides, peptides and/or fragments of this invention in other organisms on the basis of information available in the art.

The term "percent identity," as known in the art, describes a relationship between two or more polypeptide sequences or two or more polynucleotide sequences, as determined by comparing the sequences. In the art, "identity" also means the degree of sequence relatedness between polypeptide or polynucleotide sequences as determined by the match between strings of such sequences. "Identity" and "similarity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

Accordingly, the present invention further provides nucleotide sequences having significant sequence similarity or identity to the nucleotide sequences of the present invention. Significant sequence similarity or identity means at least 60%, 65%, 70%, 75%, 80%, 85%, 90%, 95%, 97%, 98%, 99%, and/or 100% similarity or identity with another nucleotide sequence.

Exemplary methods to determine identity are designed to give the best match between the sequences tested. Methods to determine identity and similarity are codified in publicly available computer programs. Sequence alignments and percent identity calculations can be performed using the Megalign program of the LASERGENE bioinformatics computing suite (DNASTAR Inc., Madison, Wis.). Multiple alignment of the sequences may be performed using the Clustal method of alignment (Higgins and Sharp (1989) CABIOS. 5:151-153) with the default parameters (GAP PENALTY=10, GAP LENGTH PENALTY=10). Exemplary default parameters for pairwise alignments using the Clustal method can be selected: KTUPLE 1, GAP PENALTY=3, WINDOW=5 and DIAGONALS SAVED=5.

The term "sequence analysis software" refers to any computer algorithm or software program that is useful for the analysis of nucleotide and/or amino acid sequences. Sequence analysis software is commercially available or can be independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA). Within the context of this application, it will be understood that where sequence analysis software is used for analysis, the results of the analysis will be based on the "default values" of the program referenced, unless otherwise specified. As used herein "default values" will mean any set of values or parameters, which originally load with the software when first initialized.

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, in one embodiment, sequence identity of sequences shorter than a sequence specifically disclosed herein, will be determined using the number of amino acids in the shorter sequence. In percent identity calculations relative weight is not assigned to various manifestations of sequence variation, such as insertions, deletions, substitutions, etc.

In other embodiments, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

The nucleotide sequences and/or nucleic acid fragments of the instant invention may be used to isolate cDNAs and genes encoding homologous proteins from the same or different organisms. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain I reaction, etc.).

For example, genes encoding other plexin-A4 and/or Sema3A polypeptides, either as cDNAs or genomic DNAs, could be isolated directly by using all or a substantial portion of the nucleic acid sequences or fragments of the present invention as DNA hybridization probes to screen libraries from any desired organism employing methodology well known to those skilled in the art. Specific oligonucleotide probes based upon the instant nucleic acid sequences can be designed and synthesized by methods known in the art (See, e.g., Sambrook et al., *Molecular Cloning; A Laboratory Manual 2nd Ed.* (Cold Spring Harbor, N.Y., 1989); Ausubel et al. Current Protocols in Molecular Biology (Green Publishing Associates, Inc. and John Wiley & Sons, Inc., New York). Moreover, the entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding the plexin-A4 genes or the Sema3A genes. Alternatively, the second primer sequence may be based upon sequences derived from the cloning vector. For example, the skilled artisan can follow the RACE protocol (Frohman et al. (1988) *Proc. Natl. Acad, Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3'RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165).

The term "therapeutically effective amount" or "effective amount," as used herein, refers to that amount of a composition of this invention that imparts a modulating effect, which, for example, can be a beneficial effect, to a subject afflicted with a disorder, disease or cosmetic condition, including improvement in the disease or disorder of the subject (e.g., in one or more symptoms), delay or reduction in the progression of the disease or disorder, prevention or delay of the onset of the disease or disorder, and/or change in clinical parameters of the disease or disorder, as would be well known in the art. The effective amount will vary with the age, general condition of the subject, the severity of the disease, disorder or condition being treated, the particular agent or composition administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science and Practice of Pharmacy* (20th ed. 2000)). For example, a therapeutically effective amount or effective amount can refer to the amount of a composition, compound, or agent that improves a disease or disorder in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

Although individual needs may vary, the determination of optimal ranges for effective amounts of a composition of this invention is within the skill of the art. Human doses can also readily be extrapolated from animal studies (Katocs et al., Chapter 27 In: Remington's Pharmaceutical Sciences, 18.sup.th Ed., Gennaro, ed., Mack Publishing Co., Easton, Pa., 1990). Generally, the dosage required to provide an effective amount of a composition of this invention, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3 In: Goodman & Gilman's The Pharmacological Basis of Therapeutics, 9.sup.th Ed., Hardman et al., eds., McGraw-Hill, New York, N.Y., 1996). In some embodiments, a daily dosage of fusion protein can be about 1 µg to 100 milligrams per kilogram of body weight. In other embodiments, the dosage can be 0.5 µg to 50 milligrams per kilogram of body weight, and preferably 1 to 10 milligrams per kilogram per day given in divided doses 1 to 6 times a day or in sustained release form is effective to obtain desired results.

The pharmaceutical compositions according to the present invention may be administered as a single dose or in multiple doses. The pharmaceutical compositions of the present invention may be administered either as individual therapeutic agents or in combination with other therapeutic agents, which when combined may be administered sequentially or simultaneously.

For antibodies, the dosage administered to a patient is typically 0.1 mg/kg to 100 mg/kg of the patient's body weight. In some aspects of the invention, the dosage administered to a patient is between 0.1 mg/kg and 20 mg/kg of the patient's body weight. In other aspects of the invention, the dosage can be 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

By the terms "treat," "treating" or "treatment of" (or grammatically equivalent terms) it is meant that the severity of the subject's disease or disorder is reduced or at least partially improved or ameliorated and/or that some alleviation, mitigation or decrease in at least one clinical symptom is achieved and/or there is a delay in the progression of the disease or disorder, as would be well known in the art. Thus, in some embodiments, the terms "treat," "treating" or "treatment of" refer only to therapeutic regimens. In other embodiments, the terms "treat," "treating" or "treatment of" (or grammatically equivalent terms) refer to both prophylactic and therapeutic regimens. As an example, a patient exhibiting bacteremia may be treated with the compositions of the present invention prior to the onset of sepsis in order to prevent the onset of said disease.

The terms "prevent," "preventing" and "prevention" (and grammatical variations thereof) refer to avoidance, prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is delayed and/or is less than what would occur in the absence of the method of the present invention.

An "effective amount," as used herein, refers to an amount that imparts a desired effect, which is optionally a therapeutic or prophylactic effect.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

Pharmaceutical compositions comprising the plexin-A4/Fc IgG fusion proteins, plexin-A4 antibodies and/or fragments thereof of this invention, and a pharmaceutically acceptable carrier are also provided. Additionally provided herein are pharmaceutical compositions comprising the Sema3A/Fc IgG fusion proteins, Sema3A antibodies and/or fragments thereof of this invention, and a pharmaceutically acceptable carrier. The compositions described herein can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

Exemplary modes of administration of the proteins, peptides, fragments, nucleic acids and/or vectors of this invention can include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intraperitoneal, intradermal, intrapleural, intracerebral, intracranial, and intraarticular), topical (e.g., to both skin and mucosal surfaces, including airway surfaces, and transdermal administration, and the like, as well as direct tissue or organ injection (e.g., to liver, skeletal muscle, cardiac muscle, diaphragm muscle or brain). The most suitable route in any given case will depend on the nature and severity of the condition being treated and on the nature of the particular protein, peptide, fragment, nucleic acid and/or vector that is being used.

The compositions of the present invention may be administered to a subject in need of treatment prior to, during or after onset of the disease or disorder. For instance, a patient exhibiting bacteremia may be treated with a composition of the present invention prior to onset of sepsis to prevent progression to sepsis. Thus, the compositions of the present invention can be used to treat ongoing immune-related and/or inflammatory diseases or disorders or to prevent diseases or delay the development of immune-related and/or inflammatory diseases or disorders.

In some embodiments, an effective dose or effective amount can comprise one or more (e.g., two or three or four or more) doses of the composition of this invention at any time interval (e.g., hourly, daily, weekly, monthly, yearly, as needed, etc.) so as to achieve and/or maintain the desired therapeutic benefit.

Several methods known in the art may be used to produce a polynucleotide and/or vector according to this invention. A "vector" is any nucleic acid molecule for the cloning and/or amplification of nucleic acid as well as for the transfer of nucleic acid into a subject (e.g., a cell of the subject). A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral nucleic acid molecules for introducing a nucleic acid into a cell in vitro, ex vivo, and/or in vivo.

A large number of vectors known in the art may be used to manipulate nucleic acids, incorporate response elements and promoters into genes, etc. Such vectors include, for example, plasmids or modified viruses including, for example bacteriophages such as lambda derivatives, or plasmids such as pBR322 or pUC plasmid derivatives, or the Bluescript® vector. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker.

Vectors have been used in a wide variety of gene delivery applications in cells, as well as in living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors, as well as any combination thereof. Nonlimiting examples of non-viral vectors include plasmids, liposomes, electrically charged lipids (cytofectins), nucleic acid-protein complexes, and biopolymers, as well as any combination thereof. In addition to a nucleic acid of interest, a vector may also comprise one or more regulatory regions (e.g., promoters, enhancers, termination sequences, etc.), and/or selectable markers useful in selecting, measuring, and monitoring nucleic acid transfer results (delivery to specific tissues, duration of expression, etc.).

In embodiments in which a nucleic acid of this invention is delivered in a viral vector (e.g., a virus particle), the dosage of virus particles to be administered to a subject will depend upon the mode of administration, the disease or disorder to be treated, the individual subject's condition, the particular virus vector, and the nucleic acid to be delivered, and can be determined in a routine manner. Exemplary doses are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units.

The present invention further provides a method of identifying a substance having an inhibitory effect on plexin-A4 activity, comprising contacting the substance with macrophage/dendritic cells under conditions whereby plexin-A4 activity can occur and measuring the amount of plexin-A4 activity in the presence and absence of the substance, whereby a decrease in plexin-A4 activity in the presence of the substance as compared to the amount of plexin-A4 activity in the absence of the substance identifies a substance having an inhibitory effect on plexin-A4 activity.

In addition, the present invention provides a method of identifying a substance having an inhibitory effect on plexin-A4 expression, comprising contacting the substance with macrophage/dendritic cells under conditions whereby plexin-A4 expression can occur and measuring the amount of plexin-A4 expression in the presence and absence of the substance, whereby a decrease in plexin-A4 expression in the presence of the substance as compared to the amount of plexin-A4 expression in the absence of the substance identifies a substance having an inhibitory effect on plexin-A4 expression.

Plexin-A4 activity and expression can be measured by many means as known in the art. For example, plexin-A4 expression can be measured at the RNA level by conventional protocols including, but not limited to, Northern blots, real-time PCR, reverse transcribed PCR, RNase protection protocols, and/or in situ hybridization. Plexin-A4 protein can be measured by protocols including, but not limited to, immunodetection such as ELISA, flow cytometric analysis, binding to Sema3A, and/or a combination of microscopic and immunolabelling and immunoblot methods. The activity of plexin-A4 protein can be measured by its ability optimize TLR activation by TLR agonists in the absence or presence of plexin-A4 fusion protein. TLR activation can be measured by events such as the secretion of proinflammatory cytokines (non-limiting examples of which are IL-6 and TNF) and chemokines, and by the activation of Rac, NF-kB and MAP kinases.

The present invention further provides a method of identifying a substance having an inhibitory effect on Sema3A activity, comprising contacting the substance with macrophage/dendritic cells under conditions whereby SemaA3 activity can occur and measuring the amount of Sema3A activity in the presence and absence of the substance, whereby a decrease in Sema3A activity in the presence of the substance as compared to the amount of Sema3A activity in the absence of the substance identifies a substance having an inhibitory effect on Sema3A activity.

In addition, the present invention provides a method of identifying a substance having an inhibitory effect on Sema3A expression, comprising contacting the substance with macrophage/dendritic cells under conditions whereby Sema3A expression can occur and measuring the amount of Sema3A expression in the presence and absence of the substance, whereby a decrease in Sema3A expression in the presence of the substance as compared to the amount of Sema3A expression in the absence of the substance identifies a substance having an inhibitory effect on Sema3A expression.

Sema3A activity and expression can be measured by many means as known in the art. For example, Sema3A expression can be measured at the RNA level by conventional protocols including, but not limited to, Northern blots, real-time PCR, reverse transcribed PCR, RNase protection protocols, and/or in situ hybridization. Sema3A protein can be measured by protocols including, but not limited to, immunodetection such as ELISA, flow cytometric analysis, binding to plexin-A4, and/or a combination of microscopic and immunolabelling and immunoblot methods. The activity of Sema3A protein can be measured by its ability optimize TLR activation by TLR agonists in the absence or presence of Sema3A fusion protein. TLR activation can be measured by events such as the secretion of proinflammatory cytokines (non-limiting examples of which are IL-6 and TNF) and chemokines, and by the activation of Rac, NF-kB and MAP kinases.

The present invention further provides a method of identifying a substance having an enhancing effect on plexin-A4 activity or expression, said method comprising contacting the substance with macrophage/dendritic cells under conditions whereby plexin A4 activity or expression can occur and measuring the amount of plexin-A4 activity or expression in the presence and absence of the substance, whereby an increase in plexin-A4 activity or expression in the presence of the substance as compared to the amount of plexin-A4 activity or expression in the absence of the substance identifies a substance having an enhancing effect on plexin-A4 activity or expression. Methods for detecting plexin-A4 activity or expression are known in the art and discussed above.

The present invention additionally provides a method of identifying a substance having an enhancing effect on Sema3A activity or expression, said method comprising contacting the substance with macrophage/dendritic cells under conditions whereby Sema3A activity or expression can occur and measuring the amount of Sema3A activity or expression in the presence and absence of the substance, whereby an increase in Sema3A activity or expression in the presence of the substance as compared to the amount of Sema3A activity or expression in the absence of the substance identifies a substance having an enhancing effect on Sema3A activity or expression. Methods for detecting Sema3A activity or expression are known in the art and discussed above.

The following examples are included to demonstrate various embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Mice.

C57BL/6 mice were purchased from the Jackson Laboratory. Plxna4$^{-/-}$ mice were provided by M. Tessier-Lavigne (Stanford University) (Yaron et al., 2005) and were backcrossed for nine generations onto the C57BL/6 background. OT-II TCR-transgenic mice were obtained from M. Croft (La Jolla Institute of Allergy and Immunology). Mice were treated in accordance with the National Institute of Health Guide for the Care and Use of Laboratory Animals. The Institutional Animal Care and Use Committee (IACUC) of the University of North Carolina at Chapel Hill approved all experimental procedures.

Reagents.

Pam3Cys, poly(I:C), Ultrapure LPS, imiquimod (R837) and mouse CpG-B (ODN 1826) were from InvivoGen. LPS (*E. coli* 0111:B4) used for the in vivo injections was purchased from Sigma. Recombinant human Sema3A-Fc (1250-S3), human Sema6A-Fc (1146-S6) and human IgG$_1$ Fc (110-HG) were from R&D. The Rac1 inhibitor NSC23766 (Gao et al., 2004) was from Calbiochem. In immunoblotting experiments, the primary antibodies specific for NF-κB p65 (3034), NF-κB p65 phosphorylated at Ser536 (93H1; 3033), IκBα phosphorylated at Ser32 (14D4; 2859), phospho-ERK1/2 (Thr202/Thr204) (197G2; 4377), phospho-JNK1/2 (Thr183/Tyr185) (81E11; 4668) and phospho-p38 (Thr180/Tyr182) (9211) were from Cell Signaling Technology, Anti-β-actin (C-11; sc-1615 HRP) was from Santa Cruz Biotechnology. Antibody specific for mouse plexin-A4 has been previously described (Suto et al., 2007) and was kindly provided by F. Suto (Tohoku University). In ChIP analysis, the antibodies specific for NF-κB p65 (A) X (sc-109) and c-Jun phosphorylated at Ser63 (9261) were from Santa Cruz Biotechnology (Santa Cruz, Calif.) and Cell Signaling Technology (Danvers, Mass.), respectively. In assays for GTP-bound Rac1, Cdc42 and RhoA, glutathione-SEPHAROSE™ (crosslinked polysaccharide polymer) beads conjugated with either GST-Pak1 PBD (for GTP-bound Rac1 and Cdc42) or GST-rhotekin RBD (for GTP-bound RhoA) were kindly provided by K. Burridge (University of North Carolina at Chapel Hill). The primary antibodies specific for Rac1 (C-14; sc-217), Cdc42 (B-8; sc-8401) and RhoA (26C4; sc-418) were from Santa Cruz Biotechnology.

Example 2

Peritoneal Macrophage Isolation and In Vitro Stimulation

Total peritoneal cells were harvested from the peritoneal cavities of naïve WT or Plxna4$^{-/-}$ mice with two 10 ml cold sterile PBS wash. Lavage was pooled for mice in the same group. RBCs were lysed in ammonium chloride buffer (150 mM NH$_4$CL, 10 mM NaHCO3, 1 mM EDTA-tetrasodium). The remaining cells were thoroughly washed with PBS and counted in a hemocytometer. Cytospins were prepared and stained with Diff-Quik solutions, and the number of peritoneal macrophages was determined. Cells were resuspended at a concentration of 10$^6$ macrophages/ml in RPMI 1640 medium supplemented with 10% FCS, 2 mM L-glutamine, 100 U/ml penicillin, and 100 µg streptomycin. Macrophages were plated in 96-well cell culture plate (2×10$^5$/well) and incubated for 2 h at 37° C. Non-adherent cells were removed, and adherent cells were washed with complete RPMI 1640 medium, followed by stimulation with various reagents. In some experiments, cells were pretreated with 200 µM NSC23766 for 1 h followed by the stimulation with TLR agonists.

Example 3

Bacterial Infection in Vitro

*L. monocytogenes* and *S. typhimurium* were from the ATCC (ATCC 43251 and ATCC14028, respectively). *E. coli* strain LF82 has been previously described (Carvalho et al., 2008) and was provided by R. Balfour Sartor (University of North Carolina at Chapel Hill). *S. aureus* strain RN6390 has been previously described (Labandeira-Rey et al., 2007) and was provided by M. Gabriela Bowden (Texas A&M University). All bacterial strains were grown to the late exponential phase. The number of viable bacteria used in each experiment was calibrated by colony counting. After three washes with sterile cold PBS, bacteria were added to peritoneal macrophages at a multiplicity of infection (MOI) of 40. After incubation for 1 h at 37° C., cells were treated with 100 µg/ml gentamicin to kill extracellular bacteria and were further incubated for various time periods (*S. typhimurium* for 1 h; *L. monocytogenes, E. coli* and *S. aureus* for 3 h).

Example 4

ELISA

Cytokines generated by in vitro cultured peritoneal macrophages were quantified using the ELISA Set for mouse TNF-α or IL-6 (BD Biosciences) and mouse IFN-β ELISA Kit (PBL InterferonSource). For the in vivo experiments, concentrations of TNF-α, IL-1β, IL-6, IL-12p70, CCL2 and CCL3 were measured in cell-free peritoneal lavage fluid, serum, and lung homogenate using a Customized Mouse Cytokine 6-plex Panel (BioLegend) and a Luminex Bio-Plex 200 system (Bio-Rad Laboratories).

Example 5

Immunoblotting

Electrophoresis of proteins was performed by using the NuPAGE system (Invitrogen) according to the manufacturer's protocol. Briefly, peritoneal macrophage stimulated with LPS or left unstimulated were collected and lysed with buffer (50 mM Tris-HCl pH 7.4, 150 mM NaCl, 2 mM EDTA, 1% TRITON™ X-100 (a non-ionic surfactant), 0.1% SDS, and protease inhibitor cocktail). Proteins were separated on a NuPAGE® (SDS PAGE) gel and were transferred onto nitrocellulose membranes (Bio-Rad Laboratories). The membranes were blocked with 10% milk proteins in 1×PBS and 0.1% TWEEN-20 and then probed with the primary antibodies, Appropriate HRP-conjugated secondary antibodies were used and proteins were detected using an Enhanced Chemiluminescent (ECL) Western Blotting Substrate reagent (peroxidase substrate) from Thermo Scientific.

Example 6

Chromatin Immunoprecipitation (ChIP) Assay

ChIP assays were performed as described previously (Wen et al., 2008). Briefly, resident peritoneal macrophages were stimulated with various TLR agonists for 1 hour. DNA-protein structure was then cross-linked by 1% formaldehyde for 10 min at 37° C. Cells were collected and lysed in 400 µl SDS lysis buffer. The resulting lysates were sonicated to obtain DNA fragments ranging from 200-1,000 bp using a Sonics VCX 750 (Sonics & Materials, Inc.) 4× for periods of 15 s each. After centrifugation, the supernatant containing chromatin was diluted and an aliquot (2% volume) was saved to quantitate the input DNA in each sample. The remaining chromatin fractions were pre-cleared with salmon sperm DNA/protein A agarose beads (Invitrogen) followed by immunoprecipitation overnight with primary antibodies at 4° C. with gentle rotation. Cross-linking was reversed for 4 h at 65° C. and was followed by proteinase K digestion. DNA was purified by standard phenol/chloroform and ethanol precipitation, and subjected to real-time PCR. Primers for mouse Tnfa promoter KB binding site: forward, 5'-TGAAAG-GAGAAGGCTTGTGA (SEQ ID NO:18); reverse, 5'-TAATGGGATGAGTATGGGGCA (SEQ ID NO:19). Primers for mouse Tnfa promoter c-Jun binding site: forward, 5'-CCCAACTTTCCAAACCCTCT (SEQ ID NO:20); reverse, 5'-ACCATGATCTCATGTGGAGGA (SEQ ID NO:21). Primers for mouse 116 promoter: forward, 5'-GC-CTCAAGGATGACTTAAGCA (SEQ ID NO:22); reverse, 5'-AGATTGCACAATGTGACGTCG (SEQ ID NO:23).

Example 7

Detection of GTP-bound Rac1, Cdc42 and RhoA

The assays for GTP-bound Rac1, Cdc42 and RhoA were performed as described (Noren et al., 2000). Briefly, peritoneal macrophages were stimulated with 1 µg/ml LPS for various time periods. Cells were lysed and GTP-bound Rac1 and Cdc42 were affinity precipitated using Rac1/Cdc42-binding domain of PAK (PBD) fused with GST. GTP-bound RhoA was affinity precipitated using RhoA-binding domain of rhotekin (RBD) fused with GST. Bound proteins were resolved on a NuPAGE® (SDS PAGE) gel and were transferred onto nitrocellulose membranes. Membranes were immunoblotted with the appropriate primary antibodies against Rac1, Cdc42 or RhoA.

Example 8

Experimental Sepsis Induced by CLP

CLP surgery was performed on mice as previously described with minor modifications (Wen et al., 2008). In brief, mice were anesthetized with an intraperitoneal injection of 8 mg of 2,2,2-tribromoethanol (Avertin) (Sigma). Under sterile surgical conditions, a 1-cm midline incision was made to the ventral surface of the abdomen and the cecum was exposed. The cecum was partially ligated at its base with a 3.0 silk suture and punctured two or nine times with 21-gauge needle. The cecum was returned to the peritoneal cavity and the abdominal incision was closed using surgical staples.

Mice were rehydrated with 1 ml saline subcutaneously and placed on a heating pad until they recovered from anesthetic. Sham-operated mice were subjected to a similar laparotomy without ligation and puncture. For survival studies, mice subjected to surgery were monitored for 5 days. For analysis of septic inflammatory responses, CLP mice were anesthetized and bled at 4, 24 and 72 h after surgery. Peritoneal lavage was performed with 1 ml of cold sterile PBS wash. Serum and cell-free peritoneal lavage fluid were collected for cytokine protein analyses. To determine bacterial loads after CLP surgery, peritoneal lavage fluid, EDTA-treated blood and lung homogenate from 24 h post-CLP were placed on ice and serially diluted in sterile PBS. A 10 µl aliquot of each dilution was spread on LB agar plates without antibiotics and incubated at 37° C. overnight. Colonies were counted and expressed as CFU/ml. In some experiments, recombinant human Sema3A-Fc or human IgG$_1$ Fc control protein were injected intraperitoneally at a dosage of 25 µg/kg 1 h prior to CLP procedure.

Example 9

Statistics

Statistical analysis was carried out with Prism 4 for Macintosh. In survival studies a log-rank test was used to test for significance. For all other studies results were presented as the mean±s.d., and unpaired Student's t-test (one tailed) was applied to evaluate significance. P values less than 0.05 were considered statistically significant.

Example 10

Antigen Presenting Assay

Bone marrow-derived dendritic cells (BMDCs) were generated from WT and Plxna4$^{-/-}$ mice as described previously (Eun et al., 2006). BMDCs were incubated with either 1 µg/ml OVA peptide$_{323-339}$ (ISQAVHAAHAEINEAGR (SEQ ID NO:60); New England Peptide) or 50 µg/ml OVA whole protein (Worthington Biochemical Corp.) at 37° C. overnight. Soluble antigen was removed from DC culture by washing cells two times with medium. CD4$^+$T cells isolated from spleens of OT II mice with Mouse CD4 Subset Column (R&D) were labeled with 2 µM carboxyfluorescein succinimidyl ester (CFSE) and then added to the DC culture. Two or four days later, cells were collected, and T cell proliferation was analyzed by the dilution of CFSE fluorescence detected on a CyAn ADP flow cytometer (DAKO).

Example 11

Sorting and Stimulation of Plasmacytoid DCs

Total bone marrow cells were harvested from the femurs and tibiae of mice. Single cell suspensions were prepared, and RBCs were lysed. Plasmacytoid DCs were sorted to more than 98% purity by FACS by labeling cells with 3 colors: anti-mPDCA1-PE, antiCD11c-APC and anti-B220-pacific blue (all from BD Biosciences). Sorted pDCs (B220$^+$ CD11c$^{int}$mPDCA1) were stimulated with either TLR7 ligand Imiquimod (R837) or TLR9 ligand B-type CpG oligodeoxynucleotide (ODN1826) in 96-well plates for 16 h. IFN-α protein levels in cell-free supernatant were determined using a mouse IFN-α ELISA kit (PBL InterferonSource).

Example 12

Flow Cytometry Analysis

Spleens were collected from naïve WT and Plxna4$^{-/-}$ mice and dispersed in 0.5% collagenase A (Roche). After lysing RBCs with ammonium chloride buffer, total cell numbers were determined using a hemocytometer. Fc binding was blocked via a 10 min incubation with purified rat anti-mouse CD16/CD32 (FcγIII/II receptor). The cells were stained with the following monoclonal antibodies to identify different mouse cell types: anti-CD11b-APC, anti-F4/80-PE-Cy5, anti-Ly6C-PE, anti-Ly6G-FITC, anti-B220-Pacific Blue, anti-CD11c-PE-Cy7, anti-mPDCA1-PE, anti-NK1.1-FITC, anti-CD3-PE, anti-CD4-PerCP, anti-CD8-Pacific Blue, anti-CD19-PE-Cy7. All antibodies were purchased from eBioscience, except for anti-F4/80 (Serotec). The cells were fixed in 1% paraformaldehyde and kept in the dark at 4° C. until analysis with a CyAn ADP flow cytometer (DAKO).

Example 13

Plexin-A4 is Expressed by Myeloid and Monocytic Cells

Plexin-A4 is highly expressed in the nervous system and functions as an axon guidance factor during neuronal development (Suto et al., 2007; Yaron et al., 2005). To investigate the role of plexin-A4 in the immune system, the Plxna4$^{-/-}$ mRNA expression level was analyzed in different immune subpopulations. Cells of the lymphoid lineage (T, B and NK cells) showed no detectable expression, while cells of the myeloid lineage including macrophages and conventional DCs expressed relatively high levels of the gene with the exception of plasmacytoid DCs (pDCs), which expressed a low level of the gene (FIG. 1A). The highest level of Plxna4 mRNA was observed in peritoneal macrophages. Plexin-A4 protein was detected on the surface of wild type (WT), but not of Plxna4$^{-/-}$ peritoneal macrophages as determined by immunofluorescence staining and flow cytometry analysis.

Figure 8:
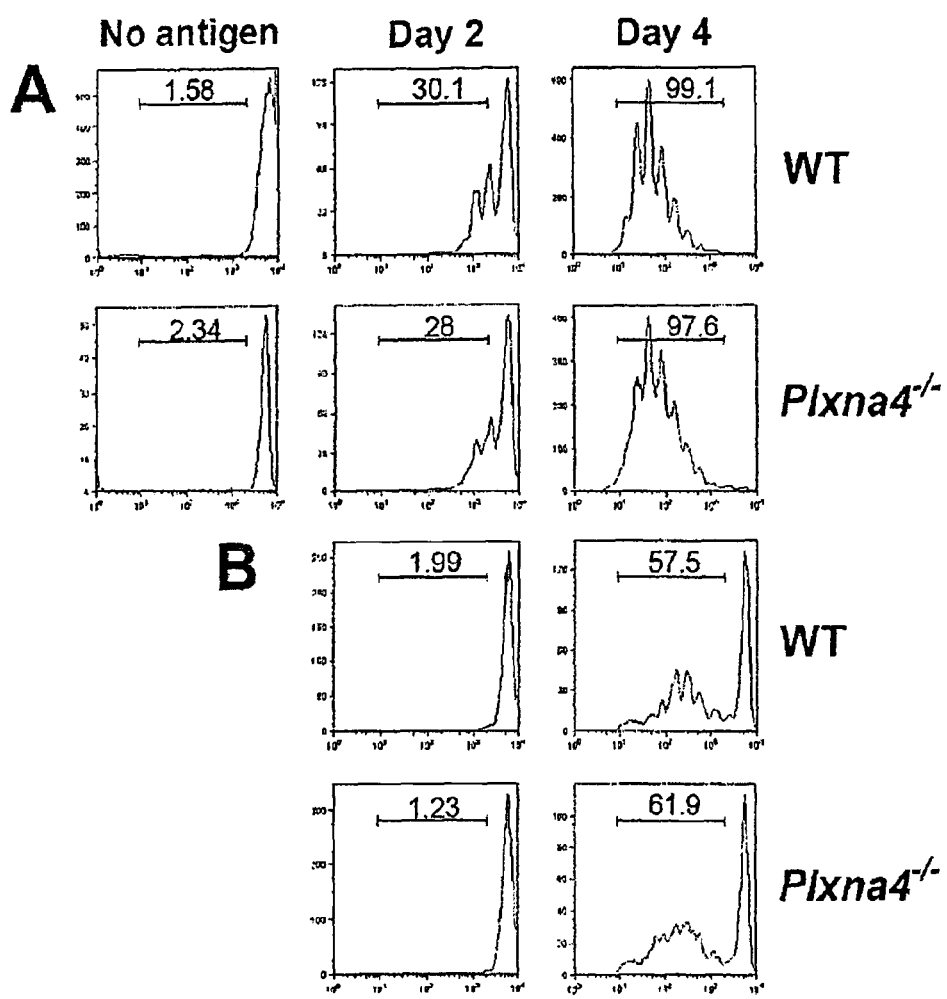
FIGS. 8A-B show that plexin-A4 does not modulate the presentation of OVA antigen by bone marrow-derived dendritic cells (BMDCs). BMDCs generated from WT or Plxna4$^{-/-}$ mice were pulsed with either 1 μg/ml OVA peptide$_{323-339}$ (FIG. 8A) or 50 μg/ml OVA whole protein (FIG. 8B), and co-cultured with carboxyfluorescein succinimidyl ester (CFSE)-labeled splenic CD4$^+$T cells isolated from naïve TCR-transgenic OTII mice. Two or four days later, T cell proliferation was analyzed by the dilution of CFSE fluorescence.
Figure 9:
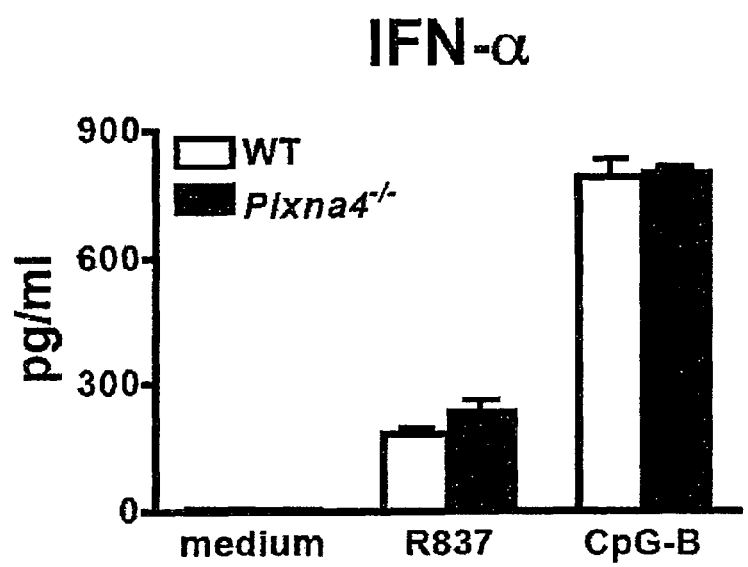
FIG. 9 shows that plexin-A4 does not affect TLR-induced IFN-α production by plasmacytoid dendritic cells (pDCs). Plasmacytoid DCs were isolated from the bone marrows of WT and Plxna4$^{-/-}$ mice by FACS, and stimulated with 10 μg/ml 8837 (TLR7) or 4 μg/ml CpG-B for 16 h. IFN-α protein levels in the supernatants were determined by ELISA.

Due to the selective expression of plexin-A4 in myeloid cells, the role of plexin-A4 was investigated in functions that are well studied in cells of this lineage. Previous work has shown that plexin-A1 on DCs mediates the activation of T cells (Takegahara et al., 2006; Wong et al., 2003). In contrast, plexin-A4 is not involved in DC antigen presentation, since OVA$_{323-339}$-specific OTII CD4$^+$T cell proliferation was comparable when stimulated with either WT or Plxna4$^{-/-}$ bone marrow-derived DCs (BMDCs) that have been loaded with either OVA$_{323-339}$ peptide or whole OVA protein (FIG. 8). The role of plexin-A4 in type I IFN production by pDCs was also evaluated. WT and Plxna4$^{-/-}$ pDCs isolated from the bone marrow generated comparable amounts of IFN-α in response to stimulation with TLR7 (R837) or TLR9 (B-type CpG oligodeoxynucleotide, CpG-B) agonists. This indicates that plexin-A4 does not play a role in type 1 IFN production by pDCs during TLR stimulation (FIG. 9).

Example 14

Plexin-A4 is Required for TNF-α and IL-6 Production in Macrophages

Figure 10:
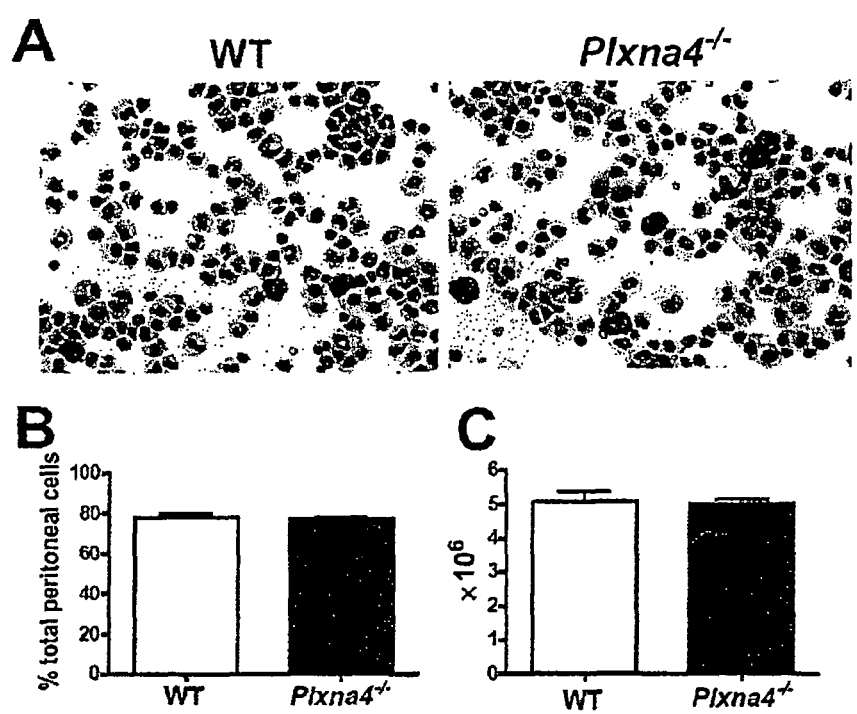
FIGS. 10A-C show that plexin-A4 does not affect the number of peritoneal macrophages. Total peritoneal cells were harvested from WT and Plxna4$^{-/-}$ mice by peritoneal lavage. Cytospins were prepared and stained by hematoxylin and eosin (FIG. 10A). The percent of peritoneal macrophages from WT and Plxna4$^{-/-}$ mice (FIG. 10B) were multiplied by the total cell count to determine the absolute numbers (FIG. 10C).
Figure 19:
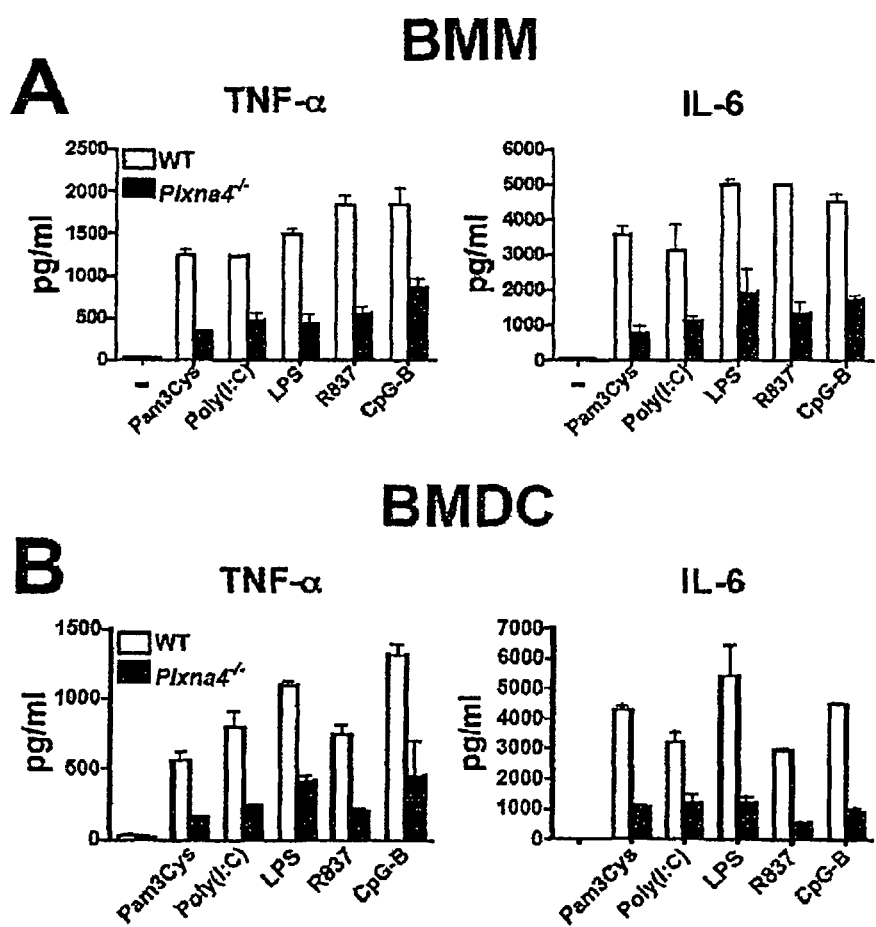
FIGS. 19A-B show that plexin-A4 is required for TLR-induced cytokine production in bone marrow-derived macrophages (BMMs) and bone marrow-derived dendritic cells (BMDCs). BMMs (FIG. 19A) and BMDCs (FIG. 19B) were generated from the bone marrow cells of WT and Plxna4$^{-/-}$ mice, and stimulated with various TLR agonists for 4 h. Protein levels of TNF-α and IL-6 in the supernatant were determined by ELISA.

The role of plexin-A4 in cytokine production in response to TLR activation was examined next. Plxna4$^{-/-}$ and WT mice showed no difference in the percent or absolute number of peritoneal macrophages as determined by the analysis of a cytospin sample (FIGS. 10A-10C). A variety of TLR agonists were used to stimulate naïve peritoneal macrophages, including Pam3Cys (TLR2), polyinosinic-polycytidylic acid (poly (I:C), TLR3), lipopolysaccharide (LPS, TLR4), R837 and CpG-B. During TLR stimulation with these diverse agonists, Plxna4$^{-/-}$ peritoneal macrophages generated significantly lower amount of TNF-α and IL-6 mRNA and protein compared to similarly treated WT controls (FIGS. 1B and 1C). In contrast, there was no difference in IFN-β production between WT and Plxna4$^{-/-}$ peritoneal macrophages upon TLR activation. In addition to peritoneal macrophages, Plxna4$^{-/-}$ bone marrow-derived macrophages (BMMs) (FIG. 19A) and BMDCs (FIG. 19B) exhibited defective TNF-α and IL-6 production upon TLR stimulation when compared to their WT counterparts. These findings show that plexin-A4 is required for TLR-initiated proinflammatory cytokines but not type 1 IFN production.

Figure 2:
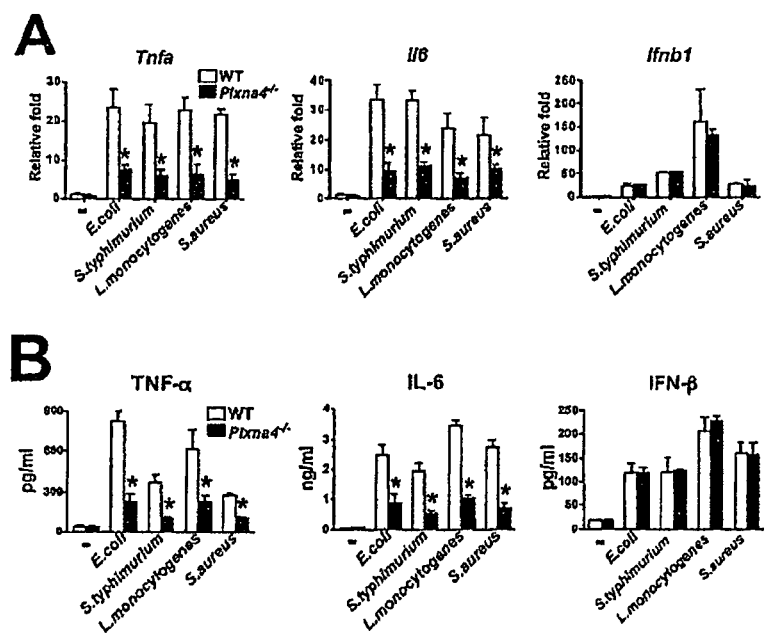
FIGS. 2A-B show that plexin-A4 is required for cytokine production in response to bacterial challenge. Peritoneal macrophages isolated from WT or Plxna4$^{-/-}$ mice were stimulated with *Escherichia coli, Salmonella typhimurium, Listeria monocytogenes* or *Staphylococcus aureus* at a multiplicity of infection (MOI) of 40. Messenger RNA (FIG. 2A) and protein (FIG. 2B) levels of TNF-α, IL-6 and IFN-β were measured by RT-PCR and ELISA, respectively. The results shown are representative of three independent experiments and are expressed as mean±s.d. * P<0.05 compared to WT peritoneal macrophages.

The role of macrophage plexin-A4 in response to bacterial challenge was further tested. Both Gram-positive (*Listeria monocytogenes, Staphylococcus aureus*) and -negative (*Escherichia coli, Salmonella typhimurium*) bacteria were used to stimulate peritoneal macrophages. In all cases, bacteria-challenged Plxna4$^{-/-}$ macrophages produced significantly reduced levels of TNF-α and IL-6 mRNA and protein, but a similar level of IFN-β when compared to WT macrophages (FIGS. 2A and 2B). These data suggest that plexin-A4 is important in the bacteria-induced, inflammatory cytokine response.

Example 15

Plexin-A4 Mediates the Activation of NF-κB and JNK but not ERK or p38

Figure 3:
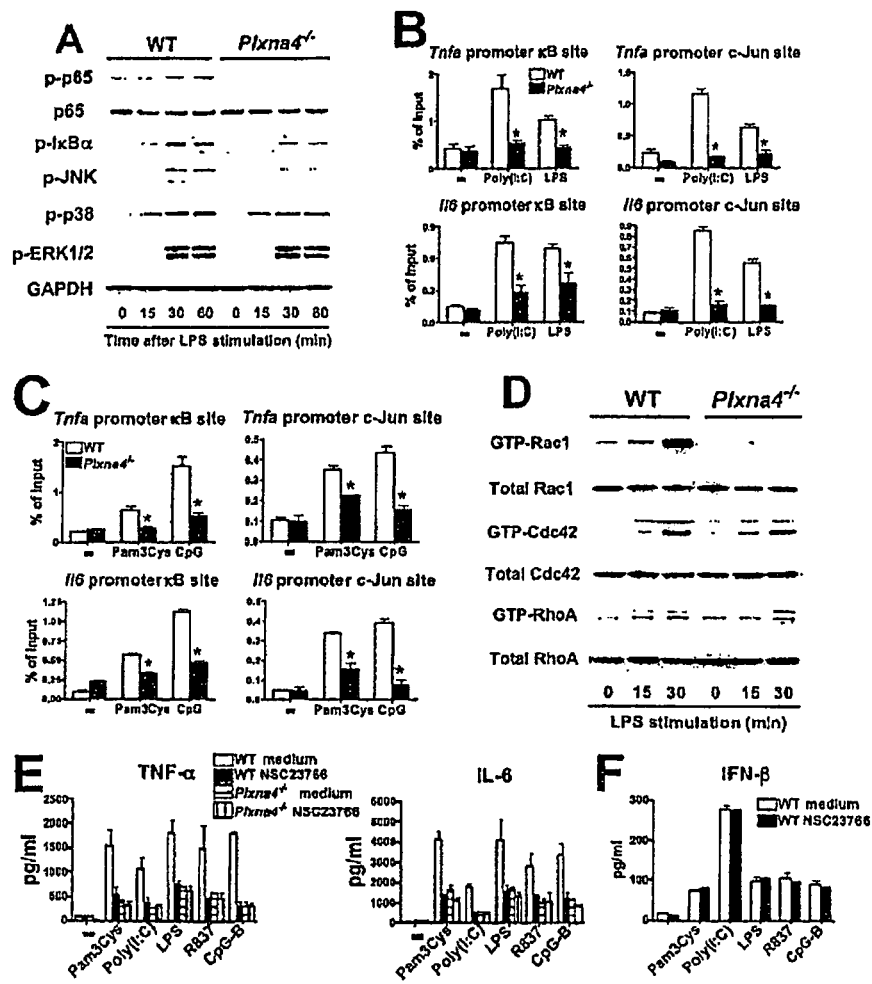
FIGS. 3A-E show that plexin-A4 is required for LPS-induced activation of nuclease factor-kappa B (NF-κB), c-Jun-N-terminal kinase (JNK) and small GTPase Rac1. Immunoblot analysis of NF-κB and mitogen-activated protein kinase (MAPK) signaling molecules was performed with WT and Plxna4$^{-/-}$ peritoneal macrophages left untreated (0) or treated for 15, 30 or 60 min with 1 μg/ml ultrapure LPS (FIG. 3A).
Figure 20:
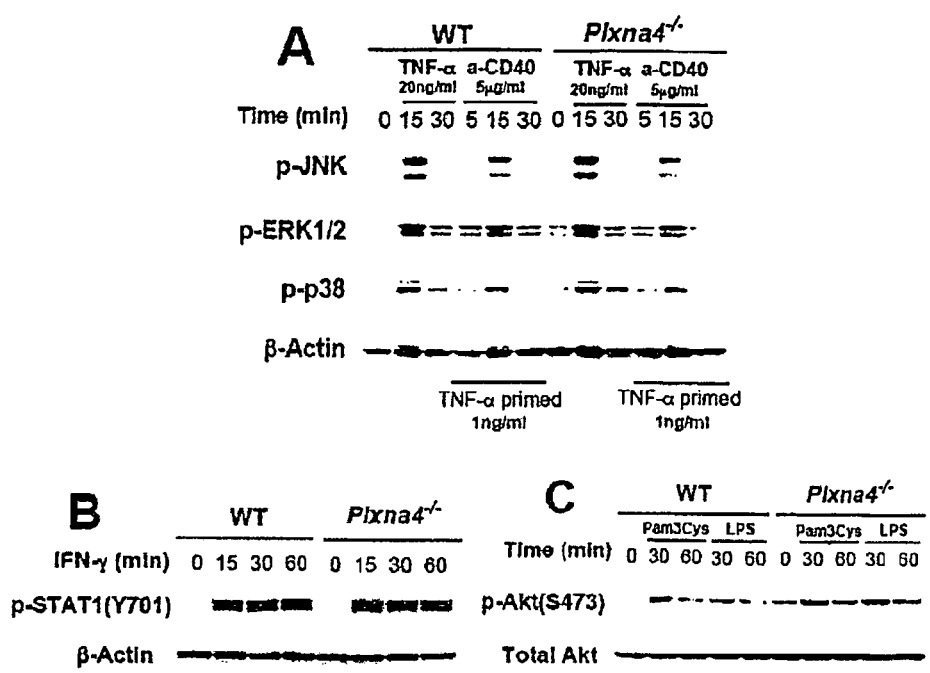
FIGS. 20A-C show that plexin-A4 does not affect TNF-α, CD40, or PI3K/Akt signaling pathways. Peritoneal macrophages were isolated from WT and Plxna4$^{-/-}$ mice by peritoneal lavage. Cells were treated either with recombinant mouse TNF-α (20 ng/ml) or anti-CD40 (5 μg/ml) after TNF-α (1 ng/ml) priming for 3 h. TNF-α priming is required to upregulate CD40 expression (Lich et al., 2007). Immunoblot of MAPK signaling molecules was performed (FIG. 20A). Cells were treated with recombinant mouse IFN-γ, and STAT1 phosphorylation at tyrosine 701 was detected by immunoblot (FIG. 19B). Cells were treated with either Pam3Cys (5 μg/ml) or LPS (1 μg/ml). Akt phosphorylated at serine 473 was detected by immunoblot (FIG. 19C).
Figure 21:
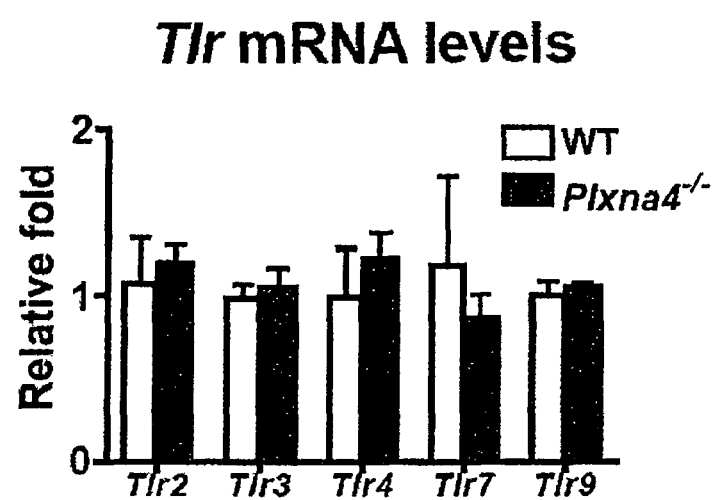
FIG. 21 shows that plexin-A4 does not affect toll-like receptor mRNA expression in peritoneal macrophages. Messenger RNA levels of Tlr2, 3, 4, 7 and 9 in WT and Plxna4$^{-/-}$ peritoneal macrophages were analyzed by RT-PCR using different primer sets, as described in Example 21, Table 1, below.

NF-κB and MAPK signaling pathways control the production of inflammatory cytokines during macrophage activation in response to TLR agonists and microbial pathogens (Vallabhapurapu and Karin, 2009). The defective production of TNF-α and IL-6 by Plxna4$^{-/-}$ macrophages prompted us to investigate the function of plexin-A4 in these signaling pathways. After LPS stimulation, naive WT peritoneal macrophages exhibited enhanced phosphorylation of p65, JNK, p38 and ERK1/2 MAPKs as expected. However, Plxna4$^{-/-}$ macrophages showed a dramatic defect in the phosphorylation of p65 and JNK, but not ERK1/2 and p38, suggesting a specific regulatory function of plexin-A4 in the activation of NF-κB and JNK kinase (FIG. 3A), Phosphorylation and activation of p65 requires phosphorylation of the inhibitor of κB (IκB). In accordance with defective p65 phosphorylation during LPS stimulation, Plxna4$^{-/-}$ macrophages showed a defect in IκB phosphorylation compared with WT macrophages (FIG. 3A). In contrast, Plxna4$^{-/-}$ macrophages were not defective in response to TNF-α, anti-CD40 and IFN-γ treatment. The phosphorylation of MAPKs upon TNF-α or anti-CD40 treatment (FIG. 20A) and of STAT1 (signal transducer activators of transcription 1) upon IFN-γ treatment (FIG. 20B) was not altered in Plxna4$^{-/-}$ macrophages. This indicates that plexin-A4 specifically mediates TLR activation. Additionally, Plxna4$^{-/-}$ peritoneal macrophages showed no defect in Akt phosphorylation in response to TLR activation by Pam3Cys and LPS stimulation (FIG. 20C). These findings indicate that plexin-A4 deficiency leads to a TLR-specific defect in NF-κB and JNK activation. Furthermore, this defect is not due to decreased TLR expression, since the mRNA levels of Tlr2, 3, 4, 7 or 9 were similar between WT and Plxna4$^{-/-}$ peritoneal macrophages (FIG. 21).

To determine if impaired NF-κB and JNK activation in Plxna4$^{-/-}$ macrophages causes defective binding of the downstream transcription factors, p65 and c-Jun, at the promoter regions of Tnfa and Il6, chromatin immunoprecipitation (ChIP) assays were performed by using specific anti-p65 and anti-phospho-c-Jun antibodies. Appropriate primer sets were designed that flanked the well-defined binding sites of κB and c-Jun at the promoter regions of Tnfa and Il6 (Galvez et al., 2009; Leng et al., 2009). One hour after stimulation with various TLR agonists, WT macrophages showed enhanced binding of p65 and c-Jun at both Tnfa and Il6 promoters, which correlated with the increased expression of these inflammatory genes (FIGS. 3B and 3C), Conversely, Plxna4$^{-/-}$ macrophages showed significantly decreased p65 and c-Jun binding at these promoters compared with similarly treated WT controls. This data suggests that plexin-A4 mediates TLR-induced TNF-α and IL-6 production by inducing the activities of NF-κB and JNK to cause the epigenetic activation of these genes, Example 15

Plexin-a4 Causes the Activation of the Small GTPase, Rac1, but not RhoA or Cdc42

Several members of the plexin family, such as plexin-B1 (Perrot et al., 2002; Swiercz et al., 2002) and plexin-A1 (Turner et al., 2004), mediate their downstream effects through the activation of Rho family of small GTPases such as RhoA, Rac1 and Cdc42. More importantly, Rac1 has been shown to serve an essential role upstream of NF-κB activation and cytokine production in response to either TLR2 (Arbibe et al., 2000) or TLR4 (Sanlioglu et al., 2001) agonists. To determine if plexin-A4 regulates the activation of small GTPases during TLR activation, a small GTPase pull-down assay was used in which the binding domain of the downstream effector of a particular GTPase was used to pull down the GTP-bound and hence activated form of that GTPase. LPS-stimulated WT macrophages displayed an increase in the GTP-bound form of Rac1 and Cdc42 when compared to unstimulated controls (FIG. 3D). LPS-stimulated Plxna4$^{-/-}$ macrophages exhibited a dramatic reduction in the quantity of GTP-bound Rac1 when compared to WT cells, while GTP-bound Cdc42 and RhoA were indistinguishable. Thus, plexin-A4 affects the activation of Rac1, which is known to promote NF-κB activation and cytokine production in TLR-stimulated macrophages (Arbibe et al., 2000; Sanlioglu et al., 2001). In support of the importance of Rac1 in TLR-stimulated gene expression, a specific Rac1 inhibitor NSC23766 (Gao et al., 2004) was used and found to significantly attenuate TNF-α and IL-6 production in WT peritoneal macrophages stimulated by various TLR agonists (FIG. 3E). However, NSC23766 showed no inhibitory effect on cytokine production by TLR-activated Plxna4$^{-/-}$ macrophages. This is compatible with the conclusion that Rac1 activation is significantly attenuated in Plxna4$^{-/-}$ macrophages such that a Rac1 inhibitor has no further suppressive effect on these cells. IFN-β production in WT macrophages was not affected by Rac1 inhibition (FIG. 3F). This is consistent with the earlier observation that plexin-A4 does not affect TLR-induced type I IFN production.

Example 16

Plxna4$^{-/-}$ Mice Exhibit Reduced Cytokine Storm and are Protected Front Lethal Challenge With LPS and Poly(I:C)

Figure 11:
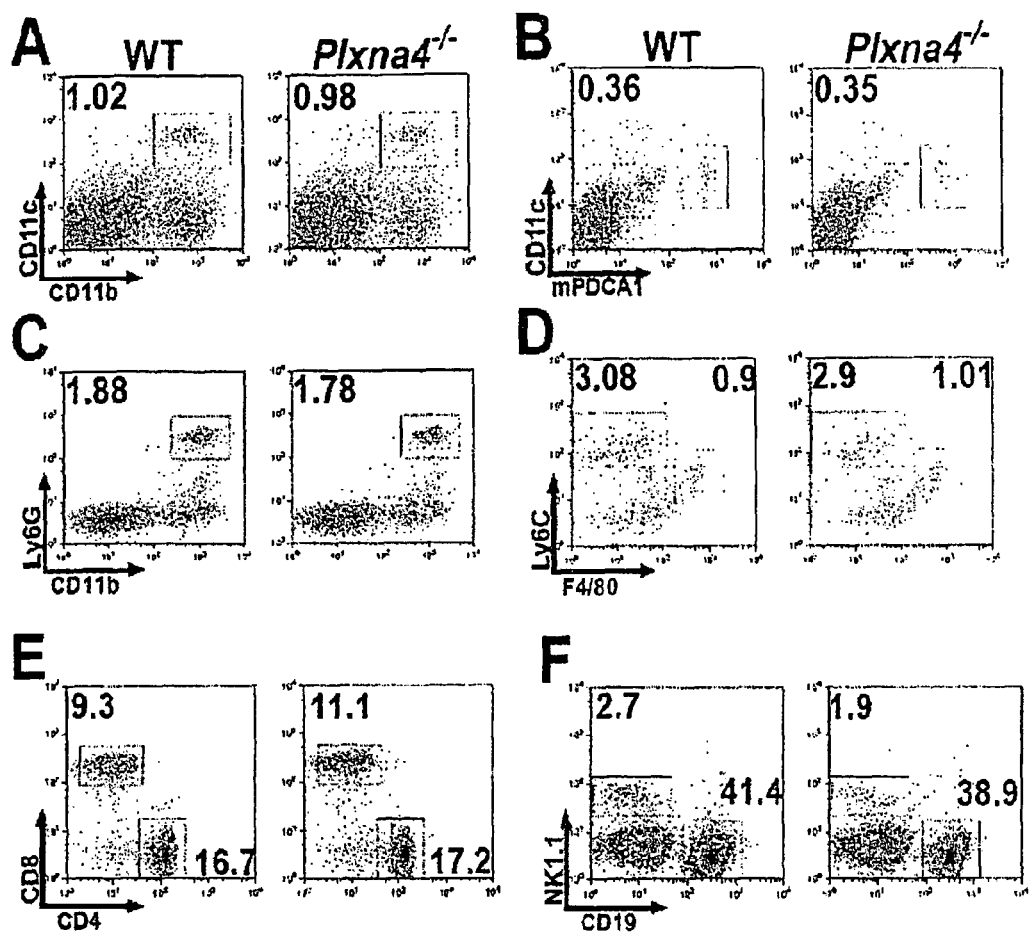
FIGS. 11A-F show that plexin-A4 does not affect immune cell composition in the spleen. Cells of myeloid or lymphoid lineage in the spleen were analyzed by FACS, including CD11b$^+$CD11c$^+$ myeloid DCs (FIG. 11A), B220$^+$mPDCA1$^+$CD11c$^{low}$pDCs (FIG. 11B), CD11b$^+$Ly6G$^+$ neutrophils (FIG. 11C), CD11b$^+$Ly6c$^+$ monocytes and CD11b$^+$F4/80$^+$ macrophages (FIG. 11D), CD3$^+$CD4$^+$T cells and CD3$^+$CD8$^+$T cells (FIG. 11E), and CD19$^+$B cells and NK1.1$^+$NK cells (FIG. 11F).

Next, the physiological relevance of these findings was evaluated. The number of immune cells in the Plxna4$^{-/-}$ mice was first determined. No apparent defect was detected for all immune cell types tested, including myeloid DCs (mDCs), pDCs, neutrophils, monocytes, macrophages, CD4$^+$ or CD8$^+$T cells, B cells, NK cells (FIG. 11). Thus, any physiological difference observed between WT and Plxna4$^{-/-}$ mice is not due to a change in immune subpopulations.

Since Plxna4$^{-/-}$ macrophages showed decreased TNF-α and IL-6 production during TLR stimulation in vitro, the in vivo role of plexin-A4 was examined next. Mice were injected intraperitoneally with either LPS (12.5 mg per kg body weight) or poly(EC) (20 mg per kg body weight), and the peritoneal lavage fluid was analyzed for inflammatory cytokines by the Multi-plex ELISA assay. Four hours after the injection of LPS or poly(I:C), both localized (FIG. 4B) and systemic (FIG. 4C) levels of inflammatory cytokines, including TNF-α, IL-1β, IL-6, IL-12p70, CCL2 and CCL3, were attenuated in Plxna4$^{-/-}$ mice compared to WT mice.

Figure 4:
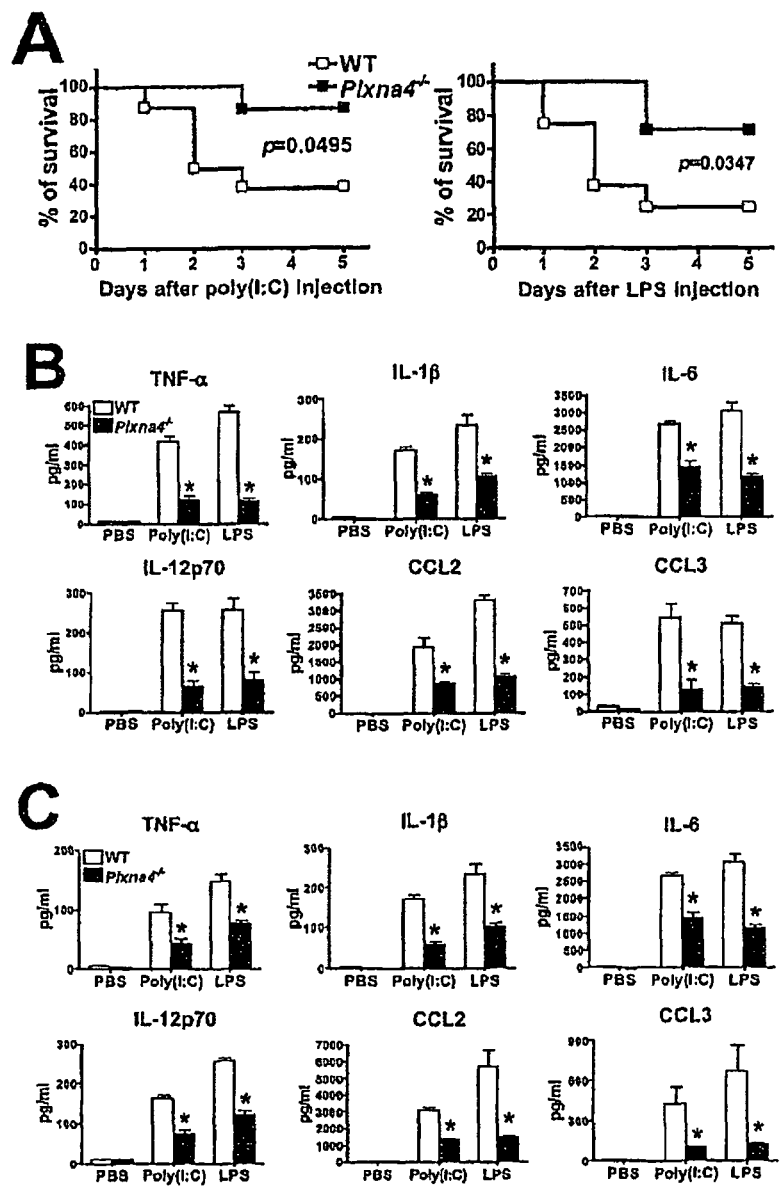
FIGS. 4A-C show that Plxna4$^{-/-}$ mice are protected from septic shock induced by poly(I:C) or LPS.
Figure 7:
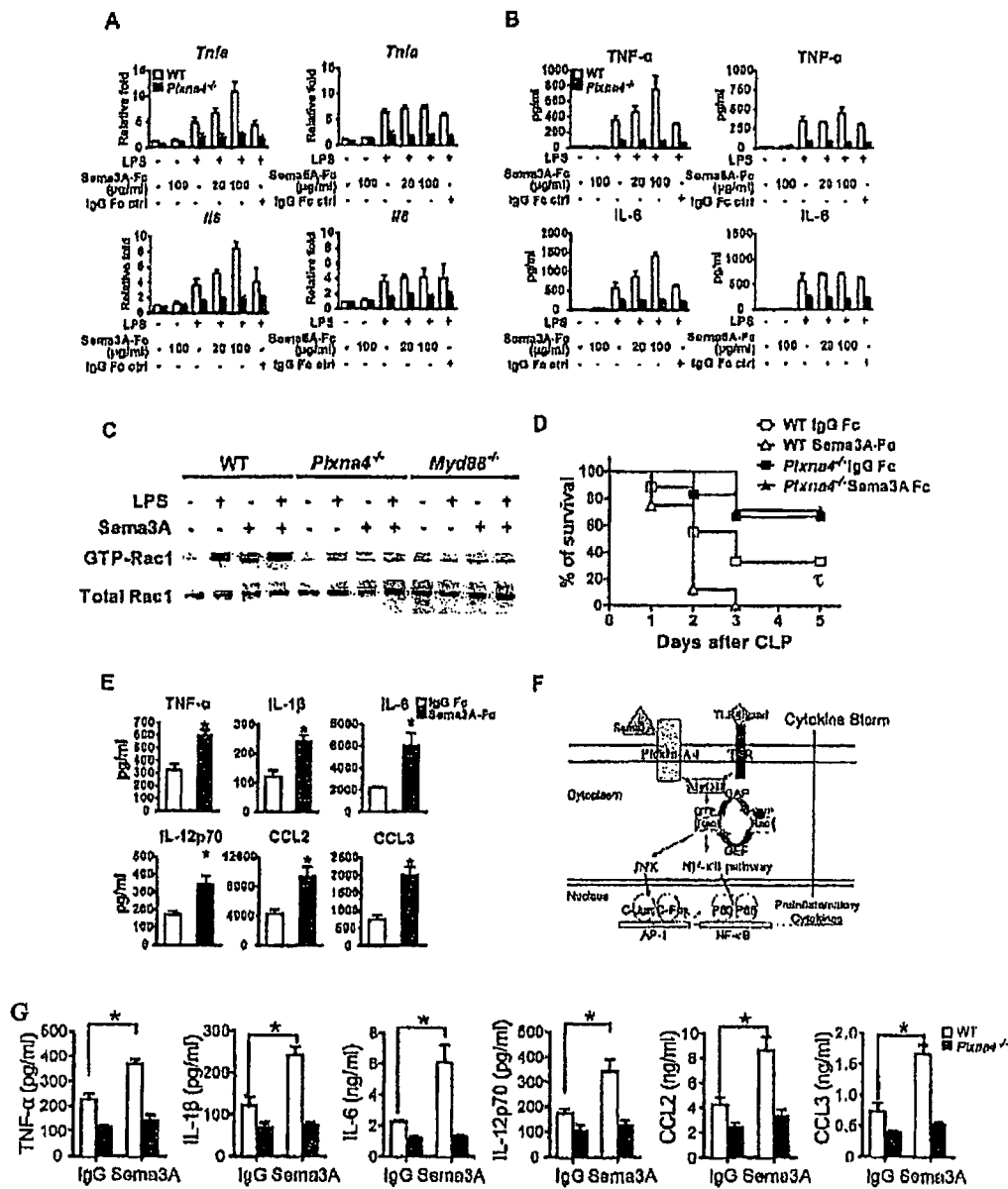
FIGS. 7A-G show that Semaphorin 3A (Sema3A) enhances LPS-induced cytokine production in a plexin-A4-dependent manner. WT and Plxna4$^{-/-}$ peritoneal macrophages were stimulated with LPS (1 μg/ml) for 4 h in the absence or presence of either Sema3A-Fc or Sema6A-Fc fusion proteins (20 or 100 μg/ml) (FIG. 7A and FIG. 7B). Messenger RNA (FIG. 7A) or protein (FIG. 7B) levels of TNF-α and IL-6 were measured by RT-PCR and ELISA, respectively. The IgG Fc fragment (100 μg/ml) was used as a negative control. WT and Plxna4$^{-/-}$ mice (n=7~9 per group) were pretreated with either Sema3A-Fc or IgG Fc control proteins at a dosage of 25 μg per kg body weight 1 h prior to CLP procedure (FIG. 7C). Survival rate was monitored for 5 days. τP<0.05 compared with WT mice pretreated with Sema3A-Fc. WT mice (n=4 per group) were pretreated with either Sema3A-Fc or IgG Fc control proteins, followed by CLP surgery (FIG. 7D). Inflammatory cytokines in peritoneal lavage collected 4 h after CLP were determined by ELISA. * P<0.05 compared to peritoneal lavage from WT mice pretreated with Sema3A-Fc (FIG. 7E).

The production of a plethora of inflammatory cytokines is frequently detrimental to the animals and referred to as the cytokine storm (FIG. 7F). Thus, morbidity among animals injected with TLR agonists was examined. While WT mice succumbed to high doses of TLR agonists, Plxna4$^{-/-}$ mice were significantly protected from LPS or poly(I:C)-induced lethality (FIG. 4A). These findings indicate that plexin-A4 enhances the in vivo inflammatory responses induced by TLR agonists.

Example 17

Plxna4$^{-/-}$ Mice are Resistant to Septic Inflammation Induced by Cecal Ligation and Puncture (CLP)

Figure 5:
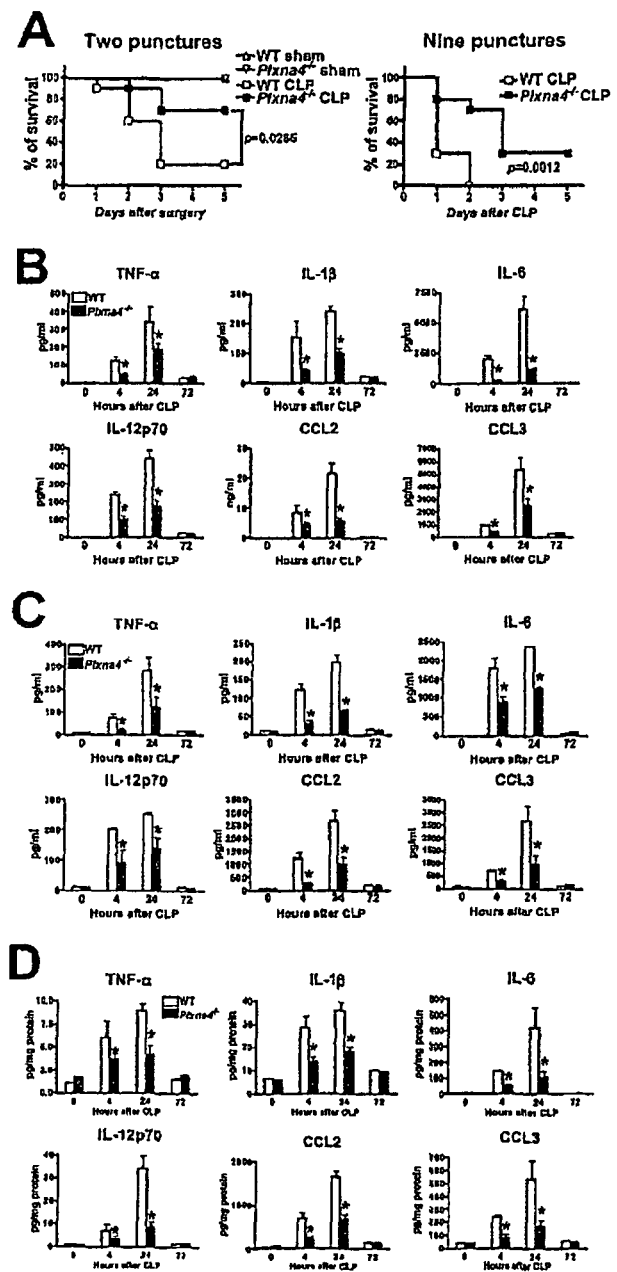
FIGS. 5A-D show that Plxna4$^{-/-}$ mice are protected from polymicrobial peritonitis induced by cecal ligation and puncture (CLP).

To further evaluate the role of plexin-A4 during in vivo bacterial infection, a well-defined CLP-induced polymicrobial peritonitis model was utilized, which closely replicates the nature and course of clinical sepsis (Hubbard et al., 2005). Acute sepsis results in a high mortality rate, which is primarily due to the overzealous production of pro inflammatory cytokines. Given that the number of cecal punctures may determine the severity of sepsis, both moderate sepsis (two punctures) and severe sepsis (nine puncture) models were employed. WT mice with two or nine punctures respectively showed 80% and 100% mortality rate as early as 3 days after CLP (FIG. 5A). However, Plxna4$^{-/-}$ mice were significantly protected from CLP-induced lethality in both moderate sepsis (p=0.0285) and severe sepsis (p=0.0012). Hence the absence of plexin-A4 provided a clear survival benefit. Inflammatory cytokine levels were also examined in the peritoneal lavage, serum, and lung homogenate before and after CLP-induced peritonitis. At 4 h and 24 h after CLP, Plxna4$^{-/-}$ mice produced significantly reduced levels of inflammatory cytokines such as TNF-α, IL-6, IL-12p70, CCL2 and CCL3 in the peritoneal lavage fluid (FIG. 5B), serum (FIG. 5C) and lung homogenate (FIG. 5D) compared to WT mice. Therefore, plexin-A4 enhances the septic inflammatory response and promotes a cytokine storm in an experimental peritonitis model.

Example 18

Plexin-A4 Shows No Role in Macrophage Phagocytosis and Bacteria Killing

Figure 6:
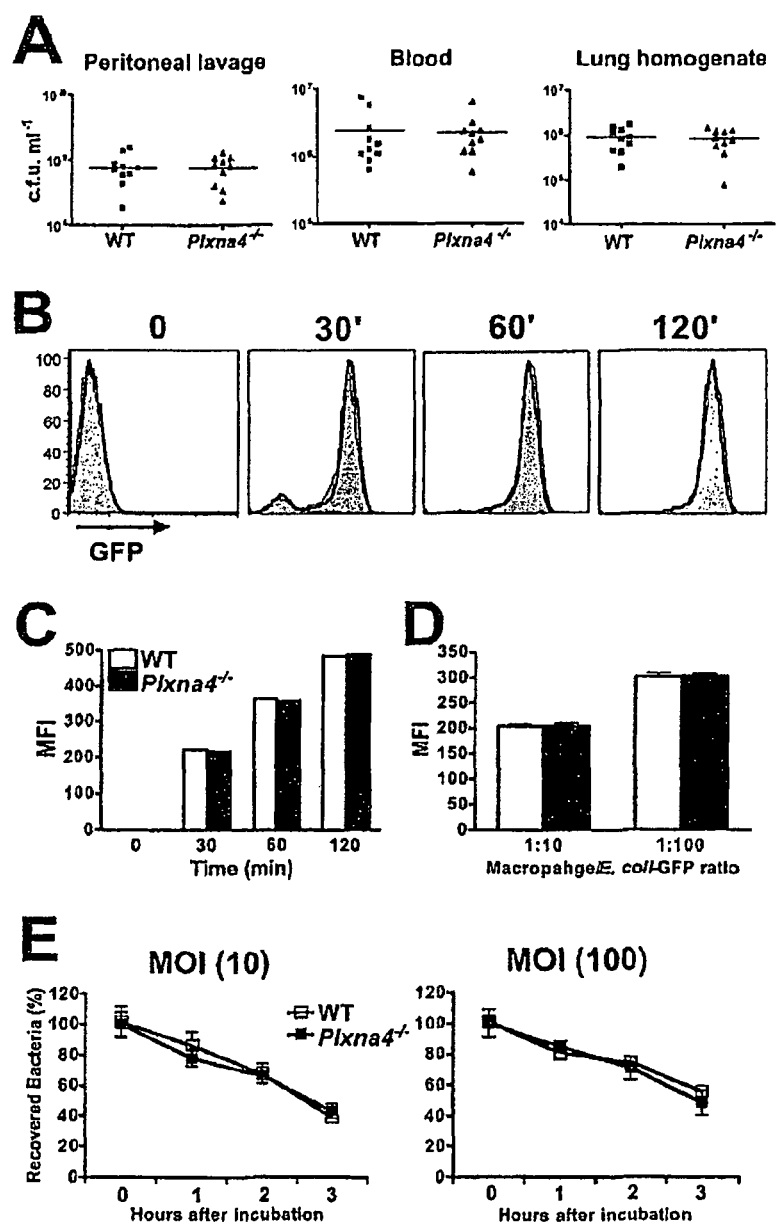
FIGS. 6A-E show that plexin-A4 is not required for macrophage phagocytosis and bacteria killing. WT and Plxna4$^{-/-}$ mice were subjected to CLP surgery (FIG. 6A). Bacterial loads in peritoneal lavage (left panel), blood (middle panel) and lung homogenate (right panel) were determined by counting the colony forming units.

Another essential factor that contributes to host survival during acute sepsis is efficient phagocytosis and killing of invading bacteria (Matsukawa et al., 2000). The dramatic survival benefit in Plxna4$^{-/-}$ mice prompted an investigation of the function of plexin-A4 in macrophage phagocytosis and bacteria killing. Twenty-four hours after CLP surgery, there were similar levels of bacterial loads in the peritoneal lavage, blood and lung homogenate from WT and Plxna4$^{-/-}$ mice, indicating that plexin-A4 is not required for bacterial clearance (FIG. 6A). WT and Plxna4$^{-/-}$ peritoneal macrophages did not differ in the in vitro phagocytosis of GFP-expressing E. coli following different points of incubation (30, 60 or 120 min) (FIG. 6B and FIG. 6C) or infection with different MOIs (10 or 100) (FIG. 6D). Furthermore, there was no difference in the bacterial killing capacity of WT and Plxna4$^{-/-}$ peritoneal macrophages, because similar numbers of E. coli were recovered from macrophages of both genotypes after the extracellular bacteria were killed by antibiotics and the E. coli loaded macrophages were incubated for different time periods (FIG. 6E). Taken together, these data suggest that plexin-A4 does not play a role in bacterial phagocytosis and killing in macrophages.

Example 19

Sema3A Enhances LPS-Induced Cytokine Production in a Plexin-A4-Dependent Manner

Figure 22:
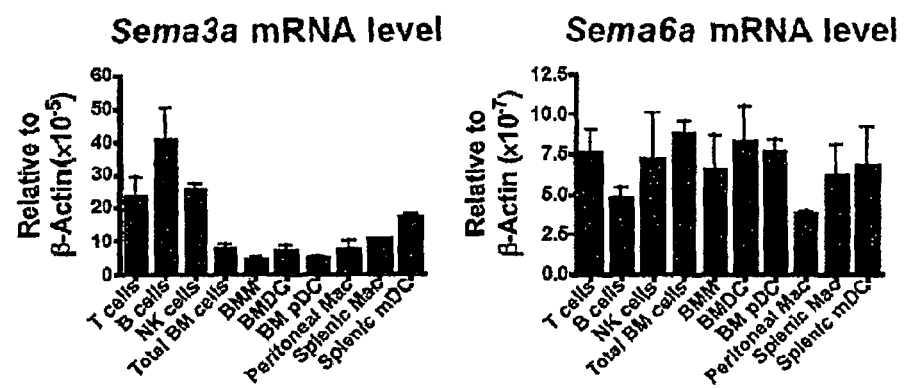
FIG. 22 shows the expression of Sema3a and Sema6a mRNA in different immune cells. Messenger RNA levels of Sema3a and Sema6a in different immune subpopulations were analyzed by RT-PCR and normalized to Actb mRNA level.

Previous studies in the CNS have identified Sema3A and Sema6A as the ligands for plexin-A4 (Suto et al., 2007; Yaron et al., 2005). Sema3a and Sema6a mRNA expression levels were first analyzed in immune subpopulations (FIG. 22). The highest level of Sema3a mRNA was observed in cells of the lymphoid lineage such as T, B and NK cells. Myeloid and monocytic cells also express Sema3a, but at a lower level. Sema6a mRNA is expressed at a relatively low level in all immune subpopulations that we analyzed. The level of Sema6a was nearly 100× lower than that of Sema3a when normalized to the Actb signal.

To determine if soluble Sema3A or Sema6A also functions in the immune system as a ligand for plexin-A4, WT or Plxna4$^{-/-}$ peritoneal macrophages were stimulated with increasing concentrations of Sema3A or Sema6A in the absence or presence of LPS. These ligands were expressed as chimeric proteins consisting of the human IgG1 Fc fragment fused to either Sema3A or Sema6A. The IgG1 Fc fragment alone was used as a negative control. Neither Sema3A nor Sema6A alone induced TNF-α and IL-6 production in macrophages. In the presence of a suboptimal concentration of LPS (50 ng/ml), Sema3A, but not Sema6A or IgG Fc control, enhanced LPS-induced TNF-α and IL-6 production in WT peritoneal macrophages in a dose-dependent manner (FIG. 7A and FIG. 7B). However, this enhancement in LPS-responsiveness was completely abolished in Plxna4$^{-/-}$ macrophages (FIG. 7A and FIG. 7B). The absence of a functional effect of Sema6A agrees with its low expression in different immune populations shown earlier.

The data presented suggest that LPS via TLR and Sema3A via plexin-A4 might synergistically induce macrophage activation. To assess a converging point for TLR and plexin-A4, we assayed for GTP-bound Rac1. WT macrophages stimulated by LPS or Sema3A resulted in Rac1 activation, while the two stimuli together enhanced this activation. However, Rac1 activation was not observed upon stimulation by either LPS or Sema3A in Plxna4$^{-/-}$ macrophages, suggesting that plexin-A4 is required for signals that emanate from the binding of TLR agonists and Sema3A (FIG. 7C). Similarly, neither Sema3A nor LPS activated Rac1 in Myd88$^{-/-}$ macrophages. This finding suggests that MyD88 lies downstream of the Sema3A/plexin-A4 axis. These findings further suggest that Sema3A and LPS both require intact MyD88 signaling to synergistically promote Rac1 activation.

We next assessed if Sema3A engagement of plexin-A4 could synergistically exacerbate CLP-induced septic inflammation. A single peritoneal injection of Sema3A or control IgG Fc at a dosage of 25 µg/kg body weight was administrated to WT and Plxna4$^{-/-}$ mice 1 h prior to CLP procedure. Sema3A, but not IgG control, significantly exacerbated CLP-induced lethality in WT mice (FIG. 7D). In contrast, Sema3A did not affect the survival rate of Plxna4$^{-/-}$ mice in the same experiment. This indicates that the observed biologic effect of Sema3A is dependent on plexin-A4. To further determine if decreased survival observed in Sema3A-pretreated WT mice was associated with dysregulated cytokine production, cytokine production in the peritoneal lavage was measured 4 h after CLP. Indeed, Sema3A-pretreated mice had significantly higher levels of inflammatory cytokines than IgG Fc-treated controls (FIG. 7E).

The above experiments were performed in cell culture with highly enriched macrophage preparations, thus it was important to assess the physiologic relevance of these findings. To address this, we assessed if Sema3A engagement of plexin-A4 could synergistically exacerbate CLP-induced septic inflammation. A single peritoneal injection of Sema3A or control IgG Fc at a dosage of 25 µg/kg body weight was administrated to WT and Plxna4$^{-/-}$ mice 1 h prior to CLP procedure. We measured cytokine production in the peritoneal lavage 4 h after CLP. Sema3A-pretreated mice had significantly higher levels of inflammatory cytokines than IgG Fc-treated controls in WT mice, but not in Plxna4$^{-/-}$ mice (FIG. 8G). Collectively, these in vitro and in vivo results suggest that plexin-A4 binding by Sema3A synergizes with TLR engagement by its agonist(s) to amplify innate inflammatory responses. Strategies to reduce Sema3A engagement of plexin-A4 should be beneficial in controlling an adverse inflammatory response associated with endotoxin shock or sepsis.

Example 20

Figure 17A:
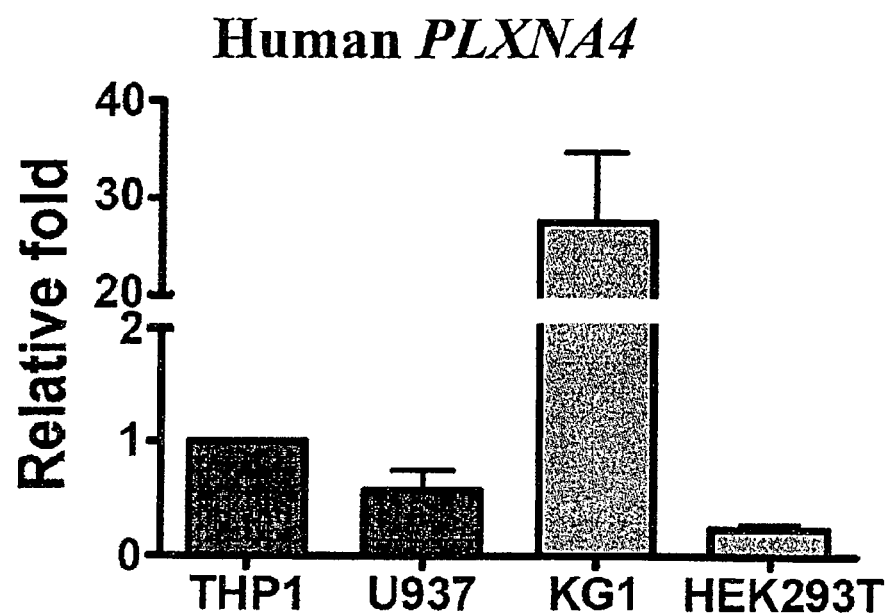

Preparation of a Fusion Protein Between Human Plexin-A4 Extracellular Fragment and Human IgG1 Fc Total RNA was isolated from human myeloid leukemia cell line KG1 cells, which expresses a relatively high PLXNA4 mRNA level (FIG. 17A). Reverse transcription was performed to yield complementary DNA. Human plexin-A4 extracellular fragment (hPLXNA4EF) (bold in FIG. 12A) was cloned using a primer set that contained HindIII (forward primer) digestion site or BamHI (reverse primer) digestion site: forward, 5'-AAGCTTGCCACCCATGAAAGCCATGCCCTGGAACT (SEQ ID NO:24); reverse, 5'-GGATCCGTCCGGGGCAATGTACACCATC (SEQ ID NO:25).

Figure 17C:
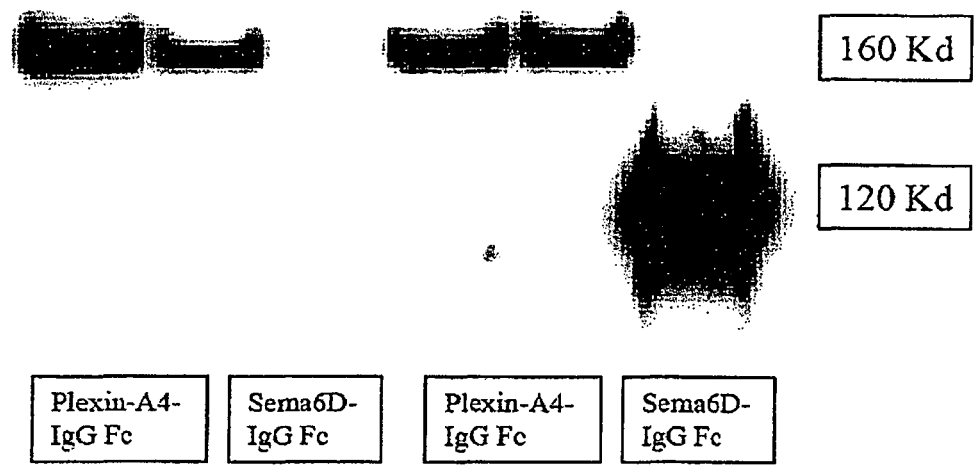

Using these enzyme digestion sites, human plexin-A4 extracellular fragment was subcloned into pcDNA3 vector containing human IgG1 Fc fragment (hIgG Fc) (bold in FIG. 17B). Then human plexin-A4 extracellular fragment is upstream of human IgG1 Fc with a linker of two amino acids between them. Human PLXNA4 EF-hIgG Fc fragment was further subcloned into pCEP4 vector to generate fusion protein between human plexin-A4 extracellular fragment and human IgG1 Fc (FIG. 15A; FIG. 17C).

Example 21

Primers

Amplifying Primers:
Full-Length hPLXNA4:

```
Forward(Hind3):
                                        SEQ ID NO: 24
AAGCTTGCCACCCATGAAAGCCATGCCCTGGAACT.

Reverse(BamHI):
                                        SEQ ID NO: 26
GGATCCAAGGACGGTTCTCAGCTGTCTA.
``` hPLXNA4 Extracellular Fragment:

```
Forward(Hind3):
                                        SEQ ID NO: 24
AAGCTTGCCACCCATGAAAGCCATGCCCTGGAACT.

Reverse(BamHI):
                                        SEQ ID NO: 25
GGATCCGTCCGGGGCAATGTACACCATC.
```

Sequencing Primers:

| | | |
|---|---|---|
| 1. | GATTGCCTGTGGGAGCCTGTA | SEQ ID NO: 27 |
| 2. | TATGTAGAGGTGCCCATTGGCT | SEQ ID NO: 28 |
| 3. | TATGAGACGGTGCAGGTGGT | SEQ ID NO: 29 |
| 4. | TTCGCCAGCACCAGCTTT | SEQ ID NO: 30 |
| 5. | TGACCCAGACTTCGCATGT | SEQ ID NO: 31 |
| 6. | AACCTGAATGCCGGAAGCAA | SEQ ID NO: 32 |
| 7. | GTGTTTGAGGCCTTTGGTCC | SEQ ID NO: 33 |
| 8. | GGATTCCGTTCCTGGACTATA | SEQ ID NO: 34 |
| 9. | TTGAGCGAGGACAAGCTCAT | SEQ ID NO: 35 |
| 10. | TGACCTGGAGAGTGGAGTCAA | SEQ ID NO: 36 |

```
Forward-Primer
                                        SEQ ID NO: 37
GCCTCTGCCATGAAAGCCA                     19

Reverse-Primer
                                        SEQ ID NO: 38
AAGGACGGTTCTCAGCTGTCTAA                 23
```

TABLE 1

Sequences of RT-PCR primers

| Mouse genes | Forward | Reverse | |
|---|---|---|---|
| Sema3a | GCCTGCAGAAGAAGGATTCA | TCAGGTTGGGGTGGTTAATG | (SEQ ID NOs: 39, 40) |
| Sema6a | AATGGCCAGATGCCCTTATG | CCGAGTAGAGTTTTCCATTGCA | (SEQ ID NOs: 41, 42) |
| Tlr2 | CTCCTGAAGCTGTTGCGTTAC | TACTTTACCCAGCTCGCTCACTAC | (SEQ ID NOs: 43, 44) |
| Tlr3 | TCTTCTTTACGAAAGTTGGACTTGTC | TTGCCAATTGTCTGGAAACACC | (SEQ ID NOs: 45, 46) |
| Tlr4 | ATGGCATGGCTTACACCACC | GAGGCCAATTTTGTCTCCACA | (SEQ ID NOs: 47, 48) |
| Tlr7 | CTGGAGTTCAGAGGCAACCATT | GTTATCACCGGCTCTCCATAGAA | (SEQ ID NOs: 49, 50) |
| Tlr9 | AGCTGAACATGAACGGCATCT | TGAGCGTGTACTTGTTGAGCG | (SEQ ID NOs: 51, 52) |
| Ifnb1 | ATGAGTGGTGGTTGCAGGC | TGACCTTTCAAATGCAGTAGATTCA | (SEQ ID NOs: 53, 54) |

Example 22

Preparation of a Fusion Protein Between Human Semaphorin 3A and Human IgG1Fc

An expression vector pCR-Blunt-TOPO containing full-length human SEMA3A was purchased from Mammalian Gene Collection (MGC). SEMA3A sequence was amplified by a primer set that contained HindIII (forward primer) digestion site or BamHI (reverse primer) digestion site: forward, 5'-AAGCTTGCCACCCATGGGCTGGTTAAC-TAGGATTGT (SEQ ID NO:55); reverse, 5'-GGATCCGA-CACTCCTGGGTGCCCTCTCA (SEQ ID NO:56). Using these enzyme digestion sites, human SEMA3A was sub-cloned into pCDNA3 vector containing human IgG1 Fc fragment (hIgG Fe) (bold portion in FIG. 17B). Then human SEMA3A is upstream of human IgG1 Fc with a linker of two amino acids between them. Human SEMA3A-hIgG Fc fragment was further subcloned into pCEP4 vector to generate fusion protein between human SEMA3A and human IgG1 Fc (FIG. 16A).

Sequencing Primers:

| 1 | TGGGAAGAGTCCATATGACCCT | (SEQ ID NO: 57) |
| 2 | ATTTTCAAGGGATCAGCCGT | (SEQ ID NO: 58) |
| 3 | CTATATATTGGTTCAACGGC | (SEQ ID NO: 59) |

Example 23

Preparation and Testing of Monoclonal Antibodies to Plexin-A4

Monoclonal antibodies were prepared against plexin-A4 using standard protocols (See, e.g., Monoclonal Antibodies. Shepherd and Dean, eds. New York: Oxford University Press, 2000; Monoclonal Antibodies: Preparation and Use of Monoclonal Antibodies and Engineered Antibody Derivatives. Heddy Zola, ed. Oxford: BIOS Scientific Publishers Limited, 2000). Western blot analysis was used to assay sixteen of the monoclonal antibodies for the ability to bind to plexin-A4. Briefly, expression vector encoding full-length human PLXNA4 was transfected into 293T cell line by using FuGENE® 6 Transfection Reagent (lipid blend for transfection) (Roche). Sixteen hours later, cell were collected and lysed with buffer (50 mM Tris-HCl pH 7.4, 150 mM NaCl, 2 mM EDTA, % TRITON™ X-100 (a non-ionic surfactant), 0.1% SDS, and protease inhibitor cocktail). Proteins were separated on a NuPAGE® (SDS PAGE) gel (Invitrogen) and were transferred onto nitrocellulose membranes (Bio-Rad Laboratories). The membranes were blocked with 10% milk proteins in 1×PBS and 0.1% TWEEN-20 and then probed with each of sixteen anti-human plexin-A4 antibodies. HRP-conjugated anti-rat secondary antibodies were used and over-expressed human plexin-A4 were detected using an Enhanced Chemiluminescent (ECL) Western Blotting Substrate reagent (peroxidase substrate) from Thermo Scientific.

Example 24

Functional Testing of Monoclonal Anti-Plexin-A4 Antibodies in Macrophages

We have identified plexin-A4 as an essential cell surface molecule involved in macrophage activation and cytokine production. Therefore, we plan to test the efficacy of monoclonal anti-plexin-A4 antibody in inhibiting macrophage cytokine production such as TNF and IL-6. Briefly, resident peritoneal macrophages are isolated and stimulated with a series of TLR agonists in the absence or presence of each of sixteen anti-plexin-A4 antibodies. The supernatants are collected and TNF and IL-6 will be measured by ELISA. Furthermore, the efficacy of anti-plexin-A4 in the treatment of experimental sepsis is tested by using polymicrobial peritonitis animal model, which has been described above.

Example 25

Prior to the present study, none of the plexin molecules had been shown to regulate TLR signaling. The present invention shows the novel intersection of the plexin-A4 and TLR pathways through the intracellular activation of Rac1, JNK and NF-κB (FIG. 7F). This intersection results in epigenetic changes at the promoters of proinflammatory genes, followed by a pan-cytokine inflammatory response in response to TLR stimulation and bacterial challenge. It cumulates in a cytokine storm that precipitates endotoxin shock induced by TLR agonists and sepsis induced by bacterial infection. The data presented herein show that the plexin-A4 ligand, Sema3A, together with endotoxin can synergistically induce cytokine production in a plexin-A4-dependent manner. Collectively, these data reveal a pivotal role of plexin-A4 in TLR-induced macrophage cytokine production through activation of Rac-1, NF-κB and JNK.

Whereas it is generally believed that TLR engagement by TLR agonists is able to fully activate immune cells, the present study identifies another requirement during this process involving the engagement of membrane plexin-A4 by Sema3A. Without wishing to be bound by any particular theory of the invention, it appears that TLR and plexin-A4 constitute components of a "two-signal" model for TLR activation. Signal 1 is initiated upon the binding of TLRs with their corresponding ligands and transduced sequentially through MyD88, IRAK, TRAF6, TAK1 kinase complex, IKK and MAPK. Meanwhile, signal 2 is initiated by plexin-A4 binding to its soluble ligand, Sema3A, which triggers Rac1, leading to the activation of NF-κB and JNK. In the absence of TLR stimulation, plexin-A4 activation by Sema3A failed to induce cytokine production, indicating that plexin-A4-mediated signal 2 is not sufficient for the induction of cytokine production. In the absence of plexin-A4, TLR signaling is significantly attenuated but not abolished, indicating that TLR signaling is amplified by plexin-A4 activation but is not initiated by this activation. The data presented herein show that in macrophages lacking MyD88, which is the adaptor for all TLRs except for TLR3, Rac1 activation is attenuated in response to Sema3A stimulation. This indicates that Sema3A/plexin-A4 signaling also requires MyD88. Whether this is achieved via direct binding of plexin-A4 and MyD88 or an indirect route remains to be elucidated. In contrast to its role in the promotion of proinflammatory cytokines, plexin-A4 is not required for TLR-induced TRIF-dependent type 1 IFN production, suggesting that plexin-A4 does not affect TRIF signaling.

The findings of the present invention show that while plexin-A4 is most highly expressed by monocytic and myeloid cell lineages and significantly reduced on lymphoid cells, Sema3A is highly expressed by lymphoid cells with reduced expression by myeloid/monocytic cell types. Thus it is possible that during an early inflammatory response, the smaller amount of Sema3A produced by myeloid and monocytic cells together with TLR ligands is sufficient to activate the higher density of plexin-A4 on macrophage membrane. Later when T cells are called in, the higher amounts of Sema3A expressed by activated T cells then serve as a feedback-loop to downregulate T cells, which express less plexin-A4 receptors.

The biologic function of plexin-A4 in the activation of a pan-cytokine response has broad clinical implications. New anti-inflammatory therapeutic methods are needed in the treatment of immune-related and/or inflammatory diseases. In addition, pathogen-induced sepsis represents a major burden to the US health care system and has become increasingly significant over the past decades (Martin et al., 2003). The hallmark of sepsis in the acute phase is an exacerbated production of proinflammatory cytokines and chemokines, leading to the cytokine storm. While these inflammatory mediators are essential in providing an immediate host defense, their overzealous production can be deleterious to the host if left uncontrolled. The present invention suggests a role for plexin-A4 in mediating the production of proinflammatory cytokines, which affects host survival in models of sepsis. Therefore, the interaction of plexin-A4 and Sema3A presents a new therapeutic target for anti-inflammatory and anti-sepsis treatment.

REFERENCES

Akira, S., and Takeda, K. (2004). Toll-like receptor signalling. Nat Rev Immunol 4, 499-511.

Akira, S., Uematsu, S., and Takeuchi, O. (2006). Pathogen recognition and innate immunity. Cell 124, 783-801.

Arbibe, L., Mira, J. P., Teusch, N., Kline, L., Guha, M., Mackman, N., Godowski, P. J., Ulevitch, R. J., and Knaus, U. G. (2000). Toll-like receptor 2-mediated NF-kappa B activation requires a Rac1-dependent pathway. Nat Immunol 1, 533-540.

Carvalho, F. A., Barnich, N., Sauvanet, P., Darcha, C., Gelot, A., and Darfeuille-Michaud, A. (2008). Crohn's disease-associated *Escherichia coli* LF82 aggravates colitis in injured mouse colon via signaling by flagellin. *Inflammatory Bowel Diseases* 14, 1051-1060.

Choi, Y. I., Duke-Cohan, J. S., Ahmed, W. B., Handley, M. A., Mann, F., Epstein, J. A., Clayton, L. K., and Reinherz, E. L. (2008). PlexinD1 glycoprotein controls migration of positively selected thymocytes into the medulla. *Immunity* 29, 888-898.

Couzin, J. MicroRNAs Make Big Impression in Disease After Disease. *Science* 319, 1782-1784 (2008).

Eun, S. Y., O'Connor, B. P., Wong, A. W., van Deventer, H. W., Taxman, D. J., Reed, W., Li, P., Blum, J. S., McKinnon, K. P., and Ting, J. P. (2006). Cutting edge: rho activation and actin polarization are dependent on plexin-A1 in dendritic cells. J Immunol 177, 4271-4275.

Forster, A. C. and R. H. Symons. Self-cleavage of plus and minus RNAs of a virusoid and a structural model for the active sites. *Cell* 49, 211-220 (1987).

Galvez, A. S., Duran, A., Linares, J. F., Pathrose, P., Castilla, E. A., Abu-Baker, S., Leitges, M., Diaz-Meco, M. T., and Moscat, J. (2009). Protein kinase Czeta represses the interleukin-6 promoter and impairs tumorigenesis in vivo. Mol Cell Biol 29, 104-115.

Gao, Y., Dickerson, J. B., Guo, F., Zheng, J., and Zheng, Y. (2004). Rational design and characterization of a Rae GTPase-specific small molecule inhibitor. *Proc Natl Acad Sci USA* 101, 7618-7623.

Gerlach, W. L. et al. Construction of a plant disease resistance gene from the satellite RNA of tobacco ringspot virus. *Nature* 328, 802-805 (1987).

Gu, C., Rodriguez, E. R., Reimert, D. V., Shu, T., Fritzsch, B., Richards, L. J., Kolodkin, A. L., and Ginty, D. D. (2003a). Neuropilin-1 conveys semaphorin and VEGF signaling during neural and cardiovascular development. *Developmental Cell* 5, 45-57.

Hubbard, W. J., Choudhry, M., Schwacha, M. G., Kerby, J. D., Rue, L. W., 3rd, Bland, K. I., and Chaudry, I. H. (2005). Cecal ligation and puncture. *Shock* 24 Suppl 1, 52-57.

Iwasaki, A., and Medzhitov, R. (2004). Toll-like receptor control of the adaptive immune responses. *Nat Immunol* 5, 987-995.

Joyce, G. F. RNA evolution and the origins of life, *Nature* 338. 217-224 (1989).

Kawai, T., and Akira, S. (2006). Innate immune recognition of viral infection. *Nat Immunol* 7, 131-137.

Kikutani, H., and Kumanogoh, A. (2003). Semaphorins in interactions between T cells and antigen-presenting cells. *Nat Rev Immunol* 3, 159-167.

Kim, S.-H. and T. R. Cech. Three-dimensional model of the active site of the self-splicing rRNA precursor of Tetrahymena. *Proc Natl Acad Sci USA* 84, 8788-8792 (1987).

Kruger, R. P., Aurandt, J., and Guan, K. L. (2005). Semaphorins command cells to move. *Nat Rev Mol Cell* Biol 6, 789-800.

Labandeira-Rey, M., Couzon, F., Boisset, S., Brown, E. L., Bes, M., Benito, Y., Barbu, E. M., Vazquez, V., Hook, M., Etienne, J., et al. (2007). Staphylococcus aureus Panton-Valentine leukocidin causes necrotizing pneumonia. Science 315, 1130-1133.

Leng, J., Butcher, B. A., Egan, C. E., Abdallah, D. S., and Denkers, E. Y. (2009). Toxoplasma gondii prevents chromatin remodeling initiated by TLR-triggered macrophage activation. J Immunol 182, 489-497.

Lich, J. D., Williams, K. L., Moore, C. B., Arthur, J. C., Davis, B. K., Taxman, D. J., and Ting, J. P. (2007). Monarch-1 suppresses non-canonical NF-kappaB activation and p52-dependent chemokine expression in monocytes. J Immunol 178, 1256-1260.

Martin, G. S., Mannino, D. M., Eaton, S., and Moss, M. (2003). The epidemiology of sepsis in the United States from 1979 through 2000. N Engl J Med 348, 1546-1554.

Matsukawa, A., Hogaboam, C. M., Lukacs, N. W., Lincoln, P. M., Evanoff, H. L., and Kunkel, S. L. (2000). Pivotal role of the CC chemokine, macrophage-derived chemokine, in the innate immune response. J Immunol 164, 5362-5368.

Michel F. and E. Westhof. Modelling of the three-dimensional architecture of group I catalytic introns based on comparative sequence analysis. J Biol Chem 216, 585-610 (1990).

Neufeld, G., and Kessler, O. (2008). The semaphorins: versatile regulators of tumour progression and tumour angiogenesis. Nature Reviews 8, 632-645.

Noren, N. K., Liu, B. P., Burridge, K., and Kreft, B. (2000). p120 catenin regulates the actin cytoskeleton via Rho family GTPases. J Cell Biol 150, 567-580.

Perrot, V., Vazquez-Prado, J., and Gutkind, J. S. (2002). Plexin B regulates Rho through the guanine nucleotide exchange factors leukemia-associated Rho GEF (LARG) and PDZ-RhoGEF. J Biol Chem 277, 43115-43120.

Reinhold-Hurek, B. and D. A. Shub. Self-splicing introns in tRNA genes of widely divergent bacteria. Nature 357, 173-176 (1992).

Sanlioglu, S., Williams, C. M., Samavati, L., Butler, N. S., Wang, G., McCray, P. B., Jr., Ritchie, T. C., Hunninghake, G. W., Zandi, E., and Engelhardt, J. F. (2001). Lipopolysaccharide induces Rac1-dependent reactive oxygen species formation and coordinates tumor necrosis factor-alpha secretion through IKK regulation of NF-kappa B. J Biol Chem 276, 30188-30198.

Sarver, N. et al. Ribozymes as potential anti-HIV-1 therapeutic agents. Science 247, 1222-1225 (1990).

Scanlon, K. J. et al. Ribozyme-mediated cleavage of c-fos mRNA reduces gene expression of DNA synthesis enzymes and metallothionein. Proc Natl Acad Sci USA 88, 10591-10595 (1991).

Serini, G., Valdembri, D., Zanivan, S., Morterra, G., Burkhardt, C., Caccavari, F., Zammataro, L., Primo, L., Tamagnone, L., Logan, M., et al. (2003). Class 3 semaphorins control vascular morphogenesis by inhibiting integrin function. Nature 424, 391-397.

Sierra, J. R., Corso, S., Caione, L., Cepero, V., Conrotto, P., Cignetti, A., Piacibello, W., Kumanogoh, A., Kikutani, H., Comoglio, P. M., et al. (2008). Tumor angiogenesis and progression are enhanced by Sema4D produced by tumor-associated macrophages. J Exp Med 205, 1673-1685.

Sioud, M. et al. Preformed Ribozyme Destroys Tumor Necrosis Factor mRNA in Human Cells, J Mol Biol 223, 831-835 (1992), Suto, F., Tsuboi, M., Kamiya, H., Mizuno, H., Kiyama, Y., Komai, S., Shimizu, M., Sanbo, M., Yagi, T., Hiromi, Y., et al. (2007). Interactions between plexin-A2, plexin-A4, and semaphorin 6A control lamina-restricted projection of hippocampal mossy fibers. Neuron 53, 535-547.

Suzuki, K., Kumanogoh, A., and Kikutani, H. (2008). Semaphorins and their receptors in immune cell interactions. Nat Immunol 9, 17-23.

Swiercz, J. M., Kuner, R., Behrens, J., and Offermanns, S. (2002). Plexin-B1 directly interacts with PDZ-RhoGEF/LARG to regulate RhoA and growth cone morphology. Neuron 35, 51-63.

Takegahara, N., Takamatsu, H., Toyofuku, T., Tsujimura, T., Okuno, T., Yukawa, K., Mizui, M., Yamamoto, M., Prasad, D. V., Suzuki, K., et al. (2006). Plexin-A1 and its interaction with DAP12 in immune responses and bone homeostasis. Nat Cell Biol 8, 615-622.

Toyofuku, T., Zhang, H., Kumanogoh, A., Takegahara, N., Yabuki, M., Harada, K., Hori, M., and Kikutani, H. (2004). Guidance of myocardial patterning in cardiac development by Sema6D reverse signalling. Nat Cell Biol 6, 1204-1211.

Tran, Kolodkin, A. L., and Bharadwaj, R. (2007). Semaphorin regulation of cellular morphology. Annu Rev Cell Developmental Biol 23, 263-292.

Turner, L. J., Nicholls, S., and Hall, A. (2004). The activity of the plexin-A1 receptor is regulated by Rac. J Biol Chem 279, 33199-33205.

Vallabhapurapu, S., and Karin, M. (2009). Regulation and function of NF-kappaB transcription factors in the immune system. Annu Rev Immunol 27, 693-733.

Waimey, K. E., Huang, P. H., Chen, M., and Cheng, H. J. (2008). Plexin-A3 and plexin-A4 restrict the migration of sympathetic neurons but not their neural crest precursors. Developmental Biology 315, 448-458.

Walzer, T., Galibert, L., and De Smedt, T. (2005). Dendritic cell function in mice lacking Plexin C1. Int Immunol 17, 943-950.

Wen, H., Dou, Y., Hogaboam, C. M., and Kunkel, S. L. (2008). Epigenetic regulation of dendritic cell-derived interleukin-12 facilitates immunosuppression after a severe innate immune response. Blood 111, 1797-1804.

Wong, A. W., Brickey, W. J., Taxman, D. J., van Deventer, H. W., Reed, W., Gao, J. X., Zheng, P., Liu, Y., Li, P., Blum, J. S., et al. (2003). CIITA-regulated plexin-A1 affects T-cell-dendritic cell interactions. Nat Immunol 4, 891-898.

Yamamoto, M., Suzuki, K., Okuno, T., Ogata, T., Takegahara, N., Takamatsu, H., Mizui, M., Taniguchi, M., Chedotal, A., Suto, F., et al. (2008). Plexin-A4 negatively regulates T lymphocyte responses. Int Immunol 20, 413-420.

Yaron, A., Huang, P. H., Cheng, H. J., and Tessier-Lavigne, M. (2005). Differential requirement for Plexin-A3 and -A4 in mediating responses of sensory and sympathetic neurons to distinct class 3 Semaphorins. Neuron 45, 513-523.

van Deventer, H. W., Serody, J. S., McKinnon, K. P., Clements, C., Brickey, W. J., and Ting, J. P. (2002). Transfection of macrophage inflammatory protein 1 alpha into B16 F10 melanoma cells inhibits growth of pulmonary metastases but not subcutaneous tumors. J Immunol 169, 1634-1639.

What is claimed is:

1. A method of treating an inflammatory disorder in a subject, comprising administering to the subject an effective amount of an inhibitor of plexin-A4 activity, wherein the inhibitor of plexin-A4 activity is an inhibitor of semaphorin 3A (Sema3A) activity and is an antibody or active fragment thereof directed to Sema3A and the inflammatory disorder is sepsis, whereby the plexin-A4 activity in said subject is reduced, thereby treating the inflammatory disorder.

2. The method of claim 1, wherein the antibody or active fragment thereof directed to Sema3A is a monoclonal antibody or is derived from a monoclonal antibody.

3. The method of claim 1, wherein the inhibitor is administered subcutaneously, intramuscularly, intraperitoneally, topically, intravenously, and any combination thereof.

* * * * *

UNITED STATES PATENT AND TRADEMARK OFFICE
CERTIFICATE OF CORRECTION

PATENT NO. : 8,871,205 B2
APPLICATION NO. : 13/511933
DATED : October 28, 2014
INVENTOR(S) : Ting et al.

It is certified that error appears in the above-identified patent and that said Letters Patent is hereby corrected as shown below:

In the Specification:
Column 35, Line 63: Please correct "mPDCA1)" to read -- mPDCA1$^+$) --

Column 38, Line 22: Please correct "genes," to read -- genes. --

Column 39, Line 65: Please correct "TNF -α, IL-6," to read -- TNF -α, IL-1β, IL-6, --

Signed and Sealed this
Twelfth Day of May, 2015

Michelle K. Lee
*Director of the United States Patent and Trademark Office*

SEQUENCE LISTING

<160> NUMBER OF SEQ ID NOS: 60

<210> SEQ ID NO 1
<211> LENGTH: 1894
<212> TYPE: PRT
<213> ORGANISM: Homo sapiens

<400> SEQUENCE: 1

```
Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
            20                  25                  30

Leu Ser Gln Lys Gln Arg Ser Phe Val Thr Phe Arg Gly Glu Pro Ala
        35                  40                  45

Glu Gly Phe Asn His Leu Val Val Asp Glu Arg Thr Gly His Ile Tyr
    50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
            100                 105                 110

Asn Val Asn Lys Met Leu Leu Ile Asp Tyr Lys Glu Asn Arg Leu Ile
        115                 120                 125

Ala Cys Gly Ser Leu Tyr Gln Gly Ile Cys Lys Leu Leu Arg Leu Glu
    130                 135                 140

Asp Leu Phe Lys Leu Gly Glu Pro Tyr His Lys Lys Glu His Tyr Leu
145                 150                 155                 160

Ser Gly Val Asn Glu Ser Gly Ser Val Phe Gly Val Ile Val Ser Tyr
                165                 170                 175

Ser Asn Leu Asp Asp Lys Leu Phe Ile Ala Thr Ala Val Asp Gly Lys
            180                 185                 190

Pro Glu Tyr Phe Pro Thr Ile Ser Ser Arg Lys Leu Thr Lys Asn Ser
        195                 200                 205

Glu Ala Asp Gly Met Phe Ala Tyr Val Phe His Asp Glu Phe Val Ala
    210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
                245                 250                 255

Leu Thr Leu Gln Pro Glu Met Val Ser Pro Pro Gly Ser Thr Thr Lys
            260                 265                 270

Glu Gln Val Tyr Thr Ser Lys Leu Val Arg Leu Cys Lys Glu Asp Thr
        275                 280                 285

Ala Phe Asn Ser Tyr Val Glu Val Pro Ile Gly Cys Glu Arg Ser Gly
    290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Leu Leu Phe
                325                 330                 335

Thr Val Phe Ser Lys Gly Gln Lys Arg Lys Met Lys Ser Leu Asp Glu
            340                 345                 350

Ser Ala Leu Cys Ile Phe Ile Leu Lys Gln Ile Asn Asp Arg Ile Lys
        355                 360                 365
```

```
Glu Arg Leu Gln Ser Cys Tyr Arg Gly Glu Gly Thr Leu Asp Leu Ala
    370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
                405                 410                 415

Asp Met Val Arg Gly Ile Pro Val Phe Thr Glu Asp Arg Asp Arg Met
            420                 425                 430

Thr Ser Val Ile Ala Tyr Val Tyr Lys Asn His Ser Leu Ala Phe Val
        435                 440                 445

Gly Thr Lys Ser Gly Lys Leu Lys Lys Ile Arg Val Asp Gly Pro Arg
    450                 455                 460

Gly Asn Ala Leu Gln Tyr Glu Thr Val Gln Val Val Asp Pro Gly Pro
465                 470                 475                 480

Val Leu Arg Asp Met Ala Phe Ser Lys Asp His Glu Gln Leu Tyr Ile
                485                 490                 495

Met Ser Glu Arg Gln Leu Thr Arg Val Pro Val Glu Ser Cys Gly Gln
            500                 505                 510

Tyr Gln Ser Cys Gly Glu Cys Leu Gly Ser Gly Asp Pro His Cys Gly
        515                 520                 525

Trp Cys Val Leu His Asn Thr Cys Thr Arg Lys Glu Arg Cys Glu Arg
    530                 535                 540

Ser Lys Glu Pro Arg Arg Phe Ala Ser Glu Met Lys Gln Cys Val Arg
545                 550                 555                 560

Leu Thr Val His Pro Asn Asn Ile Ser Val Ser Gln Tyr Asn Val Leu
                565                 570                 575

Leu Val Leu Glu Thr Tyr Asn Val Pro Glu Leu Ser Ala Gly Val Asn
            580                 585                 590

Cys Thr Phe Glu Asp Leu Ser Glu Met Asp Gly Leu Val Val Gly Asn
        595                 600                 605

Gln Ile Gln Cys Tyr Ser Pro Ala Ala Lys Glu Val Pro Arg Ile Ile
    610                 615                 620

Thr Glu Asn Gly Asp His His Val Val Gln Leu Gln Leu Lys Ser Lys
625                 630                 635                 640

Glu Thr Gly Met Thr Phe Ala Ser Thr Ser Phe Val Phe Tyr Asn Cys
                645                 650                 655

Ser Val His Asn Ser Cys Leu Ser Cys Val Glu Ser Pro Tyr Arg Cys
            660                 665                 670

His Trp Cys Lys Tyr Arg His Val Cys Thr His Asp Pro Lys Thr Cys
        675                 680                 685

Ser Phe Gln Glu Gly Arg Val Lys Leu Pro Glu Asp Cys Pro Gln Leu
    690                 695                 700

Leu Arg Val Asp Lys Ile Leu Val Pro Val Glu Val Ile Lys Pro Ile
705                 710                 715                 720

Thr Leu Lys Ala Lys Asn Leu Pro Gln Pro Ser Gly Gln Arg Gly
                725                 730                 735

Tyr Glu Cys Ile Leu Asn Ile Gln Gly Ser Glu Gln Arg Val Pro Ala
            740                 745                 750

Leu Arg Phe Asn Ser Ser Val Gln Cys Gln Asn Thr Ser Tyr Ser
        755                 760                 765

Tyr Glu Gly Met Glu Ile Asn Asn Leu Pro Val Glu Leu Thr Val Val
    770                 775                 780

Trp Asn Gly His Phe Asn Ile Asp Asn Pro Ala Gln Asn Lys Val His
```

```
                785                 790                 795                 800
Leu Tyr Lys Cys Gly Ala Met Arg Glu Ser Cys Gly Leu Cys Leu Lys
                    805                 810                 815

Ala Asp Pro Asp Phe Ala Cys Gly Trp Cys Gln Gly Pro Gly Gln Cys
                    820                 825                 830

Thr Leu Arg Gln His Cys Pro Ala Gln Glu Ser Gln Trp Leu Glu Leu
                    835                 840                 845

Ser Gly Ala Lys Ser Lys Cys Thr Asn Pro Arg Ile Thr Glu Ile Ile
850                 855                 860

Pro Val Thr Gly Pro Arg Glu Gly Gly Thr Lys Val Thr Ile Arg Gly
865                 870                 875                 880

Glu Asn Leu Gly Leu Glu Phe Arg Asp Ile Ala Ser His Val Lys Val
                    885                 890                 895

Ala Gly Val Glu Cys Ser Pro Leu Val Asp Gly Tyr Ile Pro Ala Glu
                    900                 905                 910

Gln Ile Val Cys Glu Met Gly Glu Ala Lys Pro Ser Gln His Ala Gly
                    915                 920                 925

Phe Val Glu Ile Cys Val Ala Val Cys Arg Pro Glu Phe Met Ala Arg
                    930                 935                 940

Ser Ser Gln Leu Tyr Tyr Phe Met Thr Leu Thr Leu Ser Asp Leu Lys
945                 950                 955                 960

Pro Ser Arg Gly Pro Met Ser Gly Gly Thr Gln Val Thr Ile Thr Gly
                    965                 970                 975

Thr Asn Leu Asn Ala Gly Ser Asn Val Val Met Phe Gly Lys Gln
                    980                 985                 990

Pro Cys Leu Phe His Arg Arg Ser Pro Ser Tyr Ile Val Cys Asn Thr
                    995                 1000                1005

Thr Ser Ser Asp Glu Val Leu Glu Met Lys Val Ser Val Gln Val
        1010                1015                1020

Asp Arg Ala Lys Ile His Gln Asp Leu Val Phe Gln Tyr Val Glu
        1025                1030                1035

Asp Pro Thr Ile Val Arg Ile Glu Pro Glu Trp Ser Ile Val Ser
        1040                1045                1050

Gly Asn Thr Pro Ile Ala Val Trp Gly Thr His Leu Asp Leu Ile
        1055                1060                1065

Gln Asn Pro Gln Ile Arg Ala Lys His Gly Gly Lys Glu His Ile
        1070                1075                1080

Asn Ile Cys Glu Val Leu Asn Ala Thr Glu Met Thr Cys Gln Ala
        1085                1090                1095

Pro Ala Leu Ala Leu Gly Pro Asp His Gln Ser Asp Leu Thr Glu
        1100                1105                1110

Arg Pro Glu Glu Phe Gly Phe Ile Leu Asp Asn Val Gln Ser Leu
        1115                1120                1125

Leu Ile Leu Asn Lys Thr Asn Phe Thr Tyr Tyr Pro Asn Pro Val
        1130                1135                1140

Phe Glu Ala Phe Gly Pro Ser Gly Ile Leu Glu Leu Lys Pro Gly
        1145                1150                1155

Thr Pro Ile Ile Leu Lys Gly Lys Asn Leu Ile Pro Pro Val Ala
        1160                1165                1170

Gly Gly Asn Val Lys Leu Asn Tyr Thr Val Leu Val Gly Glu Lys
        1175                1180                1185

Pro Cys Thr Val Thr Val Ser Asp Val Gln Leu Leu Cys Glu Ser
        1190                1195                1200
```

```
Pro Asn Leu Ile Gly Arg His Lys Val Met Ala Arg Val Gly Gly
    1205                1210                1215

Met Glu Tyr Ser Pro Gly Met Val Tyr Ile Ala Pro Asp Ser Pro
    1220                1225                1230

Leu Ser Leu Pro Ala Ile Val Ser Ile Ala Val Ala Gly Gly Leu
    1235                1240                1245

Leu Ile Ile Phe Ile Val Ala Val Leu Ile Ala Tyr Lys Arg Lys
    1250                1255                1260

Ser Arg Glu Ser Asp Leu Thr Leu Lys Arg Leu Gln Met Gln Met
    1265                1270                1275

Asp Asn Leu Glu Ser Arg Val Ala Leu Glu Cys Lys Glu Ala Phe
    1280                1285                1290

Ala Glu Leu Gln Thr Asp Ile His Glu Leu Thr Ser Asp Leu Asp
    1295                1300                1305

Gly Ala Gly Ile Pro Phe Leu Asp Tyr Arg Thr Tyr Thr Met Arg
    1310                1315                1320

Val Leu Phe Pro Gly Ile Glu Asp His Pro Val Leu Arg Asp Leu
    1325                1330                1335

Glu Val Pro Gly Tyr Arg Gln Glu Arg Val Glu Lys Gly Leu Lys
    1340                1345                1350

Leu Phe Ala Gln Leu Ile Asn Asn Lys Val Phe Leu Leu Ser Phe
    1355                1360                1365

Ile Arg Thr Leu Glu Ser Gln Arg Ser Phe Ser Met Arg Asp Arg
    1370                1375                1380

Gly Asn Val Ala Ser Leu Ile Met Thr Val Leu Gln Ser Lys Leu
    1385                1390                1395

Glu Tyr Ala Thr Asp Val Leu Lys Gln Leu Leu Ala Asp Leu Ile
    1400                1405                1410

Asp Lys Asn Leu Glu Ser Lys Asn His Pro Lys Leu Leu Leu Arg
    1415                1420                1425

Arg Thr Glu Ser Val Ala Glu Lys Met Leu Thr Asn Trp Phe Thr
    1430                1435                1440

Phe Leu Leu Tyr Lys Phe Leu Lys Glu Cys Ala Gly Glu Pro Leu
    1445                1450                1455

Phe Ser Leu Phe Cys Ala Ile Lys Gln Gln Met Glu Lys Gly Pro
    1460                1465                1470

Ile Asp Ala Ile Thr Gly Glu Ala Arg Tyr Ser Leu Ser Glu Asp
    1475                1480                1485

Lys Leu Ile Arg Gln Gln Ile Asp Tyr Lys Thr Leu Val Leu Ser
    1490                1495                1500

Cys Val Ser Pro Asp Asn Ala Asn Ser Pro Glu Val Pro Val Lys
    1505                1510                1515

Ile Leu Asn Cys Asp Thr Ile Thr Gln Val Lys Glu Lys Ile Leu
    1520                1525                1530

Asp Ala Ile Phe Lys Asn Val Pro Cys Ser His Arg Pro Lys Ala
    1535                1540                1545

Ala Asp Met Asp Leu Glu Trp Arg Gln Gly Ser Gly Ala Arg Met
    1550                1555                1560

Ile Leu Gln Asp Glu Asp Ile Thr Thr Lys Ile Glu Asn Asp Trp
    1565                1570                1575

Lys Arg Leu Asn Thr Leu Ala His Tyr Gln Val Pro Asp Gly Ser
    1580                1585                1590
```

Val Val Ala Leu Val Ser Lys Gln Val Thr Ala Tyr Asn Ala Val
            1595                1600                1605

Asn Asn Ser Thr Val Ser Arg Thr Ser Ala Ser Lys Tyr Glu Asn
    1610                1615                1620

Met Ile Arg Tyr Thr Gly Ser Pro Asp Ser Leu Arg Ser Arg Thr
    1625                1630                1635

Pro Met Ile Thr Pro Asp Leu Glu Ser Gly Val Lys Met Trp His
    1640                1645                1650

Leu Val Lys Asn His Glu His Gly Asp Gln Lys Glu Gly Asp Arg
    1655                1660                1665

Gly Ser Lys Met Val Ser Glu Ile Tyr Leu Thr Arg Leu Leu Ala
    1670                1675                1680

Thr Lys Gly Thr Leu Gln Lys Phe Val Asp Asp Leu Phe Glu Thr
    1685                1690                1695

Ile Phe Ser Thr Ala His Arg Gly Ser Ala Leu Pro Leu Ala Ile
    1700                1705                1710

Lys Tyr Met Phe Asp Phe Leu Asp Glu Gln Ala Asp Lys His Gly
    1715                1720                1725

Ile His Asp Pro His Val Arg His Thr Trp Lys Ser Asn Cys Leu
    1730                1735                1740

Pro Leu Arg Phe Trp Val Asn Met Ile Lys Asn Pro Gln Phe Val
    1745                1750                1755

Phe Asp Ile His Lys Asn Ser Ile Thr Asp Ala Cys Leu Ser Val
    1760                1765                1770

Val Ala Gln Thr Phe Met Asp Ser Cys Ser Thr Ser Glu His Arg
    1775                1780                1785

Leu Gly Lys Asp Ser Pro Ser Asn Lys Leu Leu Tyr Ala Lys Asp
    1790                1795                1800

Ile Pro Ser Tyr Lys Asn Trp Val Glu Arg Tyr Tyr Ser Asp Ile
    1805                1810                1815

Gly Lys Met Pro Ala Ile Ser Asp Gln Asp Met Asn Ala Tyr Leu
    1820                1825                1830

Ala Glu Gln Ser Arg Met His Met Asn Glu Phe Asn Thr Met Ser
    1835                1840                1845

Ala Leu Ser Glu Ile Phe Ser Tyr Val Gly Lys Tyr Ser Glu Glu
    1850                1855                1860

Ile Leu Gly Pro Leu Asp His Asp Asp Gln Cys Gly Lys Gln Lys
    1865                1870                1875

Leu Ala Tyr Lys Leu Glu Gln Val Ile Thr Leu Met Ser Leu Asp
    1880                1885                1890

Ser

<210> SEQ ID NO 2
<211> LENGTH: 522
<212> TYPE: PRT
<213> ORGANISM: Homo sapiens

<400> SEQUENCE: 2

Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
                20                  25                  30

Leu Ser Gln Lys Gln Arg Ser Phe Val Thr Phe Arg Gly Glu Pro Ala
            35                  40                  45

```
Glu Gly Phe Asn His Leu Val Val Asp Glu Arg Thr Gly His Ile Tyr
 50                  55                  60
Leu Gly Ala Val Asn Arg Ile Tyr Lys Leu Ser Ser Asp Leu Lys Val
 65                  70                  75                  80
Leu Val Thr His Glu Thr Gly Pro Asp Glu Asp Asn Pro Lys Cys Tyr
                 85                  90                  95
Pro Pro Arg Ile Val Gln Thr Cys Asn Glu Pro Leu Thr Thr Thr Asn
            100                 105                 110
Asn Val Asn Lys Met Leu Leu Ile Asp Tyr Lys Glu Asn Arg Leu Ile
            115                 120                 125
Ala Cys Gly Ser Leu Tyr Gln Gly Ile Cys Lys Leu Leu Arg Leu Glu
145                 135                 140
Asp Leu Phe Lys Leu Gly Glu Pro Tyr His Lys Lys Glu His Tyr Leu
145                 150                 155                 160
Ser Gly Val Asn Glu Ser Gly Ser Val Phe Gly Val Ile Val Ser Tyr
                165                 170                 175
Ser Asn Leu Asp Asp Lys Leu Phe Ile Ala Thr Ala Val Asp Gly Lys
            180                 185                 190
Pro Glu Tyr Phe Pro Thr Ile Ser Ser Arg Lys Leu Thr Lys Asn Ser
            195                 200                 205
Glu Ala Asp Gly Met Phe Ala Tyr Val Phe His Asp Glu Phe Val Ala
            210                 215                 220
Ser Met Ile Lys Ile Pro Ser Asp Thr Phe Thr Ile Ile Pro Asp Phe
225                 230                 235                 240
Asp Ile Tyr Tyr Val Tyr Gly Phe Ser Ser Gly Asn Phe Val Tyr Phe
                245                 250                 255
Leu Thr Leu Gln Pro Glu Met Val Ser Pro Gly Ser Thr Thr Lys
            260                 265                 270
Glu Gln Val Tyr Thr Ser Lys Leu Val Arg Leu Cys Lys Glu Asp Thr
            275                 280                 285
Ala Phe Asn Ser Tyr Val Glu Val Pro Ile Gly Cys Glu Arg Ser Gly
            290                 295                 300
Val Glu Tyr Arg Leu Leu Gln Ala Ala Tyr Leu Ser Lys Ala Gly Ala
305                 310                 315                 320
Val Leu Gly Arg Thr Leu Gly Val His Pro Asp Asp Leu Leu Phe
                325                 330                 335
Thr Val Phe Ser Lys Gly Gln Lys Arg Lys Met Lys Ser Leu Asp Glu
                340                 345                 350
Ser Ala Leu Cys Ile Phe Ile Leu Lys Gln Ile Asn Asp Arg Ile Lys
            355                 360                 365
Glu Arg Leu Gln Ser Cys Tyr Arg Gly Glu Gly Thr Leu Asp Leu Ala
            370                 375                 380
Trp Leu Lys Val Lys Asp Ile Pro Cys Ser Ser Ala Leu Leu Thr Ile
385                 390                 395                 400
Asp Asp Asn Phe Cys Gly Leu Asp Met Asn Ala Pro Leu Gly Val Ser
                405                 410                 415
Asp Met Val Arg Gly Ile Pro Val Phe Thr Glu Asp Arg Asp Arg Met
            420                 425                 430
Thr Ser Val Ile Ala Tyr Val Tyr Lys Asn His Ser Leu Ala Phe Val
            435                 440                 445
Gly Thr Lys Ser Gly Lys Leu Lys Lys Ser Phe Gly Thr Gly Pro Gln
            450                 455                 460
Gly Gly Ile Thr Gln Glu Trp Ile Gly Val Glu Gly Asp Pro Pro Gly
```

```
                465                 470                 475                 480
            Ala Asn Ile Ala Ser Gln Glu Gln Met Leu Cys Val Tyr Leu Gln Cys
                            485                 490                 495

Ser Ser His Lys Ala Ile Ser Asp Gln Arg Val Gln Pro Leu Leu Cys
                            500                 505                 510

Cys Phe Leu Asn Val Pro Gly Asn Ser Ser
                            515                 520

<210> SEQ ID NO 3
<211> LENGTH: 492
<212> TYPE: PRT
<213> ORGANISM: Homo sapiens

<400> SEQUENCE: 3

Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
                20                  25                  30

Leu Ser Gln Lys Gln Arg Ser Phe Val Thr Phe Arg Gly Glu Pro Ala
            35                  40                  45

Glu Gly Phe Asn His Leu Val Val Asp Glu Arg Thr Gly His Ile Tyr
        50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
            100                 105                 110

Asn Val Asn Lys Met Leu Leu Ile Asp Tyr Lys Glu Asn Arg Leu Ile
        115                 120                 125

Ala Cys Gly Ser Leu Tyr Gln Gly Ile Cys Lys Leu Leu Arg Leu Glu
    130                 135                 140

Asp Leu Phe Lys Leu Gly Glu Pro Tyr His Lys Lys Glu His Tyr Leu
145                 150                 155                 160

Ser Gly Val Asn Glu Ser Gly Ser Val Phe Gly Val Ile Val Ser Tyr
                165                 170                 175

Ser Asn Leu Asp Asp Lys Leu Phe Ile Ala Thr Ala Val Asp Gly Lys
            180                 185                 190

Pro Glu Tyr Phe Pro Thr Ile Ser Ser Arg Lys Leu Thr Lys Asn Ser
        195                 200                 205

Glu Ala Asp Gly Met Phe Ala Tyr Val Phe His Asp Glu Phe Val Ala
    210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
                245                 250                 255

Leu Thr Leu Gln Pro Glu Met Val Ser Pro Pro Gly Ser Thr Thr Lys
            260                 265                 270

Glu Gln Val Tyr Thr Ser Lys Leu Val Arg Leu Cys Lys Glu Asp Thr
        275                 280                 285

Ala Phe Asn Ser Tyr Val Glu Val Pro Ile Gly Cys Glu Arg Ser Gly
    290                 295                 300

Val Glu Tyr Arg Leu Leu Gln Ala Ala Tyr Leu Ser Lys Ala Gly Ala
305                 310                 315                 320
```

Val Leu Gly Arg Thr Leu Gly Val His Pro Asp Asp Leu Leu Phe
                325                 330                 335

Thr Val Phe Ser Lys Gly Gln Lys Arg Lys Met Lys Ser Leu Asp Glu
            340                 345                 350

Ser Ala Leu Cys Ile Phe Ile Leu Lys Gln Ile Asn Asp Arg Ile Lys
        355                 360                 365

Glu Arg Leu Gln Ser Cys Tyr Arg Gly Glu Gly Thr Leu Asp Leu Ala
    370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
            405                 410                 415

Asp Met Val Arg Gly Ile Pro Val Phe Thr Glu Asp Arg Asp Arg Met
        420                 425                 430

Thr Ser Val Ile Ala Tyr Val Tyr Lys Asn His Ser Leu Ala Phe Val
    435                 440                 445

Gly Thr Lys Ser Gly Lys Leu Lys Met Pro Gly Thr Ser Leu Cys
    450                 455                 460

Pro Thr Leu Glu Leu Gln Thr Gly Pro Arg Ser His Arg Ala Thr Val
465                 470                 475                 480

Thr Leu Glu Leu Leu Phe Ser Ser Cys Ser Ser Asn
            485                 490

<210> SEQ ID NO 4
<211> LENGTH: 5685
<212> TYPE: DNA
<213> ORGANISM: Homo sapiens

<400> SEQUENCE: 4

| | |
|---|---|
| atgaaagcca tgccctggaa ctggacctgc cttctctccc acctcctcat ggtgggcatg | 60 |
| ggctcctcca ctttgctcac ccggcagcca gccccgctgt cccagaagca gcggtcattt | 120 |
| gtcacattcc gaggagagcc cgccgagggt ttcaatcacc tggtggtgga tgagaggaca | 180 |
| ggacacattt acttgggggc cgtcaatcgg atttacaagc tctccagcga cctgaaggtc | 240 |
| ttggtgacgc atgagacagg gccggacgag gacaacccca gtgttaccc accccgcatc | 300 |
| gtccagacct gcaatgagcc cctgaccacc accaacaatg tcaacaagat gctcctcata | 360 |
| gactacaagg agaacaggct gattgcctgt gggagcctgt accaaggcat ctgcaagctg | 420 |
| ctgaggctgg aggacctctt caagctgggg gagccttatc ataaggga gcactatctg | 480 |
| tcaggtgtca acgagagcgg ctcagtcttt ggagtgatcg tctcctacag caacctggat | 540 |
| gacaagctgt tcattgccac ggcagtggat gggaagcccg agtattttcc caccatctcc | 600 |
| agccggaaac tgaccaagaa ctctgaggcg atggcatgt cgcgtacgt cttccatgat | 660 |
| gagttcgtgg cctcgatgat taagatccct tcggacacct tcaccatcat ccctgacttt | 720 |
| gatatctact atgtctatgg ttttagcagt ggcaactttg tctactttt gacccctcca | 780 |
| cctgagatgg tgtctccacc aggctccacc accaaggagc aggtgtatac atccaagctc | 840 |
| gtgaggcttt gcaaggagga cacagccttc aactcctatg tagaggtgcc cattggctgt | 900 |
| gagcgcagtg gggtggagta ccgcctgctg caggctgcct acctgtccaa gcgggggcc | 960 |
| gtgcttggca ggacccttgg agtccatcca gatgatgacc tgctcttcac cgtcttctcc | 1020 |
| aagggccaga gcggaaaat gaatccctg gatgagtcgg ccctgtgcat cttcatcttg | 1080 |
| aagcagataa atgaccgcat taaggagcgg ctgcagtctt gttaccgggg cgagggcacg | 1140 |

```
ctggacctgg cctggctcaa ggtgaaggac atcccctgca gcagtgcgct cttaaccatt    1200
gacgataact tctgtggcct ggacatgaat gctcccctgg gagtgtccga catggtgcgt    1260
ggaattcccg tcttcacgga ggacagggac cgcatgacgt ctgtcatcgc atatgtctac    1320
aagaaccact ctctggcctt tgtgggcacc aaaagtggca agctgaagaa gatccgggtg    1380
gatggaccca ggggcaacgc cctccagtat gagacggtgc aggtggtgga ccccggccca    1440
gtcctccggg atatggcctt ctccaaggac acgagcaac tctacatcat gtcagagagg     1500
cagctcacca gagtccctgt ggagtcctgt ggtcagtatc agagctgcgg cgagtgcctt    1560
ggctcaggcg accccactg tggctggtgt gtgctgcaca acacttgcac ccggaaggag      1620
cggtgtgagc ggtccaagga gccccgcagg tttgcctcgg agatgaagca gtgtgtccgg    1680
ctgacggtcc atcccaacaa tatctccgtc tctcagtaca cgtgctgct ggtcctggag     1740 acgtacaatg tcccggagct gtcagctggc gtcaactgca cctttgagga cctgtcagag    1800
atggatgggc tggtcgtggg caatcagatc cagtgctact cccctgcagc caaggaggtg    1860
ccccggatca tcacagagaa tgggaccac catgtcgtac agcttcagct caaatcaaag     1920
gagaccggca tgaccttcgc cagcaccagc tttgtcttct acaattgcag cgtccacaat    1980
tcgtgcctgt cctgcgtgga gagtccatac cgctgccact ggtgtaaata ccggcatgtc    2040
tgcacccatg accccaagac ctgctccttc caggaaggcc gagtgaagct gcccgaggac    2100 tgccccccagc tgctgcgagt ggacaagatc ctggtgcccg tggaggtgat caagcctatc    2160
acgctgaagg ccaagaacct cccccagccc cagtctgggc agcgtggcta cgaatgcatc    2220
ctcaacattc agggcagcga gcagcgagtg cccgccctgc gcttcaacag ctccagcgta    2280
cagtgccaga acacctctta ttcctatgaa gggatggaga tcaacaaacct gcccgtggag    2340 ttgacagtcg tgtggaatgg gcacttcaac attgacaacc cagctcagaa taaagttcac    2400
ctctacaagt gtggagccat gcgtgagagc tgcgggctgt gcctcaaggc tgacccagac    2460
ttcgcatgtg gctggtgcca gggcccaggc cagtgcaccc tgcgccagca ctgccctgcc    2520
caggagagcc agtggctgga gctgtctggt gccaaaagca agtgcacaaa ccccgcatc    2580 acagagataa tcccggtgac aggccccgg gaaggggca ccaaggtcac tatccgaggg     2640
gagaacctgg gcctggaatt tcgcgacatc gcctcccatg tcaaggttgc tggcgtggag    2700
tgcagccctt tagtggatgg ttacatccct gcagaacaga tcgtgtgtga gatggggag    2760 gccaagccca gccagcatgc aggcttcgtg gagatctgcg tggctgtgtg tcggcctgaa    2820
ttcatggccc ggtcctcaca gctctattac ttcatgacac tgactctctc agatctgaag    2880
cccagccggg ggcccatgtc cggagggacc caagtgacca tcacaggcac caacctgaat    2940
gccggaagca acgtggtggt gatgtttgga aagcagccct gtctcttcca caggcgatct    3000
ccatcctaca ttgtctgcaa caccacatcc tcagatgagg tgctagagat gaaggtgtcg    3060
gtgcaggtgg acagggccaa gatccaccag gacctggtct ttcagtatgt ggaagacccc    3120
accatcgtgc ggattgagcc agaatggagc attgtcagtg aaacacacc catcgccgta    3180 tgggggaccc acctggacct catacagaac ccccagatcc gtgccaagca tggagggaag    3240
gagcacatca atatctgtga ggttctgaac gctactgaga tgacctgtca ggcgcccgcc    3300
ctcgctctgg gtcctgacca ccagtcagac ctgaccgaga ggcccgagga gtttggcttc    3360
atcctggaca acgtccagtc cctgctcatc ctcaacaaga ccaacttcac ctactatccc    3420
aacccggtgt tgaggccttt tggtccctca ggaatcctgg agctcaagcc tggcacgccc    3480
atcatcctaa agggcaagaa cctgatcccg cctgtggctg ggggcaacgt gaagctgaac    3540
```

```
tacactgtgc tggttgggga gaagccgtgc accgtgaccg tgtcagatgt ccagctgctc    3600
tgcgagtccc ccaacctcat cggcaggcac aaagtgatgg cccgtgtcgg tggcatggag    3660
tactccccgg ggatggtgta cattgccccg gacagcccgc tcagcctgcc cgccatcgtc    3720
agcatcgcag tggctggcgg cctcctcatc attttcatcg tggccgtgct cattgcctat    3780
aaacgcaagt cccgcgaaag tgacctcacg ctgaagcggc tgcagatgca gatggacaac    3840
ctggagtccc gtgtggccct ggagtgcaag gaagcctttg ccgagctgca gacggacatc    3900
catgagctga ccagtgacct ggatggagcc gggattccgt tcctggacta tagaacttac    3960
accatgcggg tgctgttccc aggaattgaa gaccaccctg tcctccggga ccttgaggtc    4020
ccgggctacc ggcaggagcg tgtggagaaa ggcctgaagc tcttcgccca gctcatcaac    4080
aacaaggtgt tcctgctgtc cttcatccgc acgcttgagt cccagcgtag cttctccatg    4140
cgcgaccgtg gcaacgtggc ctcactcatc atgaccgtgc tgcagagcaa gctggagtac    4200
gccactgatg tgctgaagca gctgctggcc gacctcattg acaagaacct ggagagcaag    4260
aaccacccta gctgctgct caggaggact gagtcagtgg ctgagaagat gctgaccaat    4320
tggtttactt tcctcctcta caagttcctc aaggagtgtg ctggggagcc cctcttctcc    4380
ctgttctgtg ccatcaagca gcagatggag aagggcccca ttgacgccat cacgggcgag    4440
gcccgctact ccttgagcga ggacaagctc atccgccagc agattgacta caaaaccctg    4500
gtcctgagct gtgtcagccc agacaatgcc aacagcccccg aggtcccagt aaagatcctc    4560
aactgtgaca ccatcactca ggtcaaggag aagattctgg atgccatctt caagaatgtg    4620
ccttgctccc accggcccaa agctgcagat atggatctgg agtggcgaca aggaagtggg    4680
gcaaggatga tcttgcagga tgaagacatc accaccaaga ttgagaatga ttggaagcga    4740
ctgaacacac tggcccacta ccaggtgcca gatggttccg tggtggcatt agtgtccaag    4800
caggtgacag cctataacgc agtgaacaac tccaccgtct ccaggacctc agcaagtaaa    4860
tatgaaaaca tgatccggta cacgggcagc cccgacagcc tccgctcacg acacctatg    4920 atcactcctg acctgagag tggagtcaag atgtggcacc tagtgaagaa ccacgagcac    4980
ggagaccaga aggaggggga ccgggggagc aagatggtgt ctgaaatcta cctgacccga    5040
ctcctggcca ctaagggcac actgcagaag tttgtggatg acctctttga gaccatcttc    5100
agcacggcac accgtggctc tgccctgccc ctggccatca gtacatgtt tgacttcctg    5160 gatgagcagg ctgataaaca tggcattcat gacccgcacg tccgccatac ctggaagagc    5220
aattgcctgc ccctgaggtt ttgggtcaac atgatcaaga cccgcagtt tgtgtttgac    5280 atccataaga acagcatcac agacgcctgc ctctctgtgg tggctcagac cttcatggac    5340
tcttgctcca cgtcagagca ccggctgggc aaggactcgc cctccaacaa gctgctgtat    5400
gccaaggaca tccccagcta caagaattgg gtggagaggt attactcaga catagggaag    5460
atgccagcca tcgcgacca agacatgaac gcatacctgg ctgagcagtc ccggatgcac    5520
atgaatgagt tcaacaccat gagtgcactc tcagagatct tctcctatgt gggcaaatac    5580
agcgaggaga tccttggacc tctgaccac gatgaccagt gtgggaagca gaaactggcc    5640
tacaaactag aacaagtcat aaccctcatg agcttagaca gctga                    5685
```

<210> SEQ ID NO 5
<211> LENGTH: 13061
<212> TYPE: DNA
<213> ORGANISM: Homo sapiens

```
<400> SEQUENCE: 5
tgcgttcggg gctggggctg gaggaggcag ccacacgcgc gcacacgcac acgttcagag      60
gagggcgaga ggcagcggca taggctccat ctgcagtgtc aatgcggcgc tcccgctgaa     120
ggagggaaac gcggcgcgtc cagtagggga gactgcattg ctgagtcctg ccctctgag     180 gggacgactg tgcctgagtg ctgctgtgcc actgggaccc gcctctgcca tgaaagccat    240
gccctggaac tggacctgcc ttctctccca cctcctcatg gtgggcatgg gctcctccac    300
tttgctcacc cggcagccag ccccgctgtc ccagaagcag cggtcatttg tcacattccg    360
aggagagccc gccgagggtt tcaatcacct ggtggtggat gagaggacag gacacattta    420 cttggggggcc gtcaatcgga tttacaagct ctccagcgac ctgaaggtct tggtgacgca    480
tgagacaggg ccggacgagg acaaccccaa gtgttaccca ccccgcatcg tccagacctg    540
caatgagccc ctgaccacca ccaacaatgt caacaagatg ctcctcatag actacaagga    600
gaacaggctg attgcctgtg ggagcctgta ccaaggcatc tgcaagctgc tgaggctgga    660
ggacctcttc aagctggggg agccttatca taagaaggag cactatctgt caggtgtcaa    720
cgagagcggc tcagtctttg gagtgatcgt ctcctacagc aacctggatg acaagctgtt    780
cattgccacg gcagtggatg ggaagcccga gtattttccc accatctcca gccggaaact    840
gaccaagaac tctgaggcgg atggcatgtt cgcgtacgtc ttccatgatg agttcgtggc    900
ctcgatgatt aagatccctt cggacacctt caccatcatc cctgactttg atatctacta    960
tgtctatggt tttagcagtg caactttgt ctacttttg accctccaac ctgagatggt   1020
gtctccacca ggctccacca ccaaggagca ggtgtataca tccaagctcg tgaggctttg   1080
caaggaggac acagccttca actcctatgt agaggtgccc attggctgtg agcgcagtgg   1140
ggtggagtac cgcctgctgc aggctgccta cctgtccaaa gcggggggcc tgcttggcag   1200
gacccttgga gtccatccag atgatgacct gctcttcacc gtcttctcca agggccagaa   1260
gcggaaaatg aaatccctgg atgagtcggc cctgtgcatc ttcatcttga agcagataaa   1320
tgaccgcatt aaggagcggc tgcagtcttg ttaccggggc gagggcacgc tggacctggc   1380
ctggctcaag gtgaaggaca tcccctgcag cagtgcgctc ttaaccattg acgataactt   1440
ctgtggcctg gacatgaatg ctccccctggg agtgtccgac atggtgcgtg gaattcccgt   1500
cttcacggag gacagggacc gcatgacgtc tgtcatcgca tatgtctaca agaaccactc   1560
tctggccttt gtgggcacca aaagtggcaa gctgaagaag atccgggtgg atggacccag   1620
gggcaacgcc ctccagtatg agacggtgca ggtggtggac cccggcccag tcctccggga   1680
tatggccttc tccaaggacc acgagcaact ctacatcatg tcagagaggc agctcaccag   1740
agtccctgtg gagtcctgtg tcagtatcca gagctgcggc gagtgccttg gctcaggcga   1800 ccccactgt ggctggtgtg tgctgcacaa cacttgcacc cggaaggagc ggtgtgagcg   1860
gtccaaggag ccccgcaggt ttgcctcgga gatgaagcag tgtgtccggc tgacggtcca   1920
tcccaacaat atctccgtct ctcagtacaa cgtgctgctg gtcctggaga cgtacaatgt   1980
cccggagctg tcagctggcg tcaactgcac cttgaggac ctgtcagaga tggatgggct   2040
ggtcgtgggc aatcagatcc agtgctactc ccctgcagcc aaggaggtgc ccggatcat   2100 cacagagaat ggggaccacc atgtcgtaca gcttcagctc aaatcaaagg agaccggcat   2160
gaccttcgcc agcaccagct ttgtcttcta caattgcagc gtccacaatt cgtgcctgtc   2220
ctgcgtggag agtccatacc gctgccactg gtgtaaatac cggcatgtct gcacccatga   2280
ccccaagacc tgctccttcc aggaaggccg agtgaagctg cccgaggact gccccagct   2340
```

```
gctgcgagtg gacaagatcc tggtgcccgt ggaggtgatc aagcctatca cgctgaaggc    2400
caagaacctc ccccagcccc agtctgggca gcgtggctac gaatgcatcc tcaacattca    2460
gggcagcgag cagcgagtgc ccgccctgcg cttcaacagc tccagcgtac agtgccagaa    2520
cacctcttat tcctatgaag ggatggagat caacaacctg cccgtggagt tgacagtcgt    2580
gtggaatggg cacttcaaca ttgacaaccc agctcagaat aaagttcacc tctacaagtg    2640
tggagccatg cgtgagagct gcgggctgtg cctcaaggct gacccagact cgcatgtgg     2700 ctggtgccag ggcccaggcc agtgcaccct gcgccagcac tgccctgccc aggagagcca    2760
gtggctgagg ctgtctggtg ccaaaagcaa gtgcacaaac ccccgcatca cagagataat    2820
cccggtgaca ggcccccggg aaggggcac caaggtcact atccgagggg agaacctggg    2880
cctggaattt cgcgacatcg cctcccatgt caaggttgct ggcgtggagt gcagcccttt    2940
agtggatggt tacatccctg cagaacagat cgtgtgtgag atgggggagg ccaagcccag    3000
ccagcatgca ggcttcgtgg agatctgcgt ggctgtgtgt cggcctgaat tcatggcccg    3060
gtcctcacag ctctattact tcatgacact gactctctca gatctgaagc ccagccgggg    3120
gcccatgtcc ggagggaccc aagtgaccat cacaggcacc aacctgaatg ccggaagcaa    3180
cgtggtggtg atgtttggaa agcagccctg tctcttccac aggcgatctc atcctacat     3240 tgtctgcaac accacatcct cagatgaggt gctagagatg aaggtgtcgg tgcaggtgga    3300
cagggccaag atccaccagg acctggtctt tcagtatgtg aagaccccca ccatcgtgcg    3360
gattgagcca gaatggagca ttgtcagtgg aaacacaccc atcgccgtat gggggaccca    3420
cctggacctc atacagaacc cccagatccg tgccaagcat ggagggaagg agcacatcaa    3480
tatctgtgag gttctgaacg ctactgagat gacctgtcag gcgcccgccc tcgctctggg    3540
tcctgaccac cagtcagacc tgaccgagag gcccgaggag tttggcttca tcctggacaa    3600
cgtccagtcc ctgctcatcc tcaacaagac caacttcacc tactatccca acccggtgtt    3660
tgaggccttt ggtccctcag gaatcctgga gctcaagcct ggcacgccca tcatcctaaa    3720
gggcaagaac ctgatcccgc ctgtggctgg gggcaacgtg aagctgaact acactgtgct    3780
ggttggggag aagccgtgca ccgtgaccgt gtcagatgtc cagctgctct gcgagtcccc    3840
caacctcatc ggcaggcaca aagtgatggc ccgtgtcggt ggcatggagt actccccggg    3900
gatggtgtac attgccccgg acagcccgct cagcctgccc gccatcgtca gcatcgcagt    3960
ggctggcggc ctcctcatca ttttcatcgt ggccgtgctc attgcctata acgcaagtc     4020 ccgcgaaagt gacctcacgc tgaagcggct gcagatgcag atggacaacc tggagtcccg    4080 tgtggcctg gagtgcaagg aagcctttgc cgagctgcag acggacatcc atgagctgac     4140
cagtgacctg gatggagccg ggattccgtt cctggactat agaacttaca ccatgcgggt    4200
gctgttccca ggaattgaag accccctgt cctccgggac cttgaggtcc cgggctaccg     4260
gcaggagcgt gtggagaaag gcctgaagct cttcgcccag ctcatcaaca caaggtgtt    4320 cctgctgtcc ttcatccgca cgcttgagtc ccagcgtagc ttctccatgc gcgaccgtgg    4380
caacgtggcc tcactcatca tgaccgtgct gcagagcaag ctggagtacg ccactgatgt    4440
gctgaagcag ctgctggccg acctcattga caagaacctg agagcaaga accacccta     4500 gctgctgctc aggaggactg agtcagtggc tgagaagatg ctgaccaatt ggtttacttt    4560
cctcctctac aagttcctca aggagtgtgc tgggagccc ctcttctccc tgttctgtgc     4620
catcaagcag cagatggaga agggccccat tgacgccatc acgggcgagg cccgctactc    4680
```

```
cttgagcgag gacaagctca tccgccagca gattgactac aaaaccctgg tcctgagctg    4740
tgtcagccca gacaatgcca acagccccga ggtcccagta aagatcctca actgtgacac    4800
catcactcag gtcaaggaga agattctgga tgccatcttc aagaatgtgc cttgctccca    4860
ccggcccaaa gctgcagata tggatctgga gtggcgacaa ggaagtgggg caaggatgat    4920
cttgcaggat gaagacatca ccaccaagat tgagaatgat tggaagcgac tgaacacact    4980
ggcccactac caggtgccag atggttccgt ggtggcatta gtgtccaagc aggtgacagc    5040
ctataacgca gtgaacaact ccaccgtctc caggacctca gcaagtaaat atgaaaacat    5100
gatccggtac acgggcagcc ccgacagcct ccgctcacgg acacctatga tcactcctga    5160
cctggagagt ggagtcaaga tgtggcacct agtgaagaac cacgagcacg agaccagaa    5220 ggaggggggac cggggagca agatggtgtc tgaaatctac ctgacccgac tcctggccac    5280
taagggcaca ctgcagaagt tgtggatga cctctttgag accatcttca gcacggcaca    5340
ccgtggctct gccctgcccc tggccatcaa gtacatgttt gacttcctgg atgagcaggc    5400
tgataaacat ggcattcatg acccgcacgt ccgcctatacc tggaagagca attgcctgcc    5460
cctgaggttt tgggtcaaca tgatcaagaa cccgcagttt gtgtttgaca tccataagaa    5520
cagcatcaca gacgcctgcc tctctgtggt ggctcagacc ttcatggact cttgctccac    5580
gtcagagcac cggctgggca aggactcgcc ctccaacaag ctgctgtatg ccaaggacat    5640
ccccagctac aagaattggg tggagaggta ttactcagac ataggaagaa tgccagccat    5700
cagcgaccaa gacatgaacg catacctggc tgagcagtcc cggatgcaca tgaatgagtt    5760
caacaccatg agtgcactct cagagatctt ctcctatgtg ggcaaatacca gcgaggagat    5820 ccttggacct ctggaccacg atgaccagtg tgggaagcag aaactggcct acaaactaga    5880
acaagtcata accctcatga gcttagacag ctgagaaccg tccttccagg gccgccctgg    5940 aggggggacac accaagccgt gcctcagtct agattatcat ctttaccaag tgcaagttcc    6000
gactggcatc agcagcatcc cctgagcagc gctgtttctc tctctttctc tctgcctctt    6060
tccgtttctc cctccttcct ggatctcttc tcttccagtt gctctgccaa cacgattgga    6120
ccaagccact gaccctcagt tagtccaaga atggccaggc ccatggcaag ggagctgacc    6180
agaagatgtc agagaggcct ctgtctccca ggtgctcctg accctgtgca tgtcagcagc    6240
agggtgcaaa taacgaatga ggagccaggg acagggacca ttttctgtgct gctacttcac    6300 cttccacttt ggcagcccct gctttggtct gagccttggc ctagggaaga ggcaaggaag    6360
gacttcagta ttatctttac tgggaagaca tcacctggct ctcccttccc acagttccat    6420
ctccagtggt tcagccagtg gtctgatcgc tttgcagctg tgagaagaaa ggctacacct    6480
cctgcatgtg gctggagcag ggcatgtgtg ggcagctggg aggtgctcct tgaggctcct    6540
tctcccccac tgggctggtg tccagaggct tcctgtcctt ttccaggtct ccagagggac    6600
ctgcctgccc tgcctgctcc cccgccagta gaaagccagg caggagaaag aatagcaatt    6660
acattccacc atggagatgc tcctgacctt ttcatctgaa tcctagtagc agaaatgtaa    6720
cacaggggga gaaaggaaa gagagttgca tctaccctgg aagcagaatt tgttttccat    6780
ttaccctcaa attcaaatga gtcacaatca tagtcatagg tctagtccac taccagagcc    6840
ctgagtgctg tcaagagaaa gcatctatct ccaccctcct tgtcaaccct tcatcaaggg    6900
tcaacgtgaa atgcagagtg catctaggag attctacctc cagccatctc catggctcca    6960
tccccatcat ccttcctgag aactccatag acggctgggg ccaacagcct agtccctgtt    7020
ccctctgcag aatccggtgc cattgctatg cagatgactt tgtcactggg ctgtccagac    7080
```

```
ctctttggga atgatttcat caacatctca gctgtctctc atcattctcc ttcctcatct   7140
cttcagcagt catccttgaa agaaacagac ttaagcaaag cctcacggag acagcccaaa   7200
atgccagcca acctcagcct ccagcttgtc agatctggga gggacaaaga gtcgagctga   7260
tgggcctggc tggaattaag aagagggaca tacaaatgac cttggccttg catccatct    7320
ccccatctgt tcttacatct acagatgcac gattttagcc aggcaggcaa atgtgtgcct   7380
agaaattgat actaggtaag cagaggctat ggggagagat ggtctaatgg agggttctag   7440
gaacctttca tcctaaggag accttaggtg ctgtctggtg cagtctccca tcctaagcag   7500
gagtctctgt tggcacctct gctctggagt tgttcaccac tatgggagac aaggagaaac   7560
atcttaggtg aggttgagga gaaggattca cagtcttgcc ttcactcccc aaacatcaga   7620
catcattcct tgtcacccac tcagaatgag cccccttgg ggaagaaacc acaccatttc    7680
cagcaaagtc catggagcat ccggtacttt taagaacact tgcccctttg gatatgaata   7740
tgtgcacatg tgtgtgagca catgtatgtg tgtgtgtgtg tctgcccag gtgtaggcgg    7800
aaagctcaaa aggatttctt gtcctttgta ggaggatttt tgaagtgttc cccttctctt   7860
tccccttgct catccattca tcctgcagct tcaggacatt tcaacactta cttgctttct   7920
atgctgagag ctggtgggtg gaaggagagg gcgcttgtcc ataggaaatc agggtggtcg   7980
cctgccgagg cctggacctt ggaacagggc atcatgtgac atcgcagagg acagatggtg   8040
gaaaagacat gagcaaccta atgggaagag gaaaatggga aacaatgcat tggaagagga   8100
agaaaaaaaa taaataacca aaggttttgg caagtgcagt accaggtgga gaagcttgac   8160
ttttctatcc ttgatcattt tattccctcc caagaagtca gtcacaggac ctggaaggcc   8220
agaaagggta catgtgggag acggtctgag gaagtacctc ggtcactaca atattttgc    8280
acatataaag ggttggggag gaaagagaca caaacgtatt taacacagat ttgctggatg   8340
gaagctgcgt gtgtgaacgt gtgtatgagt gagtgcattt tgattttttt ttttttttt    8400
tgcacagtta agagaaaaaa tcaaacaagc agaaaaaaaa aagaaaaaag acttatcacg   8460
gttctgctga agcttttatt ttttactgga tgatgattat tgttattgtt actttggcgg   8520
tacaggactt tattttattc catgtttttg ttataagaaa aatttcaaac acctcagaga   8580
aatagaaagg ttaggaagaa agaggagaca aggacagaca aattttctgg ctgtccccat   8640
ttctcctggg ggaggggttt ggggctggtt tgacttaat  tggtgggtgg gttgtttctg   8700
ccgctctgtt tgctgcagtc cccgtggcct gcttgggac  tgagaaattt gagccaggta   8760
tccagagcca cagcccatct tgcttataaa aattatcttc tgctgtttgt tttccatttc   8820
ttccgtttgg attcttggtg cacgtgtgat atggtattta aaagcaaaga caagcaacat   8880
tgtcaaaaag ctgtccttgc ccccatccc  ccacccaaat cttttttcca aactccccca   8940
gggatcttcc ttaccccact ggcagagcaa acatccaggg gctgtccatg tggcttgcgg   9000
gctcccagag aaaggaattg ggccaacttt gtcctgtggg atggaggccc cttcacggcc   9060
tccctcgagg caaagttaat tgtagggtc  accattatgt tgagtcatga gcagacagaa   9120
ggagagaaaa ggccatcttc cttaccttcc cctccaactt atcccgtacc ctcccaggga   9180
aaatggtacc agactgagcc atcaaaatca ctgacaaagt ttaggtggga attttttttg   9240
catgttggag agagaagggc ttaaggtagc agggaagaag ggggctttgt ggggtcctaa   9300
attttaagga ataagtagag gaagacaaga aacagagtgg taggctggtc atttctcctg   9360
gccacaagtc cccccagatg cagcttttac ccattctttg tccttcccca taaggagaga   9420
```

```
ccctgacatt tcttggtagc tgcaaatagt gccactaagt gaaggtggcc atcatgccag    9480
ttacttcctc aggaaaatat tttcttgcct tcttctttca gtatggtttt aaatttggga    9540
acagtggata acccaagtgt cccacaggcc aaggtacatt ccaatggcag catgatccct    9600
gcacccaaag ccagcccta aagcctaccc cttgtgcacc cgcagcctgg taagtgagct     9660
tggctgcttg tgaggagcta caagtgaaag agaagttatt ttaaataaat cccaaagttt    9720
gaggcagact gtccaggact gttcccagga agaagcagga gttacccaca ggaaaagtct    9780
ctgacctggt cccctcaggc ccagctacct gcgcccacca gcagtgaagg ttgatgtact    9840
ggcccagcat ctccacctcc cccatgcaac caggtccctg gtaccgtgtc cccgttgca    9900 tgtctggctt ctgcctgtgc cctcctgcc acagcatcc tccctgtccc tcctcattcc      9960
accgtgtctc tcctgcacac atagcctctg tcccagggcg atttatccac ttgagtacag   10020
gagctgctca gacctctcag cccagccctc tgtgactgcc ccagccccat cctacccac    10080 ccaaagctgc cttcctggct gtaggagctc cctcgtctag ccaaggccct atgggtcccc   10140
atccgaggat ccacaagcaa tgacttccca aatgacctcc actgcaagaa gaatccttac   10200 cactgttttcc agagccgtga acgatgctgt gatgggccca ggtctcagca ccaccctctg  10260
tgacctaaaa agaaaagctc aatttccatc tgtcttcttt cccaggacca aggggacaca   10320
gtaatgtgaa gtcaaatact taaccgagca aagggccagt attgttatca gtcaaggaca   10380
aacctcccac ctcacagaca gccaagcagt gagggaaaga cagacagaca taggtaggaa   10440
ggtgctctgc aggcacaagg cccagagaag cccctctccg ggaacttccc ctgctccttc   10500
caggaacagt gagcccagtg agcagcccca gccagctctt caaggccttc aagggggtctt 10560 tccatgactg agtcacctcc aggagctcac ctgaccccca gagaagacct accccaggca   10620
gctccgtgcc ctggcttctc cccatgcccc aaatcccccc ccgccatccc tcctggtcct   10680
cgtctacatc aagggcctct tcccctcttc ctgccagctc tcaggacagg tgactgggag   10740
gccttgaacc ctcagcctct tcctttaaaa aaacaaaac aaaacaaaac tgtgggccat    10800
ttatttggga ttttggagtt gtttggtttt tgtttgtata tcttaatagt tcgaaagtaa   10860
gaagggagcc ctgctatgga tgttaagtcc aaattactcg gttagtggga gcaaaaccta   10920
tgacttccaa ggggatgagg agaggttcag aggacaggag gagcctcccc cattgaaaaa   10980
aaaaaatggg tcaggacatt ccctggatga ggacaatgct aggggtggca tctcacatgg   11040
ctgctgctat tcctggtgct tccccacact tttgacagat ggagtccttc tcctaccgcc   11100
tcctgccacc tcaccctaca ggcattctct atgtaggaaa caagagcctt attttataga   11160
gtggggagct gagacacagc ctcaggtaac actgacacag ctcccgaatg aggctgggac   11220
actctgcaaa cctctcctca tggtgctaag ggtggcatgc tcttgacagg aaacctaaat   11280
gaccactcct ctcatttgga aagtaatcca ctgcagtaaa agtttcagac atgcaagaga   11340 gagtttttt ttttttacta caaattttg ctccccata aaattatttt attagaggga      11400
gtatccaagt tttaaaagta tatagaattt tttggttgta agagaaatac atactcatta   11460
ggatcccgat taaattcctt gagtagactg gtgcctacca gaaagcaaag caaagttaaa   11520
caaaacgaaa caaaatcctt catatacaaa agaactttc tgtttgtatt ggcagaggta    11580
gtgaggtgat tcaggtaggc tgaaaatcct gggttgcggg agcctcactt tattccattc   11640
ccacccgctt tgatgtctat gcttggctct ctgggctgcc cctggtactg ccgaatccta   11700
cacatctctt atcagctttc ctcaaacttt aaggaggctc tgtgagggat gggtcatggg   11760
aagacccaag cttcccctcc gccaggattg caaaagcaag tagacttggt ctatgcagct   11820
```

```
cttcttccag caatttcttt atttggaatt agaacttcct tgttagtat ctttgatctt    11880 ttgactcaag cacattttgg aagggctccc ttacaaaagt agaatttaaa acagaggata    11940
cagttaaaga gcaacccaaa ggacgcttaa gaaaccgaga ccacttcacc aaacaggact    12000
aaggaacact ttcgtgcaca gaagtcagcc gcaatccagg cacaggacga agatgggata    12060
cacgtgctca tctgtctgtc ctcctttcct ctccctcccc gacgttctag ttagcttgtt    12120
gacttgttaa accttctgtt cttaaaatga aaagctagct tacctcaaag aatcttgttt    12180
ccattcggaa accaacgatt tgtgttttta gaatggacag ccctcccctc accactccct    12240
accttggcct ggtgtccttg agacatacgg tctttgctta gtcgtgtgtt ggctgctttg    12300
agcaggaaca aggcctccag gccctgaggt gggaaggaag gattggatgc cactgccctc    12360
ctccccactt tagcatgtag gggccagccc atctcttcca gcagggtcct gctgagttac    12420
catagcaacc agcaactcca gggtaccaca acagacaatg gctcagcgag ccgacgtgtg    12480
gggatgatgc aggggttttg gcccagccag aggacccaga gttgagcttc aaatgctaga    12540
gaagggagaa aacaggatgg aagggtggtt taaggaaccg gcagggtct ttgagtcaca    12600 tagagaagcc gttgaaggag gtagggcagg ttatctctgt tccagtcacc cccttccagc    12660
cccatcccac ttctgtttca aactaaagct cccacctcga acattgaccc tttgttagaa    12720
caaagcaaag catatcttta gacaacagtg ttaaaatgag cctcaaatgt atgtggatga    12780
gatctctaag aagagggtct tctggttttg attttttaaag aagagtatcc tagtaaaata    12840
ttaaaaaaaa attaaaaagt ttttaaaaag gaaacctgtg ctatttaaat tggagcccag    12900
ttgtaacttg gtaaaggcaa gcttctgtac ctttgttata attaattgta tacctgtgta    12960
tgtaaatata aggcattcct attttgcagt tcagaacaaa aaaaacttat ttgtaatata    13020
gaataaagtt tattaaaaaa taataaaaat gcagtttggg a                       13061
```

<210> SEQ ID NO 6
<211> LENGTH: 1466
<212> TYPE: PRT
<213> ORGANISM: Artificial
<220> FEATURE:
<223> OTHER INFORMATION: Plexin-A4 fusion protein sequence

<400> SEQUENCE: 6

```
Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
            20                  25                  30

Leu Ser Gln Lys Gln Arg Ser Phe Val Thr Phe Arg Gly Glu Pro Ala
        35                  40                  45

Glu Gly Phe Asn His Leu Val Val Asp Glu Arg Thr Gly His Ile Tyr
    50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
            100                 105                 110

Asn Val Asn Lys Met Leu Leu Ile Asp Tyr Lys Glu Asn Arg Leu Ile
        115                 120                 125

Ala Cys Gly Ser Leu Tyr Gln Gly Ile Cys Lys Leu Leu Arg Leu Glu
    130                 135                 140
```

```
Asp Leu Phe Lys Leu Gly Glu Pro Tyr His Lys Glu His Tyr Leu
145                 150                 155                 160

Ser Gly Val Asn Glu Ser Gly Ser Val Phe Gly Val Ile Val Ser Tyr
            165                 170                 175

Ser Asn Leu Asp Asp Lys Leu Phe Ile Ala Thr Ala Val Asp Gly Lys
                180                 185                 190

Pro Glu Tyr Phe Pro Thr Ile Ser Ser Arg Lys Leu Thr Lys Asn Ser
            195                 200                 205

Glu Ala Asp Gly Met Phe Ala Tyr Val Phe His Asp Glu Phe Val Ala
210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
                245                 250                 255

Leu Thr Leu Gln Pro Glu Met Val Ser Pro Pro Gly Ser Thr Thr Lys
            260                 265                 270

Glu Gln Val Tyr Thr Ser Lys Leu Val Arg Leu Cys Lys Glu Asp Thr
        275                 280                 285

Ala Phe Asn Ser Tyr Val Glu Val Pro Ile Gly Cys Glu Arg Ser Gly
    290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Leu Leu Phe
                325                 330                 335

Thr Val Phe Ser Lys Gly Gln Lys Arg Lys Met Lys Ser Leu Asp Glu
            340                 345                 350

Ser Ala Leu Cys Ile Phe Ile Leu Lys Gln Ile Asn Asp Arg Ile Lys
        355                 360                 365

Glu Arg Leu Gln Ser Cys Tyr Arg Gly Glu Gly Thr Leu Asp Leu Ala
    370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
                405                 410                 415

Asp Met Val Arg Gly Ile Pro Val Phe Thr Glu Asp Arg Asp Arg Met
            420                 425                 430

Thr Ser Val Ile Ala Tyr Val Tyr Lys Asn His Ser Leu Ala Phe Val
        435                 440                 445

Gly Thr Lys Ser Gly Lys Leu Lys Lys Ile Arg Val Asp Gly Pro Arg
    450                 455                 460

Gly Asn Ala Leu Gln Tyr Glu Thr Val Gln Val Asp Pro Gly Pro
465                 470                 475                 480

Val Leu Arg Asp Met Ala Phe Ser Lys Asp His Glu Gln Leu Tyr Ile
                485                 490                 495

Met Ser Glu Arg Gln Leu Thr Arg Val Pro Val Glu Ser Cys Gly Gln
            500                 505                 510

Tyr Gln Ser Cys Gly Glu Cys Leu Gly Ser Gly Asp Pro His Cys Gly
        515                 520                 525

Trp Cys Val Leu His Asn Thr Cys Thr Arg Lys Glu Arg Cys Glu Arg
    530                 535                 540

Ser Lys Glu Pro Arg Arg Phe Ala Ser Glu Met Lys Gln Cys Val Arg
545                 550                 555                 560
```

```
Leu Thr Val His Pro Asn Asn Ile Ser Val Ser Gln Tyr Asn Val Leu
                565                 570                 575

Leu Val Leu Glu Thr Tyr Asn Val Pro Glu Leu Ser Ala Gly Val Asn
            580                 585                 590

Cys Thr Phe Glu Asp Leu Ser Glu Met Asp Gly Leu Val Val Gly Asn
        595                 600                 605

Gln Ile Gln Cys Tyr Ser Pro Ala Ala Lys Glu Val Pro Arg Ile Ile
    610                 615                 620

Thr Glu Asn Gly Asp His His Val Val Gln Leu Gln Leu Lys Ser Lys
625                 630                 635                 640

Glu Thr Gly Met Thr Phe Ala Ser Thr Ser Phe Val Phe Tyr Asn Cys
                645                 650                 655

Ser Val His Asn Ser Cys Leu Ser Cys Val Glu Ser Pro Tyr Arg Cys
            660                 665                 670

His Trp Cys Lys Tyr Arg His Val Cys Thr His Asp Pro Lys Thr Cys
        675                 680                 685

Ser Phe Gln Glu Gly Arg Val Lys Leu Pro Glu Asp Cys Pro Gln Leu
    690                 695                 700

Leu Arg Val Asp Lys Ile Leu Val Pro Val Glu Val Ile Lys Pro Ile
705                 710                 715                 720

Thr Leu Lys Ala Lys Asn Leu Pro Gln Pro Gln Ser Gly Gln Arg Gly
                725                 730                 735

Tyr Glu Cys Ile Leu Asn Ile Gln Gly Ser Glu Gln Arg Val Pro Ala
            740                 745                 750

Leu Arg Phe Asn Ser Ser Ser Val Gln Cys Gln Asn Thr Ser Tyr Ser
        755                 760                 765

Tyr Glu Gly Met Glu Ile Asn Asn Leu Pro Val Glu Leu Thr Val Val
    770                 775                 780

Trp Asn Gly His Phe Asn Ile Asp Asn Pro Ala Gln Asn Lys Val His
785                 790                 795                 800

Leu Tyr Lys Cys Gly Ala Met Arg Glu Ser Cys Gly Leu Cys Leu Lys
                805                 810                 815

Ala Asp Pro Asp Phe Ala Cys Gly Trp Cys Gln Gly Pro Gly Gln Cys
            820                 825                 830

Thr Leu Arg Gln His Cys Pro Ala Gln Glu Ser Gln Trp Leu Glu Leu
        835                 840                 845

Ser Gly Ala Lys Ser Lys Cys Thr Asn Pro Arg Ile Thr Glu Ile Ile
    850                 855                 860

Pro Val Thr Gly Pro Arg Glu Gly Gly Thr Lys Val Thr Ile Arg Gly
865                 870                 875                 880

Glu Asn Leu Gly Leu Glu Phe Arg Asp Ile Ala Ser His Val Lys Val
                885                 890                 895

Ala Gly Val Glu Cys Ser Pro Leu Val Asp Gly Tyr Ile Pro Ala Glu
            900                 905                 910

Gln Ile Val Cys Glu Met Gly Glu Ala Lys Pro Ser Gln His Ala Gly
        915                 920                 925

Phe Val Glu Ile Cys Val Ala Val Cys Arg Pro Glu Phe Met Ala Arg
    930                 935                 940

Ser Ser Gln Leu Tyr Tyr Phe Met Thr Leu Thr Leu Ser Asp Leu Lys
945                 950                 955                 960

Pro Ser Arg Gly Pro Met Ser Gly Gly Thr Gln Val Thr Ile Thr Gly
                965                 970                 975

Thr Asn Leu Asn Ala Gly Ser Asn Val Val Val Met Phe Gly Lys Gln
```

-continued

```
                980             985             990
    Pro Cys Leu Phe His Arg Arg Ser Pro Ser Tyr Ile Val Cys Asn Thr
                    995             1000            1005

Thr Ser Ser Asp Glu Val Leu Glu Met Lys Val Ser Val Gln Val
        1010            1015            1020

Asp Arg Ala Lys Ile His Gln Asp Leu Val Phe Gln Tyr Val Glu
        1025            1030            1035

Asp Pro Thr Ile Val Arg Ile Glu Pro Glu Trp Ser Ile Val Ser
        1040            1045            1050

Gly Asn Thr Pro Ile Ala Val Trp Gly Thr His Leu Asp Leu Ile
        1055            1060            1065

Gln Asn Pro Gln Ile Arg Ala Lys His Gly Gly Lys Glu His Ile
        1070            1075            1080

Asn Ile Cys Glu Val Leu Asn Ala Thr Glu Met Thr Cys Gln Ala
        1085            1090            1095

Pro Ala Leu Ala Leu Gly Pro Asp His Gln Ser Asp Leu Thr Glu
        1100            1105            1110

Arg Pro Glu Glu Phe Gly Phe Ile Leu Asp Asn Val Gln Ser Leu
        1115            1120            1125

Leu Ile Leu Asn Lys Thr Asn Phe Thr Tyr Tyr Pro Asn Pro Val
        1130            1135            1140

Phe Glu Ala Phe Gly Pro Ser Gly Ile Leu Glu Leu Lys Pro Gly
        1145            1150            1155

Thr Pro Ile Ile Leu Lys Gly Lys Asn Leu Ile Pro Pro Val Ala
        1160            1165            1170

Gly Gly Asn Val Lys Leu Asn Tyr Thr Val Leu Val Gly Glu Lys
        1175            1180            1185

Pro Cys Thr Val Thr Val Ser Asp Val Gln Leu Leu Cys Glu Ser
        1190            1195            1200

Pro Asn Leu Ile Gly Arg His Lys Val Met Ala Arg Val Gly Gly
        1205            1210            1215

Met Glu Tyr Ser Pro Gly Met Val Tyr Ile Ala Pro Asp Gly Cys
        1220            1225            1230

Val Glu Pro Lys Ser Cys Asp Lys Thr His Thr Cys Pro Pro Cys
        1235            1240            1245

Pro Ala Pro Glu Leu Leu Gly Gly Pro Ser Val Phe Leu Phe Pro
        1250            1255            1260

Pro Lys Pro Lys Asp Thr Leu Met Ile Ser Arg Thr Pro Glu Val
        1265            1270            1275

Thr Cys Val Val Val Asp Val Ser His Glu Asp Pro Glu Val Lys
        1280            1285            1290

Phe Asn Trp Tyr Val Asp Gly Val Glu Val His Asn Ala Lys Thr
        1295            1300            1305

Lys Pro Arg Glu Glu Gln Tyr Asn Ser Thr Tyr Arg Val Val Ser
        1310            1315            1320

Val Leu Thr Val Leu His Gln Asp Trp Leu Asn Gly Lys Glu Tyr
        1325            1330            1335

Lys Cys Lys Val Ser Asn Lys Ala Leu Pro Ala Pro Ile Glu Lys
        1340            1345            1350

Thr Ile Ser Lys Ala Lys Gly Gln Pro Arg Glu Pro Gln Val Tyr
        1355            1360            1365

Thr Leu Pro Pro Ser Arg Asp Glu Leu Thr Lys Asn Gln Val Ser
        1370            1375            1380
```

```
Leu Thr Cys Leu Val Lys Gly Phe Tyr Pro Ser Asp Ile Ala Val
    1385                1390                1395

Glu Trp Glu Ser Asn Gly Gln Pro Glu Asn Asn Tyr Lys Thr Thr
    1400                1405                1410

Pro Pro Val Leu Asp Ser Asp Gly Ser Phe Phe Leu Tyr Ser Lys
    1415                1420                1425

Leu Thr Val Asp Lys Ser Arg Trp Gln Gln Gly Asn Val Phe Ser
    1430                1435                1440

Cys Ser Val Met His Glu Ala Leu His Asn His Tyr Thr Gln Lys
    1445                1450                1455

Ser Leu Ser Leu Ser Pro Gly Lys
    1460                1465

<210> SEQ ID NO 7
<211> LENGTH: 1231
<212> TYPE: PRT
<213> ORGANISM: Homo sapiens

<400> SEQUENCE: 7

Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
                20                  25                  30

Leu Ser Gln Lys Gln Arg Ser Phe Val Thr Phe Arg Gly Glu Pro Ala
            35                  40                  45

Glu Gly Phe Asn His Leu Val Val Asp Glu Arg Thr Gly His Ile Tyr
        50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
            100                 105                 110

Asn Val Asn Lys Met Leu Leu Ile Asp Tyr Lys Glu Asn Arg Leu Ile
        115                 120                 125

Ala Cys Gly Ser Leu Tyr Gln Gly Ile Cys Lys Leu Leu Arg Leu Glu
    130                 135                 140

Asp Leu Phe Lys Leu Gly Glu Pro Tyr His Lys Lys Glu His Tyr Leu
145                 150                 155                 160

Ser Gly Val Asn Glu Ser Gly Ser Val Phe Gly Val Ile Val Ser Tyr
                165                 170                 175

Ser Asn Leu Asp Asp Lys Leu Phe Ile Ala Thr Ala Val Asp Gly Lys
            180                 185                 190

Pro Glu Tyr Phe Pro Thr Ile Ser Ser Arg Lys Leu Thr Lys Asn Ser
        195                 200                 205

Glu Ala Asp Gly Met Phe Ala Tyr Val Phe His Asp Glu Phe Val Ala
    210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
                245                 250                 255

Leu Thr Leu Gln Pro Glu Met Val Ser Pro Pro Gly Ser Thr Thr Lys
            260                 265                 270

Glu Gln Val Tyr Thr Ser Lys Leu Val Arg Leu Cys Lys Glu Asp Thr
```

```
                275                 280                 285
Ala Phe Asn Ser Tyr Val Glu Val Pro Ile Gly Cys Glu Arg Ser Gly
290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Asp Leu Leu Phe
                325                 330                 335

Thr Val Phe Ser Lys Gly Gln Lys Arg Lys Met Lys Ser Leu Asp Glu
                340                 345                 350

Ser Ala Leu Cys Ile Phe Ile Leu Lys Gln Ile Asn Asp Arg Ile Lys
                355                 360                 365

Glu Arg Leu Gln Ser Cys Tyr Arg Gly Glu Gly Thr Leu Asp Leu Ala
                370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
                405                 410                 415

Asp Met Val Arg Gly Ile Pro Val Phe Thr Glu Asp Arg Asp Arg Met
                420                 425                 430

Thr Ser Val Ile Ala Tyr Val Tyr Lys Asn His Ser Leu Ala Phe Val
                435                 440                 445

Gly Thr Lys Ser Gly Lys Leu Lys Lys Ile Arg Val Asp Gly Pro Arg
450                 455                 460

Gly Asn Ala Leu Gln Tyr Glu Thr Val Gln Val Asp Pro Gly Pro
465                 470                 475                 480

Val Leu Arg Asp Met Ala Phe Ser Lys Asp His Glu Gln Leu Tyr Ile
                485                 490                 495

Met Ser Glu Arg Gln Leu Thr Arg Val Pro Val Glu Ser Cys Gly Gln
                500                 505                 510

Tyr Gln Ser Cys Gly Glu Cys Leu Gly Ser Gly Asp Pro His Cys Gly
                515                 520                 525

Trp Cys Val Leu His Asn Thr Cys Thr Arg Lys Glu Arg Cys Glu Arg
530                 535                 540

Ser Lys Glu Pro Arg Arg Phe Ala Ser Glu Met Lys Gln Cys Val Arg
545                 550                 555                 560

Leu Thr Val His Pro Asn Asn Ile Ser Val Ser Gln Tyr Asn Val Leu
                565                 570                 575

Leu Val Leu Glu Thr Tyr Asn Val Pro Glu Leu Ser Ala Gly Val Asn
                580                 585                 590

Cys Thr Phe Glu Asp Leu Ser Glu Met Asp Gly Leu Val Val Gly Asn
                595                 600                 605

Gln Ile Gln Cys Tyr Ser Pro Ala Ala Lys Glu Val Pro Arg Ile Ile
                610                 615                 620

Thr Glu Asn Gly Asp His His Val Val Gln Leu Gln Leu Lys Ser Lys
625                 630                 635                 640

Glu Thr Gly Met Thr Phe Ala Ser Thr Ser Phe Val Phe Tyr Asn Cys
                645                 650                 655

Ser Val His Asn Ser Cys Leu Ser Cys Val Glu Ser Pro Tyr Arg Cys
                660                 665                 670

His Trp Cys Lys Tyr Arg His Val Cys Thr His Asp Pro Lys Thr Cys
                675                 680                 685

Ser Phe Gln Glu Gly Arg Val Lys Leu Pro Glu Asp Cys Pro Gln Leu
690                 695                 700
```

```
Leu Arg Val Asp Lys Ile Leu Val Pro Val Glu Val Ile Lys Pro Ile
705                 710                 715                 720

Thr Leu Lys Ala Lys Asn Leu Pro Gln Pro Gln Ser Gly Gln Arg Gly
            725                 730                 735

Tyr Glu Cys Ile Leu Asn Ile Gln Gly Ser Glu Gln Arg Val Pro Ala
            740                 745                 750

Leu Arg Phe Asn Ser Ser Val Gln Cys Gln Asn Thr Ser Tyr Ser
            755                 760                 765

Tyr Glu Gly Met Glu Ile Asn Asn Leu Pro Val Glu Leu Thr Val Val
770                 775                 780

Trp Asn Gly His Phe Asn Ile Asp Asn Pro Ala Gln Asn Lys Val His
785                 790                 795                 800

Leu Tyr Lys Cys Gly Ala Met Arg Glu Ser Cys Gly Leu Cys Leu Lys
                805                 810                 815

Ala Asp Pro Asp Phe Ala Cys Gly Trp Cys Gln Gly Pro Gly Gln Cys
                820                 825                 830

Thr Leu Arg Gln His Cys Pro Ala Gln Glu Ser Gln Trp Leu Glu Leu
                835                 840                 845

Ser Gly Ala Lys Ser Lys Cys Thr Asn Pro Arg Ile Thr Glu Ile Ile
850                 855                 860

Pro Val Thr Gly Pro Arg Glu Gly Gly Thr Lys Val Thr Ile Arg Gly
865                 870                 875                 880

Glu Asn Leu Gly Leu Glu Phe Arg Asp Ile Ala Ser His Val Lys Val
                885                 890                 895

Ala Gly Val Glu Cys Ser Pro Leu Val Asp Gly Tyr Ile Pro Ala Glu
                900                 905                 910

Gln Ile Val Cys Glu Met Gly Glu Ala Lys Pro Ser Gln His Ala Gly
                915                 920                 925

Phe Val Glu Ile Cys Val Ala Val Cys Arg Pro Glu Phe Met Ala Arg
                930                 935                 940

Ser Ser Gln Leu Tyr Tyr Phe Met Thr Leu Thr Leu Ser Asp Leu Lys
945                 950                 955                 960

Pro Ser Arg Gly Pro Met Ser Gly Gly Thr Gln Val Thr Ile Thr Gly
                965                 970                 975

Thr Asn Leu Asn Ala Gly Ser Asn Val Val Val Met Phe Gly Lys Gln
                980                 985                 990

Pro Cys Leu Phe His Arg Arg Ser Pro Ser Tyr Ile Val Cys Asn Thr
                995                 1000                1005

Thr Ser Ser Asp Glu Val Leu Glu Met Lys Val Ser Val Gln Val
    1010                1015                1020

Asp Arg Ala Lys Ile His Gln Asp Leu Val Phe Gln Tyr Val Glu
    1025                1030                1035

Asp Pro Thr Ile Val Arg Ile Glu Pro Glu Trp Ser Ile Val Ser
    1040                1045                1050

Gly Asn Thr Pro Ile Ala Val Trp Gly Thr His Leu Asp Leu Ile
    1055                1060                1065

Gln Asn Pro Gln Ile Arg Ala Lys His Gly Gly Lys Glu His Ile
    1070                1075                1080

Asn Ile Cys Glu Val Leu Asn Ala Thr Glu Met Thr Cys Gln Ala
    1085                1090                1095

Pro Ala Leu Ala Leu Gly Pro Asp His Gln Ser Asp Leu Thr Glu
    1100                1105                1110
```

```
Arg Pro Glu Glu Phe Gly Phe Ile Leu Asp Asn Val Gln Ser Leu
    1115                1120                1125

Leu Ile Leu Asn Lys Thr Asn Phe Thr Tyr Tyr Pro Asn Pro Val
    1130                1135                1140

Phe Glu Ala Phe Gly Pro Ser Gly Ile Leu Glu Leu Lys Pro Gly
    1145                1150                1155

Thr Pro Ile Ile Leu Lys Gly Lys Asn Leu Ile Pro Pro Val Ala
    1160                1165                1170

Gly Gly Asn Val Lys Leu Asn Tyr Thr Val Leu Val Gly Glu Lys
    1175                1180                1185

Pro Cys Thr Val Thr Val Ser Asp Val Gln Leu Leu Cys Glu Ser
    1190                1195                1200

Pro Asn Leu Ile Gly Arg His Lys Val Met Ala Arg Val Gly Gly
    1205                1210                1215

Met Glu Tyr Ser Pro Gly Met Val Tyr Ile Ala Pro Asp
    1220                1225                1230

<210> SEQ ID NO 8
<211> LENGTH: 233
<212> TYPE: PRT
<213> ORGANISM: Artificial
<220> FEATURE:
<223> OTHER INFORMATION: IgG Fc portion of plexin-A4 fusion protein

<400> SEQUENCE: 8

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 9
<211> LENGTH: 4398
<212> TYPE: DNA
<213> ORGANISM: Artificial
<220> FEATURE:
<223> OTHER INFORMATION: Coding sequence for plexin-A4 fusion protein

<400> SEQUENCE: 9

| | | | | | |
|---|---|---|---|---|---|
| atgaaagcca | tgccctggaa | ctggacctgc | cttctctccc | acctcctcat | ggtgggcatg | 60 |
| ggctcctcca | ctttgctcac | ccggcagcca | gccccgctgt | cccagaagca | gcggtcattt | 120 |
| gtcacattcc | gaggagagcc | cgccgagggt | ttcaatcacc | tggtggtgga | tgagaggaca | 180 |
| ggacacattt | acttgggggc | cgtcaatcgg | atttacaagc | tctccagcga | cctgaaggtc | 240 |
| ttggtgacgc | atgagacagg | gccggacgag | acaaccccca | gtgttaccca | cccccgcatc | 300 |
| gtccagacct | gcaatgagcc | cctgaccacc | accaacaatg | tcaacaagat | gctcctcata | 360 |
| gactacaagg | agaacaggct | gattgcctgt | gggagcctgt | accaaggcat | ctgcaagctg | 420 |
| ctgaggctgg | aggacctctt | caagctgggg | gagccttatc | ataagaagga | gcactatctg | 480 |
| tcaggtgtca | acgagagcgg | ctcagtcttt | ggagtgatcg | tctcctacag | caacctggat | 540 |
| gacaagctgt | tcattgccac | ggcagtggat | gggaagcccg | agtattttcc | caccatctcc | 600 |
| agccggaaac | tgaccaagaa | ctctgaggcg | gatggcatgt | tcgcgtacgt | cttccatgat | 660 |
| gagttcgtgg | cctcgatgat | taagatccct | tcggacacct | tcaccatcat | ccctgacttt | 720 |
| gatatctact | atgtctatgg | ttttagcagt | ggcaactttg | tctactttt | gaccctccaa | 780 |
| cctgagatgg | tgtctccacc | aggctccacc | accaaggagc | aggtgtatac | atccaagctc | 840 |
| gtgaggcttt | gcaaggagga | cacagccttc | aactcctatg | tagaggtgcc | cattggctgt | 900 |
| gagcgcagtg | gggtggagta | ccgcctgctg | caggctgcct | acctgtccaa | agcgggggcc | 960 |
| gtgcttggca | ggacccttgg | agtccatcca | gatgatgacc | tgctcttcac | cgtcttctcc | 1020 |
| aagggccaga | gcggaaaat | gaatccctg | gatgagtcgg | ccctgtgcat | cttcatcttg | 1080 |
| aagcagataa | atgaccgcat | taaggagcgg | ctgcagtctt | gttaccgggg | cgagggcacg | 1140 |
| ctggacctgg | cctggctcaa | ggtgaaggac | atccccctgca | gcagtgcgct | cttaaccatt | 1200 |
| gacgataact | tctgtggcct | ggacatgaat | gctcccctgg | gagtgtccga | catggtgcgt | 1260 |
| ggaattcccg | tcttcacgga | ggacagggac | cgcatgacgt | ctgtcatcgc | atatgtctac | 1320 |
| aagaaccact | ctctggcctt | tgtgggcacc | aaaagtggca | agctgaagaa | gatccgggtg | 1380 |
| gatggaccca | ggggcaacgc | cctccagtat | gagacggtgc | aggtggtgga | ccccggccca | 1440 |
| gtcctccggg | atatggcctt | ctccaaggac | cacgagcaac | tctacatcat | gtcagagagg | 1500 |
| cagctcacca | gagtccctgt | ggagtcctgt | ggtcagtatc | agagctgcgg | cgagtgcctt | 1560 |
| ggctcaggcg | accccactg | tggctggtgt | gtgctgcaca | acacttgcac | ccggaaggag | 1620 |
| cggtgtgagc | ggtccaagga | gcccgcagg | tttgcctcgg | agatgaagca | gtgtgtccgg | 1680 |
| ctgacggtcc | atcccaacaa | tatctccgtc | tctcagtaca | acgtgctgct | ggtcctggag | 1740 |
| acgtacaatg | tcccggagct | gtcagctggc | gtcaactgca | cctttgagga | cctgtcagag | 1800 |
| atggatgggc | tggtcgtggg | caatcagatc | cagtgctact | cccctgcagc | caaggaggtg | 1860 |
| ccccggatca | tcacagagaa | tggggaccac | catgtcgtac | agcttcagct | caaatcaaag | 1920 |
| gagaccggca | tgaccttcgc | cagcaccagc | tttgtcttct | acaattgcag | cgtccacaat | 1980 |
| tcgtgcctgt | cctgcgtgga | gagtccatac | cgctgccact | ggtgtaaata | ccggcatgtc | 2040 |
| tgcacccatg | accccaagac | ctgctcctc | caggaaggcc | gagtgaagct | gcccgaggac | 2100 |

```
tgcccccagc tgctgcgagt ggacaagatc ctggtgcccg tggaggtgat caagcctatc    2160
acgctgaagg ccaagaacct cccccagccc cagtctgggc agcgtggcta cgaatgcatc    2220
ctcaacattc agggcagcga gcagcgagtg cccgccctgc gcttcaacag ctccagcgta    2280
cagtgccaga acacctctta ttcctatgaa gggatggaga tcaacaacct gcccgtggag    2340
ttgacagtcg tgtggaatgg gcacttcaac attgacaacc cagctcagaa taaagttcac    2400
ctctacaagt gtggagccat gcgtgagagc tgcgggctgt gcctcaaggc tgacccagac    2460
ttcgcatgtg ctggtgcca gggcccaggc cagtgcaccc tgcgccagca ctgccctgcc    2520
caggagagcc agtggctgga gctgtctggt gccaaaagca agtgcacaaa cccccgcatc    2580
acagagataa tcccggtgac aggcccccgg aagggggca ccaaggtcac tatccgaggg    2640
gagaacctgg gcctggaatt cgcgacatc gcctcccatg tcaaggttgc tggcgtggag    2700
tgcagccctt tagtggatgg ttacatccct gcagaacaga tcgtgtgtga tgggggag    2760
gccaagccca ccagcatgc aggcttcgtg gagatctgcg tggctgtgtg tcggcctgaa    2820
ttcatggccc ggtcctcaca gctctattac ttcatgacac tgactctctc agatctgaag    2880
cccagccggg ggcccatgtc cggagggacc caagtgacca tcacaggcac caacctgaat    2940
gccggaagca acgtggtggt gatgtttgga aagcagccct gtctcttcca caggcgatct    3000
ccatcctaca ttgtctgcaa caccacatcc tcagatgagg tgctagagat gaaggtgtcg    3060
gtgcaggtgg acagggccaa gatccaccag gacctggtct ttcagtatgt ggaagacccc    3120
accatcgtgc ggattgagcc agaatggagc attgtcagtg gaaacacacc catcgccgta    3180
tgggggaccc acctggacct catacagaac ccccagatcc gtgccaagca tggagggaag    3240
gagcacatca atatctgtga ggttctgaac gctactgaga tgacctgtca ggcgcccgcc    3300
ctcgctctgg gtcctgacca ccagtcagac ctgaccgaga ggcccgagga gtttggcttc    3360
atcctggaca acgtccagtc cctgctcatc ctcaacaaga ccaacttcac ctactatccc    3420
aacccggtgt ttgaggcctt tggtccctca ggaatcctgg agctcaagcc tggcacgccc    3480
atcatcctaa agggcaagaa cctgatcccg cctgtggctg ggggcaacgt gaagctgaac    3540
tacactgtgc tggttgggga aagccgtgc accgtgaccg tgtcagatgt ccagctgctc    3600
tgcgagtccc ccaacctcat cggcaggcac aaagtgatgg cccgtgtcgg tggcatggag    3660
tactccccgg ggatggtgta cattgccccg gacggatccg agcccaaatc ttgtgacaaa    3720
actcacacat gcccaccgtg cccagcacct gaactcctgg gggaccgtc agtcttcctc    3780
ttcccccaa aacccaagga caccctcatg atctcccgga cccctgaggt cacatgcgtg    3840
gtggtggacg tgagccacga agaccctgag gtcaagttca actggtacgt ggacggcgtg    3900
gaggtgcata atgccaagac aaagccgcgg gaggagcagt acaacagcac gtaccgtgtg    3960
gtcagcgtcc tcaccgtcct gcaccaggac tggctgaatg gcaaggagta caagtgcaag    4020
gtctccaaca agccctcccc agcccccatc gagaaaacca tctccaaagc caagggcag    4080
ccccgagaac cacaggtgta caccctgccc ccatcccggg atgagctgac caagaaccag    4140
gtcagcctga cctgcctggt caaaggcttc tatcccagcg acatcgccgt ggagtgggag    4200
agcaatgggc agccggagaa caactacaag accacgcctc ccgtgctgga ctccgacggc    4260
tccttcttcc tctacagcaa gctcaccgtg gacaagagca ggtggcagca ggggaacgtc    4320
ttctcatgct ccgtgatgca tgaggctctg cacaaccact acacgcagaa gagcctctcc    4380
ctgtctccgg gtaaatga                                                  4398
```

<210> SEQ ID NO 10
<211> LENGTH: 3693
<212> TYPE: DNA
<213> ORGANISM: Homo sapiens

<400> SEQUENCE: 10

```
atgaaagcca tgccctggaa ctggacctgc cttctctccc acctcctcat ggtgggcatg      60
ggctcctcca ctttgctcac ccggcagcca gccccgctgt cccagaagca gcggtcattt     120
gtcacattcc gaggagagcc cgccgagggt ttcaatcacc tggtggtgga tgagaggaca     180
ggacacattt acttggggc cgtcaatcgg atttacaagc tctccagcga cctgaaggtc     240
ttggtgacgc atgagacagg gccggacgag acaaccccca gtgttaccc accccgcatc     300 gtccagacct gcaatgagcc cctgaccacc accaacaatg tcaacaagat gctcctcata     360
gactacaagg agaacaggct gattgcctgt gggagcctgt accaaggcat ctgcaagctg     420
ctgaggctgg aggacctctt caagctgggg gagccttatc ataagaagga gcactatctg     480
tcaggtgtca acgagagcgg ctcagtcttt ggagtgatcg tctcctacag caacctggat     540
gacaagctgt tcattgccac ggcagtggat gggaagcccg agtattttcc caccatctcc     600
agccggaaac tgaccaagaa ctctgaggcg atggcatgt cgcgtacgt cttccatgat     660 gagttcgtgg cctcgatgat taagatccct tcggacacct tcaccatcat ccctgacttt     720
gatatctact atgtctatgg ttttagcagt ggcaactttg tctactttt gaccctccaa     780 cctgagatgg tgtctccacc aggctccacc accaaggagc aggtgtatac atccaagctc     840
gtgaggcttt gcaaggagga cacagccttc aactcctatg tagaggtgcc cattggctgt     900
gagcgcagtg gggtggagta ccgcctgctg caggctgcct acctgtccaa agcggggcc     960 gtgcttggca ggacccttgg agtccatcca tgatgatgacc tgctcttcac cgtcttctcc    1020
aagggccaga gcggaaaat gaaatccctg gatgagtcgg ccctgtgcat cttcatcttg    1080
aagcagataa atgaccgcat taaggagcgg ctgcagtctt gttaccgggg cgagggcacg    1140
ctggacctgg cctggctcaa ggtgaaggac atcccctgca gcagtgcgct cttaaccatt    1200
gacgataact tctgtggcct ggacatgaat gctccccctgg gagtgtccga catggtgcgt    1260
ggaattcccg tcttcacgga ggacagggac cgcatgacgt ctgtcatcgc atatgtctac    1320
aagaaccact ctctggcctt tgtgggcacc aaaagtggca agctgaagaa gatccgggtg    1380
gatggaccca ggggcaacgc cctccagtat gagacggtgc aggtggtgga ccccggccca    1440
gtcctccggg atatggcctt ctccaaggac cacgagcaac tctacatcat gtcagagagg    1500
cagctcacca gagtccctgt ggagtcctgt ggtcagtatc agagctgcgg cgagtgcctt    1560
ggctcaggcg acccccactg tggctggtgt gtgctgcaca acacttgcac ccggaaggag    1620
cggtgtgagc ggtccaagga gccccgcagg tttgcctcgg agatgaagca gtgtgtccgg    1680
ctgacggtcc atcccaacaa tatctccgtc tctcagtaca cgtgctgct ggtcctggag    1740 acgtacaatg tcccggagct gtcagctggc gtcaactgca cctttgagga cctgtcagag    1800
atggatgggc tggtcgtggg caatcagatc cagtgctact cccctgcagc caaggaggtg    1860
ccccggatca tcacagagaa tgggaccac catgtcgtac agcttcagct caaatcaaag    1920
gagaccggca tgaccttcgc cagcaccagc tttgtcttct acaattgcag cgtccacaat    1980
tcgtgcctgt cctgcgtgga gagtccatac cgctgccact ggtgtaaata ccggcatgtc    2040
tgcacccatg accccaagac ctgctcttc caggaaggcc gagtgaagct gcccgaggac    2100
tgcccccagc tgctgcgagt ggacaagatc ctggtgcccg tggaggtgat caagcctatc    2160
```

```
acgctgaagg ccaagaacct cccccagccc cagtctgggc agcgtggcta cgaatgcatc    2220
ctcaacattc agggcagcga gcagcgagtg cccgccctgc gcttcaacag ctccagcgta    2280
cagtgccaga acacctctta ttcctatgaa gggatggaga tcaacaacct gcccgtggag    2340
ttgacagtcg tgtggaatgg gcacttcaac attgacaacc cagctcagaa taaagttcac    2400
ctctacaagt gtggagccat gcgtgagagc tgcgggctgt gcctcaaggc tgacccagac    2460
ttcgcatgtg ctggtgcca gggcccaggc cagtgcaccc tgcgccagca ctgccctgcc    2520
caggagagcc agtggctgga gctgtctggt gccaaaagca agtgcacaaa ccccgcatc     2580 acagagataa tcccggtgac aggcccccgg aagggggca ccaaggtcac tatccgaggg     2640
gagaacctgg gctggaatt tcgcgacatc gcctcccatg tcaaggttgc tggcgtggag     2700 tgcagcccctt tagtggatgg ttacatccct gcagaacaga tcgtgtgtga gatggggag     2760 gccaagccca ccagcatgc aggcttcgtg gagatctgcg tggctgtgtg tcggcctgaa    2820
ttcatggccc ggtcctcaca gctctattac ttcatgacac tgactctctc agatctgaag    2880
cccagccggg ggcccatgtc cggagggacc caagtgacca tcacaggcac caacctgaat    2940
gccggaagca acgtggtggt gatgtttgga aagcagccct gtctcttcca caggcgatct    3000
ccatcctaca ttgtctgcaa caccacatcc tcagatgagg tgctagagat gaaggtgtcg    3060
gtgcaggtgg acagggccaa gatccaccag gacctggtct ttcagtatgt ggaagacccc    3120
accatcgtgc ggattgagcc agaatggagc attgtcagtg aaacacacc catcgccgta    3180 tgggggaccc acctggacct catacagaac ccccagatcc gtgccaagca tggagggaag    3240
gagcacatca atatctgtga ggttctgaac gctactgaga tgacctgtca ggcgcccgcc    3300
ctcgctctgg gtcctgacca ccagtcagac ctgaccgaga ggcccgagga gtttggcttc    3360
atcctggaca cgtccagtc cctgctcatc ctcaacaaga ccaacttcac ctactatccc    3420
aacccggtgt ttgaggcctt tggtccctca ggaatcctgg agctcaagcc tggcacgccc    3480
atcatcctaa agggcaagaa cctgatcccg cctgtggctg ggggcaacgt gaagctgaac    3540
tacactgtgc tggttgggga aagccgtgc accgtgaccg tgtcagatgt ccagctgctc    3600
tgcgagtccc ccaacctcat cggcaggcac aaagtgatgg cccgtgtcgg tggcatggag    3660 tactcccccgg ggatggtgta cattgcccccg gac                                 3693
```

<210> SEQ ID NO 11  
<211> LENGTH: 699  
<212> TYPE: DNA  
<213> ORGANISM: Artificial  
<220> FEATURE:  
<223> OTHER INFORMATION: Coding sequence for IgG Fc portion of plexin-A4 fusion protein

<400> SEQUENCE: 11

```
gagcccaaat cttgtgacaa aactcacaca tgcccaccgt gcccagcacc tgaactcctg      60 ggggaccgt cagtcttcct cttccccccca aacccaagg acaccctcat gatctcccgg      120 accccctgagg tcacatgcgt ggtggtggac gtgagccacg aagaccctga ggtcaagttc      180
aactggtacg tggacggcgt ggaggtgcat aatgccaaga caaagccgcg ggaggagcag      240
tacaacagca cgtaccgtgt ggtcagcgtc ctcaccgtcc tgcaccagga ctggctgaat      300
ggcaaggagt acaagtgcaa ggtctccaac aaagccctcc cagcccccat cgagaaaacc      360
atctccaaag ccaaagggca gccccgagaa ccacaggtgt acaccctgcc cccatcccgg      420
gatgagctga ccaagaacca ggtcagcctg acctgcctgg tcaaaggctt ctatcccagc      480
```

```
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga gagcctctc cctgtctccg ggtaaatga                            699
```

<210> SEQ ID NO 12
<211> LENGTH: 475
<212> TYPE: PRT
<213> ORGANISM: Homo sapiens

<400> SEQUENCE: 12

```
Met Glu Phe Gly Leu Ser Cys Val Phe Leu Val Ala Ile Phe Lys Gly
1               5                   10                  15

Val His Cys Glu Val Gln Leu Val Glu Ser Gly Gly Gly Leu Val Gln
            20                  25                  30

Pro Gly Gly Ser Leu Arg Leu Ser Cys Val Ala Ser Ala Phe Thr Leu
        35                  40                  45

Ser Arg His Ala Met His Trp Val Arg Gln Ala Pro Gly Lys Gly Leu
    50                  55                  60

Glu Tyr Val Ser Gly Ile Ser Asn Ser Glu Asn Ser Thr Tyr Tyr Ala
65                  70                  75                  80

Asp Ser Val Lys Gly Arg Phe Thr Ile Ser Arg Asp Asn Tyr Lys Asn
                85                  90                  95

Thr Leu Tyr Leu Gln Leu Gly Ser Leu Arg Ala Glu Asp Lys Ala Val
            100                 105                 110

Tyr Tyr Cys Ala Arg Ala Arg Cys Arg Gly Asp Thr Cys Leu Asn Phe
        115                 120                 125

Tyr Tyr Gly Leu Asp Val Trp Gly Gln Gly Thr Thr Val Ile Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335
```

```
Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 13
<211> LENGTH: 771
<212> TYPE: PRT
<213> ORGANISM: Homo sapiens

<400> SEQUENCE: 13

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
            35                  40                  45

Asn Gly Leu Ala Asn Ser Ser Ser Tyr His Thr Phe Leu Leu Asp Glu
            50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
            85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
            115                 120                 125

Leu Tyr Ala Cys Gly Thr Gly Ala Phe His Pro Ile Cys Thr Tyr Ile
            130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
            165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
            195                 200                 205

His Pro Ile Arg Thr Glu Gln His Asp Ser Arg Trp Leu Asn Asp Pro
            210                 215                 220

Lys Phe Ile Ser Ala His Leu Ile Ser Glu Ser Asp Asn Pro Glu Asp
```

-continued

```
        225                 230                 235                 240
Asp Lys Val Tyr Phe Phe Phe Arg Glu Asn Ala Ile Asp Gly Glu His
                245                 250                 255
Ser Gly Lys Ala Thr His Ala Arg Ile Gly Gln Ile Cys Lys Asn Asp
                260                 265                 270
Phe Gly Gly His Arg Ser Leu Val Asn Lys Trp Thr Thr Phe Leu Lys
                275                 280                 285
Ala Arg Leu Ile Cys Ser Val Pro Gly Pro Asn Gly Ile Asp Thr His
            290                 295                 300
Phe Asp Glu Leu Gln Asp Val Phe Leu Met Asn Phe Lys Asp Pro Lys
305                 310                 315                 320
Asn Pro Val Val Tyr Gly Val Phe Thr Thr Ser Ser Asn Ile Phe Lys
                325                 330                 335
Gly Ser Ala Val Cys Met Tyr Ser Met Ser Asp Val Arg Arg Val Phe
            340                 345                 350
Leu Gly Pro Tyr Ala His Arg Asp Gly Pro Asn Tyr Gln Trp Val Pro
            355                 360                 365
Tyr Gln Gly Arg Val Pro Tyr Pro Arg Pro Gly Thr Cys Pro Ser Lys
        370                 375                 380
Thr Phe Gly Gly Phe Asp Ser Thr Lys Asp Leu Pro Asp Asp Val Ile
385                 390                 395                 400
Thr Phe Ala Arg Ser His Pro Ala Met Tyr Asn Pro Val Phe Pro Met
                405                 410                 415
Asn Asn Arg Pro Ile Val Ile Lys Thr Asp Val Asn Tyr Gln Phe Thr
            420                 425                 430
Gln Ile Val Val Asp Arg Val Asp Ala Glu Asp Gly Gln Tyr Asp Val
        435                 440                 445
Met Phe Ile Gly Thr Asp Val Gly Thr Val Leu Lys Val Val Ser Ile
    450                 455                 460
Pro Lys Glu Thr Trp Tyr Asp Leu Glu Glu Val Leu Leu Glu Glu Met
465                 470                 475                 480
Thr Val Phe Arg Glu Pro Thr Ala Ile Ser Ala Met Glu Leu Ser Thr
                485                 490                 495
Lys Gln Gln Gln Leu Tyr Ile Gly Ser Thr Ala Gly Val Ala Gln Leu
                500                 505                 510
Pro Leu His Arg Cys Asp Ile Tyr Gly Lys Ala Cys Ala Glu Cys Cys
            515                 520                 525
Leu Ala Arg Asp Pro Tyr Cys Ala Trp Asp Gly Ser Ala Cys Ser Arg
        530                 535                 540
Tyr Phe Pro Thr Ala Lys Arg Arg Thr Arg Arg Gln Asp Ile Arg Asn
545                 550                 555                 560
Gly Asp Pro Leu Thr His Cys Ser Asp Leu His His Asp Asn His His
                565                 570                 575
Gly His Ser Pro Glu Glu Arg Ile Ile Tyr Gly Val Glu Asn Ser Ser
            580                 585                 590
Thr Phe Leu Glu Cys Ser Pro Lys Ser Gln Arg Ala Leu Val Tyr Trp
        595                 600                 605
Gln Phe Gln Arg Arg Asn Glu Glu Arg Lys Glu Ile Arg Val Asp
        610                 615                 620
Asp His Ile Ile Arg Thr Asp Gln Gly Leu Leu Leu Arg Ser Leu Gln
625                 630                 635                 640
Gln Lys Asp Ser Gly Asn Tyr Leu Cys His Ala Val Glu His Gly Phe
                645                 650                 655
```

Ile Gln Thr Leu Leu Lys Val Thr Leu Glu Val Ile Asp Thr Glu His
                660                 665                 670

Leu Glu Glu Leu Leu His Lys Asp Asp Gly Asp Gly Ser Lys Thr
            675                 680                 685

Lys Glu Met Ser Asn Ser Met Thr Pro Ser Gln Lys Val Trp Tyr Arg
    690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Arg Gln Arg
                725                 730                 735

Pro Gly His Thr Pro Gly Asn Ser Asn Lys Trp Lys His Leu Gln Glu
            740                 745                 750

Asn Lys Lys Gly Arg Asn Arg Arg Thr His Glu Phe Glu Arg Ala Pro
        755                 760                 765

Arg Ser Val
    770

<210> SEQ ID NO 14
<211> LENGTH: 2316
<212> TYPE: DNA
<213> ORGANISM: Homo sapiens

<400> SEQUENCE: 14

| | | | | | |
|---|---|---|---|---|---|
| atgggctggt | taactaggat | tgtctgtctt | ttctggggag | tattacttac | agcaagagca | 60 |
| aactatcaga | tgggaagaa | caatgtgcca | aggctgaaat | tatcctacaa | agaaatgttg | 120 |
| gaatccaaca | atgtgatcac | tttcaatggc | ttggccaaca | gctccagtta | tcatacctc | 180 |
| cttttggatg | aggaacggag | taggctgtat | gttggagcaa | aggatcacat | attttcattc | 240 |
| gacctggtta | atatcaagga | ttttcaaaag | attgtgtggc | agtatcttca | caccagaaga | 300 |
| gatgaatgca | agtgggctgg | aaaagacatc | ctgaaagaat | gtgctaattt | catcaaggta | 360 |
| cttaaggcat | ataatcagac | tcacttgtac | gcctgtggaa | cgggggcttt | tcatccaatt | 420 |
| tgcacctaca | ttgaaattgg | acatcatcct | gaggacaata | ttttaagct | ggagaactca | 480 |
| catttgaaa | acggccgtgg | gaagagtcca | tgacccta | agctgctgac | agcatccctt | 540 |
| ttaatagatg | gagaattata | ctctggaact | gcagctgatt | ttatggggcg | agactttgct | 600 |
| atcttccgaa | ctcttgggca | ccaccaccca | atcaggacag | agcagcatga | ttccaggtgg | 660 |
| ctcaatgatc | caaagttcat | tagtgcccac | ctcatctcag | agagtgacaa | tcctgaagat | 720 |
| gacaaagtat | actttttctt | ccgtgaaaat | gcaatagatg | gagaacactc | tggaaaagct | 780 |
| actcacgcta | gaataggtca | gatatgcaag | aatgactttg | agggcacag | aagtctggtg | 840 |
| aataaatgga | caacattcct | caaagctcgt | ctgatttgct | cagtgccagg | tccaaatggc | 900 |
| attgacactc | attttgatga | actgcaggat | gtattcctaa | tgaactttaa | agatcctaaa | 960 |
| aatccagttg | tatatggagt | gtttacgact | tccagtaaca | ttttcaaggg | atcagccgtg | 1020 |
| tgtatgtata | gcatgagtga | tgtgagaagg | gtgttccttg | gtccatatgc | ccacagggat | 1080 |
| ggacccaact | atcaatgggt | gccttatcaa | ggaagagtcc | cctatccacg | gccaggaact | 1140 |
| tgtcccagca | aaacatttgg | tggttttgac | tctacaaagg | accttcctga | tgatgttata | 1200 |
| acctttgcaa | gaagtcatcc | agccatgtac | aatccagtgt | tcctatgaa | caatcgccca | 1260 |
| atagtgatca | aaacggatgt | aaattatcaa | tttacacaaa | ttgtcgtaga | ccgagtggat | 1320 |
| gcagaagatg | gacagtatga | tgttatgttt | atcggaacag | atgttgggac | cgttcttaaa | 1380 |

| | |
|---|---:|
| gtagttttcaa ttcctaagga gacttggtat gatttagaag aggttctgct ggaagaaatg | 1440 |
| acagttttc gggaaccgac tgctatttca gcaatggagc tttccactaa gcagcaacaa | 1500 |
| ctatatattg gttcaacggc tggggttgcc cagctccctt tacaccggtg tgatatttac | 1560 |
| gggaaagcgt gtgctgagtg ttgcctcgcc cgagacccct actgtgcttg ggatggttct | 1620 |
| gcatgttctc gctatttcc cactgcaaag agacgcacaa gacgacaaga tataagaaat | 1680 |
| ggagacccac tgactcactg ttcagactta caccatgata atccacatgg ccacagccct | 1740 |
| gaagagagaa tcatctatgg tgtagagaat agtagcacat ttttggaatg cagtccgaag | 1800 |
| tcgcagagag cgctggtcta ttggcaattc cagaggcgaa atgaagagcg aaaagaagag | 1860 |
| atcagagtgg atgatcatat catcaggaca gatcaaggcc ttctgctacg tagtctacaa | 1920 |
| cagaaggatt caggcaatta cctctgccat gcggtggaac atgggttcat acaaactctt | 1980 |
| cttaaggtaa ccctggaagt cattgacaca gagcatttgg aagaacttct tcataaagat | 2040 |
| gatgatggag atggctctaa gaccaaagaa atgtccaata gcatgacacc tagccagaag | 2100 |
| gtctggtaca gagacttcat gcagctcatc aaccacccca atctcaacac aatggatgag | 2160 |
| ttctgtgaac aagtttggaa aagggaccga aaacaacgtc ggcaaaggcc aggacatacc | 2220 |
| ccagggaaca gtaacaaatg gaagcactta caagaaaata gaaaggtag aaacaggagg | 2280 |
| acccacgaat tgagagggc acccaggagt gtctga | 2316 |

<210> SEQ ID NO 15
<211> LENGTH: 5672
<212> TYPE: DNA
<213> ORGANISM: Homo sapiens

<400> SEQUENCE: 15

| | |
|---|---:|
| aagcaccact gcagcagacc ttgttaattt tttttttttt tctttccaca caacagttgt | 60 |
| gcctcattat ccggtgcctg gctcggaatt tttttttttt ttttcttttt tggagggttt | 120 |
| gaagtttctg tgcttcagtg actgttacag aagaagaggt gttagtgttg ccatgagagtc | 180 |
| ttgattgtct gcatttatga atgaaactga cctaaatcac ctgttacctc cagtttccag | 240 |
| attgtttgaa cttctctggc cgcacaatac aggaaggaag actaaagcag caaagggacc | 300 |
| tacagcgtct gcagcatggg ctggttaact aggattgtct gtcttttctg gggagtatta | 360 |
| cttacagcaa gagcaaacta tcagaatggg aagaacaatg tgccaaggct gaaattatcc | 420 |
| tacaaagaaa tgttggaatc caacaatgtg atcactttca atggcttggc caacagctcc | 480 |
| agttatcata ccttccttt ggatgaggaa cggagtaggc tgtatgttgg agcaaaggat | 540 |
| cacatatttt cattcgacct ggttaatatc aaggattttc aaaagattgt gtggccagta | 600 |
| tcttacacca gaagagatga atgcaagtgg gctggaaaag acatcctgaa agaatgtgct | 660 |
| aatttcatca aggtacttaa ggcatataat cagactcact tgtacgcctg tggaacgggg | 720 |
| gcttttcatc caatttgcac ctacattgaa attggacatc atcctgagga caatattttt | 780 |
| aagctgggaga actcacattt tgaaaacggc cgtgggaaga gtccatatga ccctaagctg | 840 |
| ctgacagcat ccctttaat agatggagaa ttatactctg gaactgcagc tgattttatg | 900 |
| gggcgagact tgctatctt ccgaactctt ggcaccacc acccaatcag acagagcag | 960 |
| catgattcca ggtggctcaa tgatccaaag ttcattagtg cccacctcat ctcagagagt | 1020 |
| gacaatcctg aagatgacaa agtatacttt ttcttccgtg aaaatgcaat agatggagaa | 1080 |
| cactctggaa aagctactca cgctagaata ggtcagatat gcaagaatga ctttggaggg | 1140 |
| cacagaagtc tggtgaataa atggacaaca ttcctcaaag ctcgtctgat ttgctcagtg | 1200 |

```
ccaggtccaa atggcattga cactcatttt gatgaactgc aggatgtatt cctaatgaac    1260
tttaaagatc ctaaaaatcc agttgtatat ggagtgttta cgacttccag taacattttc    1320
aagggatcag ccgtgtgtat gtatagcatg agtgatgtga aagggtgtt ccttggtcca     1380 tatgcccaca gggatggacc caactatcaa tgggtgcctt atcaaggaag agtccctat    1440 ccacggccag gaacttgtcc cagcaaaaca tttggtggtt ttgactctac aaaggacctt    1500
cctgatgatg ttataacctt tgcaagaagt catccagcca tgtacaatcc agtgtttcct    1560
atgaacaatc gcccaatagt gatcaaaacg gatgtaaatt atcaatttac acaaattgtc    1620
gtagaccgag tggatgcaga agatggacag tatgatgtta tgtttatcgg aacagatgtt    1680
gggaccgttc ttaaagtagt ttcaattcct aaggagactt ggtatgattt agaagaggtt    1740
ctgctggaag aaatgacagt ttttcgggaa ccgactgcta tttcagcaat ggagctttcc    1800
actaagcagc aacaactata tattggttca acggctgggg ttgcccagct ccctttacac    1860
cggtgtgata tttacgggaa agcgtgtgct gagtgttgcc tcgcccgaga cccttactgt    1920
gcttgggatg gttctgcatg ttctcgctat tttcccactg caaagagacg cacaagacga    1980
caagatataa aaatggaga cccactgact cactgttcag acttacacca tgataatcac    2040
catggccaca gccctgaaga gagaatcatc tatggtgtag agaatagtag cacattttg    2100 gaatgcagtc cgaagtcgca gagagcgctg gtctattggc aattccagag gcgaaatgaa    2160
gagcgaaaag aagagatcag agtggatgat catatcatca ggacagatca aggccttctg    2220
ctacgtagtc tacaacagaa ggattcaggc aattacctct gccatgcggt ggaacatggg    2280
ttcatacaaa ctcttcttaa ggtaaccctg gaagtcattg acacagagca tttggaagaa    2340
cttcttcata agatgatga tggagatggc tctaagacca agaaaatgtc caatagcatg    2400
acacctagcc agaaggtctg gtacagagac ttcatgcagc tcatcaacca ccccaatctc    2460
aacacaatgg atgagttctg tgaacaagtt tggaaaaggg accgaaaaca acgtcggcaa    2520
aggccaggac ataccccagg gaacagtaac aaatggaagc acttacaaga aaataagaaa    2580
ggtagaaaca ggaggaccca cgaatttgag agggcaccca ggagtgtctg agctgcatta    2640
cctctagaaa ccctcaaacaa gtagaaactt gcctagacaa taactggaaa aacaaatgca    2700
atatacatga acttttttca tggcattatg tggatgttta caatggtggg aaattcagct    2760
gagttccacc aattataaat taaatccatg agtaactttc ctaataggct ttttttccta    2820
ataccaccac ctaacagaga acacaggtga atgcagatgt tcactttagc agacttaatg    2880
tttcctatga gatttcactg tacaggtttg tctttcttct ttgcctgaga ataaaaatg     2940 tcatttgcca tattgccatc taaaggagaa aaactgcatc agcaaagcca ttgtattgaa    3000
ctaaaagttt aaaatgaact gcatggattt actaagctga tgaatattcc aaaacgtggt    3060
tggattcaag gatatatttt gtctaccggc cctcatgttt gtatgtactt gaggagtaaa    3120
atgagtaaaa tgatactgaa tgaaatgttc tgtggaaata ttaaaaaaaa aaaaaaacat    3180
aagccatcca tcatccagaa gaaaaatgga atacactgat ctactactga tgtcttcttt    3240
cagctttgat ctaaagatgt atttttattaa aactataatt taaatgtacc atgaaaaata    3300
tgcagtaaaa attagttgtt ttctaagcta gagtaggatt tgtcttacaa ttattgtgct    3360
atgtagtttt tgttttaaaa attccaatgg tgtgctgctt tctttggaca ttttattttc    3420
aattctataa gagggataga tgacattgtt ctagaaacac atatacatca ttaagagtga    3480
atctctaaaa ccaggatata aattatgctt tatttctctg agaaaatcaa acaaatggaa    3540
```

```
gctgttcaca cctcccttc tttaagcatt atctaaatta attttactt gcataatgtt      3600
cttagaaaaa aaaacagaac atttaagcag gaaaaaagga agaaacaagt tgattttaa      3660
gtgcatttta ctataatgaa tcaatgaagg gaaaaggaac tgcatatttc atgaaaataa     3720
taagcattgt cttaatatac tgttaataga aaatgtgtct taattccgtg cttgaatccc     3780
tgcatgatat ttgagactaa gatctctctt atgattctac caagaattat atctgtgtca    3840
cttaattttt ttaaaagaga gagatcaata actattcaga gcaacatgtt aaaggcaaag    3900
tttccaatca tttacatctg tatcaggtgc ctcttacctt tccttattta agacaattat    3960
ttgtacaaga aacacatgac tcttttcata tcaatgggag ggactttttct acaaagtatt   4020
ttccaggatg caacccacat ttaaacaatg taaaattctt tgtttcctgc aacaacttac   4080
aaaataaggt aaaagactaa aattcaagat ttgcttcctt cattgtccta agacgattcg   4140
ttgagaatca ctgactttga gatatttaaa actttcagca ttatactgtg gtttcttttg   4200
cactgcactc acctattcag gactcctccc ccaggttcct catcatgcac aaaaatgcaa   4260
agaaaacatc ttattagtaa ttaatgaagc aacattgaaa ttctaactct agctgtcttt   4320
ggattctaat taactcagca tcaatttctc acctcagact acagtgaatt tttatttcct   4380
atcagctgaa atatttcaca gatggaagct catgtttcag tttaatgac tgccttgaat    4440
aaacaagttg ttgccacttg tttcaaacaa aagcctaaaa ataatctaca ttcaattta    4500
ggctccattg actaatatgg tgttgctttt ggaagtactg tatatcctca catggaagcc   4560
aaattgttaa attatttgaa ggacacacca ctgtacagaa agtagtgttt caaatataaa   4620
tcgaagaaca aagagtgctc caaaaaatag gtcattcttt tattttcata aagtatctaa   4680
actgtactaa cattcagtgt tgtgtttcat tctaaatttg cagctgaaat aaatttattt    4740
gcgatagcag aaaatatctta ttattcatcc tcagaaataa aggatttgaa gggatagaga  4800
ttatatgata aatttataga agactttcag aatttgaatg cattttgttt agtgttatga   4860
aatgacaata gaaaaaagtc tcgacttcaa ttaaaagtta cacaaacaaa caaatctaca   4920
ggcatgtctt tatataccat caggtctaag ttttcaaaga aaattgtaga tataacttgc   4980
agataactca ttcagtcat aatctctgcc catgtgtatt gagaggggc agtttgcacg     5040
aaaaagaatt attggcccat ttaataattc agctttaaat agactttgtc atatgcatga   5100
atcatcagag atgaaactgt ttgagagact catgtgacct tacgaaaatt acaacagcag   5160
tcttaaagta tgaaaaagat gcatcacagc agagacatta tggcccagtt gatatcaaat   5220
gtaaatgta aatgcatgta aatgcacact tcatttatg tattatttag taatttgcag    5280
tggtatgtgt ttaatatttt tgctacctac acattaggca aaaaaagat gtaaataatt    5340
tgggagaaaa agaggaagaa cagtgtaaaa taaaactttc tataagtact ccatttcaat   5400
gtgttcaaca tcatcctaaa aggcaagatt ttcccacgca ggtgacaagg tggtttatgt   5460
actatttaag ggcggaaggt gcgtgcccgt tcaataagca tgttttttgc caggtaggaa   5520
atatgttcca tatctttact tatcattgca tttcagatgg gaactagaaa aactggagag   5580
aaaaatgtaa tgaaactgct gctgtaaatt attccttta gcatgtattc acttgctaaa    5640
tacacatttc ttcaaaataa aaaaaaaaaa aa                                  5672
```

<210> SEQ ID NO 16
<211> LENGTH: 1006
<212> TYPE: PRT
<213> ORGANISM: Artificial
<220> FEATURE:
<223> OTHER INFORMATION: Sema3A/Fc IgG fusion protein sequence

<400> SEQUENCE: 16

```
Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
```

```
            405                 410                 415
Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
            435                 440                 445

Met Phe Ile Gly Thr Asp Val Gly Thr Val Leu Lys Val Val Ser Ile
            450                 455                 460

Pro Lys Glu Thr Trp Tyr Asp Leu Glu Val Leu Leu Glu Met
465                 470                 475                 480

Thr Val Phe Arg Glu Pro Thr Ala Ile Ser Ala Met Glu Leu Ser Thr
            485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
            515                 520                 525

Leu Ala Arg Asp Pro Tyr Cys Ala Trp Asp Gly Ser Ala Cys Ser Arg
            530                 535                 540

Tyr Phe Pro Thr Ala Lys Arg Thr Arg Arg Gln Asp Ile Arg Asn
545                 550                 555                 560

Gly Asp Pro Leu Thr His Cys Ser Asp Leu His His Asp Asn His His
            565                 570                 575

Gly His Ser Pro Glu Glu Arg Ile Ile Tyr Gly Val Gly Asn Ser Ser
            580                 585                 590

Thr Phe Leu Glu Cys Ser Pro Lys Ser Gln Arg Ala Leu Val Tyr Trp
            595                 600                 605

Gln Phe Gln Arg Arg Asn Glu Glu Arg Lys Glu Glu Ile Arg Val Asp
            610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
            645                 650                 655

Ile Gln Thr Leu Leu Lys Val Thr Leu Glu Val Ile Asp Thr Glu His
            660                 665                 670

Leu Glu Glu Leu Leu His Lys Asp Asp Gly Asp Gly Ser Lys Thr
            675                 680                 685

Lys Glu Met Ser Asn Ser Met Thr Pro Ser Gln Lys Val Trp Tyr Arg
            690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Gln Arg
            725                 730                 735

Pro Gly His Thr Pro Gly Asn Ser Asn Lys Trp Lys His Leu Gln Glu
            740                 745                 750

Asn Lys Lys Gly Arg Asn Arg Thr His Glu Phe Glu Arg Ala Pro
            755                 760                 765

Arg Ser Val Gly Cys Val Glu Pro Lys Ser Cys Asp Lys Thr His Thr
            770                 775                 780

Cys Pro Pro Cys Pro Ala Pro Glu Leu Leu Gly Gly Pro Ser Val Phe
785                 790                 795                 800

Leu Phe Pro Pro Lys Pro Lys Asp Thr Leu Met Ile Ser Arg Thr Pro
            805                 810                 815

Glu Val Thr Cys Val Val Val Asp Val Ser His Glu Asp Pro Glu Val
            820                 825                 830
```

Lys Phe Asn Trp Tyr Val Asp Gly Val Glu Val His Asn Ala Lys Thr
            835                 840                 845
Lys Pro Arg Glu Glu Gln Tyr Asn Ser Thr Tyr Arg Val Val Ser Val
        850                 855                 860
Leu Thr Val Leu His Gln Asp Trp Leu Asn Gly Lys Glu Tyr Lys Cys
865                 870                 875                 880
Lys Val Ser Asn Lys Ala Leu Pro Ala Pro Ile Glu Lys Thr Ile Ser
                885                 890                 895
Lys Ala Lys Gly Gln Pro Arg Glu Pro Gln Val Tyr Thr Leu Pro Pro
            900                 905                 910
Ser Arg Asp Glu Leu Thr Lys Asn Gln Val Ser Leu Thr Cys Leu Val
        915                 920                 925
Lys Gly Phe Tyr Pro Ser Asp Ile Ala Val Glu Trp Glu Ser Asn Gly
    930                 935                 940
Gln Pro Glu Asn Asn Tyr Lys Thr Thr Pro Pro Val Leu Asp Ser Asp
945                 950                 955                 960
Gly Ser Phe Phe Leu Tyr Ser Lys Leu Thr Val Asp Lys Ser Arg Trp
                965                 970                 975
Gln Gln Gly Asn Val Phe Ser Cys Ser Val Met His Glu Ala Leu His
            980                 985                 990
Asn His Tyr Thr Gln Lys Ser Leu Ser Leu Ser Pro Gly Lys
        995                1000                1005

<210> SEQ ID NO 17
<211> LENGTH: 3018
<212> TYPE: DNA
<213> ORGANISM: Artificial
<220> FEATURE:
<223> OTHER INFORMATION: Coding sequence for Sema3A/Fc IgG fusion
      protein

<400> SEQUENCE: 17

```
atgggctggt taactaggat tgtctgtctt ttctggggag tattacttac agcaagagca      60
aactatcaga tgggaagaa caatgtgcca aggctgaaat atcctacaa agaaatgttg       120
gaatccaaca atgtgatcac tttcaatggc ttggccaaca gctccagtta tcataccttc     180
cttttggatg aggaacggag taggctgtat gttggagcaa aggatcacat atttttcattc   240
gacctggtta atatcaagga ttttcaaaag attgtgtggc cagtatctta caccagaaga    300
gatgaatgca gtgggctgg aaaagacatc ctgaaagaat gtgctaattt catcaaggta     360
cttaaggcat ataatcagac tcacttgtac gcctgtggaa cggggggcttt tcatccaatt   420
tgcacctaca ttgaaattgg acatcatcct gaggacaata ttttaagct ggagaactca     480
cattttgaaa acggccgtgg gaagagtcca tgacccta gctgctgac agcatccctt        540
ttaatagatg gagaattata ctctggaact gcagctgatt ttatggggcg agactttgct    600
atcttccgaa ctcttgggca ccaccaccca atcaggacag agcagcatga ttccaggtgg    660
ctcaatgatc caaagttcat tagtgcccac ctcatctcag agagtgacaa tcctgaagat   720
gacaaagtat acttttttctt ccgtgaaaat gcaatagatg agaacactc tggaaaagct   780
actcacgcta aataggtca gatatgcaag aatgactttg agggcacag aagtctggtg     840
aataaatgga caacattcct caaagctcgt ctgatttgct cagtgccagg tccaaatggc   900
attgacactc attttgatga actgcaggat gtattcctaa tgaactttaa agatcctaaa   960
aatccagttg tatatggagt gtttacgact tccagtaaca ttttcaaggg atcagccgtg  1020
```

```
tgtatgtata gcatgagtga tgtgagaagg gtgttccttg gtccatatgc ccacagggat    1080
ggacccaact atcaatgggt gccttatcaa ggaagagtcc cctatccacg gccaggaact    1140
tgtcccagca aaacatttgg tggttttgac tctacaaagg accttcctga tgatgttata    1200
acctttgcaa gaagtcatcc agccatgtac aatccagtgt ttcctatgaa caatcgccca    1260
atagtgatca aaacggatgt aaattatcaa tttacacaaa ttgtcgtaga ccgagtggat    1320
gcagaagatg gacagtatga tgttatgttt atcggaacag atgttgggac cgttcttaaa    1380
gtagtttcaa ttcctaagga gacttggtat gatttagaag aggttctgct ggaagaaatg    1440 acagttttc gggaaccgac tgctatttca gcaatggagc tttccactaa gcagcaacaa     1500
ctatatattg gttcaacggc tggggttgcc cagctcccct tacaccggtg tgatatttac    1560
gggaaagcgt gtgctgagtg ttgcctcgcc cgagaccctt actgtgcttg gatggttct    1620 gcatgttctc gctattttcc cactgcaaag agacgcacaa gacgacaaga tataagaaat    1680
ggagacccac tgactcactg ttcagactta caccatgata atcaccatgg ccacagccct    1740
gaagagagaa tcatctatgg tgtagagaat agtagcacat ttttggaatg cagtccgaag    1800
tcgcagagag cgctggtcta ttggcaattc cagaggcgaa atgaagagcg aaaagaagag    1860
atcagagtgg atgatcatat catcaggaca gatcaaggcc ttctgctacg tagtctacaa    1920
cagaaggatt caggcaatta cctctgccat gcggtggaac atgggttcat acaaactctt    1980
cttaaggtaa ccctggaagt cattgacaca gagcatttgg aagaacttct tcataaagat    2040
gatgatggag atggctctaa gaccaaagaa atgtccaata gcatgacacc tagccagaag    2100
gtctggtaca gagacttcat gcagctcatc aaccaccca atctcaacac aatggatgag    2160
ttctgtgaac aagtttggaa aagggaccga aaacaacgtc ggcaaaggcc aggacatacc    2220
ccagggaaca gtaacaaatg gaagcactta caagaaaata gaaaggtag aaacaggagg    2280 acccacgaat ttgagagggc acccaggagt gtcggatccg agcccaaatc ttgtgacaaa    2340
actcacacat gcccaccgtg cccagcacct gaactcctgg ggggaccgtc agtcttcctc    2400
ttccccccaa aacccaagga caccctcatg atctcccgga cccctgaggt cacatgcgtg    2460
gtggtggacg tgagccacga agaccctgag gtcaagttca actggtacgt ggacggcgtg    2520
gaggtgcata atgccaagac aaagccgcgg gaggagcagt acaacagcac gtaccgtgtg    2580
gtcagcgtcc tcaccgtcct gcaccaggac tggctgaatg gcaaggagta caagtgcaag    2640
gtctccaaca aagccctccc agcccccatc gagaaaacca tctccaaagc caaagggcag    2700
ccccgagaac cacaggtgta caccctgccc ccatcccggg atgagctgac caagaaccag    2760
gtcagcctga cctgcctggt caaaggcttc tatcccagcg acatcgccgt ggagtgggag    2820
agcaatgggc agccggagaa caactacaag accacgcctc ccgtgctgga ctccgacggc    2880
tccttcttcc tctacagcaa gctcaccgtg gacaagagca ggtggcagca ggggaacgtc    2940
ttctcatgct ccgtgatgca tgaggctctg cacaaccact acacgcagaa gagcctctcc    3000
ctgtctccgg gtaaatga                                                  3018
```

<210> SEQ ID NO 18
<211> LENGTH: 20
<212> TYPE: DNA
<213> ORGANISM: Artificial
<220> FEATURE:
<223> OTHER INFORMATION: PCT primer

<400> SEQUENCE: 18
tgaaaggaga aggcttgtga                                                  20

```
<210> SEQ ID NO 19
<211> LENGTH: 21
<212> TYPE: DNA
<213> ORGANISM: Artificial
<220> FEATURE:
<223> OTHER INFORMATION: PCR primer

<400> SEQUENCE: 19
taatgggatg agtatggggc a                                              21

<210> SEQ ID NO 20
<211> LENGTH: 20
<212> TYPE: DNA
<213> ORGANISM: Artificial
<220> FEATURE:
<223> OTHER INFORMATION: PCR primer

<400> SEQUENCE: 20
cccaactttc caaaccctct                                                20

<210> SEQ ID NO 21
<211> LENGTH: 21
<212> TYPE: DNA
<213> ORGANISM: Artificial
<220> FEATURE:
<223> OTHER INFORMATION: PCR primer

<400> SEQUENCE: 21
accatgatct catgtggagg a                                              21

<210> SEQ ID NO 22
<211> LENGTH: 21
<212> TYPE: DNA
<213> ORGANISM: Artificial
<220> FEATURE:
<223> OTHER INFORMATION: PCR primer

<400> SEQUENCE: 22
gcctcaagga tgacttaagc a                                              21

<210> SEQ ID NO 23
<211> LENGTH: 21
<212> TYPE: DNA
<213> ORGANISM: Artificial
<220> FEATURE:
<223> OTHER INFORMATION: PCR primer

<400> SEQUENCE: 23
agattgcaca atgtgacgtc g                                              21

<210> SEQ ID NO 24
<211> LENGTH: 35
<212> TYPE: DNA
<213> ORGANISM: Artificial
<220> FEATURE:
<223> OTHER INFORMATION: Cloning primer

<400> SEQUENCE: 24
aagcttgcca cccatgaaag ccatgccctg gaact                               35

<210> SEQ ID NO 25
<211> LENGTH: 28
<212> TYPE: DNA
<213> ORGANISM: Artificial
<220> FEATURE:
```

```
<223> OTHER INFORMATION: Cloning primer

<400> SEQUENCE: 25
ggatccgtcc ggggcaatgt acaccatc                                28

<210> SEQ ID NO 26
<211> LENGTH: 28
<212> TYPE: DNA
<213> ORGANISM: Artificial
<220> FEATURE:
<223> OTHER INFORMATION: Cloning primer

<400> SEQUENCE: 26
ggatccaagg acggttctca gctgtcta                                28

<210> SEQ ID NO 27
<211> LENGTH: 21
<212> TYPE: DNA
<213> ORGANISM: Artificial
<220> FEATURE:
<223> OTHER INFORMATION: Sequencing primer

<400> SEQUENCE: 27
gattgcctgt gggagcctgt a                                       21

<210> SEQ ID NO 28
<211> LENGTH: 22
<212> TYPE: DNA
<213> ORGANISM: Artificial
<220> FEATURE:
<223> OTHER INFORMATION: Sequencing primer

<400> SEQUENCE: 28
tatgtagagg tgcccattgg ct                                      22

<210> SEQ ID NO 29
<211> LENGTH: 20
<212> TYPE: DNA
<213> ORGANISM: Artificial
<220> FEATURE:
<223> OTHER INFORMATION: Sequencing primer

<400> SEQUENCE: 29
tatgagacgg tgcaggtggt                                         20

<210> SEQ ID NO 30
<211> LENGTH: 18
<212> TYPE: DNA
<213> ORGANISM: Artificial
<220> FEATURE:
<223> OTHER INFORMATION: Sequencing primer

<400> SEQUENCE: 30
ttcgccagca ccagcttt                                           18

<210> SEQ ID NO 31
<211> LENGTH: 19
<212> TYPE: DNA
<213> ORGANISM: Artificial
<220> FEATURE:
<223> OTHER INFORMATION: Sequencing primer

<400> SEQUENCE: 31
tgacccagac ttcgcatgt                                          19
```

```
<210> SEQ ID NO 32
<211> LENGTH: 20
<212> TYPE: DNA
<213> ORGANISM: Artificial
<220> FEATURE:
<223> OTHER INFORMATION: Sequencing primer

<400> SEQUENCE: 32
aacctgaatg ccggaagcaa                                              20

<210> SEQ ID NO 33
<211> LENGTH: 20
<212> TYPE: DNA
<213> ORGANISM: Artificial
<220> FEATURE:
<223> OTHER INFORMATION: Sequencing primer

<400> SEQUENCE: 33
gtgtttgagg cctttggtcc                                              20

<210> SEQ ID NO 34
<211> LENGTH: 21
<212> TYPE: DNA
<213> ORGANISM: Artificial
<220> FEATURE:
<223> OTHER INFORMATION: Sequencing primer

<400> SEQUENCE: 34
ggattccgtt cctggactat a                                            21

<210> SEQ ID NO 35
<211> LENGTH: 20
<212> TYPE: DNA
<213> ORGANISM: Artificial
<220> FEATURE:
<223> OTHER INFORMATION: Sequencing primer

<400> SEQUENCE: 35
ttgagcgagg acaagctcat                                              20

<210> SEQ ID NO 36
<211> LENGTH: 21
<212> TYPE: DNA
<213> ORGANISM: Artificial
<220> FEATURE:
<223> OTHER INFORMATION: Sequencing primer

<400> SEQUENCE: 36
tgacctggag agtggagtca a                                            21

<210> SEQ ID NO 37
<211> LENGTH: 19
<212> TYPE: DNA
<213> ORGANISM: Artificial
<220> FEATURE:
<223> OTHER INFORMATION: Sequencing primer

<400> SEQUENCE: 37
gcctctgcca tgaaagcca                                               19

<210> SEQ ID NO 38
<211> LENGTH: 23
<212> TYPE: DNA
<213> ORGANISM: Artificial
<220> FEATURE:
<223> OTHER INFORMATION: Sequencing primer
```

```
<400> SEQUENCE: 38
aaggacggtt ctcagctgtc taa                                           23

<210> SEQ ID NO 39
<211> LENGTH: 20
<212> TYPE: DNA
<213> ORGANISM: Artificial
<220> FEATURE:
<223> OTHER INFORMATION: RT-PCR primer

<400> SEQUENCE: 39
gcctgcagaa gaaggattca                                               20

<210> SEQ ID NO 40
<211> LENGTH: 20
<212> TYPE: DNA
<213> ORGANISM: Artificial
<220> FEATURE:
<223> OTHER INFORMATION: RT-PCR primer

<400> SEQUENCE: 40
tcaggttggg gtggttaatg                                               20

<210> SEQ ID NO 41
<211> LENGTH: 20
<212> TYPE: DNA
<213> ORGANISM: Artificial
<220> FEATURE:
<223> OTHER INFORMATION: RT-PCR primer

<400> SEQUENCE: 41
aatggccaga tgcccttatg                                               20

<210> SEQ ID NO 42
<211> LENGTH: 22
<212> TYPE: DNA
<213> ORGANISM: Artificial
<220> FEATURE:
<223> OTHER INFORMATION: RT-PCR primer

<400> SEQUENCE: 42
ccgagtagag ttttccattg ca                                            22

<210> SEQ ID NO 43
<211> LENGTH: 21
<212> TYPE: DNA
<213> ORGANISM: Artificial
<220> FEATURE:
<223> OTHER INFORMATION: RT-PCR primer

<400> SEQUENCE: 43
ctcctgaagc tgttgcgtta c                                             21

<210> SEQ ID NO 44
<211> LENGTH: 24
<212> TYPE: DNA
<213> ORGANISM: Artificial
<220> FEATURE:
<223> OTHER INFORMATION: RT-PCR primer

<400> SEQUENCE: 44
tactttaccc agctcgctca ctac                                          24

<210> SEQ ID NO 45
<211> LENGTH: 26
```

```
<212> TYPE: DNA
<213> ORGANISM: Artificial
<220> FEATURE:
<223> OTHER INFORMATION: RT-PCR primer

<400> SEQUENCE: 45
tcttctttac gaaagttgga cttgtc                                        26

<210> SEQ ID NO 46
<211> LENGTH: 22
<212> TYPE: DNA
<213> ORGANISM: Artificial
<220> FEATURE:
<223> OTHER INFORMATION: RT-PCR primer

<400> SEQUENCE: 46
ttgccaattg tctggaaaca cc                                            22

<210> SEQ ID NO 47
<211> LENGTH: 20
<212> TYPE: DNA
<213> ORGANISM: Artificial
<220> FEATURE:
<223> OTHER INFORMATION: RT-PCR primer

<400> SEQUENCE: 47
atggcatggc ttacaccacc                                               20

<210> SEQ ID NO 48
<211> LENGTH: 21
<212> TYPE: DNA
<213> ORGANISM: Artificial
<220> FEATURE:
<223> OTHER INFORMATION: RT-PCR primer

<400> SEQUENCE: 48
gaggccaatt ttgtctccac a                                             21

<210> SEQ ID NO 49
<211> LENGTH: 22
<212> TYPE: DNA
<213> ORGANISM: Artificial
<220> FEATURE:
<223> OTHER INFORMATION: RT-PCR primer

<400> SEQUENCE: 49
ctggagttca gaggcaacca tt                                            22

<210> SEQ ID NO 50
<211> LENGTH: 23
<212> TYPE: DNA
<213> ORGANISM: Artificial
<220> FEATURE:
<223> OTHER INFORMATION: RT-PCR primer

<400> SEQUENCE: 50
gttatcaccg gctctccata gaa                                           23

<210> SEQ ID NO 51
<211> LENGTH: 21
<212> TYPE: DNA
<213> ORGANISM: Artificial
<220> FEATURE:
<223> OTHER INFORMATION: RT-PCR primer

<400> SEQUENCE: 51
```
agctgaacat gaacggcatc t                                              21

<210> SEQ ID NO 52
<211> LENGTH: 21
<212> TYPE: DNA
<213> ORGANISM: Artificial
<220> FEATURE:
<223> OTHER INFORMATION: RT-PCR primer

<400> SEQUENCE: 52
tgagcgtgta cttgttgagc g                                              21

<210> SEQ ID NO 53
<211> LENGTH: 19
<212> TYPE: DNA
<213> ORGANISM: Artificial
<220> FEATURE:
<223> OTHER INFORMATION: RT-PCR primer

<400> SEQUENCE: 53
atgagtggtg gttgcaggc                                                 19

<210> SEQ ID NO 54
<211> LENGTH: 25
<212> TYPE: DNA
<213> ORGANISM: Artificial
<220> FEATURE:
<223> OTHER INFORMATION: RT-PCR primer

<400> SEQUENCE: 54
tgacctttca aatgcagtag attca                                          25

<210> SEQ ID NO 55
<211> LENGTH: 36
<212> TYPE: DNA
<213> ORGANISM: Artificial
<220> FEATURE:
<223> OTHER INFORMATION: PCR primer

<400> SEQUENCE: 55
aagcttgcca cccatgggct ggttaactag gattgt                              36

<210> SEQ ID NO 56
<211> LENGTH: 28
<212> TYPE: DNA
<213> ORGANISM: Artificial
<220> FEATURE:
<223> OTHER INFORMATION: PCR primer

<400> SEQUENCE: 56
ggatccgaca ctcctgggtg ccctctca                                       28

<210> SEQ ID NO 57
<211> LENGTH: 22
<212> TYPE: DNA
<213> ORGANISM: Artificial
<220> FEATURE:
<223> OTHER INFORMATION: Sequencing primer

<400> SEQUENCE: 57
tgggaagagt ccatatgacc ct                                             22

<210> SEQ ID NO 58
<211> LENGTH: 20
<212> TYPE: DNA
<213> ORGANISM: Artificial

```
<220> FEATURE:
<223> OTHER INFORMATION: Sequencing primer

<400> SEQUENCE: 58
attttcaagg gatcagccgt                                               20

<210> SEQ ID NO 59
<211> LENGTH: 20
<212> TYPE: DNA
<213> ORGANISM: Artificial
<220> FEATURE:
<223> OTHER INFORMATION: Sequencing primer

<400> SEQUENCE: 59
ctatatattg gttcaacggc                                               20

<210> SEQ ID NO 60
<211> LENGTH: 17
<212> TYPE: PRT
<213> ORGANISM: Artificial
<220> FEATURE:
<223> OTHER INFORMATION: OVA peptide sequence

<400> SEQUENCE: 60

Ile Ser Gln Ala Val His Ala Ala His Ala Glu Ile Asn Glu Ala Gly
1               5                   10                  15

Arg
```